US009422553B2

(12) United States Patent
Terns et al.

(10) Patent No.: US 9,422,553 B2
(45) Date of Patent: Aug. 23, 2016

(54) PROKARYOTIC RNAI-LIKE SYSTEM AND METHODS OF USE

(71) Applicant: UNIVERSITY OF GEORGIA RESEARCH FOUNDATION, INC., Athens, GA (US)

(72) Inventors: Rebecca M. Terns, Athens, GA (US); Michael P. Terns, Athens, GA (US); Caryn R. Hale, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/025,015

(22) Filed: Sep. 12, 2013

(65) Prior Publication Data
US 2014/0093941 A1    Apr. 3, 2014

Related U.S. Application Data

(62) Division of application No. 13/055,769, filed as application No. PCT/US2009/051745 on Jul. 24, 2009, now Pat. No. 8,546,553.

(60) Provisional application No. 61/083,616, filed on Jul. 25, 2008, provisional application No. 61/227,554, filed on Jul. 22, 2009, provisional application No. 61/180,656, filed on May 22, 2009.

(51) Int. Cl.
*C12N 15/11*      (2006.01)
*C12Q 1/68*       (2006.01)
*C12N 15/113*     (2010.01)
*C07H 21/04*      (2006.01)

(52) U.S. Cl.
CPC .......... *C12N 15/113* (2013.01); *C12N 2310/11* (2013.01); *C12N 2310/3519* (2013.01)

(58) Field of Classification Search
None
See application file for complete search history.

(56) References Cited

U.S. PATENT DOCUMENTS

| 4,703,004 | A | 10/1987 | Hopp |
| 4,782,137 | A | 11/1988 | Hopp |
| 5,594,115 | A | 1/1997 | Sharma |
| 5,935,824 | A | 8/1999 | Sgarlato |
| 8,546,553 | B2 | 10/2013 | Terns et al. |
| 2006/0199190 | A1 | 9/2006 | Russell |
| 2008/0124725 | A1 | 5/2008 | Barrangou |

FOREIGN PATENT DOCUMENTS

WO    2007/025097 A2    3/2007

OTHER PUBLICATIONS

Hale et al., RNA-guided RNA cleavage by a CRISPR RNA-Cas protein complex, 2009, Cell, vol. 139, pp. 945-956.*
Terns et al., CRISPR-based technologies: prokaryotic defense weapons repurposed, 2014, Trends in Genetics, vol. 30, pp. 111-118.*
Wang et al., The impact of CRISPR repeat sequence on structures of a Cas6 protein-RNA complex, 2012, Protein Science, vol. 21, pp. 405-417.*
Benda et al., Structural model of a CRISPR RNA-silencing complex reveals the RNA-target cleavage activity in Cmr4, 2014, Molecular Cell, vol. 56, pp. 43-54.*
Genbank Accession Number: National Center for Biotechnology Information, National Library of Medicine, National Institutes of Health, GenBank Locus AAL81254, Accession No. AAL81254, "Definition," hypothetical protein PF1130 [pyrococcus furiosus DSM 3638]. Bethesda, MD [retrieved on Dec. 29, 2011. Retrieved from the Internet:<URL:http://www.ncbi.nlm.nih.gov/protein/AAL81254>; 1 pg.
Genbank Accession Number: National Center for Biotechnology Information, National Library of Medicine, National Institutes of Health, GenBank Locus AAL80476, Accession No. AAL80476, "Definition," hypothetical protein PF0352 [pyrococcus furiosus DSM 3638]. Bethesda, MD [retrieved on Dec. 29, 2011, Retrieved from the Internet:<URL:http://www.ncbi.nlm.nih.gov/protein/AAL80476>; 1 pg.
Genbank Accession Number: National Center for Biotechnology Information, National Library of Medicine, National Institutes of Health, GenBank Locus AAL81253, Accession No. AAL81253, "Definition," hypothetical protein PF1129 [pyrococcus furiosus DSM 3638]. Bethesda, MD [retrieved on Dec. 29, 2011. Retrieved from the Internet:<URL:http://www.ncbi.nlm.nih.gov/protein/AAL81253>; 2 pgs.
Genbank Accession Number: National Center for Biotechnology Information, National Library of Medicine, National Institutes of Health, GenBank Locus AAL81252, Accession No. AAL81252, "Definition," hypothetical protein PF1128 [pyrococcus furiosus DSM 3638]. Bethesda, MD [retrieved on Dec. 29, 2011. Retrieved from the Internet:<URL:http://www.ncbi.nlm.nih.gov/protein/AAL81252>; 1 pg.
Genbank Accession Number: National Center for Biotechnology Information, National Library of Medicine, National Institutes of Health, GenBank Locus AAL81250, Accession No. AAL81250, "Definition," hypothetical protein PF1126 [pyrococcus furiosus DSM 3638]. Bethesda, MD [retrieved on Dec. 29, 2011. Retrieved from the Internet:<URL:http://www.ncbi.nlm.nih.gov/protein/AAL81250>; 1 pg.

(Continued)

*Primary Examiner* — Dana Shin
(74) *Attorney, Agent, or Firm* — Mueting, Raasch & Gebhardt, P.A.

(57) ABSTRACT

Provided herein are methods for inactivating a target polynucleotide. The methods use a psiRNA having a 5' region and a 3' region. The 5' region includes, but is not limited to, 5 to 10 nucleotides chosen from a repeat from a CRISPR locus immediately upstream of a spacer. The 3' region is substantially complementary to a portion of the target polynucleotide. The methods may be practiced in a prokaryotic microbe or in vitro. Also provided are polypeptides that have endonuclease activity in the presence of a psiRNA and a target polynucleotide, and methods for using the polypeptides.

20 Claims, 22 Drawing Sheets

(56) References Cited

OTHER PUBLICATIONS

Genbank Accession Number: National Center for Biotechnology Information, National Library of Medicine, National Institutes of Health, GenBank Locus AAL81249, Accession No. AAL81249, "Definition," hypothetical protein PF1125 [pyrococcus furiosus DSM 3638]. Bethesda, MD [retrieved on Dec. 29, 2011. Retrieved from the Internet:<URL:http://www.ncbi.nlm.nih.gov/protein/AAL81249>; 1 pg.
Genbank Accession Number: National Center for Biotechnology Information, National Library of Medicine, National Institutes of Health, GenBank Locus AAL81248, Accession No. AAL811248, "Definition," hypothetical protein PF1124 [pyrococcus furiosus DSM 36381. Bethesda, MD [retrieved on Dec. 29, 2011. Retrieved from the Internet:<URL:http://www.ncbi.nlm,nih.gov/protein/AAL81248>; 1 pg.
Genbank Accession Number: AB644437, Microcystis aeuginosa DNA, CRISPR-associated protein, CRISPR, partial cds and complete sequence, strain: NIES-298, submitted on Jul. 6, 2011.
PCT International Search Report / Written Opinion issued Jan. 18, 2010, PCT Application No. US2009/051745 filed Jul. 24, 2009.
PCT International Preliminary Report on Patentability issued Jan. 25, 2011, PCT Application No. US2009/051745 filed Jul. 24, 2009.
Andersson et al., "Virus Population Dynamics and Acquired Virus Resistance in Natural Microbial Communities", 2008. *Science*, 320:1047-1050.
Aravin, et al., "The Piwi-piRNA Pathway Provides an Adaptive Defense in the Transposon Arms Race", 2007, *Science*, 318:761-764.
Baker, et al., "RNA-Guided RNA modification: functional organization of the archael H/ACA RNP", 2005, *Genes Dev*, 19(10):1238-1248.
Barrangou et al., CRISPR Provides Acquired Resistance Against Viruses in Prokaryotes, 2007, *Science*, 315:1709-1712.
Bateman et al., "HMM-based databases in InterPro", 2002, *Briefings Bioinformatics*, 43):236-245.
Beloglazova et al., "A Novel Family of Sequence-specific Endoribonucleases Associated with the Clustered Regularly Interspaced Short Palindromic Repeats", 2008, *J Biol Chem*, 283(29):20361-20371.
Bolotin, et al,, "Clustered regularly interspaced short palindrome repeats (CRISPRs) have spacers of extrachromosomal origin" 2005, *Microbiology*, 151:2551-2561.
Bowie et al., "Deciphering the Message in Protein Sequences: Tolerance to Amino Acid Substitutions", 1990, *Science*, 247:1306-1310.
Brouns, Stan J. J. et al., "Small CRISPR RNAs guide antiviral defense in prokaryotes", *Science*, New York, NY, Aug. 15, 2008, 321(5891):960-964.
Brunger et al., "Crystallography & NMR System: A New Software Suite for Macromolecular Structure Determination", 1998, *Acta Crystallographica Section D Biol Crystallography*, D54:905-921.
Calvin, et al., Review. "RNA-splicing endonuclease structure and function". 2008, *Cell Mol. Life Sci*, 65(7-8):1176-1185.
Carte et at, "Cas6 is an endoribonuclease that generates guide RNAs for invader defense in prokaryotes", 2008, *Genes Dev*, 22:3489:3496.
Chapman et al. "Specialization and evolution of endogenous small RNA pathways". 2007, *Nat Rev Genet*, 8:884-896.
Deveau et al., "Phage Response to CRISPR-Encoded Resistance in *Streptococcus thermophilus*", 2008, *J. Bacteriol*, 190(4):1390-1400.
Ding et al., "Antiviral Immunity Directed by Small RNAs". 2007, *Cell*, 130(3):413-426.
Edgar, "PILER-CR: Fast and accurate identification of CRISPR repeats". 2007. *BMC Bioinformatics*. 8:18, 6 pages.
Elbashir et al., "Duplexes of 21-nucleotide RNAs mediate RNA interference in cultured mammalian cells". 2001, *Nature*, 411:494-498.
Elbashir et al., "Functional anatomy of siRNAs for mediating efficient RNAi in *Drosophila melanogaster* embryo lysate", 2001, *Embo J*, 20(23):6877-6888.
Emsley et at., "*Coot*: model-building tools for molecular graphics". 2004, *Acta Crystallogr Section D Biological Crystallography*, D60:2126-2132.
Farazi et al., "The growing catalog of small RNAs and their association with distinct Argonaute/Piwi family members". 2008, *Development*, 135:1201-1214.
Girard et al. "Conserved themes in small-RNA-mediated transposon control". 2008, *Trends Cell Biol*. 18(3):136-148.
Grissa et al., "The CRISPRdb database and tools to display CRISPRs and to generate dictionaries of spacers and repeats", 2007, *BMC Bioinformatics*, 8:172. 10 pages.
Grissa et al., "CRISPRFinder: a web tool to identify clustered regularly interspaced short palindromic repeats", *Nuc. Acids Res.*, 2007, pp. 1-6.
Godde et al. "The Repetitive DNA Elements Called CRISPRs and Their Associated Genes: Evidence of Horizontal Transfer Among Prokaryotes". 2006, *J. Mol. Evol*, 62:718-729.
Haft et al., "The TIGRFAMs database of protein families", *Nucl. Acids Res.*, 2003, 31(1):371-373.
Haft, Daniel H. et al., "A guild of 45 CRISPR-associated (Cas) protein families and multiple CRISPR/Cas subtypes exist in prokaryotic genomes." *PLoS Computational Biology*, Nov. 2005, 1(6):0474-0483.
Hale, Caryn et al., "Prokaryotic silencing (psi) RNAs in Pyrococcus furiosus", *RNA* (New York, NY), Dec. 2008, 14(12):2572-2579.
Hale, C.R. et al., "RNA-Guided RNA Cleavage by a CRISPR RNA-Cas Protein Complex", *CELL*, 139:945-956.
Hammond, "Dicing and Slicing. The Core Machinery of the RNA Interference Pathway". 2005, *FEBS Letters* 579(26):5822-5829.
Hannon, "RNA Interference". 2002, *Nature*, 418:244-251.
Hartig et al., "piRNAs—the ancient hunters of genome invaders", 2007, *Genes Dev.*, 21:1707-1713.
Heidelberg et al., "Germ Warfare in a Microbial Mat Community: CRISPRs Provide Insights into the Co-Evolution of Host and Viral Genomes". 2009, *PLoS ONE*. 4(1): e4169. 12 pages.
Horvath et al., "Diversity, Activity, and Evolution of CRISPR Loci in *Streptococcus thermophilus*". 2008, *J. Bacterial*, 190(4):1401-1412.
Hutvagner et al "Argonaute proteins: key players in RNA silencing", 2008. *Nat Rev Mol Cell Biol*, 9:22-32.
Jansen et al., "Identification of genes that are associated with DNA repeats in prokaryotes". 2002, *Mol. Microbiol*, 43(6):1565-1575.
Jaskiewicz et al., "Role of Dicer in Posttranscriptional RNA Silencing". 2008, *Curr Top Microbial Immunol*, 320:77-97.
Kim, V. Narry. "Small RNAs just got bigger: Piwi-interacting RNAs (piRNAs) in mammalian testes". 2006, *Genes Dev.*, 20:1993-1997.
Klein et al., "Noncoding RNA genes identified in AT-rich hyperthermophiles". 2002, *Proc Natl Acad Sci USA*, 99(11):7542-7547.
Kunin et al., "Evolutionary conservation of sequence and secondary structures in CRISPR repeats". 2007, *Genome Biol.*, 8(4) Article R61. R61.1-R61.7.
Laskowski et al., "Computer Programs". 1993, *Journal of Applied Crystallography*, 26(2):283-291.
Lau et al, "An Abundant Class of Tiny RNAs with Probable Regulatory Roles in *Caenorhabditis elegans*". 2001, Science, 294:858-862.
Lillestol et al., "A putative viral defence mechanism in archael cells". 2006, *Archaea*, 2:59-72.
Lillestol et al, "CRISPR families of the crenarchael genus *Sulfolobus*: bidirectional transcription and dynamic properties". 2009, *Mol. Microbiol*, 72(1):259-272.
Lim et al., "Defining the Regulated Secreted Proteome of Rodent Adipocytes upon the Induction of Insulin Resistance". 2008, *J. Proteome Res*, 7:1251-1263.
Lim, H., "piRNAs in the Germ Line", 2007, *Science*, 316:397.
Makarova et al, "A DNA repair system specific for thermophilic Archaea and bacteria predicted by genomic context analysis". 2002, *Nucleic Acids Res.*, 30(2):482-496.
Makarova, Kira S. et al., "A putative RNA-interference-based immune system in prokaryotes: computational analysis of the predicted enzymatic machinery, functional analogies with eukaryotic RNAi, and hypothetical mechanisms of action", *Biology Direct*, Biomed. Central Ltd., LO, vol. 1, No. 1, Mar. 16, 2006. 26 pages.
Maris et al., "The RNA recognition motif, a plastic RNA-binding platform to regulate post-transcriptional gene expression". 2005, *Febs J*, 272(9):2118-2131.

(56) References Cited

OTHER PUBLICATIONS

Marraffini et al., "CRISPR Interference Limits Horizontal Gene Transfer in Staphylococci by Targeting DNA", 2008, *Science*, 322:1843-1845.

Marx, "A Trace of the Earliest Plate Tectonics Turns Up in Greenland", 2007, *Science*, 315:1650-1651.

Matsumi et al., "Disruption of a Sugar Transporter Gene Cluster in a Hyperthermophilic Archaeon Using a Host-Marker System Based on Antibiotic Resistance". 2007. *J. Bacteriol.* 189(7):2683-2691.

Mojica et al., "Intervening Sequences of Regularly Spaced Prokaryotic Repeats Derive from Foreign Genetic Elements". 2005, *Mol. Evol.*, 60:174-182.

Murshudov et al., "Refinement of Macromolecular Structures by the Maximum-Likelihood Method". 1997, *Acta Crystallogr D Biol Crystallogr*, D53:240-255.

Petrey et al., "GRASP2: Visualization, Surface Properties, and Electrostatics of Macromolecular Structures and Sequences". 2003, *Methods Enzymol*, 374:492-509.

Pourcel, et al., "CRISPR elements in *Yersinia pestis* acquire new repeats by preferential uptake of bacteriophage DNA, and provide additional tools for evolutionary studies". 2005, *Microbiology*, 151:653-663.

Sambrook et al., *Molecular Cloning: A laboratory Manual*, Cold Spring Harbor Laboratory Press 1989).Title Page, Copyright page and Table of Contents. 30 pages total.

Sorek et at., CRISPR—a widespread system that provides acquired resistance against phages in bacteria and archaea. 2008, *Nat. Rev./ Microbiol.*, 6:181-186.

Tang et al., "Identification of 86 candidates for small non-messenger RNAs from the archaeon *Archaeoglobus fulgidus*", 2002, *Proc Natl Acad Sci USA*, 99(11):7536-7541.

Tang et al, "Identification of novel non-coding RNAs as potential antisense regulators in the archaeon *Sulfolobus solfataricus*". 2005, *Mol Microbiol*, 5(2):469-481.

Tatusova et al., "BLAST 2 Sequences, a new tool for comparing protein and nucleotide sequences". *FEMS Microbiol Lett* 1999, 174:247-250.

Terwilliger et al., "Automated MAD and MIR structure solution". 1999, *Acta Crystallogr Section D Biol Crystallogr*, D55:849-861.

Tyson et al. "Rapidly evolving CRISPRs implicated in acquired resistance of microorganisms to viruses". 2008, *Environ. Microbial*, 10(1):200-207.

Van Der Oost, John et al., "CRISPR based adaptive and heritable immunity in prokaryotes", *Trends in Biochemical Sciences*, Aug. 2009, 34(8):401-407.

Van Der Oost, J. et al., "RNAi: Prokaryotes Get in on the Act", 2009. *CELL*, 139:863-865.

Weatherly et al, "A Heuristic Method for Assigning a False-discovery Rate for Protein Indentifications from Mascot Database Search Results", 2005, *Mol. Cell Proteomics* 4.6. 762-772.

Wells, et al., "Mapping Sites of O-GlcNAc Modification Using Affinity Tags for Serine and. Threonine Post-translational Modifications". 2002, *Mol Cell Proteomics* 1.10, 791-804.

Youssef et al., "Dynamic interactions within sub-complexes of the H/ACA pseudouridylation guide RNP". 2007, *Nucleic Acids Res*, 35(18):6196-6206.

Zaratiegui et al., "Noncoding RNAs and Gene Silencing". 2007, *Cell*, 128:763:776.

Bernick et al., "Comparative genomic and transcriptional analyses of CRISPR systems across the genus *Pyrobaculum*," *Frontiers in Microbiology*, Jul. 2012; 3:251.

Elmore et al., "Programmable plasmid interference by the CRISPR-Cas system in *Thermococcus kodakarensis*," *RNA Biology*, May 2013; 10(5):828-840.

Hale et al., Target RNA capture and cleavage by the Cmr type III-B CRISPR-Cas effector complex, *Genes & Development*, 2014; 28:2432-2443.

Makarova et al., "Evolution and classification of the CRISPR-Cas systems," *Nature Reviews Microbiology*, Jun. 2011; (6):467-77.

Randau, "RNA processing in the minimal organism *Nanoarchaeum equitans*," *Genome Biology*, 2012; 13:R63.

Richter et al., "Characterization of CRISPR RNA processing in *Clostridium thermocellum* and *Methanococcus maripaludis*," *Nucleic Acids Research*, 2012; 40:9887-9896.

Scholz et al., "CRISPR-Cas Systems in the Cyanobacterium *Synechocystis* sp. PCC6803 Exhibit Distinct Processing Pathways Involving at Least Two Cas6 and a Cmr2 Protein," *PLoS One*, Feb. 2013; 8(2):e56470.

Terns et al., "The RNA- and DNA-targeting CRISPR-Cas immune systems of *Pyrococcus furiosus*," *Biochemical Society Transactions*, 2013; 41(6):1416-1421.

Xu et al., "Identification and Characterization of Small RNAs in the Hyperthermophilic Archaeon *Sulfolobus solfataricus*," *PLoS One*, Apr. 2012; 7(4):e35306.

* cited by examiner

CRISPR Locus 1; psiRNAs 1.01 - 1.51

7  5  2 2 1    2 2 3 1  2    1  1    2  4 1              2           1        1

CRISPR Locus 2; psiRNAs 2.01 - 2.20

2 2          2      3      1 2

CRISPR Locus 4; psiRNAs 4.01 - 4.22

3 6   2 1   2 1       1              1 3

CRISPR Locus 5; psiRNAs 5.01 - 5.30

2 3 2 2        1   3 2     1    1 1            2

CRISPR Locus 6; psiRNAs 6.01 - 6.45

3 1 1         4      1 1                                    1 1 1      1    1

CRISPR Locus 7; psiRNAs 7.01 - 7.21

6 2   7    1         1

CRISPR Locus 8; psiRNAs 8.01 - 8.11

Cmr1-1 (PF1130)

Protein sequence:
AAL81254.1
GI:18977502
SEQ ID NO:4
MFIEEFEIESITSTHLLEVLTREYPEVRSPSIKGAMRWWFRALAGSYFGDDAQKLKEIENQVFGST
KERSRVKISVTPLSSPKRLNLKEFKDKNVGYIWFSINLLGKRGTITHYYFPGSRFRVVLESPSERV
IKLATLSLWALVSLGSVGFRSRRGTGSMKIVRASSEVLEDLGLTTEFNSIDEFKDSLKRVLDVTGE
ILGVKNSETNKSLPSYATLKFSDVEVFGPGKNTWEVLAQFNNSYKEYLRRRIKKYQRIIFGLPRFK
LRGVRKDLRRASPLWFGVVEIGGKPYGRIIKFFQSTFHPEVRSKHIVDWNVLSNFDWFISSRLPVT
KVWGGWSG Gene Sequence:
NC_003413.1 1081353-1080337
SEQ ID NO:3
ATGTTTATTGAAGAATTTGAAATTGAGTCCATAACCTCCACGCATTTATTAGAGGTGCTGACCAGA
GAATACCCAGAAGTGAGAAGTCCTTCAATAAAGGGAGCAATGAGATGGTGGTTCAGAGCTTTGGCT
GGCTCATATTTTGGAGACGATGCTCAAAAACTTAAAGAAATAGAAAACCAAGTTTTTGGGAGCACA
AAGGAAAGAAGCAGAGTAAAAATTTCTGTTACACCGCTTAGTTCTCCAAAAAGATTAAACCTTAAA
GAGTTTAAGGATAAAAATGTTGGGTACATCTGGTTTTCAATAAATCTGCTCGGAAAAAGAGGGACT
ATAACTCACTATTATCCTCCTGGGAGCAGATTTAGAGTAGTTCTAGAATCACCTAGCGAAAGGGTT
ATTAAGCTGGCAACTTTATCTCTCTGGGCTCTTGTGAGCTTAGGTAGTGTTGGATTTAGAAGTAGA
CGGGGAACAGGTTCAATGAAAATCGTTAGGGCAAGTAGCGAAGTTCTGGAGGATTTGGGACTCACA
ACAGAATTCAATTCTATAGATGAATTTAAAGATTCTTTGAAAAGGGTGTTAGATGTCACAGGCGAA
ATTTTAGGAGTAAAAAATAGCGAAACTAATAAGTCCCTCCCTTCTTACGCTACTTTAAAGTTTTCA
GACGTTGAAGTATTTGGGCCAGGGAAGAATACTTGGGAGGTATTAGCTCAGTTCAACAACTCTTAC
AAGGAATACCTAAGGAGGAGAATTAAGAAGTATCAAAGGATAATATTTGGATTGCCTCGATTTAAG
CTTAGAGGCGTGAGGAAAGACCTAAGGAGAGCTTCTCCCCTTTGGTTTGGCGTTGTAGAGATAGGC
GGAAAGCCATATGGAAGGATAATCAAGTTCTTCCAATCTACATTTCATCCAGAAGTAAGAAGCAAA
CATATAGTTGATTGGAACGTTCTTTCAAATTTTGATTGGTTTATATCCTCTAGACTTCCTGTGACT
AAGGTGTGGGGTGGTTGGAGTGGTTAA

Cmr1-2 (PF0352)

Protein Sequence:
AAL80476
GI: 33359471
SEQ ID NO:6
MLCSHGGMPMYEAIFDLEAITPLFMRGADARSPEFSSASVKGVMRWWFRALAGGYFGNNIEALKEV
EEKIFGSTRNKSRVFVRAEVEDVKKGNIYRQASSWADKTIIVWSEYVDYFFPSVLDKRRNRKTKKI
DIKTRFEYFDVGSKFSISLSSTDERYFRLAEASLWMTINLGGFGFRARRGAGSLKVQMLREMLL Gene Sequence:
NC_003413.1 365628-365038
SEQ ID NO:5

Figure 14B

```
TTGCTCTGCTCTCATGGAGGGATGCCAATGTATGAGGCAATTTTTGATCTTGAAGCAATTACCCCA
CTCTTCATGCGAGGTGCTGATGCTAGAAGTCCTGAGTTTAGCTCTGCTAGTGTTAAAGGGGTTATG
AGGTGGTGGTTCAGGGCTTTGGCTGGAGGATACTTTGGGAATAATATAGAAGCTCTCAAAGAAGTA
GAGGAAAAGATTTTTGGCTCTACTAGAAACAAAAGCAGAGTTTTTGTTCGAGCTGAAGTTGAAGAT
GTTAAGAAAGGAAATATATACCGACAAGCTTCTAGTTGGGCAGATAAAACCATTATAGTATGGTCA
GAATATGTTGATTATTTCTTCTTTTCAGTGTTAGACAAACGCAGAAATAGAAAAACTAAAAAAATA
GATATAAAAACTCGTTTCGAATACTTTGATGTAGGCTCAAAGTTTAGTATTTCCTTATCTTCTACT
GATGAAAGATATTTCCGTCAGCGGAAGCTTCTCTATGGATGACAATAAACCTCGGAGGTTTTGGT
TTTCGAGCAAGACGAGGGGCAGGAAGTTTGAAAGTACAAATGCTGAGGGAGATGTTACTTTAA
```

Cmr2 (PF1129)

Protein Sequence:
AAL81253.1
GI: 18977501
SEQ ID NO:8

```
MVNIKEKLFVYLHDPPDKALKIENHEERSKKILSSGNIQYSRTDKVKQADALSSKTQRFIIRTKEN
KEFVIDFLGRSSGKYFHVGYPVFIHPISTEIKRYETLEKYIDLGRSNRGERFVNEFLERVSKLEGD
VLKEVPEDASNKFKGEESKQWAYIWQFYPVKLKEGVKEFAKSELKLKEEEAEKFAEEFVNLPADTR
FPDHAIWTHLDLTSALSVKDPTLLRIKIVPVQPFIANSRKQLDLWASSHLLSMLMYKALEVIVDKF
GPEHVIYPSLRDQPFFLKFYLGENIGDEILVANLPNKALAIVSGKEAEKIEEEIKKRIRDFLLQLY
REAVDWAVENGVVKVDRSEKDSMLKEAYLKIVREYFTVSITWVSLSEKEDIYQVTENAGLSDEDVK
KWLKFAEKKENSRVLERIAIYPLLVKILDSLGERKVTEERFEKSEQLKGWKCHVCGENLAIFGDMY
DHDNLKSLWLDEEPLCPMCLIKRYYPVWIRSKTGQKIRFESVVDVALLYKNWRKIFDEKYGKDLVS
KAREVSEDFVKDNMLVDSDLYYSSTWESGLSKKLKNKKEIDEEKVKEVVDFLNAAYKEIGNPPKYY
AILVMDGDDMGKVISGEVLGEISTRIHPNIRDYVEIPEAKYYSTPQVHVAISQALANFSIREVRSV
VKDEGLLIYAGGDDVLAILPVDKALEVAYKIRKEFGKSFENGSLLPGWKLSAGILIVHYKHPLYDA
LEKARDLLNNKAKNVPGKDTLAIGLLKRSGSYYISLVGWELIRVFYNSELRKKLLEEKGGVGKRFI
YHVLREVDTWPKVGIDEMLKFEVIRHIRGRNKEETKELREKIYGEIKDLLEHVRGNNEVEKVRGLF
TFLKIITDAEVFP
```

Gene Sequence:
NC_003413.1 1080344-1077729
SEQ ID NO:7

```
GTGGTTAACATCAAAGAGAAACTTTTTGTATACCTTCATGATCCACCAGACAAGGCTCTAAAAATT
GAAAATCATGAGGAAAGGTCAAAAAAGATATTAAGTTCTGGCAATATCCAGTACTCCAGAACGGAC
AAAGTTAAACAAGCAGATGCACTTTCTTCTAAGACTCAGAGATTTATAATTCGAACAAAGGAAAAT
AAAGAGCCAGTAATAGATTTTTTGGGTAGATCTTCAGGAAAGTACTTCCATGTTGGATATCCTGTT
TTTATACACCCCATATCCACAGAAATTAAGAGGTATGAAACACTTGAAAAGTACATAGACCTTGGC
AGGAGTAATAGAGGGGAAAGATTTGTTAACGAGTTTTTGGAAAGGGTTTCAAAGCTTGAAGGCGAT
GTTCTCAAAGAGGTCTTTGAAGATGCTAGTAACAAATTTAAAGGAGAAGAGAGTAAACAGTGGGCC
TACATCTGGCAGTTTTATCCCGTAAAACTCAAAGAAGGAGTCAAGGAATTTGCCAAGTCAGAGTTA
AAACTTAAAGAGGAAGAAGCAGAAAAGTTTGCAGAGGAATTTGTTAACCTCCCAGCTGATACAAGA
TTTCCAGATCATGCAATTTGGACCCATTTAGACTTAACTTCCGCATTATCCGTTAAGGATCCCACT
TTGCTCAGGATCAAAATAGTTCCAGTTCAACCTTTTATTGCCAATTCAAGAAAGCAGTTAGATCTC
TGGGCCTCCAGTCATCTCCTTTCAATGCTTATGTATAAAGCTTTAGAGGTGATAGTGGACAAGTTC
GGGCCAGAACATGTAATCTATCCATCTCTAAGGGATCAACCCTTCTTCTTGAAGTTCTACCTGGGG
```

Figure 14C

```
GAAAACATAGGTGATGAAATCTTAGTTGCAAACTTGCCTAACAAAGCGCTTGCAATAGTCTCAGGA
AAGGAGGCTGAAAAGATTGAAGAAGAAATCAAGAAAAGAATTAGGGATTTCCTACTCCAACTGTAC
AGAGAAGCTGTTGATTGGGCAGTTGAAAATGGAGTAGTAAAAGTGGATAGAAGTGAAAAGGATAGC
ATGCTCAAGGAAGCATATCTTAAAATTGTGAGGGAGTACTTCACCGTCTCGATAACCTGGGTATCT
CTTTCCGAAAAGGAGGATATCTATCAAGTAACAGAGAACGCGGGTCTCTCGGATGAAGATGTTAAG
AAGTGGCTAAAGTTTGCAGAAAAGAAAGAAAATAGTAGAGTTCTCGAGAGGATTGCAATATACCCA
CTTTTGGTAAAGATATTGGATAGCCTGGGAGAGAGAAAAGTTACAGAAGAAAGGTTCGAAAAAAGC
GAACAACTCAAAGGATGGAAGTGCCACGTTTGTGGTGAGAATCTTGCAATTTTTGGAGACATGTAC
GATCACGATAATCTTAAGAGTTTGTGGCTTGATGAGGAACCATTATGTCCCATGTGTTTGATAAAA
AGGTATTATCCAGTGTGGATTAGGAGTAAAACTGGACAGAAAATAAGGTTTGAGTCGGTGGTAGAT
GTTGCACTTCTGTACAAGAACTGGAGGAAGATATTTGACGAGAAGTATGAAAAGACCTAGTCTCA
AAGGCTAGGGAAGTTAGTGAAGACTTCGTAAAGGACAATATGCTAGTAGATTCGGATCTATACTAT
TCTTCAACCTGGGAATCTGGACTTTCTAAAAAGCTCAAAAATAAGAAAGAGATTGATGAGGAAAAA
GTTAAGGAAGTTGTTGACTTCTTAAATGCGGCTTATAAAGAAATCGGTAATCCACCAAAGTACTAT
GCTATTCTAGTTATGGATGGCGACGATATGGGGAAAGTTATTTCAGGAGAGGTGCTTGGAGAAATA
TCAACTAGAATTCATCCAAATATTAGGGATTACGTTGAAATTCCAGAAGCAAAATATTACTCCACC
CCGCAGGTTCACGTGGCTATAAGCCAAGCATTGGCTAACTTTTCGATAAGGGAAGTTAGATCCGTA
GTTAAAGACGAGGGATTGCTAATATACGCTGGAGGGGATGATGTCCTAGCAATTTTGCCAGTCGAC
AAAGCTTTAGAAGTTGCATATAAGATAAGGAAAGAATTTGGCAAGAGCTTTGAAAATGGTTCTCTT
CTCCCAGGTTGGAAGTTGAGTGCTGGAATTTTGATAGTCCATTATAAGCATCCATTGTATGACGCC
CTAGAAAAGGCAAGAGATCTTCTCAATAATAAAGCAAAAAACGTTCCAGGAAAAGATACACTAGCT
ATAGGCCTACTTAAGAGGAGTGGTTCCTACTATATCTCCCTAGTGGGATGGGAATTAATTAGGGTC
TTCTACAACTCAGAGCTGAGGAAAAAGCTATTGGAAGAGAAAGGTGGAGTGGGAAAGAGGTTCATT
TATCATGTGCTCAGAGAAGTTGATACTTGGCCAAAAGTTGGAATAGACGAGATGCTTAAGTTTGAG
GTGATTAGACATATCAGGGGAAGGAACAAAGAAGAAACTAAAGAGCTCAGAGAAAAGATCTATGGA
GAAATAAAGGATCTTCTTGAGCATGTAAGAGGGAACAATGAAGTTGAAAAAGTTAGAGGCTTATTC
ACATTTCTAAAAATAATCACGGACGCGGAGGTGTTTCCATGA
```

Cmr3 (PF1128)

Protein Sequence:
AAL81252.1
GI: 18977500
SEQ ID NO:10
MIEVTFTPYDVLLFRESRPFDAGSESVARSIIPLPQTVAGAIRTLLFYKGLKNCVGVGEEEPEFTL
VGIAIGTEKGRIYPLPFNIIKSEKFYKVVNPGRFLGKLILPPKGKYKSGYVTESILEKYLKGELKE
VEENKVIRIEKEKRIGIKLSREKKVVEEGMLYTVEFLRIEKIYAWIEDPGCGIKDILSSYEFLTLG
GESRVAFVEVDDKTPDIFNRELGSTKKALFYFSTPTIGKVGEIVQELEKRLNAKIDDYLLVSSRPT
AISGWDMHEKKPKGTKFAIPPGSVLFVEFKEEVEVPPYIKLGKLKKLGYGLALGGIWE Gene Sequence:
NC_003413.1 1077732-1076764
SEQ ID NO:9
```
ATGATTGAGGTTACTTTTACTCCTTATGATGTCCTCTTATTTAGAGAAAGTAGGCCTTTTGATGCA
GGAAGTGAAAGTGTGGCAAGATCAATTATTCCTCTTCCCCAAACAGTCGCTGGCGCTATAAGGACT
CTTTTATTCTACAAAGGCCTCAAGAATTGTGTTGGAGTGGGTGAGGAGGAACCCGAATTTACGTTA
GTTGGGATTGCAATTGGAACAGAGAAAGGCAGAATTTACCCCCTTCCCTTCAATATCATAAAAAGC
```

Figure 14D

```
GAGAAATTCTACAAAGTTGTCAACCCAGGTAGATTTTTAGGGAAGTTAATTCTTCCTCCAAAAGGA
AAGTACAAGAGTGGCTATGTAACTGAAAGCATATTGGAAAAGTATTTGAAGGGAGAATTAAAAGAA
GTAGAAGAAATAAAGTAATAAGGATTGAAAAGGAAAAAAGGATTGGCATTAAGCTTTCTAGAGAG
AAGAAAGTAGTTGAAGAGGGAATGCTATATACTGTTGAATTCCTAAGAATTGAGAAAATTTACGCT
TGGATAGAAGACCCAGGATGCGGAATCAAAGATATTTTGTCATCATATGAGTTCTTAACGTTAGGA
GGAGAAAGTAGAGTTGCTTTTGTGGAAGTGGACGACAAAACACCCGATATATTTAATAGAGAATTA
GGATCAACAAAGAAAGCCCTCTTCTATTTCTCAACTCCCACAATAGGGAAAGTTGGAGAAATAGTA
CAAGAACTTGAGAAAGATTGAATGCAAAAATTGATGATTATCTTCTTGTTTCCTCTAGACCTACA
GCAATTTCTGGGTGGGATATGCATGAAAAGAAGCCAAAAGGTACTAAATTTGCGATACCTCCTGGT
TCAGTTCTCTTTGTAGAGTTTAAGGAGGAAGTAGAAGTTCCCCCCTACATTAAGCTTGGTAAGTTA
AAGAAACTTGGCTATGGGCTTGCTTTAGGAGGGATATGGGAATGA
```

Cmr4 (PF1126)

Protein Sequence:
AAL81250.1
GI: 18977498
SEQ ID NO:12
MKAYLVGLYTLTPTHPGSGTELGVVDQPIQRERHTGFPVIWGQSLKGVLRSYLKLVEKVDEEKINK
IFGPPTEKAHEQAGLISVGDAKILFPPVRSLKGVYAYVTSPLVLNRFKRDLELAGVKNFQTEIPEL
TDTAIASEEITVDNKVILEEFAILIQKDDKGILESVVKAIEQAFGNEMAEKIKGRIAIIPDDVFRD
LVELSTEIVARIRINAETGTVETGGLWYEEYIPSDTLFYSLILVTPRAKDNDMALIKEVLGKINGK
YLQIGGNETVGKGFVKVTLKEVTNNGGTHAK Gene Sequence:
NC_003413.1 1075334-1074447
SEQ ID NO:11
```
ATGAAGGCATATTTAGTTGGGTTATATACCTTAACTCCAACCCACCCGGGAAGTGGAACTGAGCTT
GGAGTGGTAGACCAACCAATTCAGAGAGAAAGACACACAGGATTTCCAGTAATTTGGGGCCAGAGT
CTCAAGGGTGTATTAAGGAGCTACCTTAAATTGGTAGAAAAGGTTGATGAGGAGAAGATAAACAAA
ATATTTGGCCCACCGACAGAAAAAGCTCATGAGCAGGCTGGGCTAATAAGTGTCGGAGATGCAAAG
ATACTATTCTTCCCTGTTAGAAGTCTAAAAGGTGTTTACGCATACGTAACTTCTCCACTAGTTCTT
AACAGGTTCAAAAGAGACTTAGAGCTAGCTGGGGTTAAGAATTTTCAGACAGAAATTCCCGAGTTA
ACAGATACCGCAATTGCAAGTGAAGAAATTACAGTTGATAACAAGGTGATTCTTGAAGAATTTGCA
ATTCTCATTCAAAAGGATGACAAGGGAATTTTGGAAAGTGTAGTTAAAGCTATTGAACAAGCCTTT
GGAAATGAAATGGCAGAGAAAATAAAGGGTAGAATTGCCATAATCCCAGATGACGTGTTTAGAGAT
TTAGTGGAGCTGTCGACAGAAATAGTAGCTAGGATAAGAATTAATGCTGAGACAGGAACTGTAGAA
ACTGGAGGACTGTGGTATGAGGAGTATATTCCTTCGGACACATTGTTCTACTCACTAATACTTGTA
ACTCCCAGGGCAAAGGATAATGATATGGCCCTAATCAAAGAAGTTCTAGGAAAGATTAACGGCAAA
TATCTCCAGATTGGAGGTAATGAAACCGTTGGGAAGGGCTTCGTCAAAGTTACTCTTAAAGAGGTG
ACCAACAATGGAGGTACACATGCTAAGTAA
```

Cmr5 (PF1125)

Protein Sequence:
AAL81249.1
SEQ ID NO:14

Figure 14E

MEVHMLSKDNKKSIRKTLEQRRGEYAYYVIKEVADLNDKQLEEKYASLVKKAFVMILSNGLLQTLA
FLLAKAETSPEKANQILSRVNEYPPRFIEKLGNDKDEHLLLYLHIVYWLRENVDRNIDVKTLLSQD
YSKVLWATKRAIALLNWMRRFAVAMLKEEGKENEGSS

Gene Sequence:
NC_003413.1 1074469-1073960
SEQ ID NO:13
ATGGAGGTACACATGCTAAGTAAAGATAACAAGAAAAGCATAAGAAAAACTCTAGAACAGCGGAGG
GGCGAGTATGCTTACTATGTGATAAAAGAAGTGGCAGATCTTAATGACAAGCAACTTGAGGAAAAG
TATGCCTCCCTAGTTAAGAAAGCCCCAGTCATGATATTGTCCAATGGTCTCCTTCAGACGCTTGCA
TTTTTACTTGCAAAGGCCGAGACTTCACCAGAAAAAGCTAATCAGATCTTGAGTAGAGTCAATGAA
TACCCACCTAGGTTCATCGAAAAGCTTGGGAATGACAAAGACGAGCACCTTCTCCTGTACCTTCAC
ATAGTCTACTGGTTGAGGGAAAATGTGACAGAAACATCGATGTGAAAACTCTATTATCCCAGGAT
TATTCAAAAGTTCTGTGGGCAACAAAAGAAGCAATAGCGCTCCTGAACTGGATGAGGAGATTCGCT
GTTGCAATGCTCAAGGAAGAGGGGAAAGAGAATGAAGGAAGTAGTTAA

Cmr6 (PF1124)

Protein Sequence:
AAL81248.1
SEQ ID NO:16
MKEVVKLVLLGERQNSLNLSLYFNKYPPTIIYPEVLEDRNKKLASPSGSQRKISLLVLNQGVLQFN
KIKETIEKSLPIETKVKLFPQKAYELYKKYYQDYTDMLNSLHAITGKFKTQSRLVVGLGDESVYETS
IRLLRNYGVPYIPGSAIKGVTRHLTYYVLAEFINEGNDFYKRAKTVQDAFMKGDPKEILSNAKVPE
RCSRLCKEFLRIFGEKKVPEIIDELIRIFGTQKKEGEVVFFDAIPIAEEIADKPILELDIMNPHYG
PYYQSGEKNVPPPGDWYDPIPIFFLTVPKDVPFLVAVGGRDRELTEKAFSLVKLALRDLGVGAKTS
LGYGRLVEYV Gene Sequence:
NC_003413.1 1073976-1072954
SEQ ID NO:15
ATGAAGGAAGTAGTTAAATTGGTTCTCCTGGGGGAGAGACAGAACTCCCTTAACCTCTCACTATAC
TTCAACAAATATCCTCCAACCATAATCTATCCAGAGGTACTGGAAGATAGGAACAAGAAACTTGCT
TCACCCTCAGGATCACAGAGAAAGATATCCCTCTTGGTCTTAAATCAAGGGGTTCTTCAGTTTAAC
AAAATAAAAGAGACAATAGAAAAGTCGTTGCCAATTGAAACTAAGGTAAAACTTCCTCAAAAAGCA
TATGAATTGTACAAGAAATACTACCAGGATTACACTGACATGCTTAACTCATTACACGCCATTACT
GGAAAGTTTAAGACTCAATCAAGGCTCGTAGTTGGGCTTGGTGATGAAAGCGTTTATGAGACAAGC
ATAAGGCTTCTTAGAAACTATGGAGTGCCTTACATTCCTGGGTCCGCAATTAAGGGAGTTACTAGG
CACTTAACTTACTACGTTCTAGCAGAATTTATCAATGAAGGAAATGATTTCTATAAGAGGGCAAAG
ACTGTTCAGGATGCATTTATGAAAGGTGATCCTAAAGAAATTCTTTCCAATGCTAAGGTACCGGAA
AGGTGTAGTAGGCTTTGTAAAGAATTTCTCAGAATATTTGGAGAGAAAAAGGTTCCAGAGATTATA
GATGAACTCATAAGAATCTTCGGAACCCAGAAAAAAGAAGGAGAAGTTGTATTCTTTGATGCAATA
CCCATAGCTGAAGAGATAGCAGATAAGCCGATCTTGGAGTTAGACATAATGAATCCTCACTATGGG
CCGTATTATCAAAGTGGAGAGAAAAATGTCCCACCTCCTGGGGACTGGTATGATCCCATCCCAATA
TTCTTCCTCACAGTACCAAAGGATGTCCCCTTCCTAGTTGCCGTTGGTGGCAGAGATAGAGAACTT
ACAGAAAAGGCCTTTAGCCTCGTTAAGTTGGCCCTTAGAGACCTTGGTGTTGGTGCAAAAACTTCT
CTTGGCTATGGGAGGCTTGTTGAATATGTTTAG

Figure 15A

```
Cmr1-1
PF03787: domain 1 of 1, from 6 to 161: score 95.8, E = 1.8e-25
                *->lklktlTplhiGsGkeegeigqivkkliDnpivrdphlfkdeiakkk
                   ++++ +T +h    ++++
         Cmr1-1    6  FEIESITSTHLLEVLTREYP------------------------- 25 tglPiyIPGSSiRGalRwwfralygsllerklgkelkeeeskeekekiFG
                   ++++    SiKGa+Rwwfral+   ++ +++++lke+e     +++FG
         Cmr1-1   26  -----EVRSPSIKGAMRWWFRALA-GSYFGDDAQKLKEIE------NQVFG  64 steeesdfagrvifsDAPtdAlLlfPVrSigvfayvTsPlvlrflevivg
                   st+e      +rv++s
         Cmr1-1   65  STKE----RSRVKIS------------------------------------ 78 ellevkkqleakledlkkklikrlailsddlfsdivk.yleektevainr
                    +   +    + +  l  ++k+  + ++      in
         Cmr1-1   76  --------------VTPLSSPKRLNLKEFKdRNVGYIWFSINL 104 ktgtaeegialryeEyvyelpagtkfffelilksedelyfeeikekesg
                   +++        +y+  p+g++ f+  ++i+s++e
         Cmr1-1  105  LGKRG------TITHYY---PPGSR-FR--VVLESPSE----------- 130 nlflnfflldeeeedlkklkellkll..dlglGgktsrGyGlvk<-*
                    + +k++  +L++l +++  +G++ +rG G++k
         Cmr1-1  131  -----------RVIKLATLSLWALvsLGSVGFRSRRGTGSMK   161

TIGR01894: domain 1 of 1, from 8 to 164: score 235.1, E = 2.1e-67
                *->leaiTPifmgGarkpvsrkyrgyyeeevRstsIkGllRWWfRalarg
                   +e iT+++ ++ +  r-y      +evRs+sIkG++RWWfRala
         Cmr1-1    8  IESITSTHLLEVLT---REY-----PEVRSPSIKGAMRWWFRALA--- 44 igsyfgnnlekIkeaEkekekkedrkglkclaeeiFGStnrkSrvrleVe
                   gsyfg++ +klke+E+            ++FGSt+++Srv+++V+
         Cmr1-1   45  -GSYFGDDAQKLKEIEN-----------------QVFGSTKERSRVKISVT  77 deqNFiTisKAiWDFiiRivsknlniaetknikignvkLsknevrkkgee
                   + +          ++k+ln++e+k++++q++++s+n  ++k+g++
         Cmr1-1   78  PLS---------------SPKRLNLKEFKDRNVGYIWFSINLLGKRGTI 111 qekvkkkrelrdpnntlrillegddkkiialinnsliskkirdelknkLl
                   ++++     +p++++r++le++++++i+l++  sl++
         Cmr1-1  112  THYY-------PPGSRFRVVLESPSERVIKLATLSLWA---------- 142 ilssFggIGrklartrRGfGsieiks<-*
                   l+s+g++G   +r+rRG+Gs++i++
         Cmr1-1  143  -LVSLGSVG---FRSRRGTGSMKIVR   164

Cmr2
TIGR02577: domain 1 of 1, from 220 to 739: score 737.8, E = 9.7e-219
                *->vLvvvitiqFVQeflakARKlrDLWaqSyLLSyliwkaieflvekyGp
                   +L+ +i +i+PVQ+fIa++RK+  DLWa+S+LLS+l++ka+e++v+k+Gp
         Cmr2    220  TLLRIKIVFVQPFIANSRKQLDLWASSHLLSMLMYKALEVIVDKFGP 266 dhviffPalrgnpffdsllankvvkefevdvgpKevvevvketilikikee
                   +hvi+P+lr++pff ++++    +++++                ++
```

Figure 15B

```
Cmr2    267 EHVIYPSLRDQPFFLKFYLGENIGD----------------------------------EIL 294 vaelpnlflailpakdekileklecetinlkikselaallikkavgkelieg
             va+lpn++lai++      k++ek+ee+i++++i+++l +ll+++av ++ +e+
Cmr2    295 VANLPNKALAIVSG------KEAEKIEEGIKKRIRDFLLQLYREAV--DWAVEN 340 eavivdleegIkqleealkkllekradlrlfapskivvdiegekeevyks
             +v+vd++e++++l+ea++k++++++++++++++s++      eke++y+
Cmr2    341 GVVKVDRSEKDSMLKEAYLKIVREYFTVSITWVSLS----------EKEDIYQV 384 vkngvveaglnkkivskylsfeeivlklsekekrkeliriylklresrsf
             ++n      agl++++v+k+l+f+e++      e+++  e+i iy++l  ++
Cmr2    385 TEN------AGLSDEDVKKWLKFAEKK-----ENSRVLERIAIYPLLVKI--- 423 ykldaigltkrkserlekqlelpqikcllegedlaiagvkekllekvydd
             Ld++g++k+++ar+ek+++i+g+kc++cge+lai+g     ++++
Cmr2    424 --LDSLGERKVTEERFEKSEQLKGWKCHVCGENLAIFG----DMYD------- 463 elkdlkallqeeerlcplclikRqlpklliedlrvlvevekkvpiesvkdv
             +++ik+l+  +ee+lcp+clikR++p++i+      +++++k+++esv+dv
Cmr2    464 -HDNLKSIWLDEEPLCPMCLIKRYYPVWIR---------SKTGQKIRFESVVDV 507 aekRreaegkewkeefdellGrlfpkkellipsikevaesekeqkilvdg
             a+++++      w++++fde++G       ++l+++  +ev+e+++++++++lvd+
Cmr2    508 ALLYKN------WRKIFDEKYG-------KDLVSKAREVSEDFVKDNMLVDS 546 elkvdkeyleelkkgleeskenEveKlkvDekkpciqkvkevsdrlnale
             +l+     y ++++gl+++++n   K+++De+k      vkev+d+lna++
Cmr2    547 DLY------YSSTWESGLSKKLKN----KKEIDEEK-----VKEVVDFLNAAY 584 kvrknprpYYAiLkaDGDrMGkllLrgeirpeekerihpkvieeevkeeekv
             k++++np++YYAiL++DGD+MGk+++ge+++e+++rihp++++       +v
Cmr2    585 KEIGNPPKYYAILVMDGDDMGKVISGEVLGEISTRIHPNIRD--------YV 628 kknaikRalkfliktlsnkdslaKvvlkkkkltttpaaHraiSraLaeFsl
             +++                         ++k+++tp++H+aiS+aLa+Fs+
Cmr2    629 EIP---------------------------EAKYYSTPQVEVAISQALANFSI 654 kevkiVveehrdDWiYeGvLVYaGGDDVLAiLPvdtNaLdvAkeLrkeFs
             +ev++Vv++      eG L+YaGGDDVLA+LPvd+  aL+vA+++rkeF+
Cmr2    655 REVRSVVKD---------EGLLIYAGGDDVLAILPVDK-ALEVAYKIRKEFG 696 ealekelgkerikpyesEkvvrYqgeKPseytsleeptlSaGlvIvHhke
             +s+e+ + ++                          +++lSaG++IvH+k+
Cmr2    697 KSFENGSLLP----------------------------GWKLSAGILIVHYKH 721

PLydALelarellkrAKe<-*
             PLydALe+ar+ll+++ +
Cmr2    722 PLYDALEKARDLLNNKAK        739
```

Cmr3
TIGR01888: domain 1 of 1, from 4 to 321: score 458.3, E = 1.3e-134

```
             *-->ilikPlDvlfFResrpFdagnegsaasVvsSifPsPtTiAGavrtaL
                 ++++P+Dvl+FResrpFdag+e     sV++Si+P+P+T+AGa+rt+L
Cmr3     4  VTFTPYDVLLFRESRPFDAGSE------SVARSIIPLPQTVAGAIRTLL 46 lekaakdlsrlldyvrkiereakpGeliefsiyGpfvvekgpeaiirelk
             ++k+  l++++  +++e +p   ef+++G++++++++         +
Cmr3    47  FYKG----LKNCVG-----VGEE-EP-------EFTLVGIAIGTEK---------G 76
```

Figure 15C

```
            pffPlpsdiafYEdedGalavdllrveellk.ekyfkvvdkalieeigkl
            +++Plp++i              +k+ek++kvv++++    lgkl
   Cmr3  77 RIYPLPFNI---------------IKSEKFYKVVNPGRF----LGKL 104 plppgkqekkeiipqflNKseskiskyLkqeiselkkydllkNVAGeeei
            +lpp   k  ++++g++  +es+l+kyLkge++e+++    +k    +++i
   Cmr3 105 ILPP----KGKYKSGYV--TESILEKYLRGELKEVEE---NK----VIRI 141 fkkEeRiDtDKDVHFLPGIkLdkekkvvreigsRkeKEgaLYsqefIkfk
            +k E+Ri          GIkL++ekkvv         +Eg+LY++efIR++
   Cmr3 142 EK-EKRI-----------GIKLSREKKVV---------EEGMLYTVEELRIE 172 rfkevdqvqlivwvedpveaedekikelleslkdikfeelnkkivtLGGE
              +    +++w+edp     +++ik++l+s+            +++tLGGE
   Cmr3 173 ------K----IYAWIEDP-----GCGIKDILSSY--------EFLTLGGE 200 rrlaklevdeenedtfngekWelkssLkegkkvkfylltPaifleggEYF
            +r+a++evd++++d+fn+e      L+++kk+  fy++tP+i++  q+
   Cmr3 201 SRVAFVEVDDRTPDIFNRE-------LGSTKKALFYFSTPTIGKVGE--- 240

VvlsdlkdllledeifakllorkgdkvlvvtlgvrkqevsGwdyvekkGN
            ++++l+++l+     ak+++        ++ +++r++++sGwd++ekk
   Cmr3 241 -IVQELEKRLN-----AKIDD------YLLVSSRPTAISGWDMHEKK-- 275

EpKptleAvppGSVlflkakeevelellnfpvsededdalliklgkfeki
            pK t++A+ppGSVlf+++keeve++    p+          iklgk++k+
   Cmr3 276 -PKGTKFAIPPGSVLFVEFKEEVEVP----PY---------IKLGKLKKL 311

GyGlaligew<-*
            GyGlal g+w
   Cmr3 312 GYGLALGGIW    321
```

Cmr4
TIGR02580: domain 1 of 1, from 4 to 280: score 533.7, E = 2.7e-157

```
            *->ylvllyalTPvHvGaGqssiGvVDlPiQRErhTGyPiIyGkSsLEGa
               ylv+ly+lTP+H+G+G+  ++GvVD+PiQRErhTG+P+I+G +sLKG+
   Cmr4   4 YLVGLYTLTPTHPGSGT-ELGVVDQPIQRERHTGFPVIWG-QSLKGV  48

LRsylakqaskdldyvdakeekkveavFGsepkeeaeesaGkvsvsDArl
            LRsyl+  +++d         e+k++++FG +p+e+a+e+aG++sv+DA++
   Cmr4  49 LRSYLKLVEKVD---------EEKINKIFG-PPTEKAHEQAGLISVGDAKI  89

LiyPVriiPiSKsldGvfayvTsPylLeRfkrdleaaGvlngskeleene
            L++PVr      sl+Gv+ayvTsP++L+Rfkrdle+aGv+n+++e++e +
   Cmr4  90 LFFPVR------SLKGVYAYVTSPLVLNRFKRDLELAGVKNFQTEIPELT 133 glekkLsldeddallasgeevlaikegkvlLeeikleailneavgeLedv
                      d++as+e    ++++kv+Lee+++++++++++  +++v
   Cmr4 134 ----------DTAIASEE---ITVDNKVILEEFAILTQKDDKGILESVV 169 laiktfkspdelvellesrlvvvsDdlFrdlVnsslEvvtRIRINqetKT
            +ai++++  ++e++e+++r++++Dd+FrdlV+  s+E+v+RIR+N+et+T
   Cmr4 170 KAIEQAF-GNEMAEKIKGRIATLPDDVFRDLVELSTEIVARIRINAEFGT 218

VeeGGLWYEEyiPaeTiFyslilvdevsndyceelnkkesnkeeifkefs
            Ve+GGLWYEEyiP++T+Fyslilv++        +++++    ++++ke++
   Cmr4 219 VETGGLWYEEYIPSDTLFYSLILVTP-------RAKDND---MALIKEVL 258
```

Figure 15D

```
                    kkinnkgisvldkvlqIGGkETvGKGlvr<-*
                    +kin+       k+lqIGG+ETvGKG+v+
        Cmr4   259  GKING--------KYLQIGGNETVGKGFVK    280

PF03787: domain 1 of 1, from 6 to 280: score 272.3, E = 1.3e-78
                *->lklktlTplhiGsGkeegeiggivkkliDnpivrdphlfkdeiakkk
                   + l+tlTp+h GsG+e g +       D pi+r++h
        Cmr4     6  VGLYTLTPTHPGSGTELGVV---------DQPIQRERH----------- 34 tglPiyIPGSSiKGalRwwfralygsllerklgkelkeeeskeekekiFG
                   tg+P +I+G+S-KG+lR       s+l + + +++++       +kiFG
        Cmr4    35  TGFP-VIWGQSLKGVLR--------SYLKLVEKVDEEKI-------NKIFG 69

.steeesdfagrvifsDAPtdA.lLlfPVrSi.gvfayvTsPlvl.rf..
                   ++te++ ++ag +++ D    A++L+fPVrS++gv+ayvTsPlvl+rf++
        Cmr4    70  pPTEKAHEQAGLISVGD-----AkILFFPVRSLEGVYAYVTSPLVLnRFkr 115

..........................................lev.l.vg
                   + +  + ++ +++  ++ +-+    +++ + +++    ++     ++ +++++
        Cmr4   116  dlelagvknfqteipeltdtaiaseeitvdnkvileefailiQKDdKgII 165 ell.evkkql.eakledlkkklikrlailsddlfsdlvk.yleektevai
                   e++ + ++q+      +++ +k++ r+ai++dd+f+dlv+ ++e++++++i
        Cmr4   166  ESVvKAIEQAfG---NEMAEKIKGRIAIIPDDVFRDLVElSTEIVARIRI 212 nrktgtaeegialryeEyvyelpagtkffffelilksedelyfeeikeke
                   n +tgt+e g +l+yeEy+    p++t+f++  lil+ ++
        Cmr4   213  NAETGTVETG-GLWYEEYI----PSDTLFYS--LILVTPRA--------- 246 sgnlflnffldeeeedlkklkelLkll...dlglGgktsrGyGlvk<-*
                   +++d+ ++ke+L +++++++l++Gg++++G+G+vk
        Cmr4   247  -----------KDNDMALIKEVLGKIngkYLQIGGNETVGKGFVK   280
```

Cmr5
```
TIGR01881: domain 1 of 1, from 15 to 161: score 261.4, E = 2.5e-75
                *->mktleqeraklAlkvveEvekkkkDkklrekYaSrvrkiPsmIlsNG
                   +ktleq+r+++A++v++Ev++ + Dk+l+ekYaS+v+k+P+mIlsNG
        CMR5    15  RKTLEQRRGEYAYYVIKEVADLN-DKQLEEKYASLVKKAFVMILSNG 60

LlpTlaFylSKaeleaenk..ilsaLnnykssskkeklGnseeasYlkvya
                   Ll+TlaF+l+Kae+++e+++++ils+n+y+++++eklGn++ +++l++y
        CMR5    61  LLQFLAFLLAKAETSPEKAnqILSRVNEYPPRFIEKIGNDK-DEHLLLYL 109 hilywLkerelkekkeilLdelkPKnnvtqSAdalkeLlekdysdvrtYL
                   hi+ywL+e+++++                  +++k+Ll++dys+v+
        CMR5   110  RIVYWLRENVDRN----------------IDVKTLLSQDYSKVL---- 137 iaTeesLrllnWlKRlAEAlLkeE<-*
                   +aT+ea++llnW++R+A+A+LkeE
        CMR5   138  WATKEAIALLNWMRRFAVAMLKEE   161
```

Cmr6
```
TIGR01898: domain 1 of 1, from 111 to 337: score 455.2, E = 1.1e-133
                *->fklkTcssrLlvGlGteheiNKPADEKGKKVEGDKEDDAPevyEtgl
                   k+kT +srL+vGlG+e+                         vyEt++
        Cmr6   111  GKFKT-QSRLVVGLGDES-----------------------VYETSI 133
```

Figure 15E

```
                tLdpiyGvPYIPGSaiKGvlRsatfevlaeeeekGeeilkiaksVkddlk
                +L ++yGvPYIPGSaiKGv+R+++++vlae++++G++++k+ak+V+d+++
    Cmr6   134  RLLRNYGVPYIPGSAIKGVTRHLTYYVLAEFINEGNDFYKRAKTVQDAFM  183 kriikedelknqvkredeklakkrfredfGkkkrpelpeeladklFGtqe
                k+++k ++l+n++++e++++++++k+f+++fG+kk+pe+ +++++++FGtq+
    Cmr6   184  KGDPK-EILSNAKVPERCSRLCKEFLRIFGEKKVPEI-IDELIRIFGTQK  231 kSieGeviFLDAyPipdenkdkpsilelDIINPHYqpYyqqeekn.kPFg
                k  eGev+F+DA+Pi+++e++dkp+ lelDI+NPHY+pYyq++ekn +PFg
    Cmr6   232  K--EGEVVFFDAIPIAEEIADKPI-LELDIMNPHYGPYYQSGEKNvPPPG  278

DwvnPiPikFLtVkkGvtFqfvvlfddlraEeLkKekifeeVknelLdel
                Dw++PiPi+FLtV+k+v+F ++v ++d+                    +
    Cmr6   279  DWYDPIPIFFLTVPKDVPFLVAVGGRDR--------------------E---  307 lldvlekLlKellkealtefGiGAKTslGYGrfe<--*
                l++++++L+K     al+++G+GAKTslGYGr++
    Cmr6   308  LTEKAFSLVK----LALRDLGVGAKTSLGYGRLV        337

PF03787: domain 1 of 1, from 111 to 337: score 144.7, E = 3.3e-40
                *-->lklktlTplhiGsGkeegeiggivkkliDnpivrdphlfkdeiakkk
                    +k+kt ++l +G G+e+++          ++++i+ ++
    Cmr6   111  GKFKTQSRLVVGLGDESVY----------ETSIRLLRN----------  138 tglPiyIPGSSiKGalRwwfralygsllerklgkelkeeeskeek.....
                +g+P yIPGS+iKG+ R        +l +++l++ +e++ ++++ ++ +
    Cmr6   139  YGVP-YIPGSAIKGVTR--------HLTYYVLAEFINEGNDFYKRaktvq  179

............................................ekiFGs
                +  ++++++ ++ + +++ ++  ++ +  ++++ ++  ++ ++iFG+
    Cmr6   180  dafmkgdpkeilsnakvpercsrlckeflrifgekkvpeiidelIRIFGT  229 teeesdfagrvifsDA.Pt.dAlLlfPVrSigvfayvTsPivlrflevlv
                +++     +g v+f+DA P+ +
    Cmr6   230  QKK----EGEVVFFDAiPIaE------------------------------  246 gellevkkqleakledlkkklikrlailsddlfsdlvk.yleektevain
                                +i ++ il++d++++++ +y+++ +++
    Cmr6   247  ---------------EIADKPILELDIMNPHYGpYYQSGEKNV--  274 rktgtaeegialryeEyvyelpagtkfffelilksedelyfeeikekes
                +  +g+++++  ++++ +v   p++ f   + + +d
    Cmr6   275  PPPGDWYDP-IPIFFLTV----PKDVP-FL--VAVGGRDR--------  306 gnlfinffldeeeedlkklkelLkll..dlglGgktsrGyGlvk<--*
                               e+ +k+ l kl  +dlg+G+kts+GyG++
    Cmr6   307  ---------------ELTEKAFSLVKLAlRDLGVGAKTSLGYGRLV   337
```

PROKARYOTIC RNAI-LIKE SYSTEM AND METHODS OF USE

CONTINUING APPLICATION DATA

This application is a divisional of U.S. patent application Ser. No. 13/055,769, filed 1 Apr. 2009, which is the §371 U.S. National Stage of International Application No. PCT/US2009/051745, filed 24 Jul. 2009, which claims the benefit of U.S. Provisional Application Ser. No. 61/083,616, filed Jul. 25, 2008, Ser. No. 61/180,656, filed May 22, 2009, and Ser. No. 61/227,554, filed Jul. 22, 2009, all of which are incorporated by reference herein.

SEQUENCE LISTING

This application contains a Sequence Listing electronically submitted via EFS-Web to the United States Patent and Trademark Office as an ASCII text filed entitled "235-01230102_SequenceListing_ST25.txt" having a size of 101 kilobytes and created on Jun. 13, 2016. The information contained in the Sequence Listing is incorporated by reference herein.

GOVERNMENT FUNDING

The present invention was made with government support under Grant No. R01GM054682, awarded by the NIH. The Government has certain rights in this invention.

BACKGROUND

Small, non-coding (nc)RNAs are found in all domains of life and function in a wide array of essential cellular processes. In eukaryotes, small ncRNAs including siRNAs and microRNAs have been shown to function in post-transcriptional gene silencing by targeting exogenous or endogenous RNAs, respectively, in a process called RNA interference, or RNAi (Hannon, 2002, Nature, 418:244-251). Another class of small RNAs referred to as piRNAs (piwi-associated) or rasiRNAs (repeat associated small interfering) regulate spreading of selfish genetic elements such as transposons or repeat elements in organisms including mammals, plants and flies (Kim V. N., 2006, Genes Dev, 20:1993-1997; Nishida and Siomi, 2006, Tanpakushitsu Kakusan Koso, 51:2450-2455; Aravin et al., 2007, Science 318:761-764; Hartig et al., 2007, Genes Dev, 21:1707-1713; Lin H., 2007, Science, 316: 397).

An RNAi-like system that functions in genome defense has recently been proposed to exist in prokaryotes (Markova et al., 2006, Biol Direct, 1:7; Deveau et al., 2008, J Bacteriol, 190:1390-1400; Sorek et al., 2008, Nat Rev Microbiol, 6:181-186; Tyson and Banfield, 2008, Environ Microbiol, 10:200-207). The hallmark of the proposed prokaryotic RNAi (or pRNAi) system is the CRISPR locus, a cluster of short direct repeats that separate short variable sequences (i.e. clustered regularly interspaced short palindromic repeat). A number of the variable sequences (also sometimes called "spacers") found in CRISPR loci display complementarity (or identity) to known prokaryotic viruses, plasmids and transposons (Bolotin et al., 2005, Microbiology, 151:2551-2561; Mojica et al., 2005, Mol Evol, 60:174-182; Pourcel et al., 2005, Microbiology, 151:653-663; Lillestol et al., 2006, Archaea, 2:59-72; Markova et al., 2006, Biol Direct, 1:7). The other signature component of the hypothesized pRNAi system is a set of protein-coding genes referred to as CRISPR-associated or Cas genes that are found in CRISPR-containing genomes (Jansen et al., 2002, Mol Microbiol, 43:1565-1575; Markarova et al., 2002, Nucleic Acids Res, 30:482-496; Haft et al., 2005, PLoS Comput Biol, 1:e60; Markova et al., 2006, Biol Direct, 1:7). The Cas genes are predicted to encode nucleases, helicases, RNA-binding proteins and a polymerase (Jansen et al., 2002, Mol Microbiol, 43:1565-1575; Markarova et al., 2002, Nucleic Acids Res, 30:482-496; Haft et al., 2005, PLoS Comput Biol, 1:e60; Markova et al., 2006, Biol Direct, 1:7). These bioinformuatically-predicted properties of the CRISPR and Cas gene products led to the hypothesis that they comprise an RNAi-like system of genome defense in prokaryotes, in which RNAs derived from the variable regions of CRISPR loci (prokaryotic silencing or psiRNAs) guide the silencing (e.g., degradation) of genome invaders by Cas proteins (Bolotin et al., 2005, Microbiology, 151:2551-2561; Lillestol et al., 2006, Archaea, 2:59-72; Markova et al., 2006, Biol Direct, 1:7). The Cas proteins are also expected to function in the processing of the psiRNAs and in the integration of new psiRNA genes (directed against newly encountered pathogens) into the genome.

Recent studies have provided strong evidence for a role of CRISPR loci in viral resistance in prokaryotes. Several groups have observed that virus exposure leads to the appearance of new virus-derived sequence elements within the CRISPR loci of surviving (resistant) isolates (Barrangou et al., 2007, Science 315:1709-1712; Deveau et al., 2008, J Bacteriol, 190:1390-1400; Horvath et al., 2008, J Bacteriol, 190:1401-1412). In addition, Barrangou et al. showed that an alteration of an organism's CRISPR sequences that generates or destroys correspondence with a viral sequence results in viral resistance and viral sensitivity, respectively (Barrangou et al., 2007, Science 315:1709-1712). However, the pathway by which CRISPR loci confer viral resistance remains hypothetical and undefined.

CRISPR loci are present in about half of bacterial genomes and nearly all archaeal genomes (Godde and Bickerton, 2006, J Mol Evol, 62:718-729; Markova et al., 2006, Biol Direct, 1:7). A given locus can contain as few as 2, and as many as several hundred repeat-psiRNA units (Grissa et al., 2007, Bioinformatics, 8:172; Sorek et al., 2008, Nat Rev Microbiol, 6:181-186). The repeat sequences are generally 25 to 45 nucleotides long and often weakly palindromic at the 5' and 3' termini (Jansen et al., 2002, Mol Microbiol, 43:1565-1575). Interspersed between the repeats are the variable, putative psiRNA-encoding sequences, which are usually similar in length to the repeats. RNAs arising from CRISPR loci have been detected by RNA cloning and/or Northern blotting in 3 archaeal species: Archaeoglobus fulgidus, Sulfolobus solfataricus and Sulfolobus acidocaldarius (Tang et al., 2002, Proc Natl Acad Sci USA, 99:7536-7541; Tang et al., 2005, Mol Microbiol, 55:469-481; Lillestol et al., 2006, Archaea, 2:59-72). These studies provided convincing evidence of transcription of entire CRISPR loci from the predicted transcriptional leader sequences that are found at one end of the loci, and of a discrete series of smaller RNAs that correspond in length to multiples of repeat-psiRNA units (e.g. ~70, 140, 210, 280 nts, etc. (Tang et al., 2002, Proc Natl Acad Sci USA, 99:7536-7541; Tang et al., 2005, Mol Microbiol, 55:469-481)). These findings along with RNA sequence analysis led to a hypothesized biogenesis pathway in which primary CRISPR transcripts are endonucleolytically cleaved within repeat sequences to produce psiRNAs flanked by repeat sequence at both the 5' and 3' ends (Tang et al., 2002, Proc Natl Acad Sci USA, 99:7536-7541; Tang et al., 2005, Mol Microbiol, 55:469-481).

SUMMARY OF THE INVENTION

Provided herein are methods for inactivating a target polynucleotide in a microbe. The methods may include introducing into the microbe a psiRNA that includes a 5' region and a 3' region. The 5' region may be a psiRNA-tag that includes 5 to 10 nucleotides chosen from a repeat from a CRISPR locus immediately upstream of a spacer. As described herein, the skilled person can easily identify nucleotides sequences suitable for use as a psiRNA-tag. Optionally, the psiRNA-tag nucleotide sequence is chosen from a CRISPR locus present in the microbe into which the psiRNA is introduced. An example of a useful psiRNA-tag is 5'-AUUGAAAS, wherein S is G or C. The 3' region may include at least 18 nucleotides, and in some aspects, no greater than 75 nucleotides. The 3' region is typically substantially complementary, optionally complementary, to a portion of the target polynucleotide.

The target polynucleotide may be cleaved in the region that is substantially complementary to the 3' region. The psiRNA may be introduced into the cell as an RNA polynucleotide, or as a DNA polynucleotide encoding the psiRNA. In some aspects the psiRNA-tag is 8 nucleotides. The target polynucleotide may be DNA or RNA, and may be an endogenous polynucleotide. Methods described herein may be used, for example, for immunizing a microbe against an exogenous polynucleotide. The target polynucleotide that is inactivated may be the exogenous polynucleotide, or the target polynucleotide may be encoded by the exogenous polynucleotide. In one aspect, the exogenous polynucleotide is a bacteriophage polynucleotide. Also provided herein are genetically modified microbes that include the psiRNAs described herein.

Provided herein are methods for inactivating a target polynucleotide. The methods include incubating under suitable conditions a composition that includes a target polynucleotide, and a psiRNA that includes a 5' region and a 3' region. The 5' region may be a psiRNA-tag of between 5 and 10 nucleotides chosen from a repeat from a CRISPR locus immediately upstream of a spacer. An example of a useful psiRNA-tag is 5'-AUUGAAAS, wherein S is G or C. The 3' region may include 5'-NNNNNNNNNNNNNNNNN↓NNNNNNNNNNNNNNN (SEQ ID NO:24) or 5'NNNNNNN-NNNNNNNNNNNNNNNNN↓NNNNNNNNNNNNNNNN-NNNNN (SEQ ID NO:25), wherein the 3' region is substantially complementary, optionally complementary, to a portion of the target polynucleotide. The composition also contains a Cmr1 polypeptide, a Cmr2 polypeptide, a Cmr3 polypeptide, a Cmr4 polypeptide, and a Cmr6 polypeptide. Optionally, the composition may further include a Cmr5 polypeptide. The target polynucleotide may be cleaved in the region that is substantially complementary to the 3' region of SEQ ID NO:24 or SEQ ID NO:25. In some aspects the psiRNA-tag is 8 nucleotides. The target polynucleotide may be cleaved opposite the position defined by the arrow. The method may be performed in vitro or in vivo. Examples of suitable cells include *Pyrococcus furiosus*, a *Sulfolobus solfataricus*, or a *S. tokodaii* cell.

The amino acid sequence of the Cmr1 polypeptide and the amino acid sequence of SEQ ID NO:4 may have at least 80% identity. The amino acid sequence of the Cmr2 polypeptide and the amino acid sequence of SEQ ID NO:8 may have at least 80% identity. The amino acid sequence of the Cmr3 polypeptide and the amino acid sequence of SEQ ID NO:10 may have at least 80% identity. The amino acid sequence of the Cmr4 polypeptide and the amino acid sequence of SEQ ID NO:12 may have at least 80% identity. The amino acid sequence of the Cmr6 polypeptide and the amino acid sequence of SEQ ID NO:16 may have at least 80% identity. The polypeptides have endonuclease activity, for instance, endoribonuclease activity. The amino acid sequence of an optional Cmr5 polypeptide and the amino acid sequence of SEQ ID NO:14 may have at least 80% identity.

Also provided herein are methods for inactivating a target polynucleotide in a microbe. The methods may include introducing into a microbe a psiRNA that includes a 5' region and a 3' region. The 5' region may be a psiRNA-tag that includes 5 to 10 nucleotides chosen from a repeat from a CRISPR locus immediately upstream of a spacer. Optionally, the psiRNA-tag nucleotide sequence is chosen from a CRISPR locus present in the microbe into which the psiRNA is introduced. An example of useful psiRNA-tag is 5'-AUUGAAAS, wherein S is G or C. The 3' region may include at least 18 nucleotides, and in some aspects, no greater than 75 nucleotides. The 3' region is typically substantially complementary, optionally complementary, to a portion of the target polynucleotide. The psiRNA introduced into the cell as an RNA polynucleotide, or as a DNA polynucleotide encoding the psiRNA. Examples of suitable cells include *Pyrococcus furiosus, Sulfolobus solfataricus*, or a *S. tokodaii* cell.

The microbe into which the psiRNA is introduced may be a genetically modified microbe, wherein the genetically modified microbe includes an exogenous Cmr1 polypeptide, an exogenous Cmr2 polypeptide, an exogenous Cmr3 polypeptide, an exogenous Cmr4 polypeptide, and an exogenous Cmr6 polypeptide. The amino acid sequence of the Cmr1 polypeptide and the amino acid sequence of SEQ ID NO:4 may have at least 80% identity. The amino acid sequence of the Cmr2 polypeptide and the amino acid sequence of SEQ ID NO:8 may have at least 80% identity. The amino acid sequence of the Cmr3 polypeptide and the amino acid sequence of SEQ ID NO:10 may have at least 80% identity. The amino acid sequence of the Cmr4 polypeptide and the amino acid sequence of SEQ ID NO:12 may have at least 80% identity. The amino acid sequence of the Cmr6 polypeptide and the amino acid sequence of SEQ ID NO:16 may have at least 80% identity. The polypeptides have endonuclease activity, for instance, endoribonuclease activity. Optionally, the genetically modified microbe may further include a Cmr5 polypeptide. The amino acid sequence of Cmr5 polypeptide and the amino acid sequence of SEQ ID NO:14 may have at least 80% identity.

Further provided herein are compositions that include enriched polypeptides, wherein the polypeptides are a Cmr1 polypeptide, a Cmr2 polypeptide, a Cmr3 polypeptide, a Cmr4 polypeptide, a Cmr5 polypeptide, a Cmr6 polypeptide, or a combination thereof. Optionally, the polypeptides are isolated.

Provided herein are enriched, optionally isolated polynucleotides that include a 5' region and a 3' region. The 5' region may be a psiRNA-tag that includes 5 to 10 nucleotides chosen from a repeat from a CRISPR locus immediately upstream of a spacer, and the 3' region may include at least 18 nucleotides, or the complement of the polynucleotides. The polynucleotides may be RNA or DNA. A polynucleotide may further include an additional polynucleotide, for instance, a target polynucleotide, that is hybridized to the 3' region. Also provided are vectors that include the isolated polynucleotide, and vectors that encode the polynucleotide. Further provided are genetically modified microbes that include such vectors, and genetically modified microbes encoding an exogenous polynucleotide that includes a 5' region and a 3' region.

Also provided herein are (a) Cmr1 polypeptides, wherein the amino acid sequence of the polypeptide and the amino acid sequence of SEQ ID NO:4 have at least 80% identity, wherein the polypeptide has endonuclease activity, for instance, endoribonuclease activity, when incubated with a psiRNA, a target polynucleotide, and Cmr2, Cmr3, Cmr4, Cmr5, and Cmr6 polypeptides having amino acid sequences SEQ ID NO:8, SEQ ID NO:10, SEQ ID NO:12, SEQ ID NO:14, and SEQ ID NO:16, respectively; (b) Cmr1 polypeptides, wherein the amino acid sequence of the polypeptide and the amino acid sequence of SEQ ID NO:6 have at least 80% identity, wherein the polypeptide has endonuclease activity, for instance, endoribonuclease activity, when incubated with a psiRNA, a target polynucleotide, and Cmr2, Cmr3, Cmr4, Cmr5, and Cmr6 polypeptides having amino acid sequences SEQ ID NO:8, SEQ ID NO:10, SEQ ID NO:12, SEQ ID NO:14, and SEQ ID NO:16, respectively; (c) Cmr2 polypeptides, wherein the amino acid sequence of the polypeptide and the amino acid sequence of SEQ ID NO:8 have at least 80% identity, wherein the polypeptide has endonuclease activity, for instance, endoribonuclease activity, when incubated with a psiRNA, a target polynucleotide, and Cmr1, Cmr3, Cmr4, Cmr5, and Cmr6 polypeptides having amino acid sequences SEQ ID NO:4, SEQ ID NO:10, SEQ ID NO:12, SEQ ID NO:14, and SEQ ID NO:16, respectively; (d) Cmr3 polypeptides, wherein the amino acid sequence of the polypeptide and the amino acid sequence of SEQ ID NO:10 have at least 80% identity, wherein the polypeptide has endonuclease activity, for instance, endoribonuclease activity, when incubated with a psiRNA, a target polynucleotide, and Cmr1, Cmr2, Cmr4, Cmr5, and Cmr6 polypeptides having amino acid sequences SEQ ID NO:4, SEQ ID NO:8, SEQ ID NO:12, SEQ ID NO:14, and SEQ ID NO:16, respectively; (e) Cmr4 polypeptides, wherein the amino acid sequence of the polypeptide and the amino acid sequence of SEQ ID NO:12 have at least 80% identity, wherein the polypeptide has endonuclease activity, for instance, endoribonuclease activity, when incubated with a psiRNA, a target polynucleotide, and Cmr1, Cmr2, Cmr3, Cmr5, and Cmr6 polypeptides having amino acid sequences SEQ ID NO:4, SEQ ID NO:8, SEQ ID NO:10, SEQ ID NO:14, and SEQ ID NO:16, respectively; (f) Cmr5 polypeptides, wherein the amino acid sequence of the polypeptide and the amino acid sequence of SEQ ID NO:14 have at least 80% identity, wherein the polypeptide has endonuclease activity, for instance, endoribonuclease activity, when incubated with a psiRNA, a target polynucleotide, and Cmr1, Cmr2, Cmr3, Cmr 4, and Cmr6 polypeptides having amino acid sequences SEQ ID NO:4, SEQ ID NO:8, SEQ ID NO:10, SEQ ID NO:12 and SEQ ID NO:16, respectively; and (g) Cmr6 polypeptides, wherein the amino acid sequence of the polypeptide and the amino acid sequence of SEQ ID NO:16 have at least 80% identity, wherein the polypeptide has endonuclease activity, for instance, endoribonuclease activity, when incubated with a psiRNA, a target polynucleotide, and Cmr1, Cmr2, Cmr3, Cmr4, and Cmr5 polypeptides having amino acid sequences SEQ ID NO:4, SEQ ID NO:8, SEQ ID NO:10, SEQ ID NO:12, and SEQ ID NO:14, respectively. Also provided are polynucleotides encoding such polypeptides. Optionally, such polynucleotides also include a heterologous polynucleotide, such as a regulatory sequence operably linked to the polynucleotide, or a vector. A genetically modified microbe, such as *E. coli*, may include an exogenous polynucleotide encoding one or more of these polypeptides.

Further provided are kits. An example of a kit contains enriched, optionally isolated polypeptides, wherein the polypeptides are a Cmr1 polypeptide, a Cmr2 polypeptide, a Cmr3 polypeptide, a Cmr4 polypeptide, a Cmr6 polypeptide, and optionally, a Cmr5 polypeptide.

As used herein, an "enriched" polynucleotide means that a polynucleotide constitutes a significantly higher fraction of the total DNA or RNA present in a mixture of interest than in cells from which the sequence was taken. A person skilled in the art could enrich a polynucleotide by preferentially reducing the amount of other polynucleotides present, or preferentially increasing the amount of the specific polynucleotide, or both. However, polynucleotide enrichment does not imply that there is no other DNA or RNA present, the term only indicates that the relative amount of the sequence of interest has been significantly increased. The term "significantly" qualifies "increased" to indicate that the level of increase is useful to the person using the polynucleotide, and generally means an increase relative to other nucleic acids of at least 2 fold, or more preferably at least 5 to 10 fold or more. The term also does not imply that there is no polynucleotide from other sources. Other polynucleotides may, for example, include DNA from a bacterial genome, or a cloning vector.

As used herein, an "enriched" polypeptide defines a specific amino acid sequence constituting a significantly higher fraction of the total of amino acids present in a mixture of interest than in cells from which the polypeptide was separated. A person skilled in the art can preferentially reduce the amount of other amino acid sequences present, or preferentially increase the amount of specific amino acid sequences of interest, or both. However, the term "enriched" does not imply that there are no other amino acid sequences present. Enriched simply means the relative amount of the sequence of interest has been significantly increased. The term "significant" indicates that the level of increase is useful to the person making such an increase. The term also means an increase relative to other amino acids of at least 2 fold, or more preferably at least 5 to 10 fold, or even more. The term also does not imply that there are no amino acid sequences from other sources. Other amino acid sequences may, for example, include amino acid sequences from a host organism.

As used herein, an "isolated" substance, such as a polynucleotide or a polypeptide, is one that has been removed from its natural environment, produced using recombinant techniques, or chemically or enzymatically synthesized. For instance, a polypeptide or a polynucleotide can be isolated. A substance may be purified, i.e., is at least 60% free, preferably at least 75% free, and most preferably at least 90% free from other components with which it is naturally associated.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, enzyme, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region" and "coding sequence" are used interchangeably and refer to a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

A polynucleotide, such as a polynucleotide that includes a coding region, may include heterologous nucleotides on one or both sides of the polynucleotide. As used herein, "heterologous nucleotides" and "heterologous polynucleotides" are used interchangeably and refer to nucleotides that are not normally present flanking a polynucleotide, such as a coding region, that is present in a wild-type cell. For instance, a coding region present in a wild-type microbe and encoding a Cmr1 polypeptide described herein is flanked by homologous sequences, and any other nucleotide sequence flanking the coding region is considered to be heterologous. Examples of heterologous nucleotides include, but are not limited to regulatory sequences. Typically, heterologous nucleotides are present in a polynucleotide disclosed herein through the use of standard genetic and/or recombinant methodologies well known to one skilled in the art. A polynucleotide disclosed herein may be included in a suitable vector.

As used herein, an "exogenous polynucleotide" refers to a polynucleotide that is not normally or naturally found in a microbe. As used herein, the term "endogenous polynucleotide" refers to a polynucleotide that is normally or naturally found in a microbe, e.g., genomic DNA is endogenous. An "endogenous polynucleotide" is also referred to as a "native polynucleotide."

The terms "complement" and "complementary" as used herein, refer to the ability of two single stranded polynucleotides to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The terms "substantial complement," "substantially complementary," and "substantial complementarity" as used herein, refer to a polynucleotide that is capable of selectively hybridizing to a specified polynucleotide under stringent hybridization conditions. Stringent hybridization for RNA molecules can take place under a number of pH, salt and temperature conditions. The pH can vary from 6 to 9, and may be 7 to 8, such as 7.4, and can be attained using 20 mM to 40 mM HEPES, such as 30 mM HEPES. The salt concentration can vary from 90 mM to 110 mM potassium acetate, such as 100 mM potassium acetate, and 1 mM to 3 mM magnesium acetate, such as 2 mM magnesium acetate. The temperature of the hybridization reaction may be incubation at 37° C. after a brief incubation at a higher temperature, such as 95° C. Thus, a polynucleotide is typically "substantially complementary" to a second polynucleotide if hybridization occurs between the polynucleotide and the second polynucleotide.

As used herein, "identity" refers to sequence similarity between two polypeptides or two polynucleotides. The sequence similarity between two polypeptides may be determined by aligning the residues of the two polypeptides (e.g., a candidate amino acid sequence and a reference amino acid sequence, such as SEQ ID NO:4, 6, 8, 10, 12, 14, or 16) to optimize the number of identical amino acids along the lengths of their sequences; gaps in either or both sequences are permitted in making the alignment in order to optimize the number of shared amino acids, although the amino acids in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence analysis techniques such as the BESTFIT or GAP algorithm in the GCG package (Madison Wis.), or the Blastp program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, sequence similarity between two amino acid sequences is determined using the Blastp program of the BLAST 2 search algorithm. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, sequence similarity is referred to as "identities."

The sequence similarity between two polynucleotides may be determined by aligning the residues of the two polynucleotides (e.g., a candidate nucleotide sequence and a reference nucleotide sequence, such as SEQ ID NO:3, 5, 7, 9, 11, 13, or 15) to optimize the number of identical nucleotides along the lengths of their sequences; gaps in either or both sequences are permitted in making the alignment in order to optimize the number of shared nucleotides, although the nucleotides in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as GCG FastA (Genetics Computer Group, Madison, Wis.), MacVector 4.5 (Kodak/IBI software package) or other suitable sequence analysis programs or methods known in the art. Preferably, sequence similarity between two nucleotide sequences is determined using the Blastn program of the BLAST 2 search algorithm, as described by Tatusova, et al. (1999, *FEMS Microbiol. Lett.*, 174:247-250), and available through the World Wide Web, for instance at the internet site maintained by the National Center for Biotechnology Information, National Institutes of Health.

Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. In the comparison of two nucleotide sequences using the BLAST search algorithm, sequence similarity is referred to as "identities."

As used herein, "genetically modified microbe" refers to a microbe which has been altered by a person. A genetically modified microbe includes a microbe into which has been introduced a polynucleotide, such as an exogenous polynucleotide. Genetically modified microbe also refers to a microbe that has been genetically manipulated such that endogenous nucleotides have been altered to include a mutation, such as a deletion, an insertion, a transition, a transversion, or a combination thereof. For instance, an endogenous coding region could be deleted. Such mutations may result in a polypeptide having a different amino acid sequence than was encoded by the endogenous polynucleotide. Another example of a genetically modified microbe is one having an altered regulatory sequence, such as a promoter, to result in increased or decreased expression of an operably linked endogenous coding region.

Conditions that are "suitable" for an event to occur, such as cleavage of a polynucleotide, or "suitable" conditions are conditions that do not prevent such events from occurring. Thus, these conditions permit, enhance, facilitate, and/or are conducive to the event.

As used herein, "in vitro" refers to an artificial environment and to processes or reactions that occur within an artificial environment. In vitro environments can consist of, but are not limited to, test tubes. The term "in vivo" refers to the natural environment (e.g., a cell, including a genetically modified microbe) and to processes or reactions that occur within a natural environment.

As used herein "prokaryotic microbe" and "microbe" are used interchangeably and refer to members of the domains Bacteria and Archaea.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. *P. furiosus* CRISPR loci and distribution of cloned psiRNAs. The seven *P. furiosus* CRISPR loci are illustrated. The psiRNA numbers associated with each locus are indicated above. Each psiRNA is represented by a box. Shaded psiRNAs were cloned at least once in this work and the number of clones isolated is indicated below the shaded box. The genome coordinates of each *P. furiosus* CRISPR locus are as follows: 1: 27091-30618; 2: 260714-262113; 4: 312405-313931; 5: 623119-625176; 6: 695937-698992; 7: 1064076-1065543; 8: 1091089-1091857.

FIG. 14. Amino acid sequences of Cmr polypeptides and nucleotide sequences encoding the polypeptides.

FIG. 15. Alignments between Cmr polypeptide regions and domains of hidden Markov models present in the TIGRFAM database of protein families. Cmr1-1 (amino acids 6 to 161 or 8 to 164 of SEQ ID NO:4), domain present in PF03787 (SEQ ID NO:269), domain present in TIGR01894 (SEQ ID NO:270), Cmr2 (amino acids 220 to 739 of SEQ ID NO:8), domain present in TIGR02577 (SEQ ID NO:271), Cmr3 (amino acids 4 to 321 of SEQ ID NO: 10), domain present in TIGR01888 (SEQ ID NO:272), Cmr4 (amino acids 4 to 280 or 6 to 280 of SEQ ID NO: 12), domain present in PF03787 (SEQ ID NO:269). domain present in TIGR02580 (SEQ ID NO:273), Cmr5 (amino acids 15 to 161 of SEQ ID NO:14), domain present in TIGR01881 (SEQ ID NO:274), Cmr6 (amino acids 111 to 337 of SEQ ID NO:16), domain present in TIGR01898 (SEQ ID NO:275), domain present in PF03787 (SEQ ID NO:269).

DETAILED DESCRIPTION OF ILLUSTRATIVE EMBODIMENTS

Figure 2:
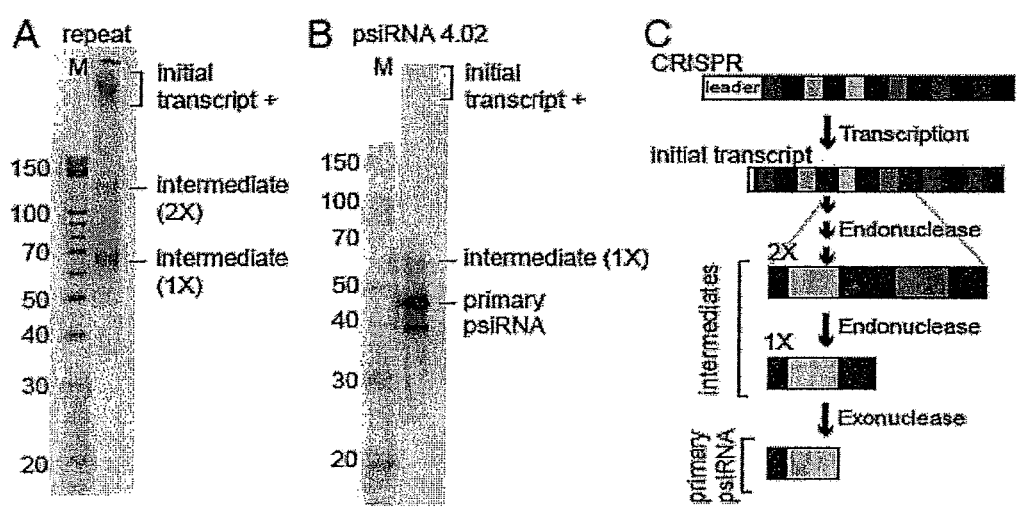
FIG. 2. Northern analysis of RNAs containing CRISPR repeat and psiRNA 4.02 sequences. A and B) Northern blots were performed with 10 µg total RNA using a degenerate oligonucleotide probe designed to detect the repeat sequences for CRISPR loci 1, 5, and 6 (A) or a probe for psiRNA 4.02 sequence (B). Radiolabeled RNA marker sizes are indicated (M). The positions of the initial transcript and large intermediates, 2× intermediate, 1× intermediate and primary psiRNA described in the text and FIG. 4C are indicated. C) Proposed psiRNA biogenesis pathway. The CRISPR locus is transcribed from a start site within the leader sequence to produce an initial transcript that includes a portion of the leader and the alternating psiRNA and repeat sequences. The initial transcript is cleaved within the repeats to produce intermediates. The endonucleolytic cleavage site may be asymmetrically located within the repeat. The 2× intermediate and 1× intermediates are illustrated. Our results indicate that the 1× intermediate is further processed by an exonuclease to remove most of the repeat sequence, resulting in a primary psiRNA species that contains 5-10 nucleotides of the repeat sequence.

The present invention includes aspects that represent an advance in the art of inactivating polynucleotides, preferably cleaving polynucleotides in a prokaryotic microbe. A CRISPR locus of a prokaryotic microbe includes, from 5' to 3', a repeat followed immediately by a spacer (referred to herein as a "repeat-spacer unit"). Typically, a CRISPR locus includes multiple repeat-spacer units. In a CRISPR locus, each repeat is nearly identical (Barrangou et al., U.S. Published Patent Application 2008/0124725). In contrast to the repeats, each spacer of a CRISPR locus is typically a different nucleotide sequence.

As described herein, a CRISPR locus is transcribed in a microbe and subsequently processed to produce psiRNAs, and the psiRNAs are proposed to be primary agents in guiding the inactivation of target polynucleotides. A target polynucleotide is inactivated when it is no longer able to carry out its biological function. For instance, an mRNA is no longer able to carry out its biological function when it no longer encodes an active polypeptide. Inactivation may occur by degradation, such as by cleavage. As described in the examples below, the first 5 to 10 nucleotides, preferably, the first 8 nucleotides, of a psiRNA may be derived from the repeat of a repeat-spacer unit. The remaining nucleotides of a psiRNA may be derived from the spacer of the repeat-spacer unit. Thus, for any psiRNA derived from a repeat-spacer unit, the nucleotides derived from the repeat are those nucleotides immediately upstream of the spacer, and the nucleotides derived from the spacer are those nucleotides immediately downstream of the repeat.

Accordingly, an aspect of the present invention includes polynucleotides having a 5' region and a 3' region. Such polynucleotides may be referred to herein as a "psiRNA," and may be enriched or isolated. While the term psiRNA suggests the nucleotides are ribonucleotides, polynucleotides described herein also include the corresponding deoxyribonucleotide sequence, and the RNA and DNA complements thereof. It should be understood that the sequences disclosed herein as DNA sequences can be converted from a DNA sequence to an RNA sequence by replacing each thymidine nucleotide with a uracil nucleotide. The 5' region of a polynucleotide, also referred to herein as a "tag" or some variant thereof, such as "psiRNA-tag" or "psi-tag," includes at least 5, at least 6, at least 7, at least 8, at least 9, or at least 10 nucleotides. In some aspects, a psi-tag is 5, 6, 7, 8, 9, or 10 nucleotides. The nucleotide sequence of a psiRNA-tag is identical to or has sequence similarity with the nucleotide sequence of a repeat (from a CRISPR locus) that is immediately upstream of a spacer.

The nucleotide sequence of a psiRNA-tag of a polynucleotide described herein is identical to or has sequence similarity with the 5 to 10 nucleotides of a repeat from a CRISPR locus that is immediately upstream of a spacer and present in a microbe that contains a CRISPR locus. psiRNA-tag nucleotide sequences that can be present in a polynucleotide of the present invention can easily be identified in any microbe that includes a CRISPR locus. For instance, the genomic sequences of many microbes are known, and the location of CRISPR loci in these microbes is often known, or can easily be located using routine bioinformatic methods known in the art. For instance, Edgar (BMC Bioinformatics, 2007, 8:18) describes a computer program specifically designed for the identification and analysis of CRISPR repeats, and includes a list of predicted repeats based on 346 prokaryotic genomes (see Edgar, Supplementary Table 1). Grissa et al. (BMC Bioinformatics, 2007, 8:172, and Nucl. Acids Res., 2007, 35(Web Server issue):W52-W57) describe a computer program which identifies CRISPRs from genomic sequences, extracts the repeat and spacer sequences, and constructs a database which is automatically updated monthly using newly released genome sequences. Thus, the nucleotide sequence of a repeat that is immediately upstream of a spacer in a CRISPR locus can be determined by the skilled person using routine methods.

The psiRNAs of the present invention include 5' nucleotide sequences identical to or having sequence similarity with the nucleotide sequence of a repeat from a CRISPR locus that is immediately upstream of a spacer; however, due to the ease of identifying repeats from CRISPR loci, the psiRNAs of the present invention are not intended to be limited to any specific CRISPR locus repeat sequence. Examples of psiRNA-tag nucleotide sequences include sequences disclosed in Kunin et al. (Genome Biol., 2007, 8:R61.1-R61.7), Godde and Bickerton (J. Mol. Evol., 62:718-729), and Edgar (BMC Bioinformatics, 2007, 8:18). An example of a psiRNA-tag of a polynucleotide of the present invention is 5' ATTGAAAG (or 5' AUUGAAAG when the polynucleotide is RNA) or 5' ATTGAAAC (or 5' AUUGAAAC when the polynucleotide is RNA), and polynucleotides having sequence similarity with ATTGAAAG or ATTGAAAC.

In some aspects a nucleotide sequence of a psiRNA-tag of a polynucleotide of the present invention may further include additional nucleotides that are identical or have sequence similarity to the other nucleotides of a repeat from a CRISPR locus that is immediately upstream of a spacer. Thus, in some embodiments, a psiRNA-tag may include nucleotides that are identical or have sequence similarity with an entire repeat, or a subset of nucleotides present in the repeat. Typically, if a psiRNA-tag includes nucleotides identical or have sequence similarity with a subset of nucleotides present in a repeat, the subset of nucleotides present in the psiRNA-tag are typically from the 3' end of the repeat. For instance, an example of a repeat present in *Pyrococcus furiosus* is GTTCCAATAA-GACTAAAATAGAATTGAAAG (SEQ ID NO:276). Examples of psi RNA-tags of a polynucleotide of the present invention include having a subset of nucleotides present in this repeat are, but are not limited to, TTCCAATAAGAC-TAAAATAGAATTGAAAG (nucleotides 2-30 of SEQ ID NO:276), TCCAATAAGACTAAAATAGAATTGAAAGU (nucleotides 3-30 of SEQ ID NO:276), and CCAATAAGAC-TAAAATAGAATTGAAAG (nucleotides 4-30 of SEQ ID NO:276). Thus, in some embodiments, a psiRNA-tag of a polynucleotide of the present invention includes at least 5, at least 6, at least 7, at least 8, at least 9, at least 10, and so on up to inclusion of nucleotides from an entire repeat. In other embodiments, a psiRNA of the present invention does not include additional nucleotides located upstream of the psiRNA-tag.

The 3' region of a psiRNA of the present invention is immediately downstream of the 5' region and may be referred to herein as a spacer sequence or a guide sequence. Without intending to be limited by theory, the guide sequence directs a psiRNA of the invention to identify a specific polynucleotide, referred to herein as a target polynucleotide, optionally resulting in inactivation of the target polynucleotide. The target polynucleotide may be DNA or RNA. In some aspects, the target polynucleotide is preferably RNA. Accordingly, in one aspect the guide sequence of a psiRNA of the present invention may be either substantially complementary or complementary to the target polynucleotide. The 3' region of a psiRNA includes a number of nucleotides that is an integer greater than 17 (e.g., at least 18, at least 19, at least 20). In some aspects, the 3' region of a psiRNA may be an integer less than 76 (e.g., no greater than 75, no greater than 74, no greater than 73, and so on). In some embodiments, the 3' region of a psiRNA is at least 28, at least 30, at least 31, at least 32, at least 33, at least 34, at least 35, at least 36, at least 37, at least 38, or at least 39 nucleotides. Thus, a psiRNA of the present invention may be at least 23 nucleotides in length, or greater. In some aspects, a psiRNA of the present invention may be 39 nucleotides or 45 nucleotides in length, for instance, an 8 nucleotide tag and a guide of 31 or 37 nucleotides.

The 3' region of a psiRNA may be any nucleotide sequence. As discussed below, one aspect of the present invention includes methods for cleaving a specific target polynucleotide at a specific location, e.g., using a psiRNA as a restriction endonuclease that cleaves a polynucleotide, such as an RNA polynucleotide. Thus, in one aspect, since the 3' region of a psiRNA is substantially complementary or complementary to the target polynucleotide, the sequence of the target polynucleotide will dictate the nucleotide sequence of a psiRNA 3' region. Specific examples of nucleotide sequences that can be present in a psiRNA 3' region are described hereinbelow.

Also provided herein are polypeptides that have endonuclease activity, for instance, endoribonuclease activity, when used together. The polypeptides are referred to herein as Cmr1, Cmr2, Cmr3, Cmr4, Cmr5, and Cmr6.

Examples of Cmr1 polypeptides are depicted at Genbank Accession No. AAL81254 (SEQ ID NO:4), Genbank Accession No. AAL80476 (SEQ ID NO:6), and FIG. 14. The Cmr1 polypeptide having SEQ ID NO:6 is expected to have endonuclease activity, for instance, endoribonuclease activity, under the conditions described herein. Other examples of Cmr1 polypeptides provided herein include those having sequence similarity with the amino acid sequence of SEQ ID NO:4 or the amino acid sequence of SEQ ID NO:6. A Cmr1 polypeptide having sequence similarity with the amino acid sequence depicted at SEQ ID NO:4 or SEQ ID NO:6 has endonuclease activity, for instance, endoribonuclease activity, when incubated with a psiRNA, a target polynucleotide, and Cmr2, Cmr3, Cmr4, Cmr5 and Cmr6 polypeptides having amino acid sequences SEQ ID NO:8, SEQ ID NO:10, SEQ ID NO:12, SEQ ID NO:14, and SEQ ID NO:16.

Examples of Cmr2 polypeptides are depicted at Genbank Accession No. AAL81253 (SEQ ID NO:8) and FIG. 14. Other examples of Cmr2 polypeptides provided herein include those having sequence similarity with the amino acid sequence of SEQ ID NO:8. A Cmr2 polypeptide having sequence similarity with the amino acid sequence depicted at SEQ ID NO:8 has endonuclease activity, for instance, endoribonuclease activity, when incubated with a psiRNA, a target polynucleotide, and Cmr1, Cmr3, Cmr4, Cmr5, and Cmr6 polypeptides having amino acid sequences SEQ ID NO:4, SEQ ID NO:10, SEQ ID NO:12, SEQ ID NO:14, and SEQ ID NO:16.

Examples of Cmr3 polypeptides are depicted at Genbank Accession No. AAL81252 (SEQ ID NO:10) and FIG. 14. Other examples of Cmr3 polypeptides provided herein include those having sequence similarity with the amino acid sequence of SEQ ID NO:10. A Cmr3 polypeptide having sequence similarity with the amino acid sequence depicted at SEQ ID NO:10 has endonuclease activity, for instance, endoribonuclease activity, when incubated with a psiRNA, a target polynucleotide, and Cmr1, Cmr2, Cmr4, Cmr5, and Cmr6 polypeptides having amino acid sequences SEQ ID NO:4, SEQ ID NO:8, SEQ ID NO:12, SEQ ID NO:14, and SEQ ID NO:16.

Examples of Cmr4 polypeptides are depicted at Genbank Accession No. AAL81250 (SEQ ID NO:12) and FIG. 14. Other examples of Cmr4 polypeptides provided herein include those having sequence similarity with the amino acid sequence of SEQ ID NO:12. A Cmr4 polypeptide having sequence similarity with the amino acid sequence depicted at SEQ ID NO:12 has endonuclease activity, for instance, endoribonuclease activity, when incubated with a psiRNA, a target polynucleotide, and Cmr1, Cmr2, Cmr3, Cmr5, and Cmr6 polypeptides having amino acid sequences SEQ ID NO:4, SEQ ID NO:8, SEQ ID NO:10, SEQ ID NO:14, and SEQ ID NO:16.

Examples of Cmr5 polypeptides are depicted at Genbank Accession No. AAL81249 (SEQ ID NO:14) and FIG. 14. Other examples of Cmr5 polypeptides provided herein include those having sequence similarity with the amino acid sequence of SEQ ID NO:14. A Cmr5 polypeptide having sequence similarity with the amino acid sequence depicted at SEQ ID NO:14 has endonuclease activity, for instance, endoribonuclease activity, when incubated with a psiRNA, a target polynucleotide, and Cmr1, Cmr2, Cmr3, Cmr4, and Cmr6 polypeptides having amino acid sequences SEQ ID NO:4, SEQ ID NO:8, SEQ ID NO:10, SEQ ID NO:12 and SEQ ID NO:16.

Examples of Cmr6 polypeptides are depicted at Genbank Accession No. AAL81248 (SEQ ID NO:16) and FIG. 14. Other examples of Cmr6 polypeptides provided herein include those having sequence similarity with the amino acid sequence of SEQ ID NO:16. A Cmr6 polypeptide having sequence similarity with the amino acid sequence depicted at SEQ ID NO:16 has endonuclease activity, for instance, endoribonuclease activity, when incubated with a psiRNA, a target polynucleotide, and Cmr1, Cmr2, Cmr3, and Cmr4 polypeptides having amino acid sequences SEQ ID NO:4, SEQ ID NO:8, SEQ ID NO:10, SEQ ID NO:12, and SEQ ID NO:14.

A composition including a Cmr1 polypeptide chosen from SEQ ID NO:4 and SEQ ID NO:6, preferably SEQ ID NO:4, a Cmr2 polypeptide, a Cmr3 polypeptide, a Cmr4 polypeptide, and a Cmr6 polypeptide has endonuclease activity. Optionally, a composition also includes a Cmr5 polypeptide. The endonuclease activity of a composition of five, optionally six, of the polypeptides described herein acts to inactivate a target polynucleotide. Inactivation may be by cleavage of a target polynucleotide, preferably at a specific site. When determining whether a composition of five, optionally six, of the polypeptides described herein have endonuclease activity, a suitable psiRNA is 5'-AUUGAAAGUUGUAGUAUGCG-GUCCUUGCGGCUGAGAGCACUUCAG (where the first 8 nucleotides are the 5' region and the remaining nucleotides are the 3' region, SEQ ID NO:17) and a suitable target polynucleotide is 5'-CUGAAGUG-CUCUCA↓GCCGCAAGGACCGCAUACUACAA (SEQ ID NO:18), where the target polynucleotide is optionally cleaved, for example, between the nucleotides as defined by the arrow. Suitable conditions for cleavage of this polynucleotide by a composition of the polypeptides described herein include those described in Example 2.

The amino acid sequence of a polypeptide having sequence similarity to SEQ ID NO:4, SEQ ID NO:6, SEQ ID NO:8, SEQ ID NO:10, SEQ ID NO:12, SEQ ID NO:14, or SEQ ID NO:16 may include conservative substitutions of amino acids present in an amino acid sequence. A conservative substitution is typically the substitution of one amino acid for another that is a member of the same class. For example, it is well known in the art of protein biochemistry that an amino acid belonging to a grouping of amino acids having a particular size or characteristic (such as charge, hydrophobicity, and/or hydrophilicity) may generally be substituted for another amino acid without substantially altering the secondary and/or tertiary structure of a polypeptide. For the purposes of this invention, conservative amino acid substitutions are defined to result from exchange of amino acids residues from within one of the following classes of residues: Class I: Gly, Ala, Val, Leu, and Ile (representing aliphatic side chains); Class II: Gly, Ala, Val, Leu, Ile, Ser, and Thr (representing aliphatic and aliphatic hydroxyl side chains); Class III: Tyr, Ser, and Thr (representing hydroxyl side chains); Class IV: Cys and Met (representing sulfur-containing side chains); Class V: Glu, Asp, Asn and Gln (carboxyl or amide group-containing side chains); Class VI: His, Arg and Lys (representing basic side chains); Class VII: Gly, Ala, Pro, Trp, Tyr, Ile, Val, Leu, Phe and Met (representing hydrophobic side chains); Class VIII: Phe, Trp, and Tyr (representing aromatic side chains); and Class IX: Asn and Gln (representing amide side chains). The classes are not limited to naturally occurring amino acids, but also include artificial amino acids, such as beta or gamma amino acids and those containing non-natural side chains, and/or other similar monomers such as hydroxyacids.

Guidance concerning how to make phenotypically silent amino acid substitutions is provided in Bowie et al. (1990, Science, 247:1306-1310), wherein the authors indicate proteins are surprisingly tolerant of amino acid substitutions. For example, Bowie et al. disclose that there are two main approaches for studying the tolerance of a polypeptide sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As stated by the authors, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, and the references cited therein.

Cmr2 polypeptides typically include polymerase/nuclease domains (see Makarova et al., 2002, Nucleic Acids Res., 30:482-496, and Makarova et al., 2006, Biol. Direct 1:7). Cmr1, Cmr3, Cmr4, and Cmr6 are members of the RAMP superfamily (Markova et al., 2002, Nucl. Acids Res., 30:482-496), and may include the characteristics of polypeptides that are members of that superfamily. Cmr1 polypeptides may include domains present in the TIGRFAM database at accession numbers PF03787 and TIGR11894, as shown in FIG. 15. The TIGRFAM database includes families of polypeptides for which function is conserved (Haft et al., Nucl. Acids Res., 2003, 31:371-373, Bateman and Haft, 2002, Briefings Bioinformatics, 3:236-245, and Haft et al., 2005, PLoS Computational Biol., 1(6):e60). Cmr2 polypeptides may include domains present in the TIGRFAM database at accession number TIGR02577, as shown in FIG. 15. Cmr3 polypeptides may include domains present in the TIGRFAM database at accession number TIGR01888, as shown in FIG. 15. Cmr4 polypeptides may include domains present in the TIGRFAM database at accession numbers TIGR02580 and PF03787, as shown in FIG. 15. Cmr5 polypeptides may include domains present in the TIGRFAM database at accession numbers TIGR01881, as shown in FIG. 15. Cmr6 polypeptides may include domains present in the TIGRFAM database at accession numbers TIGR01898 and PF03787, as shown in FIG. 15.

A Cmr1, a Cmr2, a Cmr3, a Cmr4, a Cmr5, or a Cmr6 polypeptide may be produced using recombinant techniques, or chemically or enzymatically synthesized using routine methods. A Cmr1, a Cmr2, a Cmr3, a Cmr4, a Cmr5, or a Cmr6 polypeptide may be isolated from a prokaryotic microbes having CRISPR loci. Examples of prokaryotic microbes with known whole genomic sequences containing coding regions expected to encode a polypeptide of the present invention include *Archaeoglobus fulgidus* DSM4304, Clostridium botulinum A ATCC 19397, Clostridium botulinum A Hall, Clostridium botulinum F Langeland, Clostridium botulinum Hall A Sanger, Deinococcus geothermalis DSM 11300, Methanosaeta thermophila PT, Methanosarcina acetivorans C2A, Myxococcus xanthus DK 1622, Pyrococcus furiosus DSM 3638, Rubrobacter xylanophilus DSM 9941, Sulfolobus solfataricus P2, Sulfolobus tokodaii strain 7, Synechococccus sp. OS Type A, Synechococccus sp. OS Type B prime, Syntrophus aciditrophicus SB, Thermoanaerobacter tengcongensis MB4(T), Thermobifida fusca YX, Thermotoga maritima MSB8, Thermus thermophilus HB27, Porphyromonas gingivalis W83, Methanopyrus kandleri AV19, Clostridium novyi NT, Methanococcus jannaschii DSM2661, Staphylococcus epidermidis RP62A, Sulfolobus acidocaldarius DSM 639, Methanococcus maripaludis C5, Methanocorpusculum labreanum Z, Methanosarcina barkeri fusaro, Prochlorococcus marinus str. AS9601, Campylobacter fetus subsp. fetus 82-40, Carboxydothermus hydrogenoformans Z-2901, Clostridium botulinum B1 strain Okra, Methanospirillum hungatei JF-1, Mycobacterium tuberculosis CDC1551, Nostoc sp. PCC 7120, Pyrobaculum islandicum DSM 4184, Pyrococcus horikoshii shinkaj OT3, Burkholderia cenocepacia HI2424, Neorickettsia sennetsu Miyayama, Rhodospirillum rubrum ATCC 11170, Clostridium beijerinckii NCIMB 8052, Aquifex aeolicus VF5, Bacillus halodurans C-125, Thermus thermophilus HB8, Methanosarcina mazei Goe1, Treponema pallidum Nichols, Baumannia cicadellinicola, Chlamydia muridarum strain Nigg, Clostridium perfringens ATCC13124, Methylibium petroleiphilum PM1, Mycoplasma capricolumn subsp capricolumn California kid ATCC 27343, Mycoplasma genitalium G-37, Clostridium phytofermentans ISDg, Methanobacterium thermoautotrophicum delta H, Methanothermobacter thermautotrophicus str. Delta H, Ehrlichia chaffeensis Arkansas, Campylobacter curvus 525.92, Clostridium perfringens 13, Clostridium perfringens SM101, Coxiella burnetii RSA 493, Desulfovibrio vulgaris Hildenborough, Enterococcus faecalis V583, Lactobacillus delbrueckii subsp. bulgaricus ATCC BAA-365, Leptospira interrogans Copenhageni Fiocruz L1-130, Leptospira interrogans serovar lai str. 56601, Listeria welshimeri serovar 6b str. SLCC5334, Mesoplasma florum L1, Methanococcoides burtonii DSM 6242, Prevotella intermedia 17, Pseudomonas aeruginosa PAO1, Pyrococcus abyssi GES, Staphylococcus epidermidis ATCC 12228, Streptococcus gordonii Challis NCTC7868, Streptococcus pneumoniae TIGR4, Streptomyces coelicolor A3(2), Sulfolobus islandicus filamentous virus (SIFV), Aeropyrum pernix K1, Anaplasma phagocytophilum HZ, Campylobacter concisus 13826, Campylobacter jejuni RM1221, Colwellia psychrerythraea 34H, Deinococcus radiodurans R1, Geobacter sulfurreducens PCA, Nitrosospira multiformis ATCC 25196, Prochlorococcus marinus MIT9313, Pseudomonas putida KT2440, Shewanella oneidensis MR-1, Shewanella sp. MR-4, Shewanella sp. MR-7, Streptococcus agalactiae 2603V/R, Streptococcus agalactiae A909, Synechococcus sp. CC9311, Treponema denticola ATCC 35405, Vibrio cholerae El Tor N16961, Vibrio fischeri ES114, Bacillus halodurans, Synechocystis sp. PCC 6803, Thermotoga maritima, Borrelia garini PBi, Lactococcus lactis subsp. lactis IL1403, Leuconostoc mesenteroides subsp. mesenteroides ATCC 8293, Mannheimia succiniciproducens MBEL55E, Mycobacterium bovis subsp. bovis AF2122/97, Mycobacterium tuberculosis H37Rv (lab strain), Nitrosomonas europaea ATCC 19718, Photorhabdus luminescens TTO1, Picrophilus torridus DSM 9790, Pyrobaculum aerophilum IM2, Streptococcus thermophilus CNRZ1066, Streptococcus thermophilus LMG 18311, Thermoplasma volcanium GSS1, and Vibrio vulnificus YJ016.

Also provided herein are polynucleotides, including isolated polynucleotides, encoding a Cmr1, a Cmr2, a Cmr3, a Cmr4, a Cmr5, or a Cmr6 polypeptide. Cmr1 polynucleotides may have a nucleotide sequence encoding a polypeptide having the amino acid sequence shown in SEQ ID NO:4 or SEQ ID NO:6. Cmr2, Cmr3, Cmr4, Cmr5, and Cmr6 polynucleotides may have a nucleotide sequence encoding a polypeptide having the amino acid sequence shown in SEQ ID NO:8, SEQ ID NO:10, SEQ ID NO:12, SEQ ID NO:14, or SEQ ID NO:16, respectively. An example of the class of nucleotide sequences encoding such a polypeptide is the nucleotide sequence depicted at Genbank Accession Numbers as shown in Table 1.

TABLE 1

Genbank accession numbers and PF locus numbers for Cmr polypeptides and polynucleotides.

| | Genbank nucleotide sequence (location in genome) | SEQ ID NO: | Genbank protein sequence | SEQ ID NO: | PF locus |
|---|---|---|---|---|---|
| Cmr1 | NC_003413 (1081353-1080337) | 3 | AAL81254 | 4 | PF1130 |
| Cmr1 | NC_003413 (365628-365038) | 5 | AAL80476 | 6 | PF0352 |
| Cmr2 | NC_003413 (1080344-1077729) | 7 | AAL81253 | 8 | PF1129 |
| Cmr3 | NC_003413 (1077732-1076764) | 9 | AAL81252 | 10 | PF1128 |
| Cmr4 | NC_003413 (1075334-1074447) | 11 | AAL81250 | 12 | PF1126 |
| Cmr5 | NC_003413 (1074469-1073960) | 13 | AAL81249 | 14 | PF1125 |
| Cmr6 | NC_003413 (1073976-1072954) | 15 | AAL81248 | 16 | PF1124 |

It should be understood that a polynucleotide encoding a Cmr1, a Cmr2, a Cmr3, a Cmr4, a Cmr5, or a Cmr6 polypeptide represented by the corresponding nucleotide sequence in Table 1 is not limited to that nucleotide sequence, but also includes the class of polynucleotides encoding such polypeptides as a result of the degeneracy of the genetic code. For example, the naturally occurring nucleotide sequence SEQ ID NO:3 is but one member of the class of nucleotide sequences encoding a polypeptide having the amino acid sequence SEQ ID NO:4. The class of nucleotide sequences encoding a selected polypeptide sequence is large but finite, and the nucleotide sequence of each member of the class may be readily determined by one skilled in the art by reference to the standard genetic code, wherein different nucleotide triplets (codons) are known to encode the same amino acid.

A polynucleotide encoding a polypeptide described herein may have sequence similarity with the nucleotide sequence of SEQ ID NO:3, SEQ ID NO:5, SEQ ID NO:7, SEQ ID NO:9, SEQ ID NO:11, SEQ ID NO:13, or SEQ ID NO:15. A Cmr1, a Cmr2, a Cmr3, a Cmr4, a Cmr5, or a Cmr6 polynucleotide may be isolated from a microbe having CRIPSR loci, such as, but not limited to, Pyrococcus furiosus, or may be produced using recombinant techniques, or chemically or enzymatically synthesized using routine methods. A Cmr1, a Cmr2, a Cmr3, a Cmr4, a Cmr5, or a Cmr6 polynucleotide may further include heterologous nucleotides flanking the open reading frame encoding a Cmr1, a Cmr2, a Cmr3, a Cmr4, a Cmr5, or a Cmr6 polypeptide. Typically, heterologous nucleotides may be at the 5' end of the coding region, at the 3' end of the coding region, or the combination thereof. The number of heterologous nucleotides may be, for instance, at least 10, at least 100, or at least 1000.

The present invention also includes fragments of the polypeptides described herein, and the polynucleotides encoding such fragments, such as SEQ ID NO:4, SEQ ID NO:6, SEQ ID NO:8, SEQ ID NO:10, SEQ ID NO:12, SEQ ID NO:14, or SEQ ID NO:16, as well as those polypeptides having sequence similarity with the polypeptides. A polypeptide fragment may include a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 amino acid residues.

A polypeptide disclosed herein or a fragment thereof may be expressed as a fusion polypeptide that includes an additional amino acid sequence. For instance, the additional amino acid sequence may be useful for purification of the fusion polypeptide by affinity chromatography. Various methods are available for the addition of such affinity purification moieties to proteins. Representative examples may be found in Hopp et al. (U.S. Pat. No. 4,703,004), Hopp et al. (U.S. Pat. No. 4,782,137), Sgarlato (U.S. Pat. No. 5,935,824), and Sharma (U.S. Pat. No. 5,594,115). In another example, the additional amino acid sequence may be a carrier polypeptide. The carrier polypeptide may be used to increase the immunogenicity of the fusion polypeptide to increase production of antibodies that specifically bind to a polypeptide of the invention. The invention is not limited by the types of carrier polypeptides that may be used to create fusion polypeptides. Examples of carrier polypeptides include, but are not limited to, keyhole limpet hemacyanin, bovine serum albumin, ovalbumin, mouse serum albumin, rabbit serum albumin, and the like.

A polynucleotide disclosed herein, such as a polynucleotide encoding a psiRNA or a polynucleotide encoding a polypeptide described herein, may be present in a vector. A vector is a replicating polynucleotide, such as a plasmid, phage, or cosmid, to which another polynucleotide may be attached so as to bring about the replication of the attached polynucleotide. Construction of vectors containing a polynucleotide of the invention employs standard ligation techniques known in the art. See, e.g., Sambrook et al, Molecular Cloning: A Laboratory Manual., Cold Spring Harbor Laboratory Press (1989). A vector may provide for further cloning (amplification of the polynucleotide), i.e., a cloning vector, or for expression of the polynucleotide, i.e., an expression vector. The term vector includes, but is not limited to, plasmid vectors, viral vectors, cosmid vectors, and artificial chromosome vectors. Examples of viral vectors include, for instance, adenoviral vectors, adeno-associated viral vectors, lentiviral vectors, retroviral vectors, and herpes virus vectors. Typically, a vector is capable of replication in a microbial host, for instance, a fungus, such as *S. cerevisiae*, or a prokaryotic microbe, such as *E. coli*. Preferably the vector is a plasmid.

Selection of a vector depends upon a variety of desired characteristics in the resulting construct, such as a selection marker, vector replication rate, and the like. In some aspects, suitable host cells for cloning or expressing the vectors herein include eukaryotic cells. Suitable eukaryotic cells include fungi, such as *S. cerevisiae* and *P. pastoris*. In other aspects, suitable host cells for cloning or expressing the vectors herein include prokaryotic cells. Suitable prokaryotic cells include bacteria, such as gram-negative microbes, for example, *E. coli*. Other suitable prokaryotic cells include archeae, such as *Haloferax volcanii*. Vectors may be introduced into a host cell using methods that are known and used routinely by the skilled person. For example, calcium phosphate precipitation, electroporation, heat shock, lipofection, microinjection, and viral-mediated nucleic acid transfer are common methods for introducing polynucleotides into host cells.

Polynucleotides encoding the polypeptides disclosed herein may be obtained from microbes, for instance, members of the genus *Pyrococcus*, such as *P. furiosus*, or produced in vitro or in vivo. For instance, methods for in vitro synthesis include, but are not limited to, chemical synthesis with a conventional DNA/RNA synthesizer. Commercial suppliers of synthetic polynucleotides and reagents for such synthesis are well known. Likewise, polypeptides of the present invention may be obtained from microbes, or produced in vitro or in vivo.

An expression vector may optionally include a promoter that results in expression of an operably linked psiRNA. Promoters act as regulatory signals that bind RNA polymerase in a cell to initiate transcription of a downstream (3' direction) coding region. Promoters present in prokaryotic microbes typically include two short sequences at −10 (often referred to as the Pribnow box, or the −10 element) and −35 positions (often referred to as the −35 element), or a short sequence at −30 (often referred to as a TATA box) located 5' from the transcription start site, for bacterial and archael organisms, respectively. The promoter used may be a constitutive or an inducible promoter. It may be, but need not be, heterologous with respect to a host cell. psiRNA polynucleotides of the present invention do not encode a polypeptide, and expression of a psiRNA present in a vector results in a non-coding RNA. Thus, a vector including a psiRNA may also include a transcription start signal and/or a transcription terminator operably linked to the psiRNA, but a translation start signal and/or translation stop signal typically are not operably linked to a psiRNA. Promoters have been identified in many microbes and are known to the skilled person. Many computer algorithms have been developed to detect promoters in genomic sequences, and promoter prediction is a common element of many gene prediction methods. Thus, the skilled person can easily identify nucleotide sequences present in microbes that will function as promoters.

An expression vector may optionally include a ribosome binding site and a start site (e.g., the codon ATG) to initiate translation of the transcribed message to produce the polypeptide. It may also include a termination sequence to end translation. A termination sequence is typically a codon for which there exists no corresponding aminoacetyl-tRNA, thus ending polypeptide synthesis. A vector introduced into a host cell optionally includes one or more marker sequences, which typically encode a molecule that inactivates or otherwise detects or is detected by a compound in the growth medium. For example, the inclusion of a marker sequence may render the transformed cell resistant to a selective agent, such as an antibiotic, or it may confer compound-specific metabolism on the transformed cell. Examples of a marker sequence include, but are not limited to, sequences that confer resistance to kanamycin, ampicillin, chloramphenicol, tetracycline, streptomycin, and neomycin. Another example of a marker that renders a cell resistant to a selective agent is 3-hydroxy-3-methylglutaryl coenzyme A reductase (HMG-CoA), an enzyme used for archaeal membrane lipid biosynthesis (Matsumi et al., J. Bacteriol., 2007, 189:2683-2691). Certain statins, such as mevinolin and its analog simvastatin, inhibit HMG-CoA reductase activity, and overexpression of HMG-CoA reductase can confer resistance to mevinolin and/ or simvastatin. Yet another example of a marker is a nutritional marker. A nutritional marker is typically a coding region that, when mutated in a cell, confers on that cell a requirement for a particular compound. Cells containing such a mutation will not grow on defined medium that does not include the appropriate compound, and cells receiving a coding region that complements the mutation can grow on the defined medium in the absence of the compound. Examples of nutritional markers include, but are not limited to, coding regions encoding polypeptides in biosynthetic pathways, such as nucleic acid biosynthesis (e.g., biosynthesis of uracil), amino acid biosynthesis (e.g., biosynthesis of histidine and tryptophan), vitamin biosynthesis (e.g., biosynthesis of thiamine), carbohydrate metabolism (e.g., metabolism of cellobiose), and the like.

Polypeptides and fragments thereof useful in the present invention may be produced using recombinant DNA techniques, such as an expression vector present in a cell. Such methods are routine and known in the art. The polypeptides and fragments thereof may also be synthesized in vitro, e.g., by solid phase peptide synthetic methods. The solid phase peptide synthetic methods are routine and known in the art. A polypeptide produced using recombinant techniques or by solid phase peptide synthetic methods may be further purified by routine methods, such as fractionation on immunoaffinity or ion-exchange columns, ethanol precipitation, reverse phase HPLC, chromatography on silica or on an anion-exchange resin such as DEAE, chromatofocusing, SDS-PAGE, ammonium sulfate precipitation, gel filtration using, for example, Sephadex G-75, or ligand affinity.

Polypeptides useful in the methods described herein, such as the polypeptides described herein and other polypeptides belonging to the Cmr family, may be obtained from a microbe that has a CRISPR locus. Examples of such microbes are listed hereinabove. Methods for obtaining polypeptides useful in the methods described herein may include ion exchange chromatography of cellular extracts. Typically, obtaining polypeptides includes conditions that minimize RNAse and proteinase activity, such as by including RNAse inhibitors and protease inhibitors. For instance, an S100 extract of a microbe may be prepared by ultracentrifugation of a whole cell extract at 100,000×g, followed by fractionation on an anion exchange column, for instance, a Q-sepharose column. Retained polypeptides may be removed by a cation gradient, such as NaCl. Fractions with the polypeptides of interest may be identified by determining which fractions have psiRNAs (Hale et al., 2008, RNA 14, 2572-2579). Those fractions with psiRNAs may be further separated on a second anion exchange column, eluted with a cation gradient, and the fractions with psiRNAs identified again. Those fractions with psiRNAs may be further separated on a cation exchange column, for instance, an S-sepharose column, and bound polypeptides eluted with a cation gradient. The complex of polypeptides bound to a psiRNA may be identified by native gel Northern analysis (Hale et al., 2008, RNA 14, 2572-2579).

Optionally, the complex of polypeptides bound to a psiRNA identified by native gel Northern analysis can be subjected to tandem mass spectroscopy. Tandem mass spectroscopy analysis is routinely used by the skilled person to identify polypeptides. The data from the analysis can be used to search readily available databases containing genomic sequence data for the microbe used as a source of the polypeptides, and the coding sequences encoding the polypeptides can be easily identified. These coding sequences can be easily obtained by, for instance, PCR amplification of genomic DNA, and inserted into vectors. The cloned coding regions encoding polypeptides useful in the methods described herein may be expressed in a microbe (for use in in vivo methods described herein), and optionally obtained from the microbe for use in in vitro methods described herein. Polypeptides present in the peak fractions from the cation exchange column may also be used in in vitro methods.

The present invention also includes genetically modified microbes. A genetically modified microbe may have a polynucleotide encoding a psiRNA, a polynucleotide encoding a Cmr1, a Cmr2, a Cmr3, a Cmr4, a Cmr5, or a Cmr6 polypeptide, or a combination thereof. Compared to a control microbe that is not genetically modified according to the present invention, a genetically modified microbe may exhibit production of an exogenous polynucleotide or an exogenous polypeptide disclosed herein or a fragment thereof, or increased production of an endogenous polypeptide disclosed herein. A polynucleotide encoding a psiRNA or a polypeptide disclosed herein may be present in the microbe as a vector or integrated into a chromosome. Examples of microbes that can be genetically modified include, but are not limited to, eukaryotic cells, such as *S. cerevisiae* and *P. pastoris*, bacteria, such as gram-negative microbes, for example, *E. coli*, and archaea, such as *Haloferax volcanii*.

Also provided herein are methods for inactivating a polynucleotide. The methods include incubating under suitable conditions a composition that includes a target polynucleotide, a psiRNA, and polypeptides that will catalyze the inactivation, for instance cleavage of the specific target polynucleotide. The methods of the present invention may occur in vitro or in vivo. In some aspects of the in vivo methods, the polypeptides that will catalyze the inactivation of the target polynucleotide are endogenous to the microbe in which the in vivo method is occurring. Restriction endonucleases recognize a specific nucleotide sequence of a target polynucleotide and cleave the target at a specific location. For instance, EcoRI recognizes a target double stranded DNA at GAATTC, and cleaves the double stranded molecule at a specific and predictable location within that recognition sequence. Cleaving a target polynucleotide using the methods of the present invention permits a level of flexibility that is not available with restriction endonucleases having a specific recognition site. Target polynucleotides described herein are not limited to those possessing a specific recognition site. Moreover, using the methods presented herein, the skilled worker can determine where cleavage of a target polynucleotide is desired, and then design a psiRNA that will guide the polypeptides described herein to cleave the target at that specific location. Moreover, unlike restriction endonucleases known in the art, the target polynucleotide may be RNA.

Current evidence indicates that the psi-tag is a universal feature of the psiRNAs that function as guides for the various effector complexes of the CRISPR-Cas system in diverse prokaryotes (Marraffini et al., 2008, Science, 322:1843-1845, and Brouns et al., 2008, Science, 321:960-964). The psi-tag is found on the psiRNAs in both *Staphylococcus epidermidis* and *E. coli*, where evidence indicates that silencing occurs at the DNA level (Marraffini et al., 2008, Science, 322:1843-1845, and Brouns et al., 2008, Science, 321:960-964). The methods disclosed herein for inactivating a target polynucleotide include the use of polynucleotides having a 5' region that is present irrespective of the target polynucleotide. This is in contrast with the structure of silencing RNAs known to function in eukaryotic cells, which do not possess conserved sequence elements.

As disclosed above, a psiRNA has a 5' region and a 3' region. The 5' region of a psiRNA may be selected from a repeat disclosed herein, or may be selected as described herein from other repeats present in a microbe containing CRISPR loci. psiRNAs function with polypeptides encoded by a subset of coding regions typically physically located near CRISPR loci (referred to as cas genes) to result in inactivation of a target polynucleotide. For example, psiRNAs function with the Cmr proteins to effect cleavage of target RNA polynucleotides (Example 2). Thus, when the method includes the use of a 5' region present in a particular microbe, the method may further include the use of Cmr polypeptides from that microbe. In view of the present disclosure, the skilled person now knows which psiRNAs can be used with polypeptides having endonuclease activity, for instance, endoribonuclease activity, to result in inactivation of a target polynucleotide.

In those aspects where the method is in vitro, Cas polypeptides derived from *P. furiosus* such as those described herein may be used with a psiRNA having a psiRNA-tag that is identical to or having sequence similarity with, for instance, GAAUUGAAAG (SEQ ID NO:19), AAUUGAAAG, AUUGAAAG, UUGAAAG, UGAAAG, or GAAAG, or another psiRNA-tag present in *P. furiosus*. Alternatively, polypeptides useful in the methods may be obtained from another microbe having CRISPR loci as described herein, and these polypeptides may be used with a psiRNA having a psiRNA-tag present in that same microbe. Conditions suitable for inactivation of a target polynucleotide for example by the Cmr polypeptides described herein may include incubation for an hour at a suitable temperature such as at least 30° C., at least 40° C., at least 50° C., at least 60° C., at least 70° C., at least 80° C., and at least 90° C. Other conditions suitable for inactivation include a buffer, for instance, 20 mM HEPES, an appropriate pH, such as 7.0, and additional components such as KCl (250 mM), MgCl2 (1.5 mM), ATP (1 mM), DTT (10 mM), and an RNAse inhibitor.

In vivo methods may be used to decrease or eliminate expression of polypeptides encoded by a target polynucleotide, or decrease or eliminate activities associated with non-coding RNAs. For instance, a psiRNA may be introduced into a microbe to inactivate a target polynucleotide. Such methods may be used to decrease or eliminate expression of an endogenous polynucleotide or an exogenous polynucleotide. Such methods may be used to immunize a microbe against an exogenous polynucleotide, for instance, a bacteriophage, conjugative plasmid, or transposon. The psiRNA may be introduced as an RNA polynucleotide, or may be introduced as a vector encoding the psiRNA. The vector may be one that is unable to replicate in the microbe, able to replicate, or integrate into the microbe's genome.

In those aspects where the method is in vivo, and the microbe includes polypeptides that catalyze the inactivation of a target polynucleotide (e.g. cleavage of a polynucleotide target by the Cmr complex as described herein), the psiRNA used in the method typically includes a psiRNA-tag that is present in that microbe. For instance, when the microbe is *P. furiosus* or *Sulfolobus solfataricus*, the psiRNA-tag may be GAAUUGAAAG (SEQ ID NO:19), AAUUGAAAG, AUUGAAAG, UUGAAAG, UGAAAG, or GAAAG, or another psiRNA-tag present in *P. furiosus* or *S. solfataricus*. When the method is in vivo, and the microbe does not include polypeptides that catalyze the inactivation of a target polynucleotide, the microbe may be engineered to express the polypeptides. For instance, polynucleotides encoding Cmr polypeptides may be expressed in a cell, and a psiRNA including a psiRNA-tag present in *P. furiosus* may be used. Alternatively, polypeptides from some other microbe having CRISPR loci and Cmr (or other Cas) polypeptides may be used as the source of polynucleotides encoding polypeptides having the inactivating, for instance, endoribonuclease activity. The polynucleotides may be introduced into and expressed in a microbe, and the psiRNA used in such a microbe would likewise be obtained from the same microbe that was the source of the Cas polypeptides.

Examples of microbes that may be used in methods of the present invention include, but are not limited to, microbes useful in starter cultures, probiotic cultures, dietary supplement cultures, and cultures for use in fermentation of biomass for production of biofuels. Examples of such microbes include, but are not limited to, *Escherichia* spp., *Shigella* spp., *Salmonella* spp., *Erwinia* spp., *Yersinia* spp., *Bacillus* spp., *Vibrio* spp., *Legionella* spp., *Pseudomonas* spp., *Neisseria* spp., *Bordetella* spp., *Helicobacter* spp., *Listeria* spp., *Agrobacterium* spp., *Staphylococcus* spp., *Streptococcus* spp., *Enterococcus* spp., *Clostridium* spp., *Corynebacterium* spp., *Mycobacterium* spp., *Treponema* spp., *Borrelia* spp., *Francisella* spp., *Brucella* spp., *Bifidobacterium* spp., *Brevibacterium* spp., *Propionibacterium* spp., *Lactococcus* spp., *Lactobacillus* spp., *Pediococcus* spp., *Leuconostoc* spp., and *Oenococcus* spp.

With respect to the 3' region, typically, the nucleotide sequence of the target is known. Since the 3' region of a psiRNA used in a method disclosed herein is complementary or substantially complementary to the target polypeptide that is to be inactivated by the psiRNA, the sequence of the target polynucleotide will dictate the nucleotide sequence of a psiRNA 3' region.

The methods of the present invention are not limited to any target polynucleotide. A target polynucleotide may be an endogenous polynucleotide sequence (such as a DNA or a microbial mRNA) or an exogenous polynucleotide sequence. The genomic sequence of many bacterial and archaeal microbes are published, thus the skilled person can easily select a series of nucleotides from a genomic sequence that can be used as a target polynucleotide. In embodiments that use a target polynucleotide that is a portion of an mRNA or a non-coding RNA, computer algorithms for identifying genomic sequences encoding such RNAs, for example open reading frames, are routinely used in the art. Moreover, as the speed of acquiring microbial genomic sequences continues to increase, more microbial genomes become readily available.

In some embodiments a target polynucleotide is ribonucleotide. Examples of ribonucleotides include, but are not limited to, ribonucleotides encoding a polypeptide (e.g., mRNAs) and non-coding ribonucleotides (e.g., small non-coding RNAs, or ncRNAs). Examples of ncRNAs include, but are not limited to, ribosomal RNA, bacterial signal recognition particle RNA, transfer RNA, transfer-messenger RNA, small nuclear RNA, small nucleolar RNA, and ribonuclease P. The target polynucleotide may be the deoxynucleotide sequence that encodes such ribonucleotides.

Examples of ribonucleotides encoding a polypeptide include, but are not limited to, mRNAs encoding secreted polypeptides, polypeptides associated with the outer membrane (such as porins and receptors), polypeptides associated with the inner membrane, periplasmic polypeptides, mitochondrial polypeptides, structural polypeptides (such as fimbriae, flagella, polypeptides involved in protein export), polypeptides involved in biosynthesis (such as biosynthesis of amino acids, polypeptides, nucleotides, DNA, RNA, lipids, sugar residues, coenzymes, prosthetic groups, non-ribosomal polypeptides), polypeptides involved in metabolism (such as the phosphotransferase system for glucose and other sugars, glycolysis, the pentose phosphate pathway, the Entner-Doudoroff pathway, the tricarboxylic acid cycle, pathways for polyols, pathways for carboxylates), polypeptides involved in energy production (pathways for electrons to oxygen, pathways for anaerobic electron transport), DNA restriction and modification polypeptides, polypeptides involved in protein degradation, polypeptides involved in motility and chemotaxis, polypeptides involved in resistance to antibiotics (such as beta-lactamases), and ATP-coupled solute transport polypeptides. The target polynucleotide may be the deoxynucleotide sequence that encodes such ribonucleotids.

Other examples of ribonucleotides include RNA sequences encoded by microbial invaders such as bacteriophage able to infect a microbe that contains a CRISPR locus, conjugative plasmids, microbial transposons, and the like. The target polynucleotide may be the deoxynucleotide sequence of the bacteriophage, conjugative plasmid, or transposon. Examples of bacteriophage include, but are not limited to, members of virus families Corticoviridae, Cystoviridae, Inoviridae, Leviviridae, Microviridae, Myoviridae, Podoviridae, Siphoviridae, and Tectiviridae.

Examples of psiRNAs that may be used include the sequence 5'-$N_{5-10}$NNNNNNNN-NNNNNNNN↓NNNNNNNNNNNNNN (SEQ ID NO:1) or 5'-$N_{5-10}$NNNNNNNNNNNNNN-NNNNNNNN↓NNNNNNNNNNNNNNNNNNN (SEQ ID NO:2), where $N_{5-10}$ is the 5' region of between 5 and 10 nucleotides and the last 31 nucleotides of SEQ ID NO:1 and the last 37 nucleotides of SEQ ID NO:2 are the guide sequence and are complementary or substantially complementary to the target. The psiRNA is designed to not only be complementary to the target polynucleotide, but in some cases, also to line up the desired cleavage site on the target polynucleotide with the arrow when the psiRNA and the target polynucleotide are hybridized. Cleavage of the target polynucleotide by the Cmr complex occurs, for example, opposite the position defined by the arrow. Thus, knowledge of the nucleotide sequence of a target polynucleotide surrounding a desired cleavage site aids in the design of the appropriate psiRNA.

The present invention also provides kits. A kit may include one or more of the polynucleotides or polypeptides described herein. For instance, a kit may include a psiRNA or a vector encoding a psiRNA, or a Cmr1 polypeptide, a Cmr2 polypeptide, a Cmr3 polypeptide, a Cmr4 polypeptide, a Cmr5 polypeptide, a Cmr6 polypeptide, or a combination thereof. In another aspect, a kit may include one or more vectors encoding one or more of the polypeptides described herein. Kits may be used, for instance, for modifying a microbe to express polypeptides described herein, or for in vitro cleaving of a target polynucleotide. The kit components are present in a suitable packaging material in an amount sufficient for at least one assay. Optionally, other reagents such as buffers and solutions needed to practice the invention are also included. Instructions for use of the packaged polypeptide or primer pair are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the invention nucleic acids can be used for methods as described herein. In addition, the packaging material contains instructions indicating how the materials within the kit are employed. As used herein, the term "package" refers to a solid matrix or material such as glass, plastic, paper, foil, and the like, capable of holding within fixed limits a kit component. Thus, for example, a package can be a glass vial used to contain milligram quantities of a polypeptide or polynucleotide. "Instructions for use" typically include a tangible expression describing the reagent concentration or at least one assay method parameter.

The present invention is illustrated by the following examples. It is to be understood that the particular examples, materials, amounts, and procedures are to be interpreted broadly in accordance with the scope and spirit of the invention as set forth herein.

Example 1

In many prokaryotes, non-coding RNAs that arise from the CRISPR loci are now thought to mediate defense against viruses and other molecular invaders by an RNAi-like pathway. CRISPR (clustered regularly interspaced short palindromic repeat) loci contain multiple short regions of similarity to invader sequences separated by short repeat sequences, and are associated with resistance to infection by corresponding viruses. It is hypothesized that RNAs derived from these regions, termed prokaryotic silencing (psi)RNAs, guide Slicer-like complexes of partner proteins to destroy invader nucleic acids. Here we have investigated CRISPR-derived RNAs in the archaeon *Pyrococcus furiosus*. Northern analysis revealed multiple RNA species consistent with a proposed biogenesis pathway that includes full-length CRISPR locus transcripts and intermediates generated by endonucleolytic cleavages within the repeat sequences. However, our results identify the principal products of the CRISPR loci as small psiRNAs comprised primarily of invader-targeting sequence with perhaps only 5-10 nucleotides of CRISPR repeat sequence. These RNAs are the most abundant CRISPR RNA species in *P. furiosus* and are likely the guides for the effector complexes of the proposed prokaryotic RNAi (pRNAi) system. We analyzed cell-free extracts fractionated under non-denaturing conditions and found that the various CRISPR RNA species are components of distinct RNA-protein complexes, including at least two complexes that contain mature-length psiRNAs. Finally, RNAs are produced from all 7 CRISPR loci present in the *P. furiosus* genome and interestingly, the most recently acquired psiRNAs encoded proximal to the leader sequence of a CRISPR locus appear to be the most abundant.

Methods and Materials

Small RNA cloning and sequencing. Total RNA was isolated from *P. furiosus* cells using the Trizol reagent (Invitrogen) as indicated by the manufacturer. Approximately 300 µg of total RNA was separated on an 8×8.5 cm 15% polyacrylamide 7M urea gel using DNA size standards (pGEM markers, Promega) for size determination. RNAs between 20 and 50 nucleotides were isolated and passively eluted overnight in 0.5 M ammonium acetate, 0.1% SDS, 0.5 mM EDTA, followed by ethanol precipitation. In order to remove potential 5' triphosphates or cap structures, RNAs were treated with 50 U tobacco acid pyrophosphatase (TAP) (Epicentre) for 2 hours at 37° C. The eluted RNAs were cloned using standard microRNA cloning protocols (Lau et al., 2001, *Science*, 294: 858-862) using the following primers containing EcoRI restriction sites: 3' adapter: 5'-AppTTTAACCGCGAATTC-CAGddC-3' (IDT) (SEQ ID NO: 31), 5' adapter: 5'-ACG-GAATTCCTCACTrArArA-3' (IDT) (SEQ ID NO:32), RT/PCR primer: 5'-GACTAGCTGGAATTCGCGGT-TAAA-3' (IDT) (SEQ ID NO:33), PCR primer: 5'-CAGC-CAACGGAATTCCTCACTAAA-3' (SEQ ID NO:34). An additional PCR was performed in order to add a BanI restriction site (GGYRCC) for concatamerization of the PCR products using the following primers: PCR2 5' primer 5'-GAC-TAGCTTGGTGCCGAATTCGCGGTTAAA-3' (SEQ ID NO:35), PCR2 3' primer 5'-GAGCCAACAGGCACCGAAT-TCCTCACTAAA-3' (SEQ ID NO: 36). The products were subject to restriction digestion and DNA ligation by standard methods (Lau et al., 2001, *Science*, 294:858-862). cDNAs were cloned into the pCRII TOPO vector (Invitrogen) and transformed into TOP10 cells (Invitrogen) as described by the manufacturer. Plasmid preparation and sequencing was performed in a 96-well plate format using standard M13 forward, reverse, and T7 promoter primers. Sequences were analyzed using BLAST (NCBI). Northern analysis. Approximately 10 μg of *P. furiosus* total RNA was separated on 15% polyacrylamide 7 M urea gels (Criterion, Bio-Rad) alongside [32P]-5'-end radiolabeled RNA markers (Decade, Ambion). The RNAs were transferred onto nylon membranes (Zeta-Probe, Bio-Rad) using a Trans-Blot SD Semi-Dry Cell (Bio-Rad). Membranes were baked at 80° C. for at least an hour before pre-hybridization in a ProBlot hybridization oven (LabNet) for at least 1 hour at 42° C. Pre-hybridization and hybridization was performed in either Oligo-UltraHyb (Ambion) buffer or hybridization buffer containing 5×SSC, 7% SDS, 20 mM sodium phosphate, pH 7.0 and 1×Denhardt's solution. Deoxyribonucleotide probes (MWG) (20 pmol) were 5' end labeled with T4 Polynucleotide Kinase (Ambion) and γ-[32P]-ATP (specific activity >7,000 Ci/mmol, MP Biomedicals) using standard protocols. Labeled probes were added to the pre-hybridization buffer, followed by hybridization overnight at 42° C. Following hybridization, two washes were performed in 2×SSC, 0.5% SDS for 30 minutes at 42° C. Resulting blots were exposed to a phosphoimager screen for 24-72 hours and scanned. The probes and sequences that were used are given in Table 2.

TABLE 2

Probes.

| Probe | Sequence (SEQ ID NO:) |
|---|---|
| repeat 1, 5, 6 (antisense) | CTTTCAATTCTATTTT(AG)GTCTTATTC(GT)AAC (SEQ ID NO: 37) |
| repeat 1, 5, 6 (sense) | GTT(AC)CAATAAGAC(TC)AAAATAGAATTGAAAG (SEQ ID NO: 38) |
| repeat 2, 4, 7 (antisense) | CTTTCAATTCTTTTGTAGTCTTATTGGAAC (SEQ ID NO: 39) |
| repeat 2, 4, 7 (sense) | GTTCCAATAAGACTACAAAAGAATTGAAAG (SEQ ID NO: 40) |
| psiRNA 1.01 (antisense) | GGTCAGATCAGATTGCTTAAGACAAGAAATG (SEQ ID NO: 41) |
| psiRNA 1.01 (sense) | CATTTCTTGTCTTAAGCAATCTGATCTGACC (SEQ ID NO: 42) |
| psiRNA 2.01 (antisense) | GTGGAGCAGAGTCAGAAGAAGAAGTGCG (SEQ ID NO: 43) |
| psiRNA 2.01 (sense) | CGCACTTCTTCTTCTGACTCTGCTCCAC (SEQ ID NO: 44) |
| psiRNA 4.02 (antisense) | TCTGATAGGCTTCAAAGAGTGGCGCTTCAAC (SEQ ID NO: 45) |
| psiRNA 4.02 (sense) | GTTGAAGCGCCACTCTTTGAAGCCTATCAGA (SEQ ID NO: 46) |
| psiRNA 5.02 (antisense) | GGGAATGGTTCACGTAGTACTTGAGGGCGC (SEQ ID NO: 47) |
| psiRNA 5.02 (sense) | GCGCCCTCAAGTACTACGTGAACCATTCCC (SEQ ID NO: 48) |
| psiRNA 6.01 (antisense) | CTAAGGACATTTGTACGTCAAATTCTTCAC (SEQ ID NO: 49) |
| psiRNA 6.01 (sense) | GTGAAGAATTTGACGTACAAATGTCCTTAG (SEQ ID NO: 50) |
| psiRNA 7.01 (antisense) | GCTCTCAGCCGCAAGGACCGCATAC (SEQ ID NO: 51) |
| psiRNA 7.01 (sense) | GTATGCGGTCCTTGCGGCTGAGAGC (SEQ ID NO: 52) |
| psiRNA 7.11 (antisense) | CCTTATATGGGTGTTGTGAAGCAGGATAGAAC (SEQ ID NO: 53) |
| psiRNA 7.11 (sense) | GTTCTATCCTGCTTCACAACACCCATATAAGG (SEQ ID NO: 54) |
| psiRNA 7.21 (antisense) | GGCTCTACCTAATCATCCTCTTGACACAAC (SEQ ID NO: 55) |

TABLE 2-continued

Probes.

| Probe | Sequence (SEQ ID NO:) |
|---|---|
| psiRNA 7.21 (sense) | GTTGTGTCAAGAGGATGATTAGGTAGAGCC (SEQ ID NO: 56) |
| psiRNA 8.01 (antisense) | GACTGTGTGTGGAGCAGCTATTTGCTTCGGC (SEQ ID NO: 57) |
| psiRNA 8.01 (sense) | GCCGAAGCAAATAGCTGCTCCACACACAGTC (SEQ ID NO: 58) |

Chromatography. 15 g of *Pyrococcus furiosus* cells were lysed anerobically in 200 mL 50 mM Tris, pH 8.0 in the presence of 4 mg/L RNase-free DNase (Sigma). The extract was subject to ultracentrifugation at 113,000×g for 2 hours (Optima L-90K, Beckman-Coulter). The resulting S100 extract was applied to a 60 mL DEAE Sepharose-FF column and eluted using a 0-500 mM NaCl gradient. The resulting fractions were analyzed by isolating RNAs from 250 µl of each 30 mL fraction using the Trizol LS protocol (Invitrogen). The RNAs were separated on 10% polyacrylamide 7 M urea gels, blotted, and subject to Northern analysis as described above, using the Oligo-UltraHyb hybridization buffer for both pre-hybridization and hybridization. See above for probe sequences.

Native Northern analysis. 40 ul of DEAE fractions from peaks A-C were separated on a 4-20% polyacrylamide gel (Bio-Rad) using SDS-free running buffer (25 mM Tris, 19.2 mM glycine). De-proteininzed samples were analyzed in parallel. Gels were run at 50 V for 3-4 hours at room temperature. The gel was soaked in 5M urea, 45 mM Tris, 45 mM boric acid, 1 mM EDTA for 15 minutes, then subject to blotting and Northern analysis as described above, using Ultra-Hyb Oligo hybridization buffer (Ambion) and a probe against psiRNA 7.01.

Results psiRNAs cloned from the seven CRISPR loci in *Pyrococcus furiosus* The *P. furiosus* genome contains seven CRISPR loci, each encoding between 11 and 51, and together encoding 200 potential psiRNAs (Grissa et al., 2007, *Bioinformatics*, 8:172) (FIG. 1). To investigate whether psiRNAs are produced from the 7 CRISPR loci, we isolated and cloned small RNAs (less than 50 nucleotides) from total *P. furiosus* RNA preparations. Among 872 small RNA clones sequenced, 144 (17.3%) were derived from CRISPR loci. In addition, 42.2% corresponded to rRNA, 23.9% were derived from ORFs, and 12.4% were from sRNAs (snoRNA homologs). The remaining 4.2% of sequences were derived from tRNAs, transposons, Hhc RNAs (Klein et al., 2002, *Proc Natl Acad Sci USA*, 99:7542-7547) and intergenic sequences.

Most of the CRISPR clones consisted primarily of psiRNA (variable) sequence and included some flanking repeat sequence. The clones included 64 of the 200 potential *P. furiosus* psiRNAs and represented all seven CRISPR loci (FIG. 1). We have adopted a simple system of nomenclature for psiRNAs, in which the psiRNA is designated by a 3-digit number. The first digit indicates the locus number (1, 2 and 3-8 in *P. furiosus*) and the second two digits, separated from the first by a decimal point, indicate the position of the psiRNA within that locus (relative to the leader). For example, the first psiRNA in CRISPR locus 1 is Pf psiRNA 1.01, the first psiRNA in CRISPR locus 2 is psiRNA 2.01, and the last psiRNA in CRISPR locus 1 is psiRNA 1.51 (see FIG. 1). FIG. 1 shows the number of times each individual psiRNA was cloned. The psiRNA clones ranged between 17 and 50 nucleotides in length (see Table 3 for psiRNA clone sequences). The clones included variable amounts of the psiRNA sequence (12 to 40 nucleotides) and of repeat sequence at the 5' (0 to 8 nucleotides) and/or 3' (0 to 22 nucleotides) end. In addition to the psiRNA clones, we isolated a few CRISPR-derived clones that lacked psiRNA sequence and consisted of a portion of leader sequence upstream of a repeat (See "Leader" section of Table 3), indicating that the 3' end of the CRISPR leader is also transcribed.

TABLE 3

Cloned psiRNA sequences

| Sequence | SEQ ID NO: | psiRNA |
|---|---|---|
| Locus 1 | | |
| CTGATCTGACCAGAGCTGGTTCCAATAAGACTAAA | 59 | 1.01 |
| CTGATCTGACCAGAGCTGGTTCCAAGTAAGACTAA | 60 | 1.01 |
| CTGATCTGACCAGAGCTGGTTCCAATAAGACTAAA | 61 | 1.01 |
| CAATCTGATCTGACCAGAGCTGGTTCCAAT | 62 | 1.01 |
| CAATCTGATCTGACCAGAGCTGGTTCCAAT | 63 | 1.01 |
| ATGATTCATTTCTTGTCTTAAGCAAT | 64 | 1.01 |
| TTGTCTTAAGCAATCTGATCT | 65 | 1.01 |
| CACTAAAGTCATACTTTACTGCTACAACCCGCTCTGG | 66 | 1.04 |
| GTCATACTTTACTGCTACAACCCGCTCTGG | 67 | 1.04 |
| TACTGCTACAACCCGCTCTGGGTCGAG | 68 | 1.04 |
| TTACTGCTACAACCCGCTCTGGGTCGA | 69 | 1.04 |
| ACTGCTACAACCCGCTCTGGGTTGA | 70 | 1.04 |
| CTGACACGAACATAAACAGTTCCAATAAGACTACAGAAGA | 71 | 1.06 |
| CTGACACGAACATAAACAGTTCCAATAAGACTACAGAAGA | 72 | 1.06 |
| GAAAGGGAAATGTGCGTAAAGGTTTTCTTCCC | 73 | 1.07 |

TABLE 3-continued

Cloned psiRNA sequences

| Sequence | SEQ ID NO: | psiRNA |
|---|---|---|
| GAAAGGGAAATGTGCGTAAAGGTTTTCTTCCC | 74 | 1.07 |
| TTGACCCACCACCAGCCCTGTTCCAATAAGAC | 75 | 1.08 |
| GAAAGGCGTGCCGTGTGTTTTTATAA | 76 | 1.11 |
| GAAAGGCGTGCCGTGTGTTTTTATAA | 77 | 1.11 |
| GTTGCTGCATATCCAGTGTGG | 78 | 1.12 |
| GTTGCTGCATATCCAGTGTGG | 79 | 1.12 |
| GGCAAGTTCTGGCCTATACTGTCTCCTAATGTCT | 80 | 1.13 |
| TAGGAGACAGTATAGGCCAGAACTTGCCCAG | 81 | 1.13 |
| GACATTAGCNGACAGTATAGGCCA | 82 | 1.13 |
| TTAGCAAATTGCCGATTACTGCACATAAAAAAATAG | 83 | 1.14 |
| CTATAAGGGATTGAAAGGTCAAAGGTATAN | 84 | 1.16 |
| CTATAANGGATTGAAAGGTCAAGGGTATACT | 85 | 1.16 |
| TTCGCGGTTAAACAATCTGATCTGACCAGAGCTGGTTCCAAT | 86 | 1.19 |
| GGACAGCGTGGACACGGTGAACGGGCTCTGGA | 87 | 1.21 |
| CTGATAGAACCTTTGCCACC | 88 | 1.24 |
| CTGATAGAACCTTTGCCACC | 89 | 1.24 |
| CATACTTGCGGATACGGATCCAGTCAAAACTTGACTG | 90 | 1.26 |
| TTGCGGATATGGATCCAGTCAAAACTTGACTG | 91 | 1.26 |
| GCGGATACGGATCCAGTCAAAACTTGACTG | 92 | 1.26 |
| GAAAGCATACTTGCGGATACGGATCCAGT | 93 | 1.26 |
| CTCTGGGTCGTCTATGTTTTTGA | 94 | 1.27 |
| GAGTAGAAATGCCCAAATTCCCCTTAGGGACA | 95 | 1.36 |
| TTTGTGATAGTGTTCTTTGCAACGAAGTGCTTGCTGGTCAG | 96 | 1.43 |
| GTTTGTGATAGTGTTCTTTGCAACGAAGAGCTTGCTGG | 97 | 1.43 |
| GAGTGCCCCGAGCCGGGGGCT | 98 | 1.49 |
| Locus 2 | | |
| CTGACACGAACATAAACAGTTCCAATAAGACTACAGAAGA | 99 | 2.02 |
| CTGACACGAACATAAACAGTTCCAATAAGACTACAGAAGA | 100 | 2.02 |
| ATGGCTCGATGGAATTATGTTCCAATAAGACTACAAAAG | 101 | 2.03 |
| ATGGCTCGATGGAATTATGTTCCAATAAGACTACAAAAG | 102 | 2.03 |
| CTAACTAACATCACCAATAATTAATTGTAAGTTAG | 103 | 2.10 |
| GCTACCATGGCCATCACCAATAATTAATTGTAAGT | 104 | 2.10 |
| CTGAGCCAACCCACCACTTTGGTAAAACT | 105 | 2.13 |
| CTGAGCCAACCCACCACTTTGGTAAAACT | 106 | 2.13 |
| CTGAGCCAACCCACCACTTTGGTAAAACT | 107 | 2.13 |
| TGAGGCTGGAGAGGGCTTCTTTGTTACTACTTGCGT | 108 | 2.17 |
| TTATGTTCATGTTCCACATCTAA | 109 | 2.18 |
| TATGTTCATGTTCCACACTA | 110 | 2.18 |
| Locus 4 | | |
| TTGAAAGGAATGTTGCTCAATGCAAAGGGCTCACCGCTGCTGGTGTTCCA | 111 | 4.01 |
| CTCAATGCAAAGGGCTCACCGCTGCTGGTGTTCCAATAAGA | 112 | 4.01 |
| CTCACCGCTGCTGGTGTTCCAATAAGACTACAAAAGA | 113 | 4.01 |
| TTGAAAGTTGAGTTGAAGCGCCACTCTTTGAA | 114 | 4.02 |
| TTGAGTTGAAGCGCCACTCTTTGAAGCCTATCAGAG | 115 | 4.02 |
| ATTGAAAGTTGAGTTGAAGCGCCACTCTTTGAAGCCTATCAGA | 116 | 4.02 |
| AGTTGAGTTGAAGCGCCACTCTTTGAAGCCTATCAGAGT | 117 | 4.02 |
| GTTGAGTTGAAGCGCCACTCTTTGAAGCCTATCAGAGT | 118 | 4.02 |
| TTGAGTTGAAGCGCCACTCTTTGAAGCCTATCAGAGTT | 119 | 4.02 |
| AAGTCGGGTCCCTTGGAGTTCCGAACGGGCTCCCGAGGCTGTTCCA | 120 | 4.04 |
| GGGCTCCCGAGGCTGTTCCAATAAGAC | 121 | 4.04 |
| GTTGATTCCCTTATAGATGTTCGTTTTCCACA | 122 | 4.05 |
| ATGTTCGTTCTCGTTCACTGTTATTCTCTT | 123 | 4.07 |
| CTCGTTCACTGTTATTCTCTT | 124 | 4.07 |
| AAAACTAAAAAAAGAAGAGGTGGTGGTGAAGAAT | 125 | 4.08 |
| GAAAGTCTCAATTGGGGAGTTGCTTTAATGGCTTTT | 126 | 4.12 |
| TCAATCCGAGAATCGAATTTTCCTATACGCTTTTGTT | 127 | 4.21 |
| TTTGTTTTTGCTCCTGTGTCTTGTGGTGATAAAATG | 128 | 4.22 |
| TTTGTTTTTGCTCCTGTGTCTTGTGGTGATAAAATG | 129 | 4.22 |
| GTGATAAAATGTTACAATAAGACTACAAAAG | 130 | 4.22 |
| Locus 5 | | |
| ATTGAAAGGACCATACTCACCAGCAGCGGTGAGCCCTTTGCATTGA | 131 | 5.01 |
| ATTGAAAGGACCATACTCACCAGCAG | 132 | 5.01 |
| GTTCACGTAGTACTTGAGGGCGCTCACGTTACAATAAGACCA | 133 | 5.02 |
| TTTCANGCAGTACTTGAGGGCGCTCATGTTNCANTANGACCAA | 134 | 5.02 |
| AAGAAGGGGAATGGTTCACGTAGCTACTTGAGGGC | 135 | 5.02 |
| CAATAATACAGTCCTAATGCTCGTG | 136 | 5.03 |
| CAATAATACAGTCCTAATGCTCGTG | 137 | 5.03 |
| TTGAAAACGCTAGCAGGACTAGTGCTTGT | 138 | 5.04 |
| CGCTAGCAGGACTAGTGCTTGTG | 139 | 5.04 |

TABLE 3-continued

Cloned psiRNA sequences

| Sequence | SEQ ID NO: | psiRNA |
|---|---|---|
| CTTCTCGAATCTATCGAATTCGGTTACAATAAGACCAAAATAGA | 140 | 5.09 |
| AGCCACATAANACATTGTCATACAAAGTATGACAAAATA | 141 | 5.11 |
| CACATAAGACATTGTCATACAAAGTAGGACAAAA | 142 | 5.11 |
| AAGACATTGTCATACAAAGTAGGACAAA | 143 | 5.11 |
| GTCCTCTTGGAGACCGTTCCTGTTACAATAAGACCA | 144 | 5.12 |
| GTCACGTAATTCGCCAAGTCCNCNT | 145 | 5.12 |
| AATAGTTACAATAAGACCAAAATA | 146 | 5.15 |
| CTAGCTTTTCACACACTCT | 147 | 5.18 |
| TAAACTANGNTGATTTTGTAAT | 148 | 5.20 |
| GAAAGAGTATTCCACCGAGAATTGTGCC | 149 | 5.29 |
| GTATTCCACCGAGAATTGTGCCTTTGTACTGGACTG | 150 | 5.29 |

Locus 6

| | | |
|---|---|---|
| TCTATTTTAGTCTTATTGTAACGTTCCACTAAGGAC | 151 | 6.01 |
| TTTAGTCTTATTGTAACGTTCCACTAAGGAC | 152 | 6.01 |
| AATTTGACGTACAAATGTCCTTAGTGGAAC | 153 | 6.01 |
| TTCGGGACCTGTAGGTCGTTACAATAAGACTAAAATAGA | 154 | 6.02 |
| GTTAATGGTAAAGTTACAATAAGACTAAA | 155 | 6.03 |
| GTTCTGCCGTCCCTTTTCTCGACG | 156 | 6.09 |
| TTCTGCCGTCCCTTTTCTCGACGAACCTCATACCGA | 157 | 6.09 |
| TTCTGCCGTCCCTTTTCTCGACGAAC | 158 | 6.09 |
| TTCTGCCGTCCCTTTTCTCGACGAAC | 159 | 6.09 |
| TATAGGCGGAACTCCCT | 160 | 6.13 |
| AAGTGTTTTCGAATATTGTTACTTCTTGTGT | 161 | 6.15 |
| CTATAAGACTGAAACTTCACACCT | 162 | 6.37 |
| TTAACACTCTTAACCCCAG | 163 | 6.38 |
| GTCCAAAAACGTTACAATAAGACTAAA | 164 | 6.39 |
| TTAAGCTGGGATGGGCTATATACAAAGACAG | 165 | 6.42 |
| AATTCTGGAAGGTTGTAGAAA | 166 | 6.44 |

Locus 7

| | | |
|---|---|---|
| CGCCCACCTTTGTTACGTTCCAATAAGACT | 167 | 7.01 |
| TTGTAGTATGCGGTCCTTGCGGCTGAGAGCACTTCAG | 168 | 7.01 |
| TTGTAGTATGCGGTCCTTGCGGCTGAGAGCA | 169 | 7.01 |
| TTGTAGTATGCGGTCCTTGCGGCTGAGAGCA | 170 | 7.01 |
| GTAGTATGCGGTCCTTGCGGCTGAGAGCA | 171 | 7.01 |
| GAAAGTTGTAGTATGCGGTCCTTGC | 172 | 7.01 |
| GTCTTCGATTAGTGAAAACAGTTCCAATAAGACTACAAAAG | 173 | 7.02 |
| GTCGTTATCTCTTACGAAGTCTTCGATTAGT | 174 | 7.02 |
| GTTACACGTGAGTGCAAGNTCCAATAAGACTACAAAGA | 175 | 7.04 |
| GTTACACGTGAGTGCAAGTTCCAATAAGACTACAAAAGA | 176 | 7.04 |
| GTTACACGTGAGTGCAAGTTCCAATAAGACTACAAAAGA | 177 | 7.04 |
| GTTACACGTGAGTGCAAGTTCCAATAAGACTACAAAAGA | 178 | 7.04 |
| TTTACACGTGAGTGCAAGTTCCAATAAGACTACAAAAGA | 179 | 7.04 |
| TTTACACGTGAGTGCAAGTTCCAATAAGACTACAAAAGA | 180 | 7.04 |
| TTTACACGTGAGTGCAAGTTCCAATAAGACTACAAAAGA | 181 | 7.04 |
| ACAAAAGAATTGAAAGTTAACCTCCTT | 182 | 7.07 |
| AGTTATCTAAGCTCTGCTTAAATGGGAAATCTTATAAG | 183 | 7.14 |

Locus 8

| | | |
|---|---|---|
| GAAGAGGAAGAAATGCAGACGACGTGATAAACTACGTGAA | 184 | 8.02 |
| CAGACGACGTGATAAACTACGTGAAAGTT | 185 | 8.02 |
| AACTTTTCAACGTAGTTTATCACGTCGTCTGA | 186 | 8.02 |
| GTGCACTAAGGCACCATACGCCCAA | 187 | 8.03 |
| ATTGAAGCTTGCCCAACCTCTCTAGAAACGCCCA | 188 | 8.06 |
| AATTGAAGNNAAAATCTCTTTTTAAATCTTTGA | 189 | 8.07 |
| ATTGAAGCGCANATCTNTTTTTAAATCTTTGA | 190 | 8.07 |

Leaders

| | | |
|---|---|---|
| GTAGGAGTATTGGGGCAAAAAAGCCCCCTGTTCCAATAAGAC | 191 | before 2 or 7 |
| GGGGGGAATTGGGGCAAAAAAGCCCCCTGTTCCAATAAGACT | 192 | before 2 or 7 |
| GGGGGAATTGGGGCAAAAAAGCCCCCTGTTCCAATAAGACTAC | 193 | before 2 or 7 |
| GGGGGAATTGGGGCAAAAAAGCCCCCTGTTCCAATAAGACTAC | 194 | before 2 or 7 |
| CCCCCTGTTCCAATAAGACTACAAAAG | 195 | before 2 or 7 |
| CCCCCTGTTCCAATAAGACTACAAAAG | 196 | before 2 or 7 |
| AAGCCCCCTGTTCCAATAAGACTACAAA | 197 | before 2 or 7 |

TABLE 3-continued

Cloned psiRNA sequences

| Sequence | SEQ ID NO: | psiRNA |
|---|---|---|
| GAAAAAGCCCCCTGTTACAATAAGACCAA | 198 | before 5 |
| GAAAAAGCCCCCTGTTACAATAAGACCAAAATAGA | 199 | before 5 |
| TTAGGAGTATTGGGGCGAAAAAGCCCCCTGTTACAATAAGACTA | 200 | before 6 |
| GGGGGAATTAGGGCAAAAAGCCCACTGTTCCAATAAGACT | 201 | before 8 |
| GGGGAATTAGGGCAAAAAGCCCACTGTTCCAATA | 202 | before 8 |

Repeat sequences are indicated in bold.

Our sampling is not apparently at saturation, however, we cloned psiRNAs from the beginning, middle and end of CRISPR loci (FIG. 1), indicating that RNAs are produced from across the length of the loci. Interestingly, however, the likelihood of cloning was significantly higher for psiRNAs encoded within the first part of a CRISPR locus, suggesting a greater abundance in the organism of psiRNAs from these regions. Two-thirds of the psiRNAs that we cloned were from the first third of their CRISPR locus and 45% were one of the first four psiRNAs in a given locus (FIG. 1). With the exception of locus 2, this trend was observed within each individual CRISPR locus.

Comparison of the percentage of psiRNAs cloned from a given locus (Table 4, % of clones) to the percentage of the total psiRNAs encoded by that locus (Table 4, % of psiRNAs) revealed that most of the loci are represented proportionately within the clones. However, locus 6 seems to be significantly underrepresented in the cDNA library. Locus 6 encodes ~22% of the psiRNAs in *P. furiosus*, however only ~12% of the cloned RNAs were derived from this locus. This suggests that the psiRNAs encoded within locus 6 are less abundant in *P. furiosus* than those encoded by the six other CRISPR loci.

TABLE 4

Distribution of cloned psiRNAs.

| CRISPR locus | # of psiRNAs | # of Clones | % of psiRNAs | % of Clones |
|---|---|---|---|---|
| 1 | 51 | 40 | 25% | 30% |
| 2 | 20 | 12 | 10% | 9% |
| 4 | 22 | 20 | 11% | 15% |
| 5 | 30 | 20 | 15% | 15% |
| 6 | 45 | 16 | 22% | 12% |
| 7 | 21 | 17 | 10% | 13% |
| 8 | 11 | 7 | 5% | 5% |
| Total | 200 | 132 | | |

The results of the RNA cloning suggest the presence of novel, small psiRNAs in *P. furiosus*. However, the cloned RNAs were not of a uniform size or composition. To determine whether discrete psiRNA species are present in *P. furiosus*, we undertook additional analysis.

Northern analysis of RNAs derived from the CRISPR loci in *P. furiosus* In order to further investigate the RNAs that arise from the CRISPR loci in *P. furiosus*, we undertook Northern analysis with probes against both repeat and psiRNA sequences. Probes were designed for detection of both sense (transcription from the leader sequence) and antisense RNAs. FIG. 2A shows results obtained with a probe that recognizes the repeat sequence (sense orientation) that is common to *P. furiosus* CRISPR loci 1, 5 and 6. This probe detected a prominent band at ~65 nucleotides, a less prominent band at ~130 nucleotides, and an unresolved set of bands of greater than 150 nucleotides near the top of the gel. For this and all other probes tested, no significant differences in the patterns were observed from total RNA samples prepared with and without DNase treatment indicating that the bands represent RNAs. Consistent with the observations and CRISPR RNA processing pathway proposed by others (Tang et al., 2002, *Proc Natl Acad Sci USA*, 99:7536-7541; Tang et al., 2005, *Mol Microbiol*, 55:469-481; Lillestol et al., 2006, *Archaea*, 2:59-72; Markova et al., 2006, *Biol Direct*, 1:7; Sorek et al., 2008, *Nat Rev Microbiol*, 6:181-186), the set of bands above 150 nucleotides likely represents a mixture of primary transcripts from the 3 loci as well as larger intermediates generated by cleavages within repeat regions. The most prominent band detected with the repeat probe in *P. furiosus* (~65 nucleotides) corresponds well to the primary product of the CRISPR loci reported previously in other organisms (Tang et al., 2002, *Proc Natl Acad Sci USA*, 99:7536-7541; Tang et al., 2005, *Mol Microbiol*, 55:469-481; Lillestol et al., 2006, *Archaea*, 2:59-72), however in this work this RNA is identified as the "1× intermediate" (FIG. 2). This band corresponds in length to a psiRNA (~35-40 nts) and repeat (~30 nts), and likely represents psiRNAs with flanking repeat sequences generated by cleavages within the adjacent repeats (see FIG. 2C). The detection of this RNA by the repeat probe suggests that cleavage may be asymmetric within the repeat sequence, leaving a substantial contiguous region of the 30 nucleotide repeat on one side (e.g. the 3' end as modeled in FIG. 2C) for efficient detection by Northern probes. A less abundant band of ~130 nucleotides corresponds in length to two psiRNAs with flanking repeat sequences and likely represents the immediately upstream 2× intermediates (Tang et al., 2002, *Proc Natl Acad Sci USA*, 99:7536-7541; Tang et al., 2005, *Mol Microbiol*, 55:469-481; Lillestol et al., 2006, *Archaea*, 2:59-72) (FIG. 2C).

Figure 3:
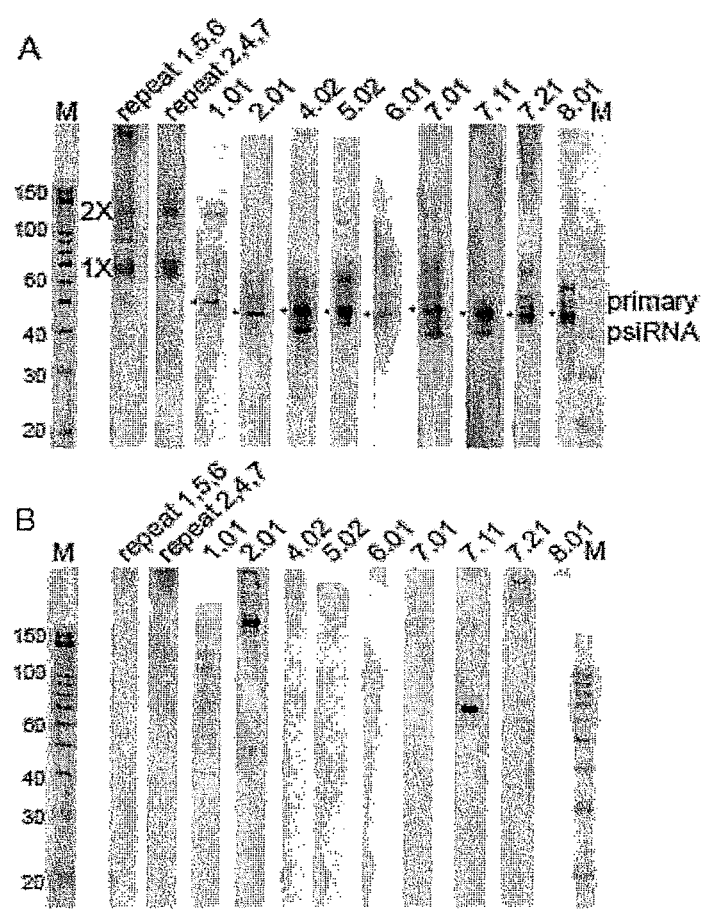
FIG. 3. Northern analysis of RNAs from the seven *P. furiosus* CRISPR loci. A and B) Northern analysis was performed with 10 µg of total RNA using probes to detect sense (A) (transcribed from the leader sequence) or anti-sense (B) psiRNA or repeat sequence-containing RNAs as indicated. Lanes are approximately aligned on the basis of adjacent marker lanes (not shown except for repeat 1, 5, 6 and psiRNA 8.01 lanes). Dots located to the left of lanes indicate the primary psiRNA species. 1× and 2× intermediates detected by repeat probes are indicated.

Northern analysis with a probe against one of the variable psiRNA sequences revealed novel CRISPR RNA species. Using a probe against psiRNA 4.02 (sense orientation), we detected a band at ~60 nucleotides and a very faint signal near the top of the gel, but the most prominent band is ~46 nucleotides (FIG. 2B) and corresponds in size to that of the psiRNA (35 nts in the case of psiRNA 4.02) and ~40 nucleotides of repeat sequence. A significant secondary band was detected at ~39 nucleotides (FIG. 2B). Importantly, similar results were observed in Northern analysis of RNAs from other CRISPR loci. Results for all RNAs analyzed, both sense and antisense, are compiled in FIG. 3. First, like the repeat 1, 5, 6 probe, a probe for the repeat sequence common to loci 2, 4 and 7 (sense orientation) detected prominent diffuse bands of ~65 and ~130 nucleotides (theoretical 1× and 2× processing intermediates, see FIG. 2C). In addition, we probed for psiRNAs from the first part of each CRISPR locus (1.01, 2.01, 4.02, 5.02, 6.01, 7.01 and 8.01) as well as for psiRNA sequences from the middle and end of locus 7 (7.11 and 7.21). Strikingly, probes for each of the psiRNA sequences (sense orientation)

detected a single predominant RNA species (indicated with dots in FIG. 3). Most of these predominant RNAs were ~43 to ~46 nucleotides. The observed size of the major RNA species was generally 5 to 10 nucleotides longer than the encoded psiRNA sequence. The psiRNA with the longest observed primary product (psiRNA 1.01) has an unusually long psiRNA sequence. These findings, together with the observation that these RNAs are recognized by psiRNA but not repeat sequence probes, suggest that the primary psiRNA species in *P. furiosus* consists of a psiRNA with ~5-10 nucleotides of repeat.

In addition to the primary psiRNA species, each of the psiRNA probes detected other RNAs. These often included an RNA close to the size of the ~65 nucleotide 1× intermediates that were detected by repeat probes, and in some cases (e.g. psiRNAs 101 and 402) an RNA was detected that was the size of the theoretical 2× intermediate. Many of the psiRNA probes detected other faint bands. However, in many cases the most prevalent secondary species was a slightly smaller RNA of ~38 to ~45 nucleotides.

We did not detect antisense RNAs with most of the CRISPR probes (FIG. 3B). Prominent bands were detected with probes from psiRNAs 2.01 and 7.11, however the absence of corresponding bands with the repeat probes suggests that these are not CRISPR locus-derived RNAs.

Figure 4:
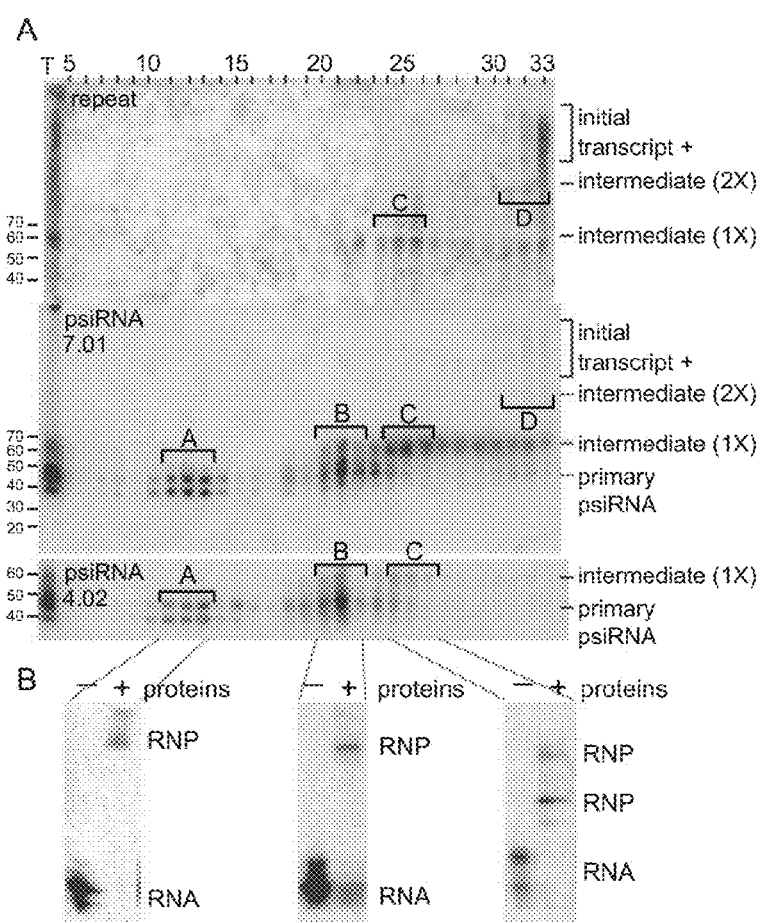
FIG. 4. CRISPR RNA-protein complexes in fractionated *P. furiosus* cell extract. A) *P. furiosus* S100 cell extract was separated by DEAE anion exchange chromatography and CRISPR RNAs present in the fractions were examined by Northern analysis using probes against repeat 1, 5, 6, and psiRNAs 7.01 and 4.02 as indicated. Unfractionated extract (T) was co-analyzed for reference. Positions of 1× intermediate, 2× intermediate and primary psiRNA, peaks A-D (see Example 1), and markers are indicated. B) Fractions corresponding to peaks A (left), B (center) and C (right) were analyzed by non-denaturing gel electrophoresis and Northern blotting using a probe against psiRNA 7.01. For comparison, proteins were extracted from a portion of each sample and analysis of the RNAs with (+) and without (−) proteins is shown. The positions of the RNAs (−proteins) and potential RNPs (+proteins) on the native gel are indicated.

Northern analysis of CRISPR RNA distribution in fractionated *P. furiosus* extract The CRISPR RNAs are hypothesized to function in complex with proteins in various aspects of RNA-guided genome defense in prokaryotes (Markova et al., 2006, *Biol Direct*, 1:7). To assess whether the CRISPR-derived RNA species that we identified may be components of distinct complexes, we analyzed the distribution of the RNAs across fractions from anion exchange chromatography of *P. furiosus* S100 cell extract performed under anaerobic conditions. Fractions were evaluated by Northern analysis using probes against the repeat sequence common to loci 1, 5 and 6, and psiRNA 4.02 and 7.01 sequences (FIG. 4). For reference, the profile of RNAs detected in unfractionated extract is shown in the first lane.

The distribution of the various RNAs across the fractions suggests the presence of several distinct CRISPR RNA-containing complexes. The novel primary and secondary psiRNAs (~45 and ~39 nts) from both loci co-fractionated in a distinct set of fractions denoted as peak A (FIG. 4, fractions 10-14). Other larger CRISPR RNA species were not observed in peak A. The primary psiRNA is also present in peak B (fractions 20-23) along with a fraction of the 1× intermediate RNA and some of the variable-size psiRNA species. However, the highest concentration of the 1× intermediate is found in a distinct set of fractions that lack small psiRNAs, termed peak C (fractions 23-26). The mixture of RNAs that likely includes full CRISPR locus transcripts and larger intermediates, and the 2× intermediate are found primarily in peak D (fractions 31-34). These results suggest the presence of multiple complexes each containing distinct subsets of CRISPR-derived RNAs in *P. furiosus*.

To verify the presence of CRISPR RNA-protein complexes in the fractionated *P. furiosus* extract, we examined the complexes on native gels. Using the probe for psiRNA 7.01, we compared the mobility of the RNAs, both in the presence of the co-fractionating proteins in peaks A, B and C and following protein extraction, by non-denaturing PAGE and Northern analysis. In each case, a significant shift in the mobility of the RNAs was observed in the presence of the proteins. Peak D was not examined on native gels. Together our results indicate that the novel primary psiRNA is a component of at least 2 distinct RNA-protein complexes (peaks A and B), the 1× intermediate is found primarily in a third complex (peak C), and a fourth complex includes larger psiRNA precursors. These complexes are likely candidates for the mediators of psiRNA production, invader destruction and CRISPR element integration in the proposed prokaryotic RNAi pathway.

Discussion

Novel CRISPR RNAs. The CRISPR loci found in many prokaryotes encode alternating repeat and "spacer" or psiRNA sequences, and have been shown to give rise to a series of RNAs that decrease in increments from the full-length locus transcript to a single psiRNA and repeat (i.e. 1× intermediate, see FIG. 2C) (Tang et al., 2002, *Proc Natl Acad Sci USA*, 99:7536-7541; Tang et al., 2005, *Mol Microbiol*, 55:469-481; Lillestol et al., 2006, *Archaea*, 2:59-72). Current evidence indicates that processing occurs by endonucleolytic cleavages within the repeat sequences (Tang et al., 2002, *Proc Natl Acad Sci USA*, 99:7536-7541; Tang et al., 2005, *Mol Microbiol*, 55:469-481). The RNA products of the CRISPR loci are hypothesized to guide silencing of viruses and other genome invaders. In this work, we have identified a novel class of smaller discrete CRISPR-derived RNAs that we have termed psiRNAs, which appear to be the ultimate gene products of the CRISPR loci (FIG. 2C).

The primary psiRNA species that we have identified is the most abundant CRISPR-derived RNA detected in *P. furiosus*. The primary psiRNAs are approximately 5 to 10 nucleotides longer than the corresponding psiRNA sequence (i.e. approximately 45 nucleotides long). These RNAs are shorter than the smallest discrete CRISPR RNA products previously reported (i.e. the ~60-65 nt 1× intermediate species) (Tang et al., 2002, *Proc Natl Acad Sci USA*, 99:7536-7541; Tang et al., 2005, *Mol Microbiol*, 55:469-481; Lillestol et al., 2006, *Archaea*, 2:59-72), and are presumably generated by exonucleolytic processing of the 1× intermediate. Our Northern and sequence analysis indicates that these RNAs are comprised primarily of psiRNA sequence and do not contain substantial repeat sequence. A secondary psiRNA of about 39 nucleotides was also consistently observed among psiRNA profiles.

CRISPR RNA-protein complexes. The common primary and secondary psiRNA species are likely candidates for the guide RNA component of the effector complex in the proposed pRNAi genome defense pathway. Both of these psiRNA species, but not larger intermediate CRISPR RNAs, are found in RNA-protein complexes in anion exchange chromatography peak A (FIGS. 4 A and B), thus peak A could contain the effector complex. The primary psiRNA is even more abundant in peak B, which contains relatively less of the secondary psiRNA but also contains some 1× intermediate RNA (FIG. 4). Peak B may also contain the effector complex and/or a complex involved in the exonucleolytic processing of the 1× intermediate to psiRNAs. The 1× intermediate RNA is most abundant in peak C, which is adjacent to peak B and processing may occur across peak B and C fractions. Longer CRISPR RNAs are found in peak D. Our results indicate that the various RNA species are components of distinct RNA-protein complexes in *P. furiosus*. Extensive purification and analysis will determine whether these hypothesized activities and the Cas proteins predicted to function in CRISPR RNA biogenesis and invader silencing (e.g. RNA binding proteins and nucleases) are present in these complexes.

psiRNA expression. The psiRNAs are hypothesized to act in a manner similar to the antibodies of the human immune system and expression would be expected even in the absence of active infection to patrol for returning invaders. Our results indicate that psiRNAs are actively produced from all 7 CRISPR loci in *P. furiosus*. Moreover, expression levels appear to be equivalent between the loci under the growth conditions examined with the possible exception of one locus that yielded 50% fewer psiRNA clones than expected (see locus 6, Table 4). Our results confirm that CRISPR RNAs are transcribed from the leader sequence in *P. furiosus* and indicate that a portion of the leader sequence is also transcribed.

Interestingly, we found evidence of significantly higher levels of expression of psiRNAs encoded proximal to the leader of a CRISPR locus. Current data indicate that these are the most recently acquired psiRNA sequences within CRISPR loci (Pourcel et al., 2005, *Microbiology*, 151:653-663; Barrangou et al., 2007, *Science* 315:1709-1712). Increased levels of these psiRNAs may be important for targeting current invaders. Distal psiRNAs may be produced at lower levels to provide surveillance for past invaders. It is not clear whether the increased level of leaderproximal psiRNAs results from differences in RNA transcription (e.g. partial transcription of the loci), processing, stability or other factors. This is an important new aspect of understanding the regulation of psiRNA expression that remains to be explored.

Example 2

Compelling evidence indicates that the CRISPR-Cas system protects prokaryotes from viruses and other potential genome invaders. The system arises from clustered regularly interspaced short palindromic repeats (CRISPRs) that harbor short invader-derived sequences, and CRISPR-associated (Cas) protein-coding genes. Here we have identified an apparent CRISPR-Cas effector complex that employs small CRISPR RNAs (termed prokaryotic silencing or psiRNAs) to recognize and destroy corresponding target RNAs. The complex consists of psiRNAs and a subset of Cas proteins termed the RAMP module (or Cmr) proteins. The psiRNA-Cmr protein complexes cleave complementary target RNAs at a fixed distance from the 3' end of the integral psiRNAs. In *Pyrococcus furiosus*, psiRNAs occur in two size forms that share a common 5' sequence tag but have distinct 3' ends that direct cleavage of a given target RNA at two distinct sites. Our results indicate that prokaryotes possess a unique RNA silencing system that functions by homology-dependent cleavage of invader RNAs recognized by the psiRNAs.

Experimental Procedures

Chromatography: *P. furiosus* S100 extract was prepared from approximately 4 grams of cells. Cells were resuspended in 20 mL of 50 mM Tris (pH 7.0), 100 U RNase-free DNase (Promega), and 0.5 mM phenylmethanesulphonyl fluoride (PMSF) at room temperature by stirring. The resulting whole cell extract was subject to ultracentrifugation at 100,000×g for 1.5 hours using an SW 41 Ti rotor (Beckman). The resulting S100 extract was loaded onto a 5 mL Q-sepharose Fast Flow (GE) pre-packed column. Proteins were eluted using a 0-1 M NaCl gradient. Fractions were analyzed by Northern analysis by isolating RNA from 100 ul of each fraction using Trizol LS (Invitrogen, following manufacturer's instructions). The RNAs were separated on 15% TBE-urea gels (Criterion, Bio-Rad), blotted and analyzed for the presence of a single guide sequence as described previously (Hale et al., 2008, *RNA*, 14:2572-2579). Peak fractions containing the psiRNA doublet were further separated on a second 5 mL Q-sepharose column, eluted with 220-430 mM NaCl. Fractions were analyzed as described above. Peak fractions were pooled, diluted in 50 mM sodium phosphate buffer, pH 7.0, and loaded onto a 5 mL S sepharose column (GE). Bound proteins were eluted with a gradient of 0-1 M NaCl. Native gel northern analysis was performed as described previously (Hale et al., 2008, *RNA*, 14:2572-2579). The secondary data shown in Table 5 was obtained from S100 extract fractionated on a DEAE column as previously described (Hale et al., 2008, *RNA*, 14:2572-2579) followed by a hydroxyapatite column eluted with a gradient of 5-500 mM sodium phosphate buffer, pH 6.5, and further purified by native gel electrophoresis.

TABLE 5

Proteins identified by tandem mass spectrometry of native RNA-protein complexes. All proteins that were identified in the S-native sample (FIG. 5), and in a native band from a separate chromatography scheme, HA-native. Numbers represent the % coverage, with the number of unique peptides in parentheses.

|  | Protein | S-native | HA-native | Annotated Function |
| --- | --- | --- | --- | --- |
| CAS Proteins | PF1129 | 56.0 (54) | 26.9 (20) | hypothetical protein PF1129 |
|  | PF1128 | 40.4 (13) | 20.5 (5) | hypothetical protein PF1128 |
|  | PF1126 | 58.3 (14) | 17.6 (3) | hypothetical protein PF1126 |
|  | PF1124 | 16.2 (5) | 11.8 (4) | hypothetical protein PF1124 |
|  | PF0352 | 28.1 (5) |  | hypothetical protein PF0352 |
|  | PF1125 | 24.9 (5) |  | hypothetical protein PF1125 |
|  | PF1130 | 3.6 (1) |  | hypothetical protein PF1130 |
| Non-Cas proteins | PF1717 | 76.2 (28) |  | translation initiation factor IF-2 gamma subunit |
|  | PF1683 | 73.6 (19) |  | N-acetyl-gamma-glutamyl-phosphate reductase |
|  | PF0990 | 60.6 (26) |  | phenylalanyl-tRNA synthetase beta subunit |
|  | PF1685 | 59.0 (20) |  | acetylornithine/acetyl-lysine aminotransferase |
|  | PF0481 | 55.7 (7) |  | translation initiation factor IF-2 beta subunit |
|  | PF1827 | 53.8 (14) | 20.8 (4) | hypothetical protein PF1827 |
|  | PF1881 | 51.6 (4) |  | chromatin protein |
|  | PF0989 | 45.1 (22) |  | phenylalanyl-tRNA synthetase alpha subunit |
|  | PF0124 | 34.3 (14) |  | hypothetical protein PF0124 |
|  | PF1140 | 30.2 (7) |  | translation initiation factor IF-2 alpha subunit |
|  | PF0495 | 29.7 (34) |  | reverse gyrase |
|  | PF1204 | 29.2 (11) |  | seryl-tRNA synthetase |
|  | PF1264 | 26.1 (3) |  | translation initiation factor IF-5A |
|  | PF0351 | 25.6 (8) |  | hypothetical protein PF0351 |
|  | PF1238 | 23.9 (14) |  | putative ABC transporter |
|  | PF1615 | 23.1 (18) |  | hypothetical protein PF1615 |
|  | PF0496 | 21.2 (5) |  | hypothetical protein PF0496 |
|  | PF0594 | 18.4 (4) | 14.3 (2) | ornithine carbamoyltransferase |

TABLE 5-continued

Proteins identified by tandem mass spectrometry of native RNA-protein complexes.
All proteins that were identified in the S-native sample (FIG. 5), and in a native band
from a separate chromatography scheme, HA-native. Numbers represent the % coverage,
with the number of unique peptides in parentheses.

| Protein | S-native | HA-native | Annotated Function |
| --- | --- | --- | --- |
| PF1405 | 16.6 (10) | 12.9 (7) | cleavage and polyadenylation specifity factor protein |
| PF0547 | 15.8 (5) | | hypothetical protein PF0547 |
| PF0969 | 14.7 (4) | | 2-ketovalerate ferredoxin oxidoreductase subunit alpha |
| PF0220 | 14.1 (6) | 13.6 (7) | hexulose-6-phosphate synthase |
| PF1375 | 13.3 (6) | | elongation factor Tu |
| PF1976 | 12.1 (6) | | L-aspartate oxidase |
| PF0666 | 11.5 (6) | | nol1-nop2-sun family putative nucleolar protein IV |
| PF1746 | 11.0 (6) | | hypothetical protein PF1746 |
| PF0251 | 11.0 (4) | | hypothetical protein PF0251 |
| PF1579 | 10.4 (7) | | DNA topoisomerase VI subunit B |
| PF0966 | 10.4 (4) | | 2-oxoglutarate ferredoxin oxidoreductase |
| PF0533 | 10.1 (7) | | indolepyruvate ferredoxin oxidoreductase subunit a |
| PF1578 | 9.2 (3) | | DNA topoisomerase VI subunit A |
| PF0026 | 8.8 (4) | | tRNA nucleotidyltransferase |
| PF1540 | 8.7 (5) | | ADP forming acetyl coenzyme A synthetase |
| PF1203 | 8.1 (5) | | formaldehyde:ferredoxin oxidoreductase |
| PF1046 | 7.9 (3) | | queuine trna-ribosyltransferase |
| PF0464 | 7.5 (4) | | glyceraldehyde-3-phosphate:ferredoxin oxidoreductase |
| PF1768 | 5.1 (2) | | 2-oxoglutarate ferredoxin oxidoreductase |
| PF0440 | 3.9 (5) | | ribonucleotide-diphosphate reductase alpha subunit |
| PF1843 | 1.7 (2) | 7.3 (6) | chromosome segregation protein smc |
| PF0102 | | 76.6 (15) | hypothetical protein PF0102 |
| PF1883 | | 74.9 (13) | small heat shock protein |
| PF1548 | | 63.3 (24) | hypothetical protein PF1548 |
| PF1931 | | 27.9 (6) | hypothetical protein PF1931 |
| PF0162 | | 11.2 (2) | hypothetical protein PF0162 |
| PF0204 | | 6.0 (2) | hypothetical protein PF0204 |
| PF1871 | | 3.7 (1) | "N(2),N(2)-dimethylguanosine tRNA methyltransferase" |
| PF1245 | | 2.2 (1) | hypothetical d-nopaline dehydrogenase |
| PF1167 | | 1.5 (1) | chromosome segregation protein |

Protein assignment by tandem mass spectrometry: In-gel and in-solution tryptic digests were performed as previously described (Lim et al., 2008, *J Proteome Res*, 7:1251-1263; Wells et al., 2002, *Mol Cell Proteomics*, 1:791-804). Desalted tryptic peptides were analyzed by nLC-MS/MS on a linear ion-trap (LTQ, ThermoFisher) as previously described (Lim et al., 2008, *J Proteome Res*, 7:1251-1263). Acquired data was searched against a *P. furiosus*-specific database (forward and inverted) using the TurboSEQUEST algorithm (ThermoFisher). Data was collated and filtered to obtain a 1% false discovery rate at the protein level using the ProteoIQsoftware package (BioInquire) that is based on the PROVALT algorithm (Weatherly et al., 2005, *Mol Cell Proteomics*, 4:762-772).

Cloning and sequencing of psiRNAs from the purified complexes: RNAs from S-column fractions (isolated as described above for Northern analysis) were treated with 1 U calf intestinal alkaline phosphatase (Promega) for 1 hour at 37° C., followed by extraction with phenol:chloroform:isoamyl alcohol (PCI; pH 5.2, Fisher) and ethanol precipitation. The resulting RNAs were separated by 15% polyacrylamide, TBEureagels (Criterion, Bio-Rad), visualized by SYBR Gold staining (Invitrogen) and the visible bands were excised. RNAs were passively eluted overnight in 0.5 M ammonium acetate, 0.1% SDS, 0.5 mM EDTA, followed by ethanol precipitation. A 5'-phosphorylated, 3' capped oligonucleotide (5'-pCTCGAGATCTGGATCCGGG-ddC3'; IDT (SEQ ID NO:26) was ligated with T4 RNA ligase to the 3' end of the RNAs. The ligated RNAs were PCI extracted, ethanol precipitated, gel purified, and subject to reverse transcription using Superscript III (Invitrogen) RT (as described by the manufacturer), followed by gel purification. The gel-purified cDNAs were polyA-tailed for 15 minutes at 37° C. using terminal deoxynucleotide transferase (Roche) using manufacturer's recommendations. PCR was performed to amplify the cDNA libraries using the following primers: 5'-CCCG-GATCCAGATCTCGAG-3' (SEQ ID NO:27), 5'-GCGAAT-TCTGCAG(T)30-3' (SEQ ID NO:28)). cDNAs were cloned into the TOPO pCRII (Invitrogen) cloning vector and transformed into TOP10 cells. White and light-blue colonies were chosen for plasmid DNA preparation, and sequencing using the M13 Reverse and T7 promoter sequencing primers was performed by the University of Georgia Sequencing and Synthesis Facility.

Small RNA deep sequencing: Small RNA libraries were prepared using the Illumina small RNA Sample preparation kit as described by the manufacturer (Illumina). Briefly, total RNA was isolated from *P. furiosus* and fractionated on a 15% polyacrylamide/urea gel, and small RNAs 18-65 nt in length were excised from the gel. 5' and 3' adapters were sequentially ligated to the small RNAs and the ligation products were gel-purified between each step. The RNAs were then reverse-transcribed and PCR-amplified for 16 cycles. The library was purified with a Qiagen QuickPrep column and quantitated using an Agilent Bioanalyzer and a nanodrop. The sample was diluted to a concentration of 2 pM and subjected to 42 cycles of sequencing on the Illumina Genome Analyzer II.

Small RNA Analysis: Sequence data was extracted from the images generated by the Illumina GenomeAnalyzer II using the software applications Firecrest and Bustard. The adapter sequences were then trimmed from the small RNA reads, which were then mapped to the *P. furiosus* genome using btbatchblast. Only reads that mapped perfectly to the genome over their entire length were used for further analysis. The location and number of reads that initiate within the CRISPR repeats were determined using a perlscript. As the maximal read length of the sequences was 42 nt, it was not possible to be certain that the 3' end of a read represented the actual 3' end of the small RNA. Therefore, the deep sequencing data was only used to determine the most frequent 5' ends and the number of reads that map to each psiRNA.

Nuclease assays: To detect target RNA cleavage, 2 μL of the peak S-column fractions (FIG. 5C) or 500 nM each of recombinant proteins was incubated with 0.05 pmoles of 32P-5' end-labeled synthetic target RNAs (FIGS. 3, 4 and 5) and 0.5 pmoles of each unlabeled psiRNA (FIG. 9) for 1 hour at 70° C. in 20 mM HEPES pH 7.0, 250 mM KCl, 1.5 mM MgCl2, 1 mM ATP, 10 mM DTT, in the presence of 1 unit of SUPERase-In ribonuclease inhibitor (Applied Biosystems). For assay with recombinant proteins, the psiRNAs were first incubated with the proteins for 30 minutes at 70° C. prior to the addition of target RNA. Reaction products were isolated by treatment with 800 ng of proteinase K for 30 minutes at room temperature, followed by PCI extraction and ethanol precipitation. The resulting RNAs were separated by 15% polyacrylamide, TBE 7M urea gels and visualized by phosphorimaging. 5' end-labeled RNA size standards (Decade Markers, Applied Biosystems) were used to determine the sizes of the observed products. Annealed RNAs were prepared by mixing equimolar amounts of RNAs in 30 mMHEPES pH 7.4, 100 mM potassium acetate, 2 mM magnesium acetate and incubating for 1 minute at 95° C., followed by 1 hour at 37° C. Annealing was confirmed by non-denaturing 8% PAGE.

Expression and purification of recombinant proteins: The genes encoding *P. furiosus* Cmr1-1 (PF1130), Cmr2 (PF1129), Cmr3 (PF1128), Cmr4 (PF1126), Cmr5 (PF1125) and Cmr6 (PF1124) were amplified by PCR from genomic DNA or existing constructs and cloned into a modified version of pET24d(PF1124, PF1125 and PF1126) or pET200D (PF1128, PF1129 and PF1130). The recombinant proteins were expressed in *E. coli* BL21-RIPL cells (DE3, Stratagene). The cells (400 mL cultures) were grown to a OD600 of 0.7, and expression of the proteins was induced with 1 mM isopropyl-"-D-thiogalactopyranoside (IPTG) overnight at room temperature. The cells were pelleted, resuspended in 20 mM sodium phosphate buffer (pH 7.6), 500 mM NaCl and 0.1 mM phenylmethylsulfonyl fluoride (PMSF), and disrupted by sonication. The sonicated sample was centrifuged at 4,500 rpm for 15 min at 4° C. The supernatant was heated at 75-78° C. for 20 min, centrifuged at 4,500 rpm for 20 min at 4° C., and filtered (0.8 μm pore size Millex filter unit, Millipore). The recombinant histidine-tagged proteins were purified by batch purification using 50 μlNi-NTA agarose beads (Qiagen) equilibrated with resuspension buffer. Following 3 washes (resuspension buffer), the bound proteins were eluted with resuspension buffer containing 500 mM imidazole. The protein samples were dialyzed at room temperature against 40 mM HEPES (pH 7.0) and 500 mM KCl prior to performing activity assays.

Synthetic psiRNAs The 45- and 39-nucleotide psiRNAs were chemically synthesized (Integrated DNATechnologies). The sequence of the 45-nucleotide psiRNA 7.01 is:AT-TGAAAGTTGTAGTATGCGGTCCTTGCG-GCTGAGAGCACTTCAG (SEQ ID NO:29). The sequence of the 39-nucleotide psiRNA 7.01 is:

(SEQ ID NO: 30)
ATTGAAAGTTGTAGTATGCGGTCCTTGCGGCTGAGAGCA.

Results

Figure 5:
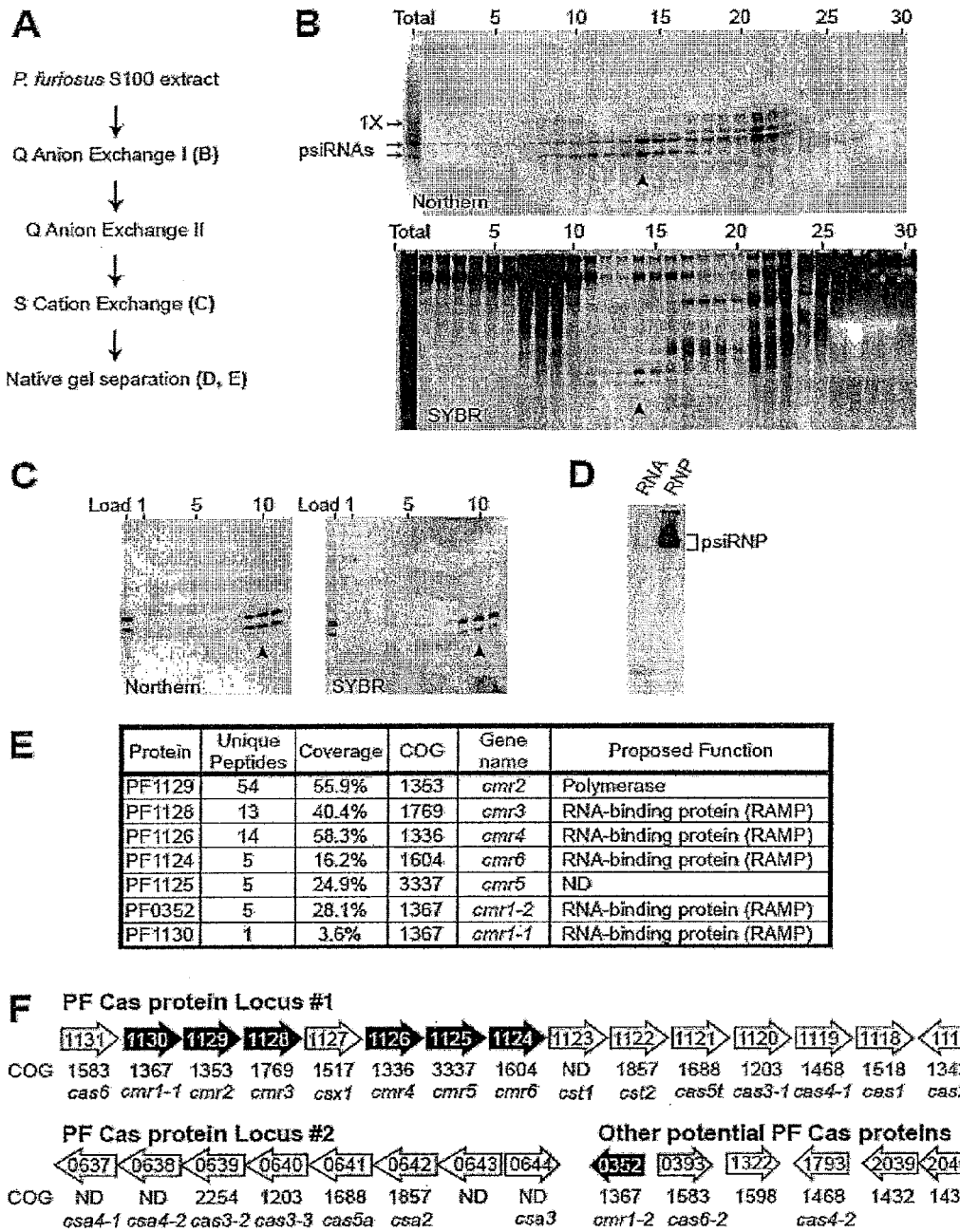
FIG. 5. Identification of a ribonucleoprotein complex containing psiRNAs and Cas proteins. A) psiRNP purification scheme. Letters indicate the location of corresponding data within the Figure. B) psiRNA (top panel) and total RNA (bottom panel) profiles across the initial Q-sepharose anion exchange fractions and an unfractionated sample (total). Northern analysis (top panel) was performed for *P. furiosus* psiRNA 7.01. The positions of the mature psiRNAs and 1× intermediate RNA (Hale et al., 2008, RNA 14, 2572-2579) are indicated. The lower panel shows all RNAs detected by SYBR Gold staining. The peak fraction is indicated by an arrow in each panel. C) psiRNA (Northern analysis of psiRNA 7.01, left panel) and total RNA (SYBR staining, right panel) profiles across the S-sepharose cation exchange fractions and starting material (load). The peak fraction is indicated by an arrow in each panel. D) Native gel Northern analysis of the psiRNP. The peak S-sepharose fraction (arrow, C) was fractionated by native gel electrophoresis and analyzed by Northern blotting for psiRNA 7.01. RNA extracted from the same fraction was co-analyzed. The position of the psiRNP is indicated. E) Cas proteins identified by tandem mass spectrometry. The isolated psiRNP (D) was subject to in-gel trypsin digestion and tandem mass spectrometry. Sequence coverage and the number of unique peptides for Cas proteins identified with 99% confidence are shown. *P. furiosus* cas gene names are as given (Haft et al., 2005, *PLoS Comput Biol*, 1:e60), and proposed functions are as predicted (Haft et al., 2005, *PLoS Comput Biol*, 1:e60; Makarova et al., 2006, *Biol. Direct* 1:7). F) Genome organization of predicted *P. furiosus* cas genes. Operon organization and COG assignments were adapted from NCBI database. Core cas genes (cas) and Cas module-RAMP (cmr), Cas subtype Apern (csa) and Cas subtype Tneap (cst) genes are indicated. Proteins identified by mass spectrometry are indicated in black.

Isolation of a complex containing mature psiRNAs and a subset of Cas proteins. PsiRNAs are hypothesized to guide Cas proteins to effect invader silencing in prokaryotes (Brouns et al., 2008, *Science*, 321:960-964; Hale et al., 2008, *RNA*, 14:2572-2579; Makarova et al., 2006, *Biol Direct*, 1:7). *P. furiosus* is a hyperthermophilic archaeon whose genome encodes 200 potential psiRNAs (organized in seven CRISPR loci) and at least 29 potential Cas proteins (largely found in 2 gene clusters), including 5 core Cas proteins and 3 sets of additional Cas proteins: the Cmr, Cst and Csa proteins (see FIG. 5F). In *P. furiosus*, most psiRNAs are processed into 2 species of ~45 nucleotides and ~39 nucleotides (Hale et al., 2008, *RNA*, 14:2572-2579). To gain insight into the functional components of the CRISPR-Cas invader defense pathway, we isolated complexes containing both of the mature psiRNA species from *P. furiosus* cellular extract through a series of steps of non-denaturing chromatography on the basis of psiRNA fractionation profiles (FIG. 5). The doublet of psiRNAs, detectable both by Northern blotting of an individual psiRNA and total RNA staining (SYBR), was purified away from larger CRISPR-derived RNAs (including the 1× intermediate; Hale et al., 2008, *RNA*, 14:2572-2579) as well as other cellular RNAs (FIG. 5C). To determine whether the psiRNAs are components of RNA-protein complexes in the purified fraction (FIG. 5C), we performed native gel northern analysis. The mobility of the psiRNAs on native gel electrophoresis was reduced in the purified fraction relative to a sample from which proteins were extracted (FIG. 5D), indicating the presence of psiRNA-protein complexes in the purified fraction.

To determine whether Cas proteins may be components of the psiRNP identified by native northern analysis (FIG. 5D), we gel purified the psiRNA-containing complex from the native gel and analyzed the sample by mass spectrometry. The sample contained a mixture of proteins that included seven Cas proteins identified with 99% confidence: Cmr1-1, Cmr1-2, Cmr2, Cmr3, Cmr4, Cmr5, and Cmr6 (FIG. 5E).

The identities of the non-Cas proteins found in the sample are listed in Table 5. Analysis of a native gel-purified psiRNP obtained by an alternate chromatography scheme revealed a similar Cas protein profile (Cmr2, Cmr3, Cmr4, and Cmr6), but few common non-Cas proteins (Table 5). The five common co-purifying non-Cas proteins are denoted in Supplemental Table 5. None of these proteins has any known link to the CRISPR-Cas system.

Remarkably, the seven Cas proteins associated with the complex are all encoded by the tightly linked cmr genes (Haft et al., 2005, *PLoS Comput Biol*, 1:e60). Moreover, the identified proteins comprise the complete set of Cmr proteins (Haft et al., 2005, *PLoS Comput Biol*, 1:e60). (The independently defined "polymerase cassette" is closely related to the RAMP module (Makarova et al., 2006, *Biol Direct*, 1:7).) There are 6 cmr genes: cmr2 encodes a predicted polymerase with HD nuclease domains, and cmr1, cmr3, cmr4, and cmr6 encode repeat-associated mysterious proteins (RAMPs)

(Haft et al., 2005, *PLoS Comput Biol*, 1:e60; Makarova et al., 2002, *Nucleic Acids Res*, 30:482-496). The *P. furiosus* genome contains two cmr1 genes and a single representative of each cmr2-cmr6, and all seven corresponding proteins were found in the purified psiRNP complex (FIG. 5E). The organization of the genes encoding the seven identified proteins is shown in FIG. 5F. Six of the seven identified Cas proteins are encoded in a nearly contiguous region of one of the two major cas gene loci in *P. furiosus*. This locus is located directly adjacent to CRISPR locus 7, and also encodes core Cas proteins Cas1-Cas4 as well as Cas6. The striking correlation between the evolutionary co-segregation and physical association of the 6 Cmr proteins strongly supports the co-function of the proteins. Our findings indicate that the two mature psiRNA species are components of complexes containing the RAMP module or Cmr proteins in *P. furiosus*.

psiRNAs possess a 5′ psiRNA-tag sequence. In order to better understand the nature of the two psiRNA species that are components of the purified complexes, each of the two RNA bands present in the final chromatography sample (FIG. 6A) was extracted and cloned. We obtained sequences of 53 RNAs (20 from the upper band and 31 from the lower band) that included psiRNAs from all seven *P. furiosus* CRISPR loci (Table 6). Six RNAs with the same guide sequence were represented in both the upper and lower bands, consistent with Northern analysis that has shown that most psiRNAs exist in both size forms (Hale et al., 2008).

TABLE 6

Cloned psiRNAs. Sequences for all of the clones obtained from both the upper and lower band of the S-column material (See FIG. 7). The length and the origin of each psiRNA is shown. For the sequences, repeat sequence is shown in bold, and the sequences are aligned by the repeat sequences.

| psiRNA sequence | length | psiRNA | SEQ ID NO. |
|---|---|---|---|
| *Upper Band* | | | |
| ATTGAAAGTTAGCAAATTGCCGATTATTGCACATAAAAAAAATAG | 45 | 1.14 | 203 |
| ATTGAAAGTTAGCAAATTGCCGATTATTGCACATAAAAAAAATAG | 45 | 1.14 | 204 |
| ATTGAAAGACTGGATTGAGAGCAACTTGTCGAATTATGTCGTCAA | 45 | 1.40 | 205 |
| AATTGAAAGTGTTCATCAGCACTTCTTCTTCTGACTCTGCTCC | 43 | 2.01 | 206 |
| AATTGAAAGTGTTCATCGCACTTCTTCTTCTGACTCTGCTCC | 42 | 2.01 | 207 |
| ATTGAAAGCTAATTTACGCTTTAGCTCGTGATCAACCCTAATC | 43 | 2.19 | 208 |
| ATTGAAAGCTAATTTACGCTTTAGCTCGTGATCAACCC | 38 | 2.19 | 209 |
| ATTGAAAGTTGAGTTGAAGCGCCACTCTTTGAAGCCTATCAGAGT | 45 | 4.02 | 210 |
| ATTGAAAGGCTTCAGGTCTTCAATATTCAATCCCGGTCCCTTTCA | 45 | 4.03 | 211 |
| ATTGAAAGGCTTCAGGTCTTCAATATTCAATCCCGGTCCCTTTCA | 45 | 4.03 | 212 |
| GAAAGTCTCTACCCTTACAAGCTTCTCGAATCTATCGAATTC | 42 | 5.09 | 213 |
| GAAAGGTCACGTAATTCGCCAAGTTCTCTTGGATACCGTTC | 41 | 5.12 | 214 |
| ATTGAAAGGTGGATAATATAATCCCTGTTTTCCCAAGA | 39 | 5.13 | 215 |
| ATTGAAAGTGGAACTCTATCAAGGTTTGCAACACCTTGCTCCCGC | 45 | 5.24 | 216 |
| GAAAGGACAAAGAACTCCCTAGCGTCCCTCCCCGTGTA | 38 | 6.07 | 217 |
| ATTGAAAGTGGGGTCTCGTCGCAATCGGTGCAGTATTCCTAAGCC | 45 | 6.26 | 218 |
| ATTGAAAGATCTCCATCATACCAATGCTGTGCAAAATCAATCTTG | 45 | 6.40 | 219 |
| ATTGAAAGTAAACTTAAGCTGGGATGGGCTATATACAAAGACAGA | 45 | 6.42 | 220 |
| AATTGAAAGTCAAGAGTTCTATCCTGCTTCACAACACCCATATAA | 46 | 7.11 | 221 |
| ATTGAAAGGCGTTAATGAACAATAAGCCTGACACGAACATAAA | 43 | 1.06, 2.02 | 222 |
| *Bottom Band* | | | |
| ATTGAAAGCCGGTTCTGCACCCGAAACTTTCATACCAAA | 39 | 1.03 | 223 |
| AATTGAAAGCCGGTTCTGCACCCGAAACTTTCATACCAA | 39 | 1.03 | 224 |
| ATTGAAAGGTAGTGAGGCGTTGAACTTGACCCACCACCA | 39 | 1.08 | 225 |
| ATTGAAAGTGAGTTGTTTAGTCTAACTCTTACACCATC | 38 | 1.19 | 226 |
| ATTGAAAGTGCGCTATTCTCGGGTCAAGCCTCCCAGCCT | 39 | 1.22 | 227 |
| GAAAGCACCACCACGATGAAGGTACCGTTTTCAAC | 35 | 1.37 | 228 |
| GAAAGCACCACCACGATGAAGGTACCGTTTTCAAC | 35 | 1.37 | 229 |
| ATTGAAAGTGTTCATCGCACTTCTTCTTCTGAC | 33 | 2.01 | 230 |
| ATTGAAAGCTTCTTCGAAGTCGTAGTTTAGTGTGTCAAG | 39 | 2.05 | 231 |
| ATTGAAAGTTCTAGAAGTTCTCTTGCGAGAGCCAGGAGC | 39 | 2.06 | 232 |
| GAAAGCTAATTTATGCTTTAGCTCGTGATCAACCCTA | 37 | 2.19 | 233 |
| GAAAGCTAATTTACGCTTTAGCTCGTGATCAACC | 34 | 2.19 | 234 |
| AGGAATGTTGCTCAATGCAAAGGGCTCACCGCT | 33 | 4.01 | 235 |
| AAAGTCTCAATTGGGGAGTGCTTTAATGGCTTTT | 34 | 4.12 | 236 |
| ATTGAAAGGGAACTCCTCGATTTTAGTACCTGTGTC | 36 | 5.05 | 237 |
| ATTGAAAGCCACATAAGACATTGTCATACAAAGTAGG | 37 | 5.11 | 238 |
| ATTGAAAGGTCACGTAATTCGCCAAGTCCTCTTGGAGA | 38 | 5.12 | 239 |
| ATTGAAAGGTGGATAATATAATCCCTGTTTTCCCAAGA | 39 | 5.13 | 240 |
| ATTGAAAGGTGGATAATATAATCCCTGTTTTCCCAAGA | 39 | 5.13 | 241 |
| ATTGAAAGGTGGATAATATAATCCCTGTTTTCCCAAGA | 39 | 5.13 | 242 |
| ATTGAAAGGTGGATAATATAATCCCTGTTTTCCCAAGA | 39 | 5.13 | 243 |
| ATTGAAAGCAGTTCTACTTTGATAAGACTGTGGTGGTTA | 39 | 6.03 | 244 |
| ATTGAAAGGACAAAGAACTCCCTAGCGTCCCTCCCCGTG | 39 | 6.07 | 245 |
| AATTGAAAGTTCTGCCGTCCCTTTCTCGACGAACCTCAT | 39 | 6.09 | 246 |
| ATTGAAAGGCACCTTCTTCACCATCGCCGTCTGGATTGC | 39 | 6.14 | 247 |
| AGTTGTAGGCTCGTGGACTTGGCTTCCACACAACTA | 36 | 6.24 | 248 |
| ATTGAAAGTATCTATTGTACAGGTACTTGTTACACGT | 37 | 7.14 | 249 |
| ATTGAA GCTTGCCCAACCTCTCTAGAAACGCCCAC | 35 | 8.06 | 250 |
| ATTGAAAGGCGTTAATGAACAATAAGCCTGACACGAAC | 38 | 1.06, 2.02 | 251 |
| ATTGAAAGTAATCTCAATAACTTTGGCTTCTTTTCTGTG | 39 | 4.14, 5.19 | 252 |

TABLE 6-continued

Cloned psiRNAs. Sequences for all of the clones obtained from both the upper and lower band of the S-column material (See FIG. 7). The length and the origin of each psiRNA is shown. For the sequences, repeat sequence is shown in bold, and the sequences are aligned by the repeat sequences.

| psiRNA sequence | length | psiRNA | SEQ ID NO. |
| --- | --- | --- | --- |
| ATTGAAAGTAATCTCAATAACTTTGGCTTCTTTTCTGTG | 39 | 4.14, 5.19 | 253 |
| ATTGAAAGACACGAATCCCCAACATTCTTCACCACCCCT | 39 | NF | 254 |
| ATTGAAAGTGACTGCCTCCCTCAGAACCTTAATGAT | 36 | NF | 255 |

Figure 6:
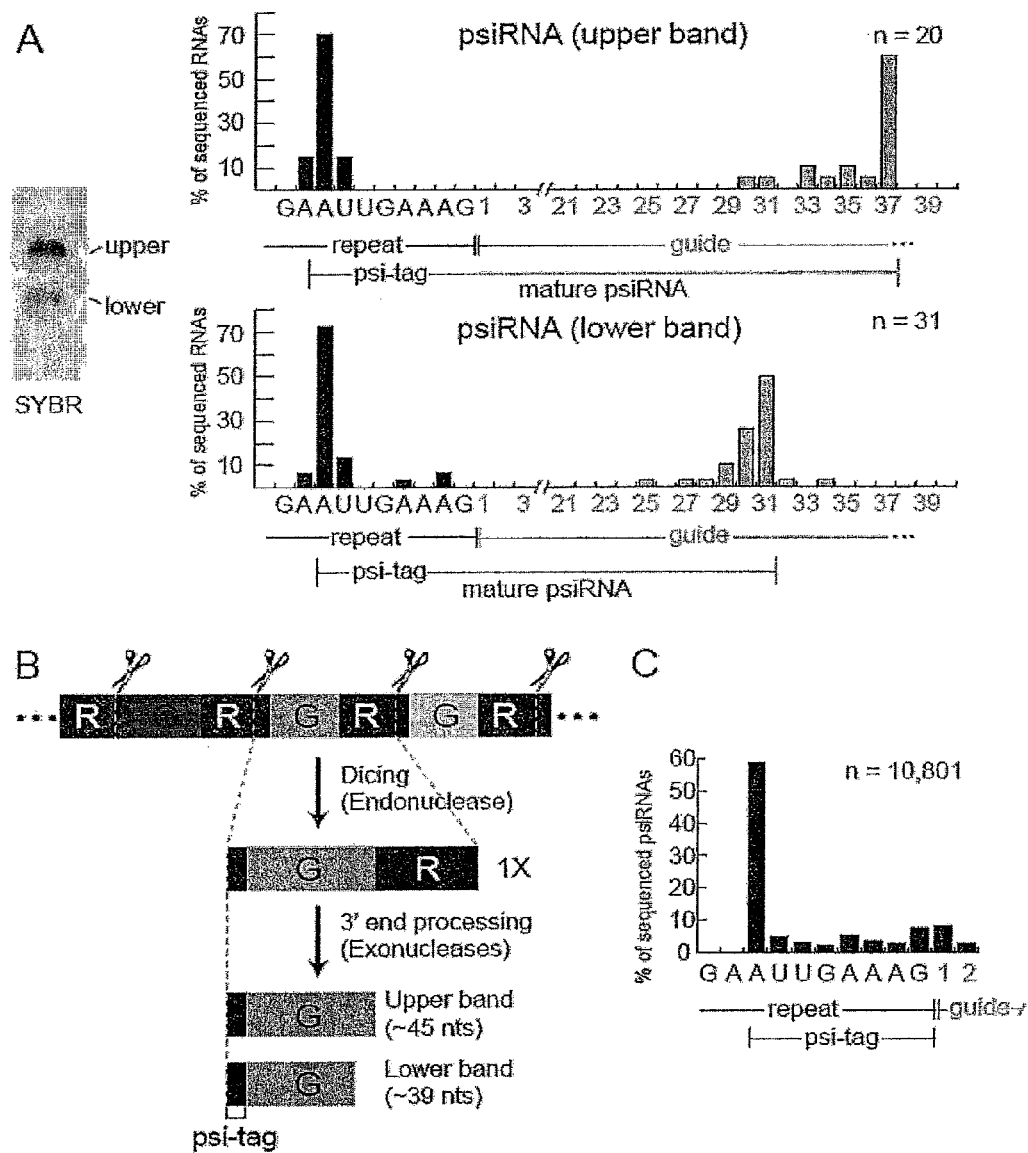
FIG. 6. psiRNA species in the RNP contain a common 5' sequence element and distinct 3' termini. A) Sequence analysis of RNAs associated with the complex. RNA species present in the S-sepharose fraction (visualized by SYBR Gold staining) are shown in left panel. RNAs in the upper and lower bands were isolated, cloned, and sequenced. Graphs show the percentage of sequenced RNAs with 5' ends located at specific positions within the repeat sequence (black), and with indicated numbers of guide sequence nucleotides downstream of the repeat sequence (orange). The average guide sequence is 37 nucleotides in *P. furiosus*. A consensus for each psiRNA species is diagrammed under each graph. The 8-nucleotide repeat sequence found at the 5' end of the majority of the psiRNAs is indicated as the psi-tag. B) Model for biogenesis of the two psiRNA species in *P. furiosus*. CRISPR locus transcripts containing alternating repeat (R, black segments) and guide (G, shaded segments) elements are cleaved at a specific site within the repeat by the Cas6 endoribonuclease (Carte et al., 2008, *Genes Dev*, 22:3489-3496), ultimately producing 1× intermediate RNAs that contain a full invader-targeting sequence flanked on both sides by segments of the repeat. The mature RNAs retain the 5' end repeat sequence (psi-tag). Uncharacterized 3' end processing of the 1× intermediate by endo- and/or exo-nucleases forms the two major mature psiRNAs: a 45-nucleotide species that contains the 8-nucleotide psi-tag and a full guide sequence, and a 39-nucleotide species that contains a shorter 31-nucleotide guide sequence. C) Deep sequencing of small RNAs from *P. furiosus* confirms the presence of the psi-tag. The 5' ends of the sequenced psiRNAs are graphed as in A. The number of total clones analyzed (n) is indicated in the graphs of panels A and C. GAAUUGAAAG; SEQ ID NO: 19.

The cloned psiRNAs consisted primarily of an individual guide (invader-targeting or "spacer") sequence, however, all of the clones retained a portion of the common repeat sequence at the 5' end. Indeed, the majority (~70%) of the RNAs in both bands contained an identical 5' end consisting of an 8-nucleotide segment of the repeat sequence (FIG. 6A). The difference between the two psiRNA size forms was found at the 3' ends. Downstream of the repeat sequence, the majority of the clones from the top band contained 37 nucleotides of guide sequence (the full length of a typical guide element in *P. furiosus*) (FIG. 6A, top panel). The 3' ends of most of the clones from the bottom band were located within the guide sequence. The majority of these RNAs contained 31 nucleotides of guide sequence downstream of the repeat sequence (FIG. 6A, bottom panel).

The psiRNAs are processed from long CRISPR locus transcripts (Brouns et al., 2008, *Science*, 321:960-964; Hale et al., 2008, *RNA*, 14:2572-2579; Lillestol et al., 2006, *Archaea*, 2:59-72; Lillestol et al., 2009, *Mol Microbiol*, 72:259-272; Tang et al., 2002, *Proc Natl Acad Sci USA*, 99:7536-7541; Tang et al., 2005, *Mol Microbial*, 55:469-481) (FIG. 6B). In *P. furiosus*, the Cas6 endoribonuclease cleaves CRISPR RNAs at a site within the repeat element located 8 nucleotides upstream of the guide sequence, generating the precise 5' end observed in the two psiRNA species found in the complex (FIG. 6B; (Carte et al., 2008, *Genes Dev*, 22:3489-3496)). Our results indicate that the 5' end generated by the Cas6 endoribonuclease is maintained in the mature psiRNAs, but that the RNAs undergo further processing at the 3' end to generate psiRNAs that contain either ~37 or ~31 nucleotides of guide sequence (FIG. 6B). The mechanism that defines the two distinct 3' end boundaries is not known. The larger ~45-nucleotide mature psiRNA species is generally more abundant than the smaller ~39-nucleotide species (Hale et al., 2008, *RNA*, 14:2572-2579, FIGS. 1 and 2A).

Figure 11:
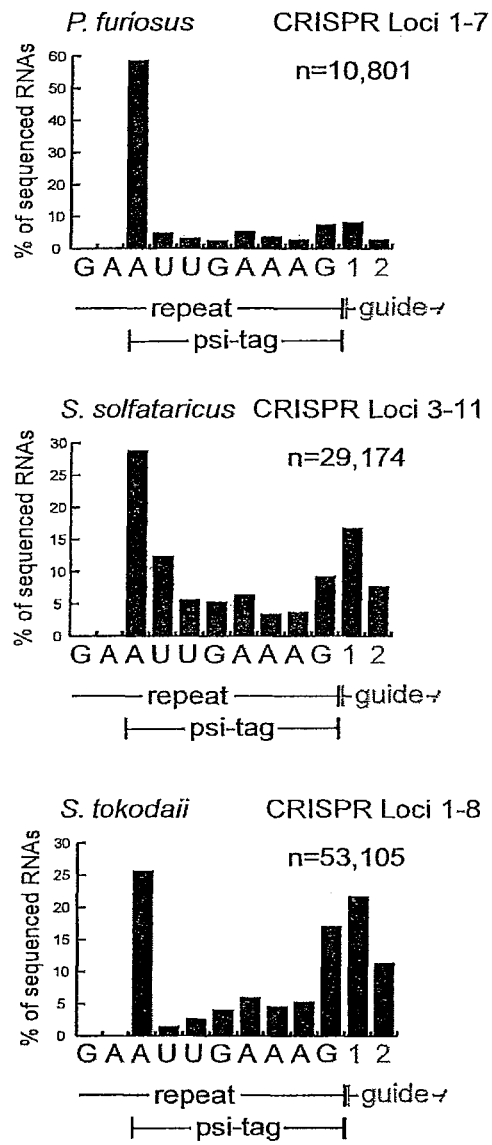
FIG. 11. Deep sequencing of small RNAs from *P. furiosus, Solfolobus solfataricus* and *Sulfolobus tokodaii* confirms the presence of the psi-tag. The 5' ends of the sequenced psiRNAs are graphed as in FIG. 6A. The number of total clones analyzed (n) is indicated. GAAUUGAAAG; SEQ ID NO:19.
Figure 12:
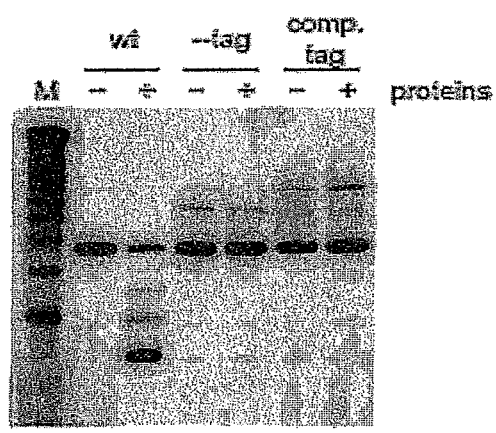
FIG. 12. The psi-tag is required for cleavage of complimentary sequences by the Cmr complex. A psiRNA with the wildtype tag (AUUGAAAG, wt) efficiently guides cleavage of a complementary RNA in the presence of Cmr1-6 (+proteins). The same psiRNA that is lacking the tag sequence (—tag) is unable to guide cleavage of the target. Mutating the tag sequence to its complement, UAACUUUC (comp. tag), also inactivates the complex. This indicates that the tag sequence, AUUGAAAG, is required for cleavage of a complementary RNA by the Cmr proteins.

The short repeat sequence that remains at the 5' end of mature psiRNAs in *P. furiosus* provides a common identifying sequence tag for the psiRNAs that could function in recognition of the RNAs by the proteins in the CRISPR-Cas pathway. In order to rigorously delineate the potentially important psiRNA-tag or "psi-tag", we purified small RNAs from *P. furiosus*, performed deep sequencing and obtained the sequences of the 5' ends of more than 10,000 CRISPR-derived RNAs (from loci 1-7). The 5' ends of the majority of the RNAs mapped 8 nucleotides upstream of the guide sequence (FIG. 6C), verifying the presence of a discrete psi-tag on small CRISPR-derived RNAs in *P. furiosus*. Analysis of RNAs isolated from *Solfolobus solfataricus* and *Sulfobus tokodaii* revealed that 8-nucleotide psi-tags (repeat-derived sequence at the 5' end of the psiRNAs, as indicated) are also present in the psiRNAs of these species (FIG. 11). The *Pyrococcus* and *Sulfolobus* species are members of the extremely phylogenetically diverse Euryarchaeta and Crenarchaeota kingdoms, respectively. These results and similar data from psiRNAs of the bacteria, *E. coli* (Brouns et al., 2008, *Science* 321, 960-964.) and *S. epidermidis* (Marraffini et al., 2008, Science, 322:1843-1845) support the highly conserved nature and functional importance of the psi-tag.

The sequences of CRISPR repeats (from which psi-tags are derived) are generally conserved within groups of organisms, but can vary widely (Godde and Bickerton, 2006, *J Mol Evol*, 62:718-729; Kunin et al, 2007, *Genome Biol*, 8:R61). Thus, while the sequence of the psi-tag found on most *P. furiosus* psiRNAs (AUUGAAAG) can be found in the repeat sequence of numerous organisms, psi-tags of distinct sequence and length would be expected in others. We found evidence to support this prediction in the psiRNAs from *P. furiosus* CRISPR locus 8, which contains a single nucleotide deletion in the psi-tag region of the repeat. Of the 640 RNAs obtained by deep sequencing that mapped to CRISPR locus 8, 60% had a 7-nucleotide AUUGAAG psi-tag. In *E. coli*, CRISPR transcripts are cleaved by a different endoribonuclease (Cse3 of the Cse complex), which nonetheless appears to generate RNAs with an 8-nucleotide AUAAACCG repeat sequence at the 5' end (Brouns et al., 2008, *Science*, 321:960-964), suggesting that this is a general feature of the psiRNAs. Interestingly, the distinct CRISPR repeat sequences found in various genomes are accompanied by specific subsets of Cas proteins (Kunin et al, 2007, *Genome Biol*, 8:R61), which may reflect coupling of specific series of Cas proteins with the psi-tagged RNAs that they recognize.

Figure 7:
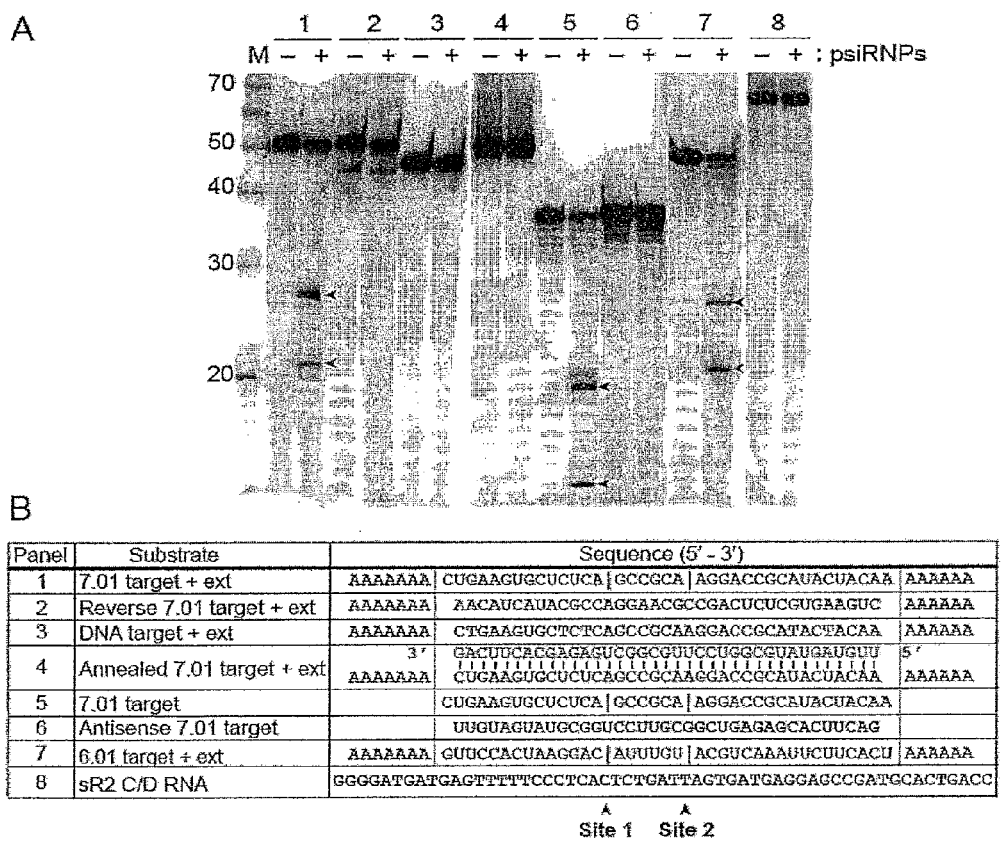
FIG. 7. Specific cleavage of complementary target RNAs. The indicated 5' endlabeled substrates were incubated in the presence (+) or absence (−) of the psiRNP (FIG. 1C). Products were resolved by denaturing gel electrophoresis. In 7A, the primary cleavage products are indicated by arrows. For each lane, the arrow at the higher molecular weight corresponds to the site of cleavage indicated by the vertical lines in the substrate sequences shown in 7B and labeled Site 2, and the arrow at the lower molecular weight corresponds to the site of cleavage indicated by the vertical lines in the substrate sequences shown in 7B and labeled Site 1. The sizes of RNA markers (M) are indicated. "Target" substrates (panel 1 (SEQ ID NO:260): panel 3 (SEQ ID NO:262); panel 4 (SEQ ID NO: 264); panel 5 (SEQ ID NO: 265); panel 7 (SEQ ID NO:267)) contain regions of perfect complementarity to the guide sequence of the indicated *P. furiosus* psiRNA. Grey bars demarcate the guide sequences in 7B. "+ext" substrates (panels 1,2,3,4,7) contain 5' and 3' polyA extensions. In panel 4, a synthetic psiRNA (SEQ ID NO: 263; sequence shown in grey) was pre-annealed to the 7.01 target RNA+ext. Panel 2 shows a reverse target sequence substrate (SEQ ID NO: 261) and panel 6 shows an antisense (AS) target substrate (SEQ ID NO: 266). Panel 3 shows a DNA substrate; all other substrates are RNA. Panel 8 shows unrelated RNA sR2 (SEQ ID NO:268).

Homology-dependent cleavage of a target RNA. One hypothesis for the mechanism by which CRISPR RNAs and Cas proteins mediate genome defense is psiRNA-guided cleavage of invader RNAs, analogous to Slicer function in eukaryotic RNAi pathways (Farazi et al., 2008, *Development*, 135:1201-1214; Girard and Hannon, 2008, *Trends Cell Biol*, 18:136-148; Hutvagner and Simard, 2008, *Nat Rev Mol Cell Biol*, 9:22-32; Makarova et al., 2006, *Biol Direct*, 1:7). Therefore, we tested the ability of the isolated psiRNP complexes to cleave a 5' end-labeled target RNA complementary to endogenous *P. furiosus* psiRNA 7.01 (first psiRNA encoded in CRISPR locus 7, which Northern analysis indicates is present in the native complexes, see FIG. 5). The 7.01 target RNA was cleaved at two sites (site 1 indicated with green vertical line and site 2 indicated with blue vertical line, FIG. 7B, panel 1) yielding 5' end-labeled products of 27 and 21 nucleotides (indicated with corresponding green and blue arrowheads, FIG. 7A, panel 1). Cleavage activity was lost in the presence of 0.1 mM EDTA indicating that the enzyme depends on divalent cations, and was restored by the addition of 1 mM $Mg^{2+}$, $Mn^{2+}$, $Ca^{2+}$, $Zn^{2+}$, $Ni^{2+}$ or $Fe^{2+}$ with no detectable change in cleavage sites with any of the metals, but was not supported by $Co^{2+}$ or $Cu^{2+}$. Cleavage did not require sequences extending beyond the 37-nucleotide region of complementarity and occurred at the same two sites in the target RNA lacking sequence extensions (FIG. 7, panel 5). No activity was observed toward RNAs that lacked homology with known *P. furiosus* psiRNAs, including the reverse 7.01 target sequence, antisense 7.01 target sequence, and a box C/D RNA (FIG. 7, panels 2, 6, and 8). A single-stranded DNA 7.01 target sequence was also not cleaved (FIG. 7, panel 3). Pre-annealing a synthetic psiRNA 7.01 to the 7.01 target RNA (to form a double-stranded RNA target) blocked cleavage by the psiRNPs in the sample (FIG. 7, panel 4). Finally, we tested a target for endogenous *P. furiosus* psiRNA 6.01 and observed cleavage that generates 2 products of the same sizes observed for the 7.01 target RNA (FIG. 7, panel 7).

These results reveal the presence of cleavage activity in *P. furiosus* that is specific for single-stranded RNAs that are complementary to psiRNAs. The activity is associated with a purified fraction that contains 2 mature psiRNA species and 7 RAMP module (Cmr) proteins.

Figure 8:
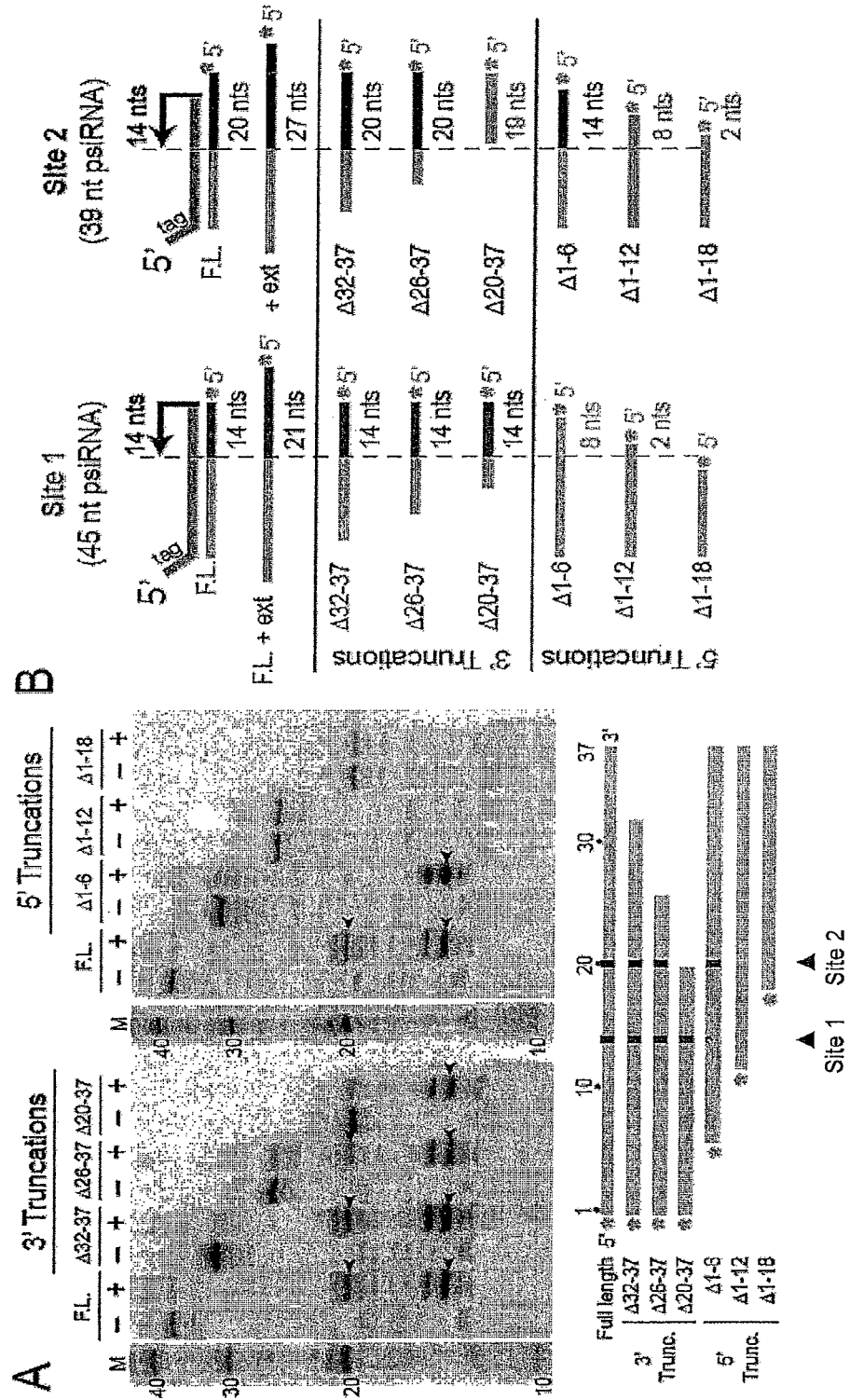
FIG. 8. Cleavages occurs 14 nucleotides from the 3' ends of the psiRNAs. A) The indicated 5' end-labeled (*) substrates were incubated in the presence (+) or absence (−) of the psiRNP (FIG. 1C). The substrates were full-length 7.01 target RNA (F.L.), and the indicated truncations as diagramed in the lower panel. As in FIG. 3, the locations of observed cleavages at sites 1 and 2 are indicated on the full-length target and truncated RNAs (lower panel) and the corresponding cleavage products are indicated with arrows in the upper panels. Question mark in the lower panel indicates cleavage that could not be assessed. B) Model for cleavage at two sites directed by two psiRNAs. The 45-nucleotide psiRNA species guides cleavage at site 1 and the 39-nucleotide psiRNA guides cleavage at site 2 on each of the substrate RNAs as indicated. In both cases, cleavage occurs 14 nucleotides from the 3' end of the psiRNA. Observed products are indicated with regular type and shaded bars, and products not observed are indicated in gray type, and correspond to products in FIGS. 3 and 4A.

Cleavage of the target RNA occurs a fixed distance from the 3' end of the psiRNA. To investigate the mechanism of psiRNA-directed RNA cleavage, we analyzed the results of cleavage assays with a series of 6-nucleotide truncations of the 7.01 target RNA (FIG. 8A). We found that the target RNA truncations analyzed did not affect the locations of the two cleavage sites. The full-length 7.01 target RNA is cleaved at sites 1 and 2 to generate 14- and 20-nucleotide 5' end-labeled products, respectively (FIGS. 3 and 4A). The 3' end-truncated target RNAs were cleaved at the same two sites to yield the same two 5' end-labeled cleavage products (except where truncation eliminated cleavage site 2, Δ20-37, FIG. 8A). On the other hand, in the case of the 5' end-truncated target RNAs, cleavage at the same sites would generate shorter 5' endlabeled cleavage products. The 14-nucleotide product that results from cleavage of the Δ1-6 target RNA at site 2 was observed (FIG. 8A), but cleavage at site 1 could not be assessed because the size of the product is below that which could be detected in the experiment. If the twelve- and eighteen-nucleotide 5' end-truncated target RNAs were cleaved at the same two sites, the products would also be outside the range of detection, however, interestingly, very little cleavage of these RNAs was observed (FIG. 8, Δ1-18 and Δ1-12, compare substrate band+/−complex).

Strikingly, the difference in the sizes of the two cleavage products observed with the various substrates is the same as the difference in the sizes of the two endogenous psiRNA species (6 nucleotides in both cases, FIG. 7). This size difference as well as the specific product sizes suggest that the two cleavages occur a fixed distance (14 nucleotides) from the 3' ends of the two psiRNAs. FIG. 8B illustrates the proposed mechanism by which the 45- and 39-nucleotide psiRNAs guide cleavage at target sites 1 and 2, respectively, for each of the target RNAs analyzed here. For example, using the full-length 7.01 target RNA we observed 20- and 14-nucleotide cleavage products (FIG. 7, panel 5) suggesting cleavage of the bound target RNA 14 nucleotides from the 3' end of the 39- and 45-nucleotide psiRNAs, respectively (FIG. 8B, F.L.). In addition, a 7-nucleotide extension at the 5' end of the target RNA resulted in a pair of 5' end-labeled products 27 and 21 nucleotides in length (FIG. 7, panel 1), consistent with cleavage of the substrate 14 nucleotides from the ends of the two psiRNAs (FIG. 8B, F.L.+ext). The anchor for this counting mechanism is the 3' end of the psiRNA. While reductions in the extent of duplex formation between the 5' end of the psiRNA and the cleavage site (3' truncations to within 6 nucleotides of the cleavage site) did not have an observable effect on cleavage efficiency, truncations that reduced duplex formation between the 3' end of the psiRNA and the cleavage site had a strong negative impact, suggesting that basepairing of the last 14 nucleotides of the psiRNA with the target is critical for cleavage activity. The results of these studies indicate that both of the mature psiRNA species are active in guiding target RNA cleavage by a mechanism that depends upon the distance from the 3' end of the psiRNA.

Figure 9:
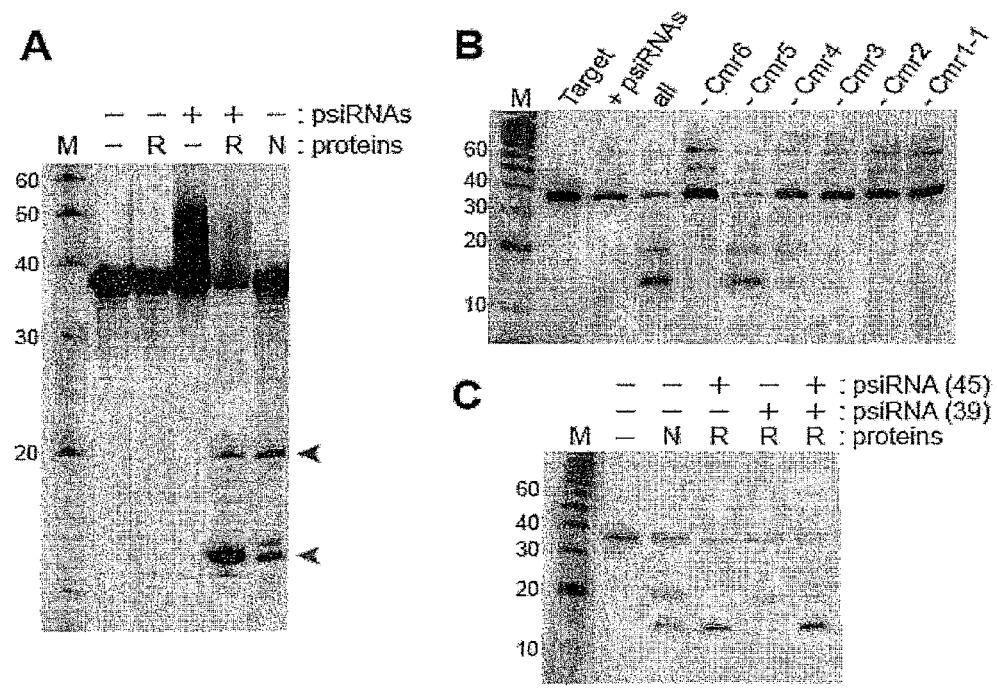
FIG. 9. Target RNA cleavage requires five Cmr proteins and a single psiRNA species. A) 5' end-labeled 7.01 target RNA was incubated in the absence of added psiRNAs or proteins, in the presence of synthetic psiRNAs or purified recombinant *P. furiosus* Cmr proteins (R) or in the presence of purified native psiRNPs (N) as indicated. The synthetic psiRNAs were the 45- and 39-nucleotide forms of psiRNA 7.01. The six added recombinant Cmr proteins were *P. furiosus* Cmr1-1, Cmr2, Cmr3, Cmr4, Cmr5 and Cmr6. Products were resolved by denaturing gel electrophoresis. The products corresponding to cleavage at site 1 and site 2 are indicated by lower and upper arrows, respectively. The sizes of RNA markers (M) are indicated. B) The 7.01 target, along with the 7.01 psiRNAs (both 39- and 45-nucleotide species, in the presence of Cmr1-6 (all), and in the absence (−) of the indicated Cmr protein. The locations of the cleavage products are indicated as above. C) The cleavage activity of the native psiRNP (N) is compared to the activity of the recombinant psiRNP (R) in the presence of either the 45-nucleotide 7.01 psiRNA, the 39-nucleotide 7.01 psiRNA, or both psiRNAs. Cleavage sites are indicated as above.

Analysis of reconstituted Cmr-psiRNA complexes. Identification of the Cmr proteins in the purified psiRNP complex (FIG. 5) along with the evolutionary evidence for their co-function with the CRISPRs (Haft et al., 2005, *PLoS Comput Biol*, 1:e60; Jansen et al., 2002, *Mol Microbiol*, 43:1565-1575; Makarova et al., 2002, *Nucleic Acids Res*, 30:482-496) strongly suggests that the Cmr proteins and psiRNAs function as a complex to cleave target RNAs (FIG. 7). In order to determine whether the Cmr proteins and psiRNAs are sufficient for function (independent of other co-purifying *P. furiosus* components), we tested the ability of purified recombinant Cmr proteins and synthetic psiRNAs to cleave target RNAs (FIG. 9). A reconstituted set of six *P. furiosus* Cmr proteins (Cmr1-1, Cmr2-Cmr6) and two mature psiRNA species (45- and 39-nucleotide psiRNA 7.01) cleaved the target RNA at 2 sites generating the same size products as those observed with the isolated native complex (FIG. 9A). While both *P. furiosus* isoforms of the Cmr1 protein are present in the isolated complexes (FIG. 5), we found that only one of the two proteins (Cmr1-1) was required for a functional reconstituted complex (FIG. 9A), suggesting that the isoforms may perform redundant functions. No activity was observed in the absence of the psiRNAs or in the absence of the Cmr proteins (FIG. 9A), indicating that both are necessary. These results demonstrate that the RAMP module Cas proteins and psiRNAs function together to cleave complementary target RNAs. In order to determine whether all of the six Cmr proteins are essential for psiRNA guided RNA cleavage, we assayed cleavage activity in the absence of each of the individual proteins. Omission of Cmr5 did not observably affect the activity of the complex (FIG. 9B). However, cleavage was significantly reduced in the absence of any one of the other proteins (FIG. 9B), indicating that 5 of the 6 RAMP module proteins are required for activity.

Finally, we had reconstituted the same cleavage activity profile observed for the native complexes using both psiRNA species (45- and 39-nucleotides) (e.g. FIG. 9A). Our model for the mechanism of cleavage predicts that each of the psiRNAs guides a distinct cleavage: the 45-nucleotide psiRNA at site 1, and the 39-nucleotide psiRNA at site 2 (see FIG. 8B). To determine whether both psiRNAs are required for activity, and whether each guides the distinct cleavage that is predicted by the model, we tested the activity of complexes reconstituted with a single psiRNA. As predicted, we found that the 45-nucleotide psiRNA guided cleavage at site 1 producing a 14-nucleotide 5' end-labeled product, and the 39-nucleotide psiRNA guided cleavage at site 2 producing a 20-nucleotide 5' end-labeled product (FIG. 9C). Based on our truncation analysis (FIG. 8, Δ20-37), the larger product of the cleavage guided by the 39-nucleotide psiRNA could act as a substrate for cleavage guided by the 45-nucleotide psiRNA, and consistent with this, we often obtain more of the smaller cleavage product in cleavage assays using both the native complex and the reconstituted complex containing both psiRNAs (e.g. FIG. 9A). The results of these experiments demonstrate that each of the psiRNA species is competent to form functional psiRNPs and guides cleavage 14 nucleotides from its 3' end.

Discussion

The findings presented here reveal the mechanism of action of an RNA-protein complex implicated in a novel RNA silencing pathway that functions in invader defense in prokaryotes. Previous work had shown that both invader-specific sequences within CRISPRs and Cas protein genes are important in virus and plasmid resistance in prokaryotes (Barrangou et al., 2007, *Science*, 315:1709-1712; Brouns et al., 2008, *Science*, 321:960-964; Deveau et al., 2008, *J Bacteriol*, 190:1390-1400). The results presented here establish how small RNAs from CRISPRs and the RAMP module Cas proteins function together to destroy RNAs recognized by the CRISPR RNAs. The major findings and models established in this work are summarized in FIG. 10.

Figure 10:
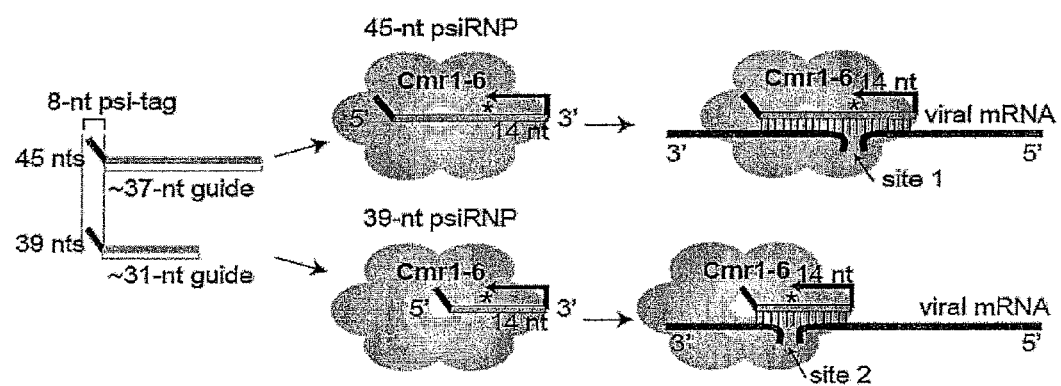
FIG. 10. Model for the function of psiRNA-Cmr protein complexes in silencing molecular invaders. Based on the results of this study, a psiRNA with a conserved 5' sequence element derived from the CRISPR repeat (psi-tag) and a region of invader targeting sequence assembles with six Cas module-RAMP proteins (Cmr1-6). The assembled psiRNP interacts with an invader RNA (e.g., viral mRNA) through base pairing between the psiRNA and invader RNA, positioning the region of the RNA-RNA duplex 14 nucleotides from the 3' end of the psiRNA in proximity to the active site (star) of the enzyme. In *P. furiosus*, there are two prominent size forms of psiRNAs with different 3' ends that guide cleavage of viral mRNAs at two distinct sites. There are also two Cmr1 proteins in *P. furiosus* that are both found in purified preparations and likely function redundantly.

Our findings indicate that the RAMP module of the CRISPR-Cas system silences invaders by psiRNA-guided cleavage of invader RNAs (FIG. 10). Specifically, the results indicate that psiRNAs present in complexes with the Cmr proteins recognize and bind an invader RNA such as a viral mRNA (via the psiRNA guide sequence co-opted from the invader by another branch of the CRISPR-Cas system), and that the complex then cleaves the invader RNA, destroying the message and presumably blocking the viral life cycle. The psiRNA-Cmr complexes cleave complementary RNAs (FIGS. 3 and 5). Five of the six Cmr proteins are required for target RNA cleavage (FIG. 9) and the component of the complex that provides catalytic activity remains to be determined. Cmr2 contains a predicted nuclease domain (Makarova et al., 2002, *Nucleic Acids Res*, 30:482-496; Makarova et al., 2006, *Biol Direct*, 1:7), however the other four essential proteins (Cmr1, 3, 4 and 6) belong to the RAMP superfamily, members of which have been found to be ribonucleases (Beloglazova et al., 2008, *J Biol Chem*, 283:20361-20371; Brouns et al., 2008, *Science*, 321:960-964; Carte et al., 2008, *Genes Dev*, 22:3489-3496).

Our results also establish a simple model for the mechanism of cleavage site selection by the psiRNA-Cmr effector complex—a 14-nucleotide ruler anchored by the 3' end of the psiRNA (FIG. 10). We found that *P. furiosus* psiRNAs occur in two lengths that share a 5' psi-tag (derived from the CRISPR repeat) and contain either ~37 or ~31 nucleotides of guide sequence (FIGS. 1 and 2). Both psiRNA species are associated with the Cmr effector complex (FIG. 5) and each guides cleavage at a distinct site (FIG. 9C). Analysis of the cleavage products of both psiRNAs and of a series of substrate RNAs (FIGS. 3, 4 and 5) indicates that the complex cleaves based on a 14-nucleotide counting mechanism anchored by the 3' end of the psiRNA. The results suggest that the 3' end of the psiRNA places the bound target RNA relative to the enzyme active site (FIG. 10). Interestingly, Argonaute 2 (a.k.a. Slicer), an enzyme with an analogous function in the eukaryotic RNAi pathway, also employs a ruler mechanism; however, in that case the site of cleavage is located ~10-11 nucleotides from the 5' end of the siRNA (Elbashir et al., 2001, *Nature*, 411:494-498; Elbashir et al., 2001, *Embo J*, 20:6877-6888).

FIG. 10 also illustrates the Cmr-psiRNA effector complex model that arises from the findings presented here. Both size classes of psiRNAs and all seven Cmr proteins are found in complexes in active, purified fractions (FIG. 5), however accurate RNAguided cleavage activity can be reconstituted with either psiRNA species and with a single Cmr1 isoform (FIG. 9). We hypothesize that each psiRNA associates with a single set of six Cmr proteins, and that Cmr1-1 and Cmr1-2 function redundantly in *P. furiosus*. Five unrelated proteins that co-purified with the complexes (Supplemental Table 1) are not essential for reconstitution of cleavage activity in vitro (FIG. 9) and are not included in our model, but could play a role in function in vivo. Recognition of the psiRNAs by the Cmr proteins, and psiRNA-Cmr complex assembly likely depend upon conserved features of the RNAs that could include 5' and 3' end groups and folded structure as well as the psi-tag. Our data reveal that the psiRNA-Cmr complex can utilize psiRNAs of different sizes to cleave a target RNA at distinct sites (FIG. 9C). Thus, the two size forms of psiRNAs present in *P. furiosus* may provide more certain and efficient target destruction.

Our data indicate that the function of the Cmr module of Cas proteins is psiRNA-guided destruction of invading target RNA. The widespread occurrence of the cmr genes in diverse archaea and bacteria indicates that invader RNA cleavage is a mechanism utilized by many prokaryotes for viral defense (Haft et al., 2005, *PLoS Comput Biol*, 1:e60; Jansen et al., 2002, *Mol Microbiol*, 43:1565-1575; Makarova et al., 2006, *Biol Direct*, 1:7). However, not all prokaryotes with the CRISPR-Cas system possess the Cmr module. In these numerous other organisms, it is possible that a different set of Cas proteins mediates psiRNA-guided RNA cleavage or that Cas proteins effect invader resistance by another mechanism. Indeed, very recent work indicates that the CRISPR-Cas system targets invader DNA in a strain of *Staphylococcus epidermis* and perhaps *E. coli* (Brouns et al., 2008, *Science*, 321:960-964; Lillestol et al., 2006, *Archaea*, 2:59-72), which possess the *Mycobacterium tuberculosis* (Csm) and *E. coli* (Cse) subtype Cas protein modules, respectively (Haft et al., 2005, *PLoS Comput Biol*, 1:e60; Jansen et al., 2002, *Mol Microbiol*, 43:1565-1575; Makarova et al., 2006, *Biol Direct*, 1:7). The prokaryotes include evolutionarily distant and very diverse organisms. Diversity in the core components of the eukaryotic RNAi machinery has led to a tremendous variety of observed RNA-mediated gene silencing pathways that can act at post-transcriptional or transcriptional levels (Chapman and Carrington, 2007, *Nat Rev Genet*, 8:884-896; Farazi et al., 2008, *Development*, 135:1201-1214; Hutvagner and Simard, 2008, *Nat Rev Mol Cell Biol*, 9:22-32; Zaratiegui et al., 2007, *Cell*, 128:763-776). The diversity of Cas proteins found in CRISPR-containing prokaryotes may reflect significantly different mechanisms of CRISPR element integration, CRISPR RNA biogenesis, and invader silencing.

Example 3

Cleavage of Target Polynucleotides by a Cmr Complex Requires a psiRNA-Tag

A psiRNA with the wildtype tag (AUUGAAAG, wt) efficiently guides cleavage of a complementary RNA in the presence of Cmr1-6 (+proteins). The same psiRNA that is lacking the tag sequence (—tag) is unable to guide cleavage of the target. Mutating the tag sequence to its complement, UAACUUUC (comp. tag), also inactivates the complex. This indicates that the tag sequence, AUUGAAAG, is required for cleavage of a complementary RNA by the Cmr proteins.

Recombinant Cmr1-6 (500 µM each protein) was added to a 20 µl reaction using conditions described in Example 1. Proteins and psiRNAs (0.25 pmol psiRNA per reaction) were incubated for 30 minutes at 70° C. [$^{32}$P]-radiolabeled target RNAs (0.05 pmol per reaction) were added and the reactions were incubated for 1 hour and 70° C. The resulting reaction was subject to proteinase K digest by 1 µg of proteinase K at 37° C. for 15 minutes, followed by PCI extraction and Ethanol precipitation. The resulting RNAs were separated on 10×10.6 cm 15% 7M urea gels and subject to autoradiography. Decade marker (Applied Biosystems) was used to determine sizes of cleavage products.

The following RNA sequences were used, Target (for all reactions),

```
                                         (SEQ ID NO: 203)
CTGUUGTGCTCTCUGCCGCUUGGUCCGCUTUCTUCUU;

(SEQ ID NO: 204)
wt psiRNA,
AUUGAAAGUUGUAGUAUGCGGUCCUUGCGGCUGAGAGCACUUCAG;
```

-continued

```
                                                (SEQ ID NO: 205)
tag psiRNA,
UUGUAGUAUGCGGUCCUUGCGGCUGAGAGCACUUCAG;

(SEQ ID NO: 206)
complement tag psiRNA,
UAACUUUCUUGUAGUAUGCGGUCCUUGCGGCUGAGAGCACUUCAG.
```

Example 4

Figure 13:
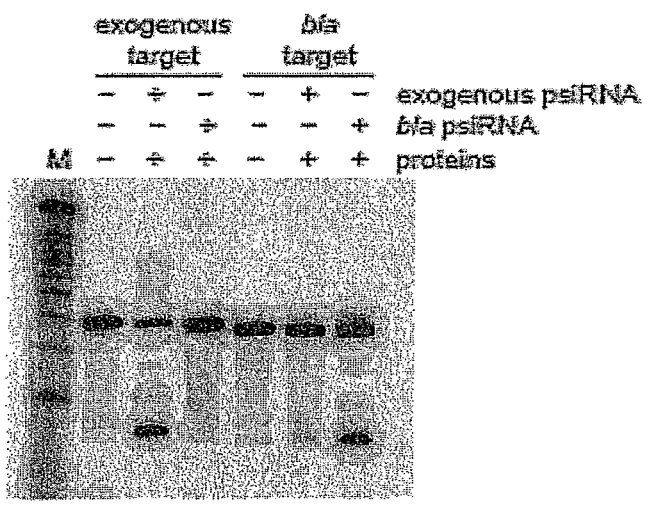
FIG. 13. The psi-tag allows for rational design of psiRNAs that cleave novel targets. psiRNAs were created to target two non-natural sequences. The first (exogenous) psiRNA targets an unrelated sequence, and the second (bla) psiRNA targets the first 37 nucleotides of the β-lactamase, or bla, mRNA, which confers antibiotic resistance in bacteria. The psiRNAs were created by adding the tag sequence, AUUGAAAG, to 37 nucleotides of guide sequence, which is complementary to the targeted sequence. The psiRNAs were incubated with the Cmr proteins and allowed to cleave both of the targets. The exogenous psiRNA was able to guide cleavage of the complementary sequence (exogenous target), but not the bla target, and the bla psiRNA was able to guide cleavage of the bla message, but not the exogenous sequence. These results indicate that addition of the psi-tag to any sequence will allow for specific cleavage of the complementary sequence by the Cmr proteins.

The Psi-Tag Allows for Rational Design of psiRNAs that Guide Inactivation of Novel Targets psiRNAs were designed to target two novel RNA sequences (not targeted by known naturally occurring psiRNAs): "exogenous target", which does not correspond to any known naturally occurring sequence, and the bla target, which corresponds to the first 37 nucleotides of the ß-lactamase or bla mRNA, which encodes a protein responsible for common forms of antibiotic resistance in bacteria. The psiRNAs were constructed by addition of the *P. furiosus* psi-tag sequence, AUUGAAAG, to 37 nucleotides of guide sequence that is complementary to the targeted sequence. The results are shown in FIG. 13. The psiRNAs and the Cmr proteins were incubated with the target RNAs. The psiRNA directed against the exogenous target ("exogenous psiRNA") directed cleavage of the exogenous target, but not the bla target RNA. The psiRNA directed against the bla target ("bla psiRNA") directed cleavage of the bla target, but not the exogenous target RNA. These results indicate that psiRNAs can be rationally designed to direct cleavage of novel target RNAs by the Cmr complex.

Cmr complex assays were performed as described in Example 1. Cmr1-6 (500 µM) was incubated with 0.25 pmol of psiRNA (described below) for 30 minutes at 70° C. in conditions described in Example 1. Radiolabeled target RNA (0.05 pmol, sequences below) was added and the reaction was allowed to continue at 70° C. for 1 hour. One microgram of proteinase K was added and incubated at 37° C. for 15 minutes. The resulting RNAs were subject to PCI extraction and ethanol precipitation. The purified RNAs were separated on 10×10.6 cm 15% 7M urea gels. The gels were dried and subject to autoradiography. Decade marker (Applied Biosystems) was used to determine sizes of cleavage products.

The following RNA sequences were used:

```
                                                (SEQ ID NO: 20)
exogenous psiRNA,
AUUGAAAGCUGAAGUGCUCUCAGCCGCAAGGACCGCAUACUACAA;

(SEQ ID NO: 21)
exogenous target,
UUGUAGUAUGCGGUCCUUGCGGCUGAGAGCACUUCAG;

(SEQ ID NO: 22)
bla psiRNA,
AUUGAAAGCUGAAGUGCUCUCAGCCGCAAGGACCGCAUACUACAA;
and (SEQ ID NO: 23)
bla target,
AUGAGUAUUCAACAUUUCCGUGUCGCCCUUAUUCCCU.
```

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for inactivating a target polynucleotide in a cell comprising:

introducing into a cell a psiRNA comprising at least 23 nucleotides, wherein the psiRNA comprises a psiRNA-tag and a guide sequence, wherein the psiRNA-tag is the first 5 to 10 nucleotides of the psiRNA and comprises a nucleotide sequence chosen from nucleotides of a repeat from a CRISPR locus that are immediately upstream of a spacer present in a microbe comprising the CRISPR locus, wherein the guide sequence is located immediately downstream of the psiRNA-tag and comprises the remaining nucleotides of the psiRNA, and wherein the guide sequence is complementary to, and hybridizes to, a target polynucleotide which is cleaved.

2. The method of claim 1 wherein the psiRNA-tag has at least 80% sequence similarity with 5'-ATTGAAAS, wherein S is G or C.

3. The method of claim 1 wherein the guide sequence comprises at least 31 nucleotides or at least 37 nucleotides.

4. The method of claim 1 wherein the guide sequence is 31 nucleotides or is 37 nucleotides.

5. The method of claim 1 wherein the psiRNA-tag is the first 8 nucleotides of the psiRNA.

6. The method of claim 1 wherein the target polynucleotide is RNA.

7. The method of claim 1 wherein the psiRNA associates in the cell with CRISPR-associated (Cas) polypeptides to form a complex having endonuclease activity, and wherein the Cas polypeptides are encoded by the cell.

8. The method of claim 7 wherein the Cas polypeptides comprise a Cmr1 polypeptide, a Cmr2 polypeptide, a Cmr3 polypeptide, a Cmr4 polypeptide, a Cmr5 polypeptide, and a Cmr6 polypeptide, and have endoribonuclease activity.

9. The method of claim 1 wherein the psiRNA is introduced into the cell as an RNA polynucleotide.

10. The method of claim 1 wherein the psiRNA introduced into the cell as a DNA polynucleotide encoding the psiRNA.

11. The method of claim 1 wherein the target polynucleotide is a polynucleotide endogenous to the cell.

12. The method of claim 1 wherein the cell is a bacterial cell.

13. The method of claim 1 wherein the cell is an archaeal cell.

14. A method for cleaving a target polynucleotide comprising:
   incubating under suitable conditions a composition comprising:
      a target polynucleotide;
      a psiRNA comprising at least 23 nucleotides, wherein the psiRNA comprises a psiRNA-tag and a guide sequence, wherein the psiRNA-tag is the first 5 to 10 nucleotides of the psiRNA and comprises a nucleotide sequence chosen from nucleotides of a repeat from a CRISPR locus that are immediately upstream of a spacer present in a microbe comprising the CRISPR locus, wherein the guide sequence is located immediately downstream of the psiRNA-tag and comprises the remaining nucleotides of the psiRNA, and wherein the guide sequence is complementary to, and hybridizes to, the target polynucleotide; and
      a Cmr1 polypeptide, a Cmr2 polypeptide, a Cmr3 polypeptide, a Cmr4 polypeptide, a Cmr5 polypeptide, and a Cmr6 polypeptide;
   wherein the target polynucleotide is cleaved.

15. The method of claim 14 wherein the psiRNA-tag has at least 80% sequence similarity with 5'-ATTGAAAS, wherein S is G or C.

16. The method of claim 14 wherein the guide sequence comprises at least 31 nucleotides or at least 37 nucleotides.

17. The method of claim 14 wherein the guide sequence is 31 nucleotides or is 37 nucleotides.

18. The method of claim 14 wherein the psiRNA-tag is the first 8 nucleotides of the psiRNA.

19. The method of claim 14 wherein the target polynucleotide is RNA.

20. The method of claim 14 wherein the method is in vivo.

* * * * *

SEQUENCE LISTING

```
<160> NUMBER OF SEQ ID NOS: 276

<210> SEQ ID NO 1
<211> LENGTH: 41
<212> TYPE: RNA
<213> ORGANISM: artificial
<220> FEATURE:
<223> OTHER INFORMATION: psiRNA
<220> FEATURE:
<221> NAME/KEY: misc_feature
<222> LOCATION: (1)..(41)
```

```
<223> OTHER INFORMATION: n may be any nucleotide
<220> FEATURE:
<221> NAME/KEY: misc_feature
<222> LOCATION: (5)..(10)
<223> OTHER INFORMATION: up to 5 of the nucleotides present at positions
      5 through 10 may be absent
<220> FEATURE:
<221> NAME/KEY: misc_feature
<222> LOCATION: (27)..(28)
<223> OTHER INFORMATION: cleavage site

<400> SEQUENCE: 1
nnnnnnnnnn nnnnnnnnnn nnnnnnnnnn nnnnnnnnnn n                           41

<210> SEQ ID NO 2
<211> LENGTH: 53
<212> TYPE: RNA
<213> ORGANISM: artificial
<220> FEATURE:
<223> OTHER INFORMATION: psiRNA
<220> FEATURE:
<221> NAME/KEY: misc_feature
<222> LOCATION: (1)..(53)
<223> OTHER INFORMATION: n may be any nucleotide
<220> FEATURE:
<221> NAME/KEY: misc_feature
<222> LOCATION: (5)..(10)
<223> OTHER INFORMATION: up to 5 of the nucleotides present at positions
      5 through 10 may be absent
<220> FEATURE:
<221> NAME/KEY: misc_feature
<222> LOCATION: (33)..(34)
<223> OTHER INFORMATION: cleavage site

<400> SEQUENCE: 2
nnnnnnnnnn nnnnnnnnnn nnnnnnnnnn nnnnnnnnnn nnnnnnnnnn nnn              53

<210> SEQ ID NO 3
<211> LENGTH: 1017
<212> TYPE: DNA
<213> ORGANISM: Pyrococcus furiosus

<400> SEQUENCE: 3
atgtttattg aagaatttga aattgagtcc ataacctcca cgcatttatt agaggtgctg        60
accagagaat acccagaagt gagaagtcct tcaataaagg gagcaatgag atggtggttc       120
agagctttgg ctggctcata ttttggagac gatgctcaaa aacttaaaga aatagaaaac       180
caagttttgt ggagcacaaa ggaaagaagc agagtaaaaa tttctgttac accgcttagt       240
tctccaaaaa gattaaacct taaagagttt aaggataaaa atgttgggta catctggttt       300
tcaataaatc tgctcggaaa aagagggact ataactcact attatcctcc tgggagcaga       360
tttagagtag ttctagaatc acctagcgaa agggttatta agctggcaac tttatctctc       420
tgggctcttg tgagcttagg tagtgttgga tttagaagta gacggggaac aggttcaatg       480
aaaatcgtta gggcaagtag cgaagttctg gaggatttgg gactcacaac agaattcaat       540
tctatagatg aatttaaaga ttcttttgaaa agggtgttag atgtcacagg cgaaattttta       600 ggagtaaaaa atagcgaaac taataagtcc ctcccttctt acgctacttt aaagttttca       660
gacgttgaag tatttgggcc agggaagaat acttgggagg tattagctca gttcaacaac       720
tcttacaagg aatacctaag gaggagaatt aagaagtatc aaaggataat atttggattg       780
cctcgattta agcttagagg cgtgaggaaa gacctaagga gagcttctcc cctttggttt       840
ggcgttgtag atataggcgg aaagccatat ggaaggataa tcaagttctt ccaatctaca       900
tttcatccag aagtaagaag caaacatata gttgattgga acgttctttc aaattttgat       960
```
tggtttatat cctctagact tcctgtgact aaggtgtggg gtggttggag tggttaa    1017

```
<210> SEQ ID NO 4
<211> LENGTH: 338
<212> TYPE: PRT
<213> ORGANISM: Pyrococcus furiosus

<400> SEQUENCE: 4
```

| Met | Phe | Ile | Glu | Glu | Phe | Glu | Ile | Glu | Ser | Ile | Thr | Ser | Thr | His | Leu |
|---|---|---|---|---|---|---|---|---|---|---|---|---|---|---|---|
| 1 | | | | 5 | | | | | 10 | | | | | 15 | |

| Leu | Glu | Val | Leu | Thr | Arg | Glu | Tyr | Pro | Glu | Val | Arg | Ser | Pro | Ser | Ile |
|---|---|---|---|---|---|---|---|---|---|---|---|---|---|---|---|
| | | | 20 | | | | | 25 | | | | | 30 | | |

| Lys | Gly | Ala | Met | Arg | Trp | Trp | Phe | Arg | Ala | Leu | Ala | Gly | Ser | Tyr | Phe |
|---|---|---|---|---|---|---|---|---|---|---|---|---|---|---|---|
| | | | 35 | | | | | 40 | | | | | 45 | | |

| Gly | Asp | Asp | Ala | Gln | Lys | Leu | Lys | Glu | Ile | Glu | Asn | Gln | Val | Phe | Gly |
|---|---|---|---|---|---|---|---|---|---|---|---|---|---|---|---|
| | | 50 | | | | | 55 | | | | | 60 | | | |

| Ser | Thr | Lys | Glu | Arg | Ser | Arg | Val | Lys | Ile | Ser | Val | Thr | Pro | Leu | Ser |
|---|---|---|---|---|---|---|---|---|---|---|---|---|---|---|---|
| 65 | | | | | 70 | | | | | 75 | | | | | 80 |

| Ser | Pro | Lys | Arg | Leu | Asn | Leu | Lys | Glu | Phe | Lys | Asp | Lys | Asn | Val | Gly |
|---|---|---|---|---|---|---|---|---|---|---|---|---|---|---|---|
| | | | | 85 | | | | | 90 | | | | | 95 | |

| Tyr | Ile | Trp | Phe | Ser | Ile | Asn | Leu | Leu | Gly | Lys | Arg | Gly | Thr | Ile | Thr |
|---|---|---|---|---|---|---|---|---|---|---|---|---|---|---|---|
| | | | 100 | | | | | 105 | | | | | 110 | | |

| His | Tyr | Tyr | Pro | Pro | Gly | Ser | Arg | Phe | Arg | Val | Val | Leu | Glu | Ser | Pro |
|---|---|---|---|---|---|---|---|---|---|---|---|---|---|---|---|
| | 115 | | | | | 120 | | | | | 125 | | | | |

| Ser | Glu | Arg | Val | Ile | Lys | Leu | Ala | Thr | Leu | Ser | Leu | Trp | Ala | Leu | Val |
|---|---|---|---|---|---|---|---|---|---|---|---|---|---|---|---|
| | 130 | | | | | 135 | | | | | 140 | | | | |

| Ser | Leu | Gly | Ser | Val | Gly | Phe | Arg | Ser | Arg | Arg | Gly | Thr | Gly | Ser | Met |
|---|---|---|---|---|---|---|---|---|---|---|---|---|---|---|---|
| 145 | | | | | 150 | | | | | 155 | | | | | 160 |

| Lys | Ile | Val | Arg | Ala | Ser | Ser | Glu | Val | Leu | Glu | Asp | Leu | Gly | Leu | Thr |
|---|---|---|---|---|---|---|---|---|---|---|---|---|---|---|---|
| | | | | 165 | | | | | 170 | | | | | 175 | |

| Thr | Glu | Phe | Asn | Ser | Ile | Asp | Glu | Phe | Lys | Asp | Ser | Leu | Lys | Arg | Val |
|---|---|---|---|---|---|---|---|---|---|---|---|---|---|---|---|
| | | | 180 | | | | | 185 | | | | | 190 | | |

| Leu | Asp | Val | Thr | Gly | Glu | Ile | Leu | Gly | Val | Lys | Asn | Ser | Glu | Thr | Asn |
|---|---|---|---|---|---|---|---|---|---|---|---|---|---|---|---|
| | | 195 | | | | | 200 | | | | | 205 | | | |

| Lys | Ser | Leu | Pro | Ser | Tyr | Ala | Thr | Leu | Lys | Phe | Ser | Asp | Val | Glu | Val |
|---|---|---|---|---|---|---|---|---|---|---|---|---|---|---|---|
| | 210 | | | | | 215 | | | | | 220 | | | | |

| Phe | Gly | Pro | Gly | Lys | Asn | Thr | Trp | Glu | Val | Leu | Ala | Gln | Phe | Asn | Asn |
|---|---|---|---|---|---|---|---|---|---|---|---|---|---|---|---|
| 225 | | | | | 230 | | | | | 235 | | | | | 240 |

| Ser | Tyr | Lys | Glu | Tyr | Leu | Arg | Arg | Ile | Lys | Lys | Tyr | Gln | Arg | Ile |
|---|---|---|---|---|---|---|---|---|---|---|---|---|---|---|
| | | | | 245 | | | | | 250 | | | | | 255 |

| Ile | Phe | Gly | Leu | Pro | Arg | Phe | Lys | Leu | Arg | Gly | Val | Arg | Lys | Asp | Leu |
|---|---|---|---|---|---|---|---|---|---|---|---|---|---|---|---|
| | | | 260 | | | | | 265 | | | | | 270 | | |

| Arg | Arg | Ala | Ser | Pro | Leu | Trp | Phe | Gly | Val | Val | Glu | Ile | Gly | Gly | Lys |
|---|---|---|---|---|---|---|---|---|---|---|---|---|---|---|---|
| | | 275 | | | | | 280 | | | | | 285 | | | |

| Pro | Tyr | Gly | Arg | Ile | Ile | Lys | Phe | Phe | Gln | Ser | Thr | Phe | His | Pro | Glu |
|---|---|---|---|---|---|---|---|---|---|---|---|---|---|---|---|
| | 290 | | | | | 295 | | | | | 300 | | | | |

| Val | Arg | Ser | Lys | His | Ile | Val | Asp | Trp | Asn | Val | Leu | Ser | Asn | Phe | Asp |
|---|---|---|---|---|---|---|---|---|---|---|---|---|---|---|---|
| 305 | | | | | 310 | | | | | 315 | | | | | 320 |

| Trp | Phe | Ile | Ser | Ser | Arg | Leu | Pro | Val | Thr | Lys | Val | Trp | Gly | Gly | Trp |
|---|---|---|---|---|---|---|---|---|---|---|---|---|---|---|---|
| | | | | 325 | | | | | 330 | | | | | 335 | |

Ser Gly

```
<210> SEQ ID NO 5
<211> LENGTH: 591
```

<212> TYPE: DNA
<213> ORGANISM: Pyrococcus furiosus

<400> SEQUENCE: 5

```
ttgctctgct ctcatggagg gatgccaatg tatgaggcaa ttttgatct tgaagcaatt     60
acccccactct tcatgcgagg tgctgatgct agaagtcctg agtttagctc tgctagtgtt    120
aaagggggtta tgaggtggtg gttcagggct ttggctggag gatactttgg gaataatata   180
gaagctctca agaagtaga ggaaaagatt tttggctcta ctagaaacaa agcagagtt     240
tttgttcgag ctgaagttga agatgttaag aaaggaaata tataccgaca agcttctagt   300
tgggcagata aaaccattat agtatggtca gaatatgttg attatttctt cttttcagtg   360
ttagacaaac gcagaaatag aaaaactaaa aaatagata taaaaactcg tttcgaatac    420
tttgatgtag gctcaaagtt tagtatttcc ttatcttcta ctgatgaaag atatttccgt    480
ctagcggaag cttctctatg gatgacaata aacctcggag gttttggttt tcgagcaaga   540
cgaggggcag gaagtttgaa agtacaaatg ctgagggaga tgttacttta a             591
```

<210> SEQ ID NO 6
<211> LENGTH: 196
<212> TYPE: PRT
<213> ORGANISM: Pyrococcus furiosus

<400> SEQUENCE: 6

```
Met Leu Cys Ser His Gly Gly Met Pro Met Tyr Glu Ala Ile Phe Asp
1               5                   10                  15

Leu Glu Ala Ile Thr Pro Leu Phe Met Arg Gly Ala Asp Ala Arg Ser
            20                  25                  30

Pro Glu Phe Ser Ser Ala Ser Val Lys Gly Val Met Arg Trp Trp Phe
        35                  40                  45

Arg Ala Leu Ala Gly Gly Tyr Phe Gly Asn Asn Ile Glu Ala Leu Lys
    50                  55                  60

Glu Val Glu Glu Lys Ile Phe Gly Ser Thr Arg Asn Lys Ser Arg Val
65                  70                  75                  80

Phe Val Arg Ala Glu Val Glu Asp Val Lys Lys Gly Asn Ile Tyr Arg
                85                  90                  95

Gln Ala Ser Ser Trp Ala Asp Lys Thr Ile Ile Val Trp Ser Glu Tyr
            100                 105                 110

Val Asp Tyr Phe Phe Phe Ser Val Leu Asp Lys Arg Arg Asn Arg Lys
        115                 120                 125

Thr Lys Lys Ile Asp Ile Lys Thr Arg Phe Glu Tyr Phe Asp Val Gly
    130                 135                 140

Ser Lys Phe Ser Ile Ser Leu Ser Ser Thr Asp Glu Arg Tyr Phe Arg
145                 150                 155                 160

Leu Ala Glu Ala Ser Leu Trp Met Thr Ile Asn Leu Gly Gly Phe Gly
                165                 170                 175

Phe Arg Ala Arg Arg Gly Ala Gly Ser Leu Lys Val Gln Met Leu Arg
            180                 185                 190

Glu Met Leu Leu
        195
```

<210> SEQ ID NO 7
<211> LENGTH: 2616
<212> TYPE: DNA
<213> ORGANISM: Pyrococcus furiosus

<400> SEQUENCE: 7

-continued

```
gtggttaaca tcaaagagaa acttttttgta taccttcatg atccaccaga caaggctcta    60
aaaattgaaa atcatgagga aaggtcaaaa aagatattaa gttctggcaa tatccagtac   120
tcgagaacgg acaaagttaa acaagcagat gcactttctt ctaagactca gagatttata   180
attcgaacaa aggaaaataa agagccagta atagatttt tgggtagatc ttcaggaaag    240
tacttccatg ttggatatcc tgtttttata caccccatat ccacagaaat taagaggtat   300
gaaacacttg aaaagtacat agaccttggc aggagtaata gaggggaaag atttgttaac   360
gagttttggg aaagggtttc aaagcttgaa ggcgatgttc tcaaagaggt ctttgaagat   420
gctagtaaca aatttaaagg agaagagagt aaacagtggg cctacatctg gcagttttat   480
cccgtaaaac tcaaagaagg agtcaaggaa tttgccaagt cagagttaaa acttaaagag   540
gaagaagcag aaaagtttgc agaggaattt gttaacctcc cagctgatac aagatttcca   600
gatcatgcaa tttggaccca tttagactta acttccgcat tatccgttaa ggatcccact   660
ttgctcagga tcaaaatagt tccagttcaa ccttttattg ccaattcaag aaagcagtta   720
gatctctggg cctccagtca tctccttca atgcttatgt ataaagcttt agaggtgata   780
gtggacaagt tcgggccaga acatgtaatc tatccatctc taagggatca acccttcttc   840
ttgaagttct acctggggga aaacataggt gatgaaatct tagttgcaaa cttgcctaac   900
aaagcgcttg caatagtctc aggaaaggag gctgaaaaga ttgaagaaga aatcaagaaa   960
agaattaggg atttcctact ccaactgtac agagaagctg ttgattgggc agttgaaaat  1020
ggagtagtaa aagtggatag aagtgaaaag gatagcatgc tcaaggaagc atatcttaaa  1080
attgtgaggg agtacttcac cgtctcgata acctgggtat ctctttccga aaaggaggat  1140
atctatcaag taacagagaa cgcgggtctc tcggatgaag atgttaagaa gtggctaaag  1200
tttgcagaaa agaaagaaaa tagtagagtt ctcgagagga ttgcaatata cccactttg   1260 gtaaagatat tggatagcct gggagagaga aaagttacag aagaaggtt cgaaaaaagc  1320 gaacaactca aaggatggaa gtgccacgtt tgtggtgaga atcttgcaat ttttggagac  1380
atgtacgatc acgataatct taagagtttg tggcttgatg aggaaccatt atgtcccatg  1440
tgtttgataa aaaggtatta tccagtgtgg attaggagta aaactggaca gaaaataagg  1500
tttgagtcgg tggtagatgt tgcacttctg tacaagaact ggaggaagat atttgacgag  1560
aagtatggaa aagacctagt ctcaaaggct agggaagtta gtgaagactt cgtaaaggac  1620
aatatgctag tagattcgga tctatactat tcttcaacct gggaatctgg actttctaaa  1680
aagctcaaaa ataagaaaga gattgatgag gaaaaagtta aggaagttgt tgacttctta  1740
aatgcggctt ataaagaaat cggtaatcca ccaaagtact atgctattct agttatggat  1800
ggcgacgata tgggaaagt tatttcagga gaggtgcttg agaaaatatc aactagaatt  1860
catccaaata ttagggatta cgttgaaatt ccagaagcaa atattactc caccccgcag   1920 gttcacgtgg ctataagcca agcattggct aactttcga taagggaagt tagatccgta  1980
gttaaagacg agggattgct aatatacgct ggaggggatg atgtcctagc aattttgcca  2040
gtcgacaaag ctttagaagt tgcatataag ataaggaaag aatttggcaa gagctttgaa  2100
aatggttctc ttctcccagg ttggaagttg agtgctggaa ttttgatagt ccattataag  2160
catccattgt atgacgccct agaaaaggca agagatcttc tcaataataa agcaaaaaac  2220
gttccaggaa aagatacact agctataggc ctacttaaga ggagtggttc ctactatatc  2280
tccctagtgg gatgggaatt aattagggtc ttctacaact cagagctgag gaaaaagcta  2340
```

-continued

```
ttggaagaga aaggtggagt gggaaagagg ttcatttatc atgtgctcag agaagttgat   2400
acttggccaa agttggaat agacgagatg cttaagtttg aggtgattag acatatcagg    2460
ggaaggaaca agaagaaac taaagagctc agagaaaaga tctatggaga aataaaggat    2520
cttcttgagc atgtaagagg gaacaatgaa gttgaaaaag ttagaggctt attcacattt   2580
ctaaaaataa tcacggacgc ggaggtgttt ccatga                              2616
```

<210> SEQ ID NO 8
<211> LENGTH: 871
<212> TYPE: PRT
<213> ORGANISM: Pyrococcus furiosus

<400> SEQUENCE: 8

```
Met Val Asn Ile Lys Glu Lys Leu Phe Val Tyr Leu His Asp Pro Pro
 1               5                  10                  15

Asp Lys Ala Leu Lys Ile Glu Asn His Glu Glu Arg Ser Lys Lys Ile
             20                  25                  30

Leu Ser Ser Gly Asn Ile Gln Tyr Ser Arg Thr Asp Lys Val Lys Gln
         35                  40                  45

Ala Asp Ala Leu Ser Ser Lys Thr Gln Arg Phe Ile Ile Arg Thr Lys
     50                  55                  60

Glu Asn Lys Glu Pro Val Ile Asp Phe Leu Gly Arg Ser Ser Gly Lys
 65                  70                  75                  80

Tyr Phe His Val Gly Tyr Pro Val Phe Ile His Pro Ile Ser Thr Glu
                 85                  90                  95

Ile Lys Arg Tyr Glu Thr Leu Glu Lys Tyr Ile Asp Leu Gly Arg Ser
            100                 105                 110

Asn Arg Gly Glu Arg Phe Val Asn Glu Phe Leu Glu Arg Val Ser Lys
        115                 120                 125

Leu Glu Gly Asp Val Leu Lys Glu Val Phe Glu Asp Ala Ser Asn Lys
    130                 135                 140

Phe Lys Gly Glu Glu Ser Lys Gln Trp Ala Tyr Ile Trp Gln Phe Tyr
145                 150                 155                 160

Pro Val Lys Leu Lys Glu Gly Val Lys Glu Phe Ala Lys Ser Glu Leu
                165                 170                 175

Lys Leu Lys Glu Glu Glu Ala Glu Lys Phe Ala Glu Glu Phe Val Asn
            180                 185                 190

Leu Pro Ala Asp Thr Arg Phe Pro Asp His Ala Ile Trp Thr His Leu
        195                 200                 205

Asp Leu Thr Ser Ala Leu Ser Val Lys Asp Pro Thr Leu Leu Arg Ile
    210                 215                 220

Lys Ile Val Pro Val Gln Pro Phe Ile Ala Asn Ser Arg Lys Gln Leu
225                 230                 235                 240

Asp Leu Trp Ala Ser Ser His Leu Leu Ser Met Leu Met Tyr Lys Ala
                245                 250                 255

Leu Glu Val Ile Val Asp Lys Phe Gly Pro Glu His Val Ile Tyr Pro
            260                 265                 270

Ser Leu Arg Asp Gln Pro Phe Phe Leu Lys Phe Tyr Leu Gly Glu Asn
        275                 280                 285

Ile Gly Asp Glu Ile Leu Val Ala Asn Leu Pro Asn Lys Ala Leu Ala
    290                 295                 300

Ile Val Ser Gly Lys Glu Ala Glu Lys Ile Glu Glu Ile Lys Lys
305                 310                 315                 320

Arg Ile Arg Asp Phe Leu Leu Gln Leu Tyr Arg Glu Ala Val Asp Trp
```

```
                    325                 330                 335
Ala Val Glu Asn Gly Val Val Lys Val Asp Arg Ser Glu Lys Asp Ser
                340                 345                 350
Met Leu Lys Glu Ala Tyr Leu Lys Ile Val Arg Glu Tyr Phe Thr Val
                355                 360                 365
Ser Ile Thr Trp Val Ser Leu Ser Glu Lys Glu Asp Ile Tyr Gln Val
                370                 375                 380
Thr Glu Asn Ala Gly Leu Ser Asp Glu Asp Val Lys Lys Trp Leu Lys
385                 390                 395                 400
Phe Ala Glu Lys Lys Glu Asn Ser Arg Val Leu Glu Arg Ile Ala Ile
                405                 410                 415
Tyr Pro Leu Leu Val Lys Ile Leu Asp Ser Leu Gly Glu Arg Lys Val
                420                 425                 430
Thr Glu Glu Arg Phe Glu Lys Ser Glu Gln Leu Lys Gly Trp Lys Cys
                435                 440                 445
His Val Cys Gly Glu Asn Leu Ala Ile Phe Gly Asp Met Tyr Asp His
                450                 455                 460
Asp Asn Leu Lys Ser Leu Trp Leu Asp Glu Glu Pro Leu Cys Pro Met
465                 470                 475                 480
Cys Leu Ile Lys Arg Tyr Tyr Pro Val Trp Ile Arg Ser Lys Thr Gly
                485                 490                 495
Gln Lys Ile Arg Phe Glu Ser Val Val Asp Val Ala Leu Leu Tyr Lys
                500                 505                 510
Asn Trp Arg Lys Ile Phe Asp Glu Lys Tyr Gly Lys Asp Leu Val Ser
                515                 520                 525
Lys Ala Arg Glu Val Ser Glu Asp Phe Val Lys Asp Asn Met Leu Val
                530                 535                 540
Asp Ser Asp Leu Tyr Tyr Ser Ser Thr Trp Glu Ser Gly Leu Ser Lys
545                 550                 555                 560
Lys Leu Lys Asn Lys Lys Glu Ile Asp Glu Glu Lys Val Lys Glu Val
                565                 570                 575
Val Asp Phe Leu Asn Ala Ala Tyr Lys Glu Ile Gly Asn Pro Pro Lys
                580                 585                 590
Tyr Tyr Ala Ile Leu Val Met Asp Gly Asp Asp Met Gly Lys Val Ile
                595                 600                 605
Ser Gly Glu Val Leu Gly Glu Ile Ser Thr Arg Ile His Pro Asn Ile
                610                 615                 620
Arg Asp Tyr Val Glu Ile Pro Glu Ala Lys Tyr Tyr Ser Thr Pro Gln
625                 630                 635                 640
Val His Val Ala Ile Ser Gln Ala Leu Ala Asn Phe Ser Ile Arg Glu
                645                 650                 655
Val Arg Ser Val Val Lys Asp Glu Gly Leu Leu Ile Tyr Ala Gly Gly
                660                 665                 670
Asp Asp Val Leu Ala Ile Leu Pro Val Asp Lys Ala Leu Glu Val Ala
                675                 680                 685
Tyr Lys Ile Arg Lys Glu Phe Gly Lys Ser Phe Glu Asn Gly Ser Leu
                690                 695                 700
Leu Pro Gly Trp Lys Leu Ser Ala Gly Ile Leu Ile Val His Tyr Lys
705                 710                 715                 720
His Pro Leu Tyr Asp Ala Leu Glu Lys Ala Arg Asp Leu Leu Asn Asn
                725                 730                 735
Lys Ala Lys Asn Val Pro Gly Lys Asp Thr Leu Ala Ile Gly Leu Leu
                740                 745                 750
```

```
Lys Arg Ser Gly Ser Tyr Tyr Ile Ser Leu Val Gly Trp Glu Leu Ile
        755                 760                 765

Arg Val Phe Tyr Asn Ser Glu Leu Arg Lys Lys Leu Leu Glu Glu Lys
        770                 775                 780

Gly Gly Val Gly Lys Arg Phe Ile Tyr His Val Leu Arg Glu Val Asp
785                 790                 795                 800

Thr Trp Pro Lys Val Gly Ile Asp Glu Met Leu Lys Phe Glu Val Ile
                805                 810                 815

Arg His Ile Arg Gly Arg Asn Lys Glu Glu Thr Lys Glu Leu Arg Glu
                820                 825                 830

Lys Ile Tyr Gly Glu Ile Lys Asp Leu Leu Glu His Val Arg Gly Asn
        835                 840                 845

Asn Glu Val Glu Lys Val Arg Gly Leu Phe Thr Phe Leu Lys Ile Ile
        850                 855                 860

Thr Asp Ala Glu Val Phe Pro
865                 870

<210> SEQ ID NO 9
<211> LENGTH: 969
<212> TYPE: DNA
<213> ORGANISM: Pyrococcus furiosus

<400> SEQUENCE: 9
atgattgagg ttacttttac tccttatgat gtcctcttat ttagagaaag taggcctttt      60
gatgcaggaa gtgaaagtgt ggcaagatca attattcctc ttccccaaac agtcgctggc     120
gctataagga ctcttttatt ctacaaaggc ctcaagaatt gtgttggagt gggtgaggag     180
gaacccgaat ttacgttagt tgggattgca attggaacag agaaaggcag aatttacccc     240
cttcccttca atatcataaa aagcgagaaa ttctacaaag ttgtcaaccc aggtagattt     300
ttagggaagt taattcttcc tccaaaagga agtacaagag tggctatgt aactgaaagc     360 atattggaaa gtatttgaa gggagaatta aaagaagtag aagaaaataa agtaataagg     420
attgaaaagg aaaaaaggat tggcattaag cttctctaga gaagaaagt agttgaagag     480 ggaatgctat atactgttga attcctaaga attgagaaaa tttacgcttg gatagaagac     540
ccaggatgcg gaatcaaaga tattttgtca tcatatgagt tcttaacgtt aggaggagaa     600
agtagagttg cttttgtgga gtggacgac aaaacacccg atatatttaa tagagaatta     660
ggatcaacaa gaaagcccct cttctatttc tcaactccca caatagggaa agttggagaa     720
atagtacaag aacttgagaa agattgaat gcaaaaattg atgattatct tcttgtttcc     780
tctagaccta cagcaatttc tgggtgggat atgcatgaaa agaagccaaa aggtactaaa     840
tttgcgatac ctcctggttc agttctcttt gtagagttta aggaggaagt agaagttccc     900
ccctacatta agcttggtaa gttaaagaaa cttggctatg gcttgctttt aggagggata     960
tgggaatga                                                            969

<210> SEQ ID NO 10
<211> LENGTH: 322
<212> TYPE: PRT
<213> ORGANISM: Pyrococcus furiosus

<400> SEQUENCE: 10

Met Ile Glu Val Thr Phe Thr Pro Tyr Asp Val Leu Leu Phe Arg Glu
1               5                   10                  15

Ser Arg Pro Phe Asp Ala Gly Ser Glu Ser Val Ala Arg Ser Ile Ile
```

```
                    20                  25                  30
Pro Leu Pro Gln Thr Val Ala Gly Ala Ile Arg Thr Leu Leu Phe Tyr
             35                  40                  45

Lys Gly Leu Lys Asn Cys Val Gly Val Gly Glu Glu Pro Glu Phe
 50                  55                  60

Thr Leu Val Gly Ile Ala Ile Gly Thr Glu Lys Gly Arg Ile Tyr Pro
 65                  70                  75                  80

Leu Pro Phe Asn Ile Ile Lys Ser Glu Lys Phe Tyr Lys Val Asn
             85                  90                  95

Pro Gly Arg Phe Leu Gly Lys Leu Ile Leu Pro Pro Lys Gly Lys Tyr
             100                 105                 110

Lys Ser Gly Tyr Val Thr Glu Ser Ile Leu Glu Lys Tyr Leu Lys Gly
     115                 120                 125

Glu Leu Lys Glu Val Glu Asn Lys Val Ile Arg Ile Glu Lys Glu
         130                 135                 140

Lys Arg Ile Gly Ile Lys Leu Ser Arg Glu Lys Lys Val Val Glu Glu
145                 150                 155                 160

Gly Met Leu Tyr Thr Val Glu Phe Leu Arg Ile Glu Lys Ile Tyr Ala
                 165                 170                 175

Trp Ile Glu Asp Pro Gly Cys Gly Ile Lys Asp Ile Leu Ser Ser Tyr
             180                 185                 190

Glu Phe Leu Thr Leu Gly Gly Glu Ser Arg Val Ala Phe Val Glu Val
         195                 200                 205

Asp Asp Lys Thr Pro Asp Ile Phe Asn Arg Glu Leu Gly Ser Thr Lys
 210                 215                 220

Lys Ala Leu Phe Tyr Phe Ser Thr Pro Thr Ile Gly Lys Val Gly Glu
225                 230                 235                 240

Ile Val Gln Glu Leu Glu Lys Arg Leu Asn Ala Lys Ile Asp Asp Tyr
                 245                 250                 255

Leu Leu Val Ser Ser Arg Pro Thr Ala Ile Ser Gly Trp Asp Met His
             260                 265                 270

Glu Lys Lys Pro Lys Gly Thr Lys Phe Ala Ile Pro Pro Gly Ser Val
         275                 280                 285

Leu Phe Val Glu Phe Lys Glu Glu Val Glu Val Pro Pro Tyr Ile Lys
 290                 295                 300

Leu Gly Lys Leu Lys Lys Leu Gly Tyr Gly Leu Ala Leu Gly Gly Ile
305                 310                 315                 320

Trp Glu

<210> SEQ ID NO 11
<211> LENGTH: 888
<212> TYPE: DNA
<213> ORGANISM: Pyrococcus furiosus

<400> SEQUENCE: 11
atgaaggcat atttagttgg gttatatacc ttaactccaa cccacccggg aagtggaact     60
gagcttggag tggtagacca accaattcag agagaaagac acacaggatt ccagtaatt    120 tgggccaga gtctcaaggg tgtattaagg agctacctta aattggtaga aaaggttgat    180
gaggagaaga taaacaaaat atttggccca ccgacagaaa agctcatga gcaggctggg    240 ctaataagtg tcggagatgc aaagatacta ttcttccctg ttagaagtct aaaaggtgtt    300
tacgcatacg taacttctcc actagttctt aacaggttca aaagagactt agagctagct    360
ggggttaaga attttcagac agaaattccc gagttaacag ataccgcaat tgcaagtgaa    420
```

```
gaaattacag ttgataacaa ggtgattctt gaagaatttg caattctcat tcaaaggat     480 gacaaaggaa ttttggaaag tgtagttaaa gctattgaac aagcctttgg aaatgaaatg     540
gcagagaaaa taaagggtag aattgccata atcccagatg acgtgtttag agatttagtg     600
gagctgtcga cagaaatagt agctaggata agaattaatg ctgagacagg aactgtagaa     660
actggaggac tgtggtatga ggagtatatt ccttcggaca cattgttcta ctcactaata     720
cttgtaactc ccagggcaaa ggataatgat atggccctaa tcaaagaagt tctaggaaag     780
attaacggca atatctcca gattggaggt aatgaaaccg ttgggaaggg cttcgtcaaa     840
gttactctta aagaggtgac caacaatgga ggtacacatg ctaagtaa                 888
```

<210> SEQ ID NO 12
<211> LENGTH: 295
<212> TYPE: PRT
<213> ORGANISM: Pyrococcus furiosus

<400> SEQUENCE: 12

```
Met Lys Ala Tyr Leu Val Gly Leu Tyr Thr Leu Thr Pro Thr His Pro
1               5                   10                  15

Gly Ser Gly Thr Glu Leu Gly Val Val Asp Gln Pro Ile Gln Arg Glu
            20                  25                  30

Arg His Thr Gly Phe Pro Val Ile Trp Gly Gln Ser Leu Lys Gly Val
        35                  40                  45

Leu Arg Ser Tyr Leu Lys Leu Val Glu Lys Val Asp Glu Glu Lys Ile
    50                  55                  60

Asn Lys Ile Phe Gly Pro Pro Thr Glu Lys Ala His Glu Gln Ala Gly
65                  70                  75                  80

Leu Ile Ser Val Gly Asp Ala Lys Ile Leu Phe Phe Pro Val Arg Ser
                85                  90                  95

Leu Lys Gly Val Tyr Ala Tyr Val Thr Ser Pro Leu Val Leu Asn Arg
            100                 105                 110

Phe Lys Arg Asp Leu Glu Leu Ala Gly Val Lys Asn Phe Gln Thr Glu
        115                 120                 125

Ile Pro Glu Leu Thr Asp Thr Ala Ile Ala Ser Glu Glu Ile Thr Val
    130                 135                 140

Asp Asn Lys Val Ile Leu Glu Glu Phe Ala Ile Leu Ile Gln Lys Asp
145                 150                 155                 160

Asp Lys Gly Ile Leu Glu Ser Val Val Lys Ala Ile Glu Gln Ala Phe
                165                 170                 175

Gly Asn Glu Met Ala Glu Lys Ile Lys Gly Arg Ile Ala Ile Ile Pro
            180                 185                 190

Asp Asp Val Phe Arg Asp Leu Val Glu Leu Ser Thr Glu Ile Val Ala
        195                 200                 205

Arg Ile Arg Ile Asn Ala Glu Thr Gly Thr Val Glu Thr Gly Gly Leu
    210                 215                 220

Trp Tyr Glu Glu Tyr Ile Pro Ser Asp Thr Leu Phe Tyr Ser Leu Ile
225                 230                 235                 240

Leu Val Thr Pro Arg Ala Lys Asp Asn Asp Met Ala Leu Ile Lys Glu
                245                 250                 255

Val Leu Gly Lys Ile Asn Gly Lys Tyr Leu Gln Ile Gly Gly Asn Glu
            260                 265                 270

Thr Val Gly Lys Gly Phe Val Lys Val Thr Leu Lys Glu Val Thr Asn
        275                 280                 285
```

Asn Gly Gly Thr His Ala Lys
    290                 295

<210> SEQ ID NO 13
<211> LENGTH: 510
<212> TYPE: DNA
<213> ORGANISM: Pyrococcus furiosus

<400> SEQUENCE: 13

```
atggaggtac acatgctaag taaagataac aagaaaagca taagaaaaac tctagaacag      60
cggaggggcg agtatgctta ctatgtgata aagaagtgg cagatcttaa tgacaagcaa      120
cttgaggaaa agtatgcctc cctagttaag aaagccccag tcatgatatt gtccaatggt      180
ctccttcaga cgcttgcatt tttacttgca aaggccgaga cttcaccaga aaaagctaat      240
cagatcttga gtagagtcaa tgaataccca cctaggttca tcgaaaagct tgggaatgac      300
aaagacgagc accttctcct gtaccttcac atagtctact ggttgaggga aatgtagac       360 agaaacatcg atgtgaaaac tctattatcc caggattatt caaaagttct gtgggcaaca     420
aaagaagcaa tagcgctcct gaactggatg aggagattcg ctgttgcaat gctcaaggaa     480 gagggaaag agaatgaagg aagtagttaa                                        510
```

<210> SEQ ID NO 14
<211> LENGTH: 169
<212> TYPE: PRT
<213> ORGANISM: Pyrococcus furiosus

<400> SEQUENCE: 14

Met Glu Val His Met Leu Ser Lys Asp Asn Lys Ser Ile Arg Lys
1               5                   10                  15

Thr Leu Glu Gln Arg Arg Gly Glu Tyr Ala Tyr Tyr Val Ile Lys Glu
            20                  25                  30

Val Ala Asp Leu Asn Asp Lys Gln Leu Glu Glu Lys Tyr Ala Ser Leu
        35                  40                  45

Val Lys Lys Ala Pro Val Met Ile Leu Ser Asn Gly Leu Leu Gln Thr
    50                  55                  60

Leu Ala Phe Leu Leu Ala Lys Ala Glu Thr Ser Pro Glu Lys Ala Asn
65                  70                  75                  80

Gln Ile Leu Ser Arg Val Asn Glu Tyr Pro Pro Arg Phe Ile Glu Lys
                85                  90                  95

Leu Gly Asn Asp Lys Asp Glu His Leu Leu Leu Tyr Leu His Ile Val
            100                 105                 110

Tyr Trp Leu Arg Glu Asn Val Asp Arg Asn Ile Asp Val Lys Thr Leu
        115                 120                 125

Leu Ser Gln Asp Tyr Ser Lys Val Leu Trp Ala Thr Lys Glu Ala Ile
    130                 135                 140

Ala Leu Leu Asn Trp Met Arg Arg Phe Ala Val Ala Met Leu Lys Glu
145                 150                 155                 160

Glu Gly Lys Glu Asn Glu Gly Ser Ser
                165

<210> SEQ ID NO 15
<211> LENGTH: 1023
<212> TYPE: DNA
<213> ORGANISM: Pyrococcus furiosus

<400> SEQUENCE: 15

```
atgaaggaag tagttaaatt ggttctcctg ggggagagac agaactccct taacctctca      60
```

-continued

```
ctatacttca acaaatatcc tccaaccata atctatccag aggtactgga agataggaac      120
aagaaacttg cttcaccctc aggatcacag agaaagatat ccctcttggt cttaaatcaa      180
ggggttcttc agtttaacaa aataaaagag acaatagaaa agtcgttgcc aattgaaact      240
aaggtaaaac ttcctcaaaa agcatatgaa ttgtacaaga atactacca ggattacact       300 gacatgctta actcattaca cgccattact ggaaagttta agactcaatc aaggctcgta      360
gttgggcttg gtgatgaaag cgtttatgag acaagcataa ggcttcttag aaactatgga      420
gtgccttaca ttcctgggtc cgcaattaag ggagttacta ggcacttaac ttactacgtt      480
ctagcagaat ttatcaatga aggaaatgat ttctataaga gggcaaagac tgttcaggat      540
gcatttatga aggtgatcc taaagaaatt ctttccaatg ctaaggtacc ggaaaggtgt       600
agtaggcttt gtaaagaatt tctcagaata tttggagaga aaaaggttcc agagattata     660
gatgaactca taagaatctt cggaacccag aaaaagaag gagaagttgt attctttgat      720
gcaataccca tagctgaaga gatagcagat aagccgatct tggagttaga cataatgaat      780
cctcactatg ggccgtatta tcaaagtgga gagaaaaatg tccccacctcc tggggactgg    840 tatgatccca tcccaatatt cttcctcaca gtaccaaagg atgtcccctt cctagttgcc     900
gttggtggca gagatagaga acttacagaa aaggccttta gcctcgttaa gttggccctt    960
agagaccttg gtgttggtgc aaaaacttct cttggctatg ggaggcttgt tgaatatgtt    1020
tag                                                                 1023
```

<210> SEQ ID NO 16
<211> LENGTH: 340
<212> TYPE: PRT
<213> ORGANISM: Pyrococcus furiosus

<400> SEQUENCE: 16

```
Met Lys Glu Val Val Lys Leu Val Leu Leu Gly Glu Arg Gln Asn Ser
1               5                   10                  15

Leu Asn Leu Ser Leu Tyr Phe Asn Lys Tyr Pro Pro Thr Ile Ile Tyr
            20                  25                  30

Pro Glu Val Leu Glu Asp Arg Asn Lys Lys Leu Ala Ser Pro Ser Gly
        35                  40                  45

Ser Gln Arg Lys Ile Ser Leu Leu Val Leu Asn Gln Gly Val Leu Gln
    50                  55                  60

Phe Asn Lys Ile Lys Glu Thr Ile Glu Lys Ser Leu Pro Ile Glu Thr
65                  70                  75                  80

Lys Val Lys Leu Pro Gln Lys Ala Tyr Glu Leu Tyr Lys Lys Tyr Tyr
                85                  90                  95

Gln Asp Tyr Thr Asp Met Leu Asn Ser Leu His Ala Ile Thr Gly Lys
            100                 105                 110

Phe Lys Thr Gln Ser Arg Leu Val Val Gly Leu Gly Asp Glu Ser Val
        115                 120                 125

Tyr Glu Thr Ser Ile Arg Leu Leu Arg Asn Tyr Gly Val Pro Tyr Ile
    130                 135                 140

Pro Gly Ser Ala Ile Lys Gly Val Thr Arg His Leu Thr Tyr Tyr Val
145                 150                 155                 160

Leu Ala Glu Phe Ile Asn Glu Gly Asn Asp Phe Tyr Lys Arg Ala Lys
                165                 170                 175

Thr Val Gln Asp Ala Phe Met Lys Gly Asp Pro Lys Glu Ile Leu Ser
            180                 185                 190
```

```
Asn Ala Lys Val Pro Glu Arg Cys Ser Arg Leu Cys Lys Glu Phe Leu
            195                 200                 205

Arg Ile Phe Gly Glu Lys Lys Val Pro Glu Ile Asp Glu Leu Ile
210                 215                 220

Arg Ile Phe Gly Thr Gln Lys Lys Glu Gly Glu Val Val Phe Phe Asp
225                 230                 235                 240

Ala Ile Pro Ile Ala Glu Glu Ile Ala Asp Lys Pro Ile Leu Glu Leu
                245                 250                 255

Asp Ile Met Asn Pro His Tyr Gly Pro Tyr Tyr Gln Ser Gly Glu Lys
            260                 265                 270

Asn Val Pro Pro Pro Gly Asp Trp Tyr Asp Pro Ile Pro Ile Phe Phe
            275                 280                 285

Leu Thr Val Pro Lys Asp Val Pro Phe Leu Val Ala Val Gly Gly Arg
            290                 295                 300

Asp Arg Glu Leu Thr Glu Lys Ala Phe Ser Leu Val Lys Leu Ala Leu
305                 310                 315                 320

Arg Asp Leu Gly Val Gly Ala Lys Thr Ser Leu Gly Tyr Gly Arg Leu
                325                 330                 335

Val Glu Tyr Val
            340

<210> SEQ ID NO 17
<211> LENGTH: 45
<212> TYPE: RNA
<213> ORGANISM: artificial
<220> FEATURE:
<223> OTHER INFORMATION: psiRNA

<400> SEQUENCE: 17
auugaaaguu guaguaugcg guccuugcgg cugagagcac uucag            45

<210> SEQ ID NO 18
<211> LENGTH: 37
<212> TYPE: RNA
<213> ORGANISM: artificial
<220> FEATURE:
<223> OTHER INFORMATION: target polynucleotide
<220> FEATURE:
<221> NAME/KEY: misc_feature
<222> LOCATION: (14)..(15)
<223> OTHER INFORMATION: cleavage site

<400> SEQUENCE: 18
cugaagugcu cucagccgca aggaccgcau acuacaa                     37

<210> SEQ ID NO 19
<211> LENGTH: 10
<212> TYPE: RNA
<213> ORGANISM: artificial
<220> FEATURE:
<223> OTHER INFORMATION: psiRNA tag

<400> SEQUENCE: 19
gaauugaaag                                                   10

<210> SEQ ID NO 20
<211> LENGTH: 45
<212> TYPE: RNA
<213> ORGANISM: artificial
<220> FEATURE:
<223> OTHER INFORMATION: exogenous psiRNA

<400> SEQUENCE: 20
```
auugaaagcu gaagugcucu cagccgcaag gaccgcauac uacaa        45

<210> SEQ ID NO 21
<211> LENGTH: 37
<212> TYPE: RNA
<213> ORGANISM: artificial
<220> FEATURE:
<223> OTHER INFORMATION: exogenous target

<400> SEQUENCE: 21
uuguaguaug cgguccuugc ggcugagagc acuucag        37

<210> SEQ ID NO 22
<211> LENGTH: 45
<212> TYPE: RNA
<213> ORGANISM: artificial
<220> FEATURE:
<223> OTHER INFORMATION: bla psiRNA

<400> SEQUENCE: 22
auugaaagcu gaagugcucu cagccgcaag gaccgcauac uacaa        45

<210> SEQ ID NO 23
<211> LENGTH: 37
<212> TYPE: RNA
<213> ORGANISM: artificial
<220> FEATURE:
<223> OTHER INFORMATION: bla target

<400> SEQUENCE: 23
augaguauuc aacauuuccg ugucgcccuu auucccu        37

<210> SEQ ID NO 24
<211> LENGTH: 31
<212> TYPE: RNA
<213> ORGANISM: artificial
<220> FEATURE:
<223> OTHER INFORMATION: 3' region of psiRNA tag
<220> FEATURE:
<221> NAME/KEY: misc_feature
<222> LOCATION: (1)..(31)
<223> OTHER INFORMATION: n may be any nucleotide
<220> FEATURE:
<221> NAME/KEY: misc_feature
<222> LOCATION: (17)..(18)
<223> OTHER INFORMATION: cleavage site

<400> SEQUENCE: 24
nnnnnnnnnn nnnnnnnnnn nnnnnnnnnn n        31

<210> SEQ ID NO 25
<211> LENGTH: 43
<212> TYPE: RNA
<213> ORGANISM: artificial
<220> FEATURE:
<223> OTHER INFORMATION: 3' region of psiRNA tag
<220> FEATURE:
<221> NAME/KEY: misc_feature
<222> LOCATION: (1)..(43)
<223> OTHER INFORMATION: n may be any nucleotide
<220> FEATURE:
<221> NAME/KEY: misc_feature
<222> LOCATION: (23)..(24)
<223> OTHER INFORMATION: cleavage site

<400> SEQUENCE: 25
nnnnnnnnnn nnnnnnnnnn nnnnnnnnnn nnnnnnnnnn nnn        43

```
<210> SEQ ID NO 26
<211> LENGTH: 20
<212> TYPE: DNA
<213> ORGANISM: artificial
<220> FEATURE:
<223> OTHER INFORMATION: oligonucleotide
<220> FEATURE:
<221> NAME/KEY: modified_base
<222> LOCATION: (1)..(1)
<223> OTHER INFORMATION: phosphorylated cytidine
<220> FEATURE:
<221> NAME/KEY: modified_base
<222> LOCATION: (20)..(20)
<223> OTHER INFORMATION: dideoxy cytidine

<400> SEQUENCE: 26
ctcgagatct ggatccgggc                                              20

<210> SEQ ID NO 27
<211> LENGTH: 19
<212> TYPE: DNA
<213> ORGANISM: artificial
<220> FEATURE:
<223> OTHER INFORMATION: primer

<400> SEQUENCE: 27
cccggatcca gatctcgag                                               19

<210> SEQ ID NO 28
<211> LENGTH: 44
<212> TYPE: DNA
<213> ORGANISM: artificial
<220> FEATURE:
<223> OTHER INFORMATION: primer

<400> SEQUENCE: 28
gcgaattctg cagttttttt tttttttttt tttttttttt tttt                   44

<210> SEQ ID NO 29
<211> LENGTH: 45
<212> TYPE: DNA
<213> ORGANISM: artificial
<220> FEATURE:
<223> OTHER INFORMATION: synthetic psiRNA

<400> SEQUENCE: 29
attgaaagtt gtagtatgcg gtccttgcgg ctgagagcac ttcag                  45

<210> SEQ ID NO 30
<211> LENGTH: 39
<212> TYPE: DNA
<213> ORGANISM: artificial
<220> FEATURE:
<223> OTHER INFORMATION: synthetic psiRNA

<400> SEQUENCE: 30
attgaaagtt gtagtatgcg gtccttgcgg ctgagagca                         39

<210> SEQ ID NO 31
<211> LENGTH: 20
<212> TYPE: DNA
<213> ORGANISM: artificial
<220> FEATURE:
<223> OTHER INFORMATION: primer
<220> FEATURE:
<221> NAME/KEY: modified_base
<222> LOCATION: (1)..(1)
<223> OTHER INFORMATION: adenylated adenine
```

```
<220> FEATURE:
<221> NAME/KEY: modified_base
<222> LOCATION: (20)..(20)
<223> OTHER INFORMATION: dideoxy cytidine

<400> SEQUENCE: 31
atttaaccgc gaattccagc                                              20

<210> SEQ ID NO 32
<211> LENGTH: 18
<212> TYPE: DNA
<213> ORGANISM: artificial
<220> FEATURE:
<223> OTHER INFORMATION: primer
<220> FEATURE:
<221> NAME/KEY: misc_RNA
<222> LOCATION: (16)..(18)
<223> OTHER INFORMATION: ribonucleotides

<400> SEQUENCE: 32
acggaattcc tcactaaa                                                18

<210> SEQ ID NO 33
<211> LENGTH: 24
<212> TYPE: DNA
<213> ORGANISM: artificial
<220> FEATURE:
<223> OTHER INFORMATION: primer

<400> SEQUENCE: 33
gactagctgg aattcgcggt taaa                                         24

<210> SEQ ID NO 34
<211> LENGTH: 24
<212> TYPE: DNA
<213> ORGANISM: artificial
<220> FEATURE:
<223> OTHER INFORMATION: primer

<400> SEQUENCE: 34
cagccaacgg aattcctcac taaa                                         24

<210> SEQ ID NO 35
<211> LENGTH: 30
<212> TYPE: DNA
<213> ORGANISM: artificial
<220> FEATURE:
<223> OTHER INFORMATION: primer

<400> SEQUENCE: 35
gactagcttg gtgccgaatt cgcggttaaa                                   30

<210> SEQ ID NO 36
<211> LENGTH: 30
<212> TYPE: DNA
<213> ORGANISM: artificial
<220> FEATURE:
<223> OTHER INFORMATION: primer

<400> SEQUENCE: 36
gagccaacag gcaccgaatt cctcactaaa                                   30

<210> SEQ ID NO 37
<211> LENGTH: 32
<212> TYPE: DNA
<213> ORGANISM: artificial
<220> FEATURE:
```

<223> OTHER INFORMATION: probe

<400> SEQUENCE: 37
ctttcaattc tattttaggt cttattcgta ac                          32

<210> SEQ ID NO 38
<211> LENGTH: 32
<212> TYPE: DNA
<213> ORGANISM: artificial
<220> FEATURE:
<223> OTHER INFORMATION: probe

<400> SEQUENCE: 38
gttaccaata agactcaaaa tagaattgaa ag                          32

<210> SEQ ID NO 39
<211> LENGTH: 30
<212> TYPE: DNA
<213> ORGANISM: artificial
<220> FEATURE:
<223> OTHER INFORMATION: probe

<400> SEQUENCE: 39
ctttcaattc ttttgtagtc ttattggaac                             30

<210> SEQ ID NO 40
<211> LENGTH: 30
<212> TYPE: DNA
<213> ORGANISM: artificial
<220> FEATURE:
<223> OTHER INFORMATION: probe

<400> SEQUENCE: 40
gttccaataa gactacaaaa gaattgaaag                             30

<210> SEQ ID NO 41
<211> LENGTH: 31
<212> TYPE: DNA
<213> ORGANISM: artificial
<220> FEATURE:
<223> OTHER INFORMATION: probe

<400> SEQUENCE: 41
ggtcagatca gattgcttaa gacaagaaat g                           31

<210> SEQ ID NO 42
<211> LENGTH: 31
<212> TYPE: DNA
<213> ORGANISM: artificial
<220> FEATURE:
<223> OTHER INFORMATION: probe

<400> SEQUENCE: 42
catttcttgt cttaagcaat ctgatctgac c                           31

<210> SEQ ID NO 43
<211> LENGTH: 28
<212> TYPE: DNA
<213> ORGANISM: artificial
<220> FEATURE:
<223> OTHER INFORMATION: probe

<400> SEQUENCE: 43
gtggagcaga gtcagaagaa gaagtgcg                               28

```
<210> SEQ ID NO 44
<211> LENGTH: 28
<212> TYPE: DNA
<213> ORGANISM: artificial
<220> FEATURE:
<223> OTHER INFORMATION: probe

<400> SEQUENCE: 44
cgcacttctt cttctgactc tgctccac                                        28

<210> SEQ ID NO 45
<211> LENGTH: 31
<212> TYPE: DNA
<213> ORGANISM: artificial
<220> FEATURE:
<223> OTHER INFORMATION: probe

<400> SEQUENCE: 45
tctgataggc ttcaaagagt ggcgcttcaa c                                    31

<210> SEQ ID NO 46
<211> LENGTH: 31
<212> TYPE: DNA
<213> ORGANISM: artificial
<220> FEATURE:
<223> OTHER INFORMATION: probe

<400> SEQUENCE: 46
gttgaagcgc cactctttga agcctatcag a                                    31

<210> SEQ ID NO 47
<211> LENGTH: 30
<212> TYPE: DNA
<213> ORGANISM: artificial
<220> FEATURE:
<223> OTHER INFORMATION: probe

<400> SEQUENCE: 47
gggaatggtt cacgtagtac ttgagggcgc                                      30

<210> SEQ ID NO 48
<211> LENGTH: 30
<212> TYPE: DNA
<213> ORGANISM: artificial
<220> FEATURE:
<223> OTHER INFORMATION: probe

<400> SEQUENCE: 48
gcgccctcaa gtactacgtg aaccattccc                                      30

<210> SEQ ID NO 49
<211> LENGTH: 30
<212> TYPE: DNA
<213> ORGANISM: artificial
<220> FEATURE:
<223> OTHER INFORMATION: probe

<400> SEQUENCE: 49
ctaaggacat ttgtacgtca aattcttcac                                      30

<210> SEQ ID NO 50
<211> LENGTH: 30
<212> TYPE: DNA
<213> ORGANISM: artificial
<220> FEATURE:
<223> OTHER INFORMATION: probe
```

<400> SEQUENCE: 50
gtgaagaatt tgacgtacaa atgtccttag                                30

<210> SEQ ID NO 51
<211> LENGTH: 25
<212> TYPE: DNA
<213> ORGANISM: artificial
<220> FEATURE:
<223> OTHER INFORMATION: probe

<400> SEQUENCE: 51
gctctcagcc gcaaggaccg catac                                     25

<210> SEQ ID NO 52
<211> LENGTH: 25
<212> TYPE: DNA
<213> ORGANISM: artificial
<220> FEATURE:
<223> OTHER INFORMATION: probe

<400> SEQUENCE: 52
gtatgcggtc cttgcggctg agagc                                     25

<210> SEQ ID NO 53
<211> LENGTH: 32
<212> TYPE: DNA
<213> ORGANISM: artificial
<220> FEATURE:
<223> OTHER INFORMATION: probe

<400> SEQUENCE: 53
ccttatatgg gtgttgtgaa gcaggataga ac                             32

<210> SEQ ID NO 54
<211> LENGTH: 32
<212> TYPE: DNA
<213> ORGANISM: artificial
<220> FEATURE:
<223> OTHER INFORMATION: probe

<400> SEQUENCE: 54
gttctatcct gcttcacaac acccatataa gg                             32

<210> SEQ ID NO 55
<211> LENGTH: 30
<212> TYPE: DNA
<213> ORGANISM: artificial
<220> FEATURE:
<223> OTHER INFORMATION: probe

<400> SEQUENCE: 55
ggctctacct aatcatcctc ttgacacaac                                30

<210> SEQ ID NO 56
<211> LENGTH: 30
<212> TYPE: DNA
<213> ORGANISM: artificial
<220> FEATURE:
<223> OTHER INFORMATION: probe

<400> SEQUENCE: 56
gttgtgtcaa gaggatgatt aggtagagcc                                30

<210> SEQ ID NO 57
<211> LENGTH: 31

<212> TYPE: DNA
<213> ORGANISM: artificial
<220> FEATURE:
<223> OTHER INFORMATION: probe

<400> SEQUENCE: 57
gactgtgtgt ggagcagcta tttgcttcgg c                                31

<210> SEQ ID NO 58
<211> LENGTH: 31
<212> TYPE: DNA
<213> ORGANISM: artificial
<220> FEATURE:
<223> OTHER INFORMATION: probe

<400> SEQUENCE: 58
gccgaagcaa atagctgctc cacacacagt c                                31

<210> SEQ ID NO 59
<211> LENGTH: 35
<212> TYPE: DNA
<213> ORGANISM: artificial
<220> FEATURE:
<223> OTHER INFORMATION: cloned psiRNA

<400> SEQUENCE: 59
ctgatctgac cagagctggt tccaataaga ctaaa                            35

<210> SEQ ID NO 60
<211> LENGTH: 35
<212> TYPE: DNA
<213> ORGANISM: artificial
<220> FEATURE:
<223> OTHER INFORMATION: cloned psiRNA

<400> SEQUENCE: 60
ctgatctgac cagagctggt tccaagtaag actaa                            35

<210> SEQ ID NO 61
<211> LENGTH: 35
<212> TYPE: DNA
<213> ORGANISM: artificial
<220> FEATURE:
<223> OTHER INFORMATION: cloned psiRNA

<400> SEQUENCE: 61
ctgatctgac cagagctggt tccaataaga ctaaa                            35

<210> SEQ ID NO 62
<211> LENGTH: 30
<212> TYPE: DNA
<213> ORGANISM: artificial
<220> FEATURE:
<223> OTHER INFORMATION: cloned psiRNA

<400> SEQUENCE: 62
caatctgatc tgaccagagc tggttccaat                                  30

<210> SEQ ID NO 63
<211> LENGTH: 30
<212> TYPE: DNA
<213> ORGANISM: artificial
<220> FEATURE:
<223> OTHER INFORMATION: cloned psiRNA

<400> SEQUENCE: 63

```
caatctgatc tgaccagagc tggttccaat                                    30

<210> SEQ ID NO 64
<211> LENGTH: 26
<212> TYPE: DNA
<213> ORGANISM: artificial
<220> FEATURE:
<223> OTHER INFORMATION: cloned psiRNA

<400> SEQUENCE: 64
atgattcatt tcttgtctta agcaat                                        26

<210> SEQ ID NO 65
<211> LENGTH: 21
<212> TYPE: DNA
<213> ORGANISM: artificial
<220> FEATURE:
<223> OTHER INFORMATION: cloned psiRNA

<400> SEQUENCE: 65
ttgtcttaag caatctgatc t                                             21

<210> SEQ ID NO 66
<211> LENGTH: 37
<212> TYPE: DNA
<213> ORGANISM: artificial
<220> FEATURE:
<223> OTHER INFORMATION: cloned psiRNA

<400> SEQUENCE: 66
cactaaagtc atactttact gctacaaccc gctctgg                            37

<210> SEQ ID NO 67
<211> LENGTH: 30
<212> TYPE: DNA
<213> ORGANISM: artificial
<220> FEATURE:
<223> OTHER INFORMATION: cloned psiRNA

<400> SEQUENCE: 67
gtcatacttt actgctacaa cccgctctgg                                    30

<210> SEQ ID NO 68
<211> LENGTH: 27
<212> TYPE: DNA
<213> ORGANISM: artificial
<220> FEATURE:
<223> OTHER INFORMATION: cloned psiRNA

<400> SEQUENCE: 68
tactgctaca acccgctctg ggtcgag                                       27

<210> SEQ ID NO 69
<211> LENGTH: 27
<212> TYPE: DNA
<213> ORGANISM: artificial
<220> FEATURE:
<223> OTHER INFORMATION: cloned psiRNA

<400> SEQUENCE: 69
ttactgctac aacccgctct gggtcga                                       27

<210> SEQ ID NO 70
<211> LENGTH: 25
<212> TYPE: DNA
<213> ORGANISM: artificial
```

```
<220> FEATURE:
<223> OTHER INFORMATION: cloned psiRNA

<400> SEQUENCE: 70
actgctacaa cccgctctgg gttga                                              25

<210> SEQ ID NO 71
<211> LENGTH: 40
<212> TYPE: DNA
<213> ORGANISM: artificial
<220> FEATURE:
<223> OTHER INFORMATION: cloned psiRNA

<400> SEQUENCE: 71
ctgacacgaa cataaacagt tccaataaga ctacagaaga                              40

<210> SEQ ID NO 72
<211> LENGTH: 40
<212> TYPE: DNA
<213> ORGANISM: artificial
<220> FEATURE:
<223> OTHER INFORMATION: cloned psiRNA

<400> SEQUENCE: 72
ctgacacgaa cataaacagt tccaataaga ctacagaaga                              40

<210> SEQ ID NO 73
<211> LENGTH: 32
<212> TYPE: DNA
<213> ORGANISM: artificial
<220> FEATURE:
<223> OTHER INFORMATION: cloned psiRNA

<400> SEQUENCE: 73
gaaagggaaa tgtgcgtaaa ggttttcttc cc                                      32

<210> SEQ ID NO 74
<211> LENGTH: 32
<212> TYPE: DNA
<213> ORGANISM: artificial
<220> FEATURE:
<223> OTHER INFORMATION: cloned psiRNA

<400> SEQUENCE: 74
gaaagggaaa tgtgcgtaaa ggttttcttc cc                                      32

<210> SEQ ID NO 75
<211> LENGTH: 32
<212> TYPE: DNA
<213> ORGANISM: artificial
<220> FEATURE:
<223> OTHER INFORMATION: cloned psiRNA

<400> SEQUENCE: 75
ttgacccacc accagccctg ttccaataag ac                                      32

<210> SEQ ID NO 76
<211> LENGTH: 26
<212> TYPE: DNA
<213> ORGANISM: artificial
<220> FEATURE:
<223> OTHER INFORMATION: cloned psiRNA

<400> SEQUENCE: 76
gaaaggcgtg ccgtgtgttt ttataa                                             26
```

<210> SEQ ID NO 77
<211> LENGTH: 26
<212> TYPE: DNA
<213> ORGANISM: artificial
<220> FEATURE:
<223> OTHER INFORMATION: cloned psiRNA

<400> SEQUENCE: 77
gaaaggcgtg ccgtgtgttt ttataa                                          26

<210> SEQ ID NO 78
<211> LENGTH: 21
<212> TYPE: DNA
<213> ORGANISM: artificial
<220> FEATURE:
<223> OTHER INFORMATION: cloned psiRNA

<400> SEQUENCE: 78
gttgctgcat atccagtgtg g                                               21

<210> SEQ ID NO 79
<211> LENGTH: 21
<212> TYPE: DNA
<213> ORGANISM: artificial
<220> FEATURE:
<223> OTHER INFORMATION: cloned psiRNA

<400> SEQUENCE: 79
gttgctgcat atccagtgtg g                                               21

<210> SEQ ID NO 80
<211> LENGTH: 34
<212> TYPE: DNA
<213> ORGANISM: artificial
<220> FEATURE:
<223> OTHER INFORMATION: cloned psiRNA

<400> SEQUENCE: 80
ggcaagttct ggcctatact gtctcctaat gtct                                 34

<210> SEQ ID NO 81
<211> LENGTH: 31
<212> TYPE: DNA
<213> ORGANISM: artificial
<220> FEATURE:
<223> OTHER INFORMATION: cloned psiRNA

<400> SEQUENCE: 81
taggagacag tataggccag aacttgccca g                                    31

<210> SEQ ID NO 82
<211> LENGTH: 24
<212> TYPE: DNA
<213> ORGANISM: artificial
<220> FEATURE:
<223> OTHER INFORMATION: cloned psiRNA
<220> FEATURE:
<221> NAME/KEY: misc_feature
<222> LOCATION: (10)..(10)
<223> OTHER INFORMATION: n may be any nucleotide

<400> SEQUENCE: 82
gacattagcn gacagtatag gcca                                            24

<210> SEQ ID NO 83
<211> LENGTH: 37

```
<212> TYPE: DNA
<213> ORGANISM: artificial
<220> FEATURE:
<223> OTHER INFORMATION: cloned psiRNA

<400> SEQUENCE: 83
ttagcaaatt gccgattact gcacataaaa aaaatag                              37

<210> SEQ ID NO 84
<211> LENGTH: 30
<212> TYPE: DNA
<213> ORGANISM: artificial
<220> FEATURE:
<223> OTHER INFORMATION: cloned psiRNA
<220> FEATURE:
<221> NAME/KEY: misc_feature
<222> LOCATION: (30)..(30)
<223> OTHER INFORMATION: n may be any nucleotide

<400> SEQUENCE: 84
ctataaggga ttgaaaggtc aaaggtatan                                     30

<210> SEQ ID NO 85
<211> LENGTH: 31
<212> TYPE: DNA
<213> ORGANISM: artificial
<220> FEATURE:
<223> OTHER INFORMATION: cloned psiRNA
<220> FEATURE:
<221> NAME/KEY: misc_feature
<222> LOCATION: (7)..(7)
<223> OTHER INFORMATION: n may be any nucleotide

<400> SEQUENCE: 85
ctataangga ttgaaaggtc aagggtatac t                                   31

<210> SEQ ID NO 86
<211> LENGTH: 42
<212> TYPE: DNA
<213> ORGANISM: artificial
<220> FEATURE:
<223> OTHER INFORMATION: cloned psiRNA

<400> SEQUENCE: 86
ttcgcggtta aacaatctga tctgaccaga gctggttcca at                       42

<210> SEQ ID NO 87
<211> LENGTH: 32
<212> TYPE: DNA
<213> ORGANISM: artificial
<220> FEATURE:
<223> OTHER INFORMATION: cloned psiRNA

<400> SEQUENCE: 87
ggacagcgtg gacacggtga acgggctctg ga                                  32

<210> SEQ ID NO 88
<211> LENGTH: 20
<212> TYPE: DNA
<213> ORGANISM: artificial
<220> FEATURE:
<223> OTHER INFORMATION: cloned psiRNA

<400> SEQUENCE: 88
ctgatagaac ctttgccacc                                                20

<210> SEQ ID NO 89
```

```
<211> LENGTH: 20
<212> TYPE: DNA
<213> ORGANISM: artificial
<220> FEATURE:
<223> OTHER INFORMATION: cloned psiRNA

<400> SEQUENCE: 89
ctgatagaac ctttgccacc                                          20

<210> SEQ ID NO 90
<211> LENGTH: 37
<212> TYPE: DNA
<213> ORGANISM: artificial
<220> FEATURE:
<223> OTHER INFORMATION: cloned psiRNA

<400> SEQUENCE: 90
catacttgcg gatacggatc cagtcaaaac ttgactg                       37

<210> SEQ ID NO 91
<211> LENGTH: 32
<212> TYPE: DNA
<213> ORGANISM: artificial
<220> FEATURE:
<223> OTHER INFORMATION: cloned psiRNA

<400> SEQUENCE: 91
ttgcggatat ggatccagtc aaaacttgac tg                            32

<210> SEQ ID NO 92
<211> LENGTH: 30
<212> TYPE: DNA
<213> ORGANISM: artificial
<220> FEATURE:
<223> OTHER INFORMATION: cloned psiRNA

<400> SEQUENCE: 92
gcggatacgg atccagtcaa aacttgactg                               30

<210> SEQ ID NO 93
<211> LENGTH: 29
<212> TYPE: DNA
<213> ORGANISM: artificial
<220> FEATURE:
<223> OTHER INFORMATION: cloned psiRNA

<400> SEQUENCE: 93
gaaagcatac ttgcggatac ggatccagt                                29

<210> SEQ ID NO 94
<211> LENGTH: 23
<212> TYPE: DNA
<213> ORGANISM: artificial
<220> FEATURE:
<223> OTHER INFORMATION: cloned psiRNA

<400> SEQUENCE: 94
ctctgggtcg tctatgtttt tga                                      23

<210> SEQ ID NO 95
<211> LENGTH: 32
<212> TYPE: DNA
<213> ORGANISM: artificial
<220> FEATURE:
<223> OTHER INFORMATION: cloned psiRNA

<400> SEQUENCE: 95
```
gagtagaaat gcccaaattc cccttaggga ca                                    32

<210> SEQ ID NO 96
<211> LENGTH: 41
<212> TYPE: DNA
<213> ORGANISM: artificial
<220> FEATURE:
<223> OTHER INFORMATION: cloned psiRNA

<400> SEQUENCE: 96
tttgtgatag tgttctttgc aacgaagtgc ttgctggtca g                          41

<210> SEQ ID NO 97
<211> LENGTH: 38
<212> TYPE: DNA
<213> ORGANISM: artificial
<220> FEATURE:
<223> OTHER INFORMATION: cloned psiRNA

<400> SEQUENCE: 97
gtttgtgata gtgttctttg caacgaagag cttgctgg                              38

<210> SEQ ID NO 98
<211> LENGTH: 21
<212> TYPE: DNA
<213> ORGANISM: artificial
<220> FEATURE:
<223> OTHER INFORMATION: cloned psiRNA

<400> SEQUENCE: 98
gagtgccccg agccgggggc t                                                21

<210> SEQ ID NO 99
<211> LENGTH: 40
<212> TYPE: DNA
<213> ORGANISM: artificial
<220> FEATURE:
<223> OTHER INFORMATION: cloned psiRNA

<400> SEQUENCE: 99
ctgacacgaa cataaacagt tccaataaga ctacagaaga                            40

<210> SEQ ID NO 100
<211> LENGTH: 40
<212> TYPE: DNA
<213> ORGANISM: artificial
<220> FEATURE:
<223> OTHER INFORMATION: cloned psiRNA

<400> SEQUENCE: 100
ctgacacgaa cataaacagt tccaataaga ctacagaaga                            40

<210> SEQ ID NO 101
<211> LENGTH: 39
<212> TYPE: DNA
<213> ORGANISM: artificial
<220> FEATURE:
<223> OTHER INFORMATION: cloned psiRNA

<400> SEQUENCE: 101
atggctcgat ggaattatgt tccaataaga ctacaaaag                             39

<210> SEQ ID NO 102
<211> LENGTH: 39
<212> TYPE: DNA

```
<213> ORGANISM: artificial
<220> FEATURE:
<223> OTHER INFORMATION: cloned psiRNA

<400> SEQUENCE: 102
atggctcgat ggaattatgt tccaataaga ctacaaaag                          39

<210> SEQ ID NO 103
<211> LENGTH: 35
<212> TYPE: DNA
<213> ORGANISM: artificial
<220> FEATURE:
<223> OTHER INFORMATION: cloned psiRNA

<400> SEQUENCE: 103
ctaactaaca tcaccaataa ttaattgtaa gttag                              35

<210> SEQ ID NO 104
<211> LENGTH: 35
<212> TYPE: DNA
<213> ORGANISM: artificial
<220> FEATURE:
<223> OTHER INFORMATION: cloned psiRNA

<400> SEQUENCE: 104
gctaccatgg ccatcaccaa taattaattg taagt                              35

<210> SEQ ID NO 105
<211> LENGTH: 29
<212> TYPE: DNA
<213> ORGANISM: artificial
<220> FEATURE:
<223> OTHER INFORMATION: cloned psiRNA

<400> SEQUENCE: 105
ctgagccaac ccaccacttt ggtaaaact                                     29

<210> SEQ ID NO 106
<211> LENGTH: 29
<212> TYPE: DNA
<213> ORGANISM: artificial
<220> FEATURE:
<223> OTHER INFORMATION: cloned psiRNA

<400> SEQUENCE: 106
ctgagccaac ccaccacttt ggtaaaact                                     29

<210> SEQ ID NO 107
<211> LENGTH: 29
<212> TYPE: DNA
<213> ORGANISM: artificial
<220> FEATURE:
<223> OTHER INFORMATION: cloned psiRNA

<400> SEQUENCE: 107
ctgagccaac ccaccacttt ggtaaaact                                     29

<210> SEQ ID NO 108
<211> LENGTH: 36
<212> TYPE: DNA
<213> ORGANISM: artificial
<220> FEATURE:
<223> OTHER INFORMATION: cloned psiRNA

<400> SEQUENCE: 108
tgaggctgga gagggcttct ttgttactac ttgcgt                             36
```

<210> SEQ ID NO 109
<211> LENGTH: 23
<212> TYPE: DNA
<213> ORGANISM: artificial
<220> FEATURE:
<223> OTHER INFORMATION: cloned psiRNA

<400> SEQUENCE: 109
ttatgttcat gttccacatc taa                                          23

<210> SEQ ID NO 110
<211> LENGTH: 20
<212> TYPE: DNA
<213> ORGANISM: artificial
<220> FEATURE:
<223> OTHER INFORMATION: cloned psiRNA

<400> SEQUENCE: 110
tatgttcatg ttccacacta                                              20

<210> SEQ ID NO 111
<211> LENGTH: 50
<212> TYPE: DNA
<213> ORGANISM: artificial
<220> FEATURE:
<223> OTHER INFORMATION: cloned psiRNA

<400> SEQUENCE: 111
ttgaaaggaa tgttgctcaa tgcaaagggc tcaccgctgc tggtgttcca             50

<210> SEQ ID NO 112
<211> LENGTH: 41
<212> TYPE: DNA
<213> ORGANISM: artificial
<220> FEATURE:
<223> OTHER INFORMATION: cloned psiRNA

<400> SEQUENCE: 112
ctcaatgcaa agggctcacc gctgctggtg ttccaataag a                      41

<210> SEQ ID NO 113
<211> LENGTH: 37
<212> TYPE: DNA
<213> ORGANISM: artificial
<220> FEATURE:
<223> OTHER INFORMATION: cloned psiRNA

<400> SEQUENCE: 113
ctcaccgctg ctggtgttcc aataagacta caaaaga                           37

<210> SEQ ID NO 114
<211> LENGTH: 32
<212> TYPE: DNA
<213> ORGANISM: artificial
<220> FEATURE:
<223> OTHER INFORMATION: cloned psiRNA

<400> SEQUENCE: 114
ttgaaagttg agttgaagcg ccactctttg aa                                32

<210> SEQ ID NO 115
<211> LENGTH: 36
<212> TYPE: DNA
<213> ORGANISM: artificial
<220> FEATURE:

<223> OTHER INFORMATION: cloned psiRNA

<400> SEQUENCE: 115
ttgagttgaa gcgccactct ttgaagccta tcagag   36

<210> SEQ ID NO 116
<211> LENGTH: 43
<212> TYPE: DNA
<213> ORGANISM: artificial
<220> FEATURE:
<223> OTHER INFORMATION: cloned psiRNA

<400> SEQUENCE: 116
attgaaagtt gagttgaagc gccactcttt gaagcctatc aga   43

<210> SEQ ID NO 117
<211> LENGTH: 39
<212> TYPE: DNA
<213> ORGANISM: artificial
<220> FEATURE:
<223> OTHER INFORMATION: cloned psiRNA

<400> SEQUENCE: 117
agttgagttg aagcgccact ctttgaagcc tatcagagt   39

<210> SEQ ID NO 118
<211> LENGTH: 38
<212> TYPE: DNA
<213> ORGANISM: artificial
<220> FEATURE:
<223> OTHER INFORMATION: cloned psiRNA

<400> SEQUENCE: 118
gttgagttga agcgccactc tttgaagcct atcagagt   38

<210> SEQ ID NO 119
<211> LENGTH: 38
<212> TYPE: DNA
<213> ORGANISM: artificial
<220> FEATURE:
<223> OTHER INFORMATION: cloned psiRNA

<400> SEQUENCE: 119
ttgagttgaa gcgccactct ttgaagccta tcagagtt   38

<210> SEQ ID NO 120
<211> LENGTH: 46
<212> TYPE: DNA
<213> ORGANISM: artificial
<220> FEATURE:
<223> OTHER INFORMATION: cloned psiRNA

<400> SEQUENCE: 120
aagtcgggtc ccttggagtt ccgaacgggc tcccgaggct gttcca   46

<210> SEQ ID NO 121
<211> LENGTH: 27
<212> TYPE: DNA
<213> ORGANISM: artificial
<220> FEATURE:
<223> OTHER INFORMATION: cloned psiRNA

<400> SEQUENCE: 121
gggctcccga ggctgttcca ataagac   27

<210> SEQ ID NO 122
<211> LENGTH: 32
<212> TYPE: DNA
<213> ORGANISM: artificial
<220> FEATURE:
<223> OTHER INFORMATION: cloned psiRNA

<400> SEQUENCE: 122
gttgattccc ttatagatgt cgttttcca ca                                    32

<210> SEQ ID NO 123
<211> LENGTH: 30
<212> TYPE: DNA
<213> ORGANISM: artificial
<220> FEATURE:
<223> OTHER INFORMATION: cloned psiRNA

<400> SEQUENCE: 123
atgttcgttc tcgttcactg ttattctctt                                      30

<210> SEQ ID NO 124
<211> LENGTH: 22
<212> TYPE: DNA
<213> ORGANISM: artificial
<220> FEATURE:
<223> OTHER INFORMATION: cloned psiRNA

<400> SEQUENCE: 124
ctcgttcact gttattctct tt                                              22

<210> SEQ ID NO 125
<211> LENGTH: 34
<212> TYPE: DNA
<213> ORGANISM: artificial
<220> FEATURE:
<223> OTHER INFORMATION: cloned psiRNA

<400> SEQUENCE: 125
aaaactaaaa aaagaagagg tggtggtgaa gaat                                 34

<210> SEQ ID NO 126
<211> LENGTH: 36
<212> TYPE: DNA
<213> ORGANISM: artificial
<220> FEATURE:
<223> OTHER INFORMATION: cloned psiRNA

<400> SEQUENCE: 126
gaaagtctca attggggagt tgctttaatg gctttt                               36

<210> SEQ ID NO 127
<211> LENGTH: 37
<212> TYPE: DNA
<213> ORGANISM: artificial
<220> FEATURE:
<223> OTHER INFORMATION: cloned psiRNA

<400> SEQUENCE: 127
tcaatccgag aatcgaattt tcctatacgc ttttgtt                              37

<210> SEQ ID NO 128
<211> LENGTH: 36
<212> TYPE: DNA
<213> ORGANISM: artificial
<220> FEATURE:
<223> OTHER INFORMATION: cloned psiRNA

```
<400> SEQUENCE: 128 tttgttttg ctcctgtgtc ttgtggtgat aaaatg                                36

<210> SEQ ID NO 129
<211> LENGTH: 36
<212> TYPE: DNA
<213> ORGANISM: artificial
<220> FEATURE:
<223> OTHER INFORMATION: cloned psiRNA

<400> SEQUENCE: 129 tttgttttg ctcctgtgtc ttgtggtgat aaaatg                                36

<210> SEQ ID NO 130
<211> LENGTH: 31
<212> TYPE: DNA
<213> ORGANISM: artificial
<220> FEATURE:
<223> OTHER INFORMATION: cloned psiRNA

<400> SEQUENCE: 130
gtgataaaat gttacaataa gactacaaaa g                                    31

<210> SEQ ID NO 131
<211> LENGTH: 46
<212> TYPE: DNA
<213> ORGANISM: artificial
<220> FEATURE:
<223> OTHER INFORMATION: cloned psiRNA

<400> SEQUENCE: 131
attgaaagga ccatactcac cagcagcggt gagccctttg cattga                    46

<210> SEQ ID NO 132
<211> LENGTH: 26
<212> TYPE: DNA
<213> ORGANISM: artificial
<220> FEATURE:
<223> OTHER INFORMATION: cloned psiRNA

<400> SEQUENCE: 132
attgaaagga ccatactcac cagcag                                          26

<210> SEQ ID NO 133
<211> LENGTH: 42
<212> TYPE: DNA
<213> ORGANISM: artificial
<220> FEATURE:
<223> OTHER INFORMATION: cloned psiRNA

<400> SEQUENCE: 133
gttcacgtag tacttgaggg cgctcacgtt acaataagac ca                        42

<210> SEQ ID NO 134
<211> LENGTH: 43
<212> TYPE: DNA
<213> ORGANISM: artificial
<220> FEATURE:
<223> OTHER INFORMATION: cloned psiRNA
<220> FEATURE:
<221> NAME/KEY: misc_feature
<222> LOCATION: (6)..(6)
<223> OTHER INFORMATION: n may be any nucleotide
<220> FEATURE:
<221> NAME/KEY: misc_feature
<222> LOCATION: (31)..(31)
<223> OTHER INFORMATION: n may be any nucleotide
```

-continued

```
<220> FEATURE:
<221> NAME/KEY: misc_feature
<222> LOCATION: (34)..(34)
<223> OTHER INFORMATION: n may be any nucleotide
<220> FEATURE:
<221> NAME/KEY: misc_feature
<222> LOCATION: (37)..(37)
<223> OTHER INFORMATION: n may be any nucleotide

<400> SEQUENCE: 134
tttcangcag tacttgaggg cgctcatgtt ncantangac caa                    43

<210> SEQ ID NO 135
<211> LENGTH: 35
<212> TYPE: DNA
<213> ORGANISM: artificial
<220> FEATURE:
<223> OTHER INFORMATION: cloned psiRNA

<400> SEQUENCE: 135
aagaagggga atggttcacg tagctacttg agggc                             35

<210> SEQ ID NO 136
<211> LENGTH: 25
<212> TYPE: DNA
<213> ORGANISM: artificial
<220> FEATURE:
<223> OTHER INFORMATION: cloned psiRNA

<400> SEQUENCE: 136
caataataca gtcctaatgc tcgtg                                        25

<210> SEQ ID NO 137
<211> LENGTH: 25
<212> TYPE: DNA
<213> ORGANISM: artificial
<220> FEATURE:
<223> OTHER INFORMATION: cloned psiRNA

<400> SEQUENCE: 137
caataataca gtcctaatgc tcgtg                                        25

<210> SEQ ID NO 138
<211> LENGTH: 29
<212> TYPE: DNA
<213> ORGANISM: artificial
<220> FEATURE:
<223> OTHER INFORMATION: cloned psiRNA

<400> SEQUENCE: 138
ttgaaaacgc tagcaggact agtgcttgt                                    29

<210> SEQ ID NO 139
<211> LENGTH: 23
<212> TYPE: DNA
<213> ORGANISM: artificial
<220> FEATURE:
<223> OTHER INFORMATION: cloned psiRNA

<400> SEQUENCE: 139
cgctagcagg actagtgctt gtg                                          23

<210> SEQ ID NO 140
<211> LENGTH: 44
<212> TYPE: DNA
<213> ORGANISM: artificial
<220> FEATURE:
```

<223> OTHER INFORMATION: cloned psiRNA

<400> SEQUENCE: 140
cttctcgaat ctatcgaatt cggttacaat aagaccaaaa taga       44

<210> SEQ ID NO 141
<211> LENGTH: 39
<212> TYPE: DNA
<213> ORGANISM: artificial
<220> FEATURE:
<223> OTHER INFORMATION: cloned psiRNA
<220> FEATURE:
<221> NAME/KEY: misc_feature
<222> LOCATION: (11)..(11)
<223> OTHER INFORMATION: n may be any nucleotide

<400> SEQUENCE: 141
agccacataa nacattgtca tacaaagtat gacaaaata            39

<210> SEQ ID NO 142
<211> LENGTH: 34
<212> TYPE: DNA
<213> ORGANISM: artificial
<220> FEATURE:
<223> OTHER INFORMATION: cloned psiRNA

<400> SEQUENCE: 142
cacataagac attgtcatac aaagtaggac aaaa                 34

<210> SEQ ID NO 143
<211> LENGTH: 28
<212> TYPE: DNA
<213> ORGANISM: artificial
<220> FEATURE:
<223> OTHER INFORMATION: cloned psiRNA

<400> SEQUENCE: 143
aagacattgt catacaaagt aggacaaa                        28

<210> SEQ ID NO 144
<211> LENGTH: 36
<212> TYPE: DNA
<213> ORGANISM: artificial
<220> FEATURE:
<223> OTHER INFORMATION: cloned psiRNA

<400> SEQUENCE: 144
gtcctcttgg agaccgttcc tgttacaata agacca               36

<210> SEQ ID NO 145
<211> LENGTH: 25
<212> TYPE: DNA
<213> ORGANISM: artificial
<220> FEATURE:
<223> OTHER INFORMATION: cloned psiRNA
<220> FEATURE:
<221> NAME/KEY: misc_feature
<222> LOCATION: (22)..(22)
<223> OTHER INFORMATION: n may be any nucleotide
<220> FEATURE:
<221> NAME/KEY: misc_feature
<222> LOCATION: (24)..(24)
<223> OTHER INFORMATION: n may be any nucleotide

<400> SEQUENCE: 145
gtcacgtaat tcgccaagtc cncnt                           25

```
<210> SEQ ID NO 146
<211> LENGTH: 24
<212> TYPE: DNA
<213> ORGANISM: artificial
<220> FEATURE:
<223> OTHER INFORMATION: cloned psiRNA

<400> SEQUENCE: 146
aatagttaca ataagaccaa aata                                          24

<210> SEQ ID NO 147
<211> LENGTH: 19
<212> TYPE: DNA
<213> ORGANISM: artificial
<220> FEATURE:
<223> OTHER INFORMATION: cloned psiRNA

<400> SEQUENCE: 147
ctagcttttc acacactct                                                19

<210> SEQ ID NO 148
<211> LENGTH: 22
<212> TYPE: DNA
<213> ORGANISM: artificial
<220> FEATURE:
<223> OTHER INFORMATION: cloned psiRNA
<220> FEATURE:
<221> NAME/KEY: misc_feature
<222> LOCATION: (8)..(8)
<223> OTHER INFORMATION: n may be any nucleotide
<220> FEATURE:
<221> NAME/KEY: misc_feature
<222> LOCATION: (10)..(10)
<223> OTHER INFORMATION: n may be any nucleotide

<400> SEQUENCE: 148
taaactangn tgattttgta at                                            22

<210> SEQ ID NO 149
<211> LENGTH: 28
<212> TYPE: DNA
<213> ORGANISM: artificial
<220> FEATURE:
<223> OTHER INFORMATION: cloned psiRNA

<400> SEQUENCE: 149
gaaagagtat tccaccgaga attgtgcc                                      28

<210> SEQ ID NO 150
<211> LENGTH: 36
<212> TYPE: DNA
<213> ORGANISM: artificial
<220> FEATURE:
<223> OTHER INFORMATION: cloned psiRNA

<400> SEQUENCE: 150
gtattccacc gagaattgtg cctttgtact ggactg                             36

<210> SEQ ID NO 151
<211> LENGTH: 36
<212> TYPE: DNA
<213> ORGANISM: artificial
<220> FEATURE:
<223> OTHER INFORMATION: cloned psiRNA

<400> SEQUENCE: 151
tctattttag tcttattgta acgttccact aaggac                             36
```

<210> SEQ ID NO 152
<211> LENGTH: 31
<212> TYPE: DNA
<213> ORGANISM: artificial
<220> FEATURE:
<223> OTHER INFORMATION: cloned psiRNA

<400> SEQUENCE: 152
tttagtctta ttgtaacgtt ccactaagga c                          31

<210> SEQ ID NO 153
<211> LENGTH: 30
<212> TYPE: DNA
<213> ORGANISM: artificial
<220> FEATURE:
<223> OTHER INFORMATION: cloned psiRNA

<400> SEQUENCE: 153
aatttgacgt acaaatgtcc ttagtggaac                             30

<210> SEQ ID NO 154
<211> LENGTH: 39
<212> TYPE: DNA
<213> ORGANISM: artificial
<220> FEATURE:
<223> OTHER INFORMATION: cloned psiRNA

<400> SEQUENCE: 154
ttcgggacct gtaggtcgtt acaataagac taaaataga                   39

<210> SEQ ID NO 155
<211> LENGTH: 29
<212> TYPE: DNA
<213> ORGANISM: artificial
<220> FEATURE:
<223> OTHER INFORMATION: cloned psiRNA

<400> SEQUENCE: 155
gttaatggta aagttacaat aagactaaa                              29

<210> SEQ ID NO 156
<211> LENGTH: 24
<212> TYPE: DNA
<213> ORGANISM: artificial
<220> FEATURE:
<223> OTHER INFORMATION: cloned psiRNA

<400> SEQUENCE: 156
gttctgccgt ccctttctc gacg                                    24

<210> SEQ ID NO 157
<211> LENGTH: 36
<212> TYPE: DNA
<213> ORGANISM: artificial
<220> FEATURE:
<223> OTHER INFORMATION: cloned psiRNA

<400> SEQUENCE: 157
ttctgccgtc cctttctcg acgaacctca taccga                       36

<210> SEQ ID NO 158
<211> LENGTH: 26
<212> TYPE: DNA
<213> ORGANISM: artificial
<220> FEATURE:
<223> OTHER INFORMATION: cloned psiRNA

```
<400> SEQUENCE: 158
ttctgccgtc ccttttctcg acgaac                                          26

<210> SEQ ID NO 159
<211> LENGTH: 26
<212> TYPE: DNA
<213> ORGANISM: artificial
<220> FEATURE:
<223> OTHER INFORMATION: cloned psiRNA

<400> SEQUENCE: 159
ttctgccgtc ccttttctcg acgaac                                          26

<210> SEQ ID NO 160
<211> LENGTH: 17
<212> TYPE: DNA
<213> ORGANISM: artificial
<220> FEATURE:
<223> OTHER INFORMATION: cloned psiRNA

<400> SEQUENCE: 160
tataggcgga actccct                                                    17

<210> SEQ ID NO 161
<211> LENGTH: 31
<212> TYPE: DNA
<213> ORGANISM: artificial
<220> FEATURE:
<223> OTHER INFORMATION: cloned psiRNA

<400> SEQUENCE: 161
aagtgttttc gaatattgtt acttcttgtg t                                    31

<210> SEQ ID NO 162
<211> LENGTH: 24
<212> TYPE: DNA
<213> ORGANISM: artificial
<220> FEATURE:
<223> OTHER INFORMATION: cloned psiRNA

<400> SEQUENCE: 162
ctataagact gaaacttcac acct                                            24

<210> SEQ ID NO 163
<211> LENGTH: 19
<212> TYPE: DNA
<213> ORGANISM: artificial
<220> FEATURE:
<223> OTHER INFORMATION: cloned psiRNA

<400> SEQUENCE: 163
ttaacactct taacccag                                                   19

<210> SEQ ID NO 164
<211> LENGTH: 27
<212> TYPE: DNA
<213> ORGANISM: artificial
<220> FEATURE:
<223> OTHER INFORMATION: cloned psiRNA

<400> SEQUENCE: 164
gtccaaaaac gttacaataa gactaaa                                         27

<210> SEQ ID NO 165
```

```
<211> LENGTH: 31
<212> TYPE: DNA
<213> ORGANISM: artificial
<220> FEATURE:
<223> OTHER INFORMATION: cloned psiRNA

<400> SEQUENCE: 165
ttaagctggg atgggctata tacaaagaca g                             31

<210> SEQ ID NO 166
<211> LENGTH: 21
<212> TYPE: DNA
<213> ORGANISM: artificial
<220> FEATURE:
<223> OTHER INFORMATION: cloned psiRNA

<400> SEQUENCE: 166
aattctggaa ggttgtagaa a                                        21

<210> SEQ ID NO 167
<211> LENGTH: 30
<212> TYPE: DNA
<213> ORGANISM: artificial
<220> FEATURE:
<223> OTHER INFORMATION: cloned psiRNA

<400> SEQUENCE: 167
cgcccacctt tgttacgttc caataagact                               30

<210> SEQ ID NO 168
<211> LENGTH: 37
<212> TYPE: DNA
<213> ORGANISM: artificial
<220> FEATURE:
<223> OTHER INFORMATION: cloned psiRNA

<400> SEQUENCE: 168
ttgtagtatg cggtccttgc ggctgagagc acttcag                       37

<210> SEQ ID NO 169
<211> LENGTH: 31
<212> TYPE: DNA
<213> ORGANISM: artificial
<220> FEATURE:
<223> OTHER INFORMATION: cloned psiRNA

<400> SEQUENCE: 169
ttgtagtatg cggtccttgc ggctgagagc a                             31

<210> SEQ ID NO 170
<211> LENGTH: 31
<212> TYPE: DNA
<213> ORGANISM: artificial
<220> FEATURE:
<223> OTHER INFORMATION: cloned psiRNA

<400> SEQUENCE: 170
ttgtagtatg cggtccttgc ggctgagagc a                             31

<210> SEQ ID NO 171
<211> LENGTH: 29
<212> TYPE: DNA
<213> ORGANISM: artificial
<220> FEATURE:
<223> OTHER INFORMATION: cloned psiRNA

<400> SEQUENCE: 171
```

-continued gtagtatgcg gtccttgcgg ctgagagca                                              29

<210> SEQ ID NO 172
<211> LENGTH: 25
<212> TYPE: DNA
<213> ORGANISM: artificial
<220> FEATURE:
<223> OTHER INFORMATION: cloned psiRNA

<400> SEQUENCE: 172
gaaagttgta gtatgcggtc cttgc                                                  25

<210> SEQ ID NO 173
<211> LENGTH: 41
<212> TYPE: DNA
<213> ORGANISM: artificial
<220> FEATURE:
<223> OTHER INFORMATION: cloned psiRNA

<400> SEQUENCE: 173
gtcttcgatt agtgaaaaca gttccaataa gactacaaaa g                                41

<210> SEQ ID NO 174
<211> LENGTH: 31
<212> TYPE: DNA
<213> ORGANISM: artificial
<220> FEATURE:
<223> OTHER INFORMATION: cloned psiRNA

<400> SEQUENCE: 174
gtcgttatct cttacgaagt cttcgattag t                                           31

<210> SEQ ID NO 175
<211> LENGTH: 39
<212> TYPE: DNA
<213> ORGANISM: artificial
<220> FEATURE:
<223> OTHER INFORMATION: cloned psiRNA
<220> FEATURE:
<221> NAME/KEY: misc_feature
<222> LOCATION: (19)..(19)
<223> OTHER INFORMATION: n may be any nucleotide

<400> SEQUENCE: 175
gttacacgtg agtgcaagnt ccaataagac tacaaaaga                                   39

<210> SEQ ID NO 176
<211> LENGTH: 39
<212> TYPE: DNA
<213> ORGANISM: artificial
<220> FEATURE:
<223> OTHER INFORMATION: cloned psiRNA

<400> SEQUENCE: 176
gttacacgtg agtgcaagtt ccaataagac tacaaaaga                                   39

<210> SEQ ID NO 177
<211> LENGTH: 39
<212> TYPE: DNA
<213> ORGANISM: artificial
<220> FEATURE:
<223> OTHER INFORMATION: cloned psiRNA

<400> SEQUENCE: 177
gttacacgtg agtgcaagtt ccaataagac tacaaaaga                                   39

<210> SEQ ID NO 178
<211> LENGTH: 39
<212> TYPE: DNA
<213> ORGANISM: artificial
<220> FEATURE:
<223> OTHER INFORMATION: cloned psiRNA

<400> SEQUENCE: 178
gttacacgtg agtgcaagtt ccaataagac tacaaaaga                               39

<210> SEQ ID NO 179
<211> LENGTH: 39
<212> TYPE: DNA
<213> ORGANISM: artificial
<220> FEATURE:
<223> OTHER INFORMATION: cloned psiRNA

<400> SEQUENCE: 179
tttacacgtg agtgcaagtt ccaataagac tacaaaaga                               39

<210> SEQ ID NO 180
<211> LENGTH: 39
<212> TYPE: DNA
<213> ORGANISM: artificial
<220> FEATURE:
<223> OTHER INFORMATION: cloned psiRNA

<400> SEQUENCE: 180
tttacacgtg agtgcaagtt ccaataagac tacaaaaga                               39

<210> SEQ ID NO 181
<211> LENGTH: 39
<212> TYPE: DNA
<213> ORGANISM: artificial
<220> FEATURE:
<223> OTHER INFORMATION: cloned psiRNA

<400> SEQUENCE: 181
tttacacgtg agtgcaagtt ccaataagac tacaaaaga                               39

<210> SEQ ID NO 182
<211> LENGTH: 27
<212> TYPE: DNA
<213> ORGANISM: artificial
<220> FEATURE:
<223> OTHER INFORMATION: cloned psiRNA

<400> SEQUENCE: 182
acaaaagaat tgaaagttaa cctcctt                                            27

<210> SEQ ID NO 183
<211> LENGTH: 39
<212> TYPE: DNA
<213> ORGANISM: artificial
<220> FEATURE:
<223> OTHER INFORMATION: cloned psiRNA

<400> SEQUENCE: 183
agttatctaa gctctgctta aatgggaaaa tcttataag                               39

<210> SEQ ID NO 184
<211> LENGTH: 40
<212> TYPE: DNA
<213> ORGANISM: artificial
<220> FEATURE:
<223> OTHER INFORMATION: cloned psiRNA

<400> SEQUENCE: 184
gaagaggaag aaatgcagac gacgtgataa actacgtgaa                              40

<210> SEQ ID NO 185
<211> LENGTH: 30
<212> TYPE: DNA
<213> ORGANISM: artificial
<220> FEATURE:
<223> OTHER INFORMATION: cloned psiRNA

<400> SEQUENCE: 185
cagacgacgt gataaactac gtgaaaagtt                                         30

<210> SEQ ID NO 186
<211> LENGTH: 32
<212> TYPE: DNA
<213> ORGANISM: artificial
<220> FEATURE:
<223> OTHER INFORMATION: cloned psiRNA

<400> SEQUENCE: 186 aactttcaa cgtagtttat cacgtcgtct ga                                       32

<210> SEQ ID NO 187
<211> LENGTH: 25
<212> TYPE: DNA
<213> ORGANISM: artificial
<220> FEATURE:
<223> OTHER INFORMATION: cloned psiRNA

<400> SEQUENCE: 187
gtgcactaag gcaccatacg cccaa                                              25

<210> SEQ ID NO 188
<211> LENGTH: 34
<212> TYPE: DNA
<213> ORGANISM: artificial
<220> FEATURE:
<223> OTHER INFORMATION: cloned psiRNA

<400> SEQUENCE: 188
attgaagctt gcccaacctc tctagaaacg ccca                                    34

<210> SEQ ID NO 189
<211> LENGTH: 33
<212> TYPE: DNA
<213> ORGANISM: artificial
<220> FEATURE:
<223> OTHER INFORMATION: cloned psiRNA
<220> FEATURE:
<221> NAME/KEY: misc_feature
<222> LOCATION: (9)..(10)
<223> OTHER INFORMATION: n may be any nucleotide

<400> SEQUENCE: 189
aattgaagnn aaaatctctt tttaaatctt tga                                     33

<210> SEQ ID NO 190
<211> LENGTH: 32
<212> TYPE: DNA
<213> ORGANISM: artificial
<220> FEATURE:
<223> OTHER INFORMATION: cloned psiRNA
<220> FEATURE:
<221> NAME/KEY: misc_feature
<222> LOCATION: (12)..(12)

```
<223> OTHER INFORMATION: n may be any nucleotide
<220> FEATURE:
<221> NAME/KEY: misc_feature
<222> LOCATION: (17)..(17)
<223> OTHER INFORMATION: n may be any nucleotide

<400> SEQUENCE: 190
attgaagcgc anatctnttt ttaaatcttt ga                                    32

<210> SEQ ID NO 191
<211> LENGTH: 42
<212> TYPE: DNA
<213> ORGANISM: artificial
<220> FEATURE:
<223> OTHER INFORMATION: cloned psiRNA

<400> SEQUENCE: 191
gtaggagtat tggggcaaaa aagcccnctg ttccaataag ac                         42

<210> SEQ ID NO 192
<211> LENGTH: 42
<212> TYPE: DNA
<213> ORGANISM: artificial
<220> FEATURE:
<223> OTHER INFORMATION: cloned psiRNA

<400> SEQUENCE: 192 gggggaatt ggggcaaaaa agccccctgt tccaataaga ct                          42

<210> SEQ ID NO 193
<211> LENGTH: 43
<212> TYPE: DNA
<213> ORGANISM: artificial
<220> FEATURE:
<223> OTHER INFORMATION: cloned psiRNA

<400> SEQUENCE: 193
gggggaattg gggcaaaaaa gcccnctgtt ccaataagac tac                        43

<210> SEQ ID NO 194
<211> LENGTH: 43
<212> TYPE: DNA
<213> ORGANISM: artificial
<220> FEATURE:
<223> OTHER INFORMATION: cloned psiRNA

<400> SEQUENCE: 194
gggggaattg gggcaaaaaa gccccctgtt ccaataagac tac                        43

<210> SEQ ID NO 195
<211> LENGTH: 27
<212> TYPE: DNA
<213> ORGANISM: artificial
<220> FEATURE:
<223> OTHER INFORMATION: cloned psiRNA

<400> SEQUENCE: 195
cccnctgttc caataagact acaaaag                                          27

<210> SEQ ID NO 196
<211> LENGTH: 27
<212> TYPE: DNA
<213> ORGANISM: artificial
<220> FEATURE:
<223> OTHER INFORMATION: cloned psiRNA

<400> SEQUENCE: 196
```

-continued

```
cccctgttc caataagact acaaaag                                             27

<210> SEQ ID NO 197
<211> LENGTH: 28
<212> TYPE: DNA
<213> ORGANISM: artificial
<220> FEATURE:
<223> OTHER INFORMATION: cloned psiRNA

<400> SEQUENCE: 197 aagcccctg ttccaataag actacaaa                                            28

<210> SEQ ID NO 198
<211> LENGTH: 29
<212> TYPE: DNA
<213> ORGANISM: artificial
<220> FEATURE:
<223> OTHER INFORMATION: cloned psiRNA

<400> SEQUENCE: 198
gaaaaagccc cctgttacaa taagaccaa                                          29

<210> SEQ ID NO 199
<211> LENGTH: 35
<212> TYPE: DNA
<213> ORGANISM: artificial
<220> FEATURE:
<223> OTHER INFORMATION: cloned psiRNA

<400> SEQUENCE: 199
gaaaaagccc cctgttacaa taagaccaaa ataga                                   35

<210> SEQ ID NO 200
<211> LENGTH: 44
<212> TYPE: DNA
<213> ORGANISM: artificial
<220> FEATURE:
<223> OTHER INFORMATION: cloned psiRNA

<400> SEQUENCE: 200
ttaggagtat tggggcgaaa aagcccctg ttcaataag acta                           44

<210> SEQ ID NO 201
<211> LENGTH: 41
<212> TYPE: DNA
<213> ORGANISM: artificial
<220> FEATURE:
<223> OTHER INFORMATION: cloned psiRNA

<400> SEQUENCE: 201
gggggaatta gggcaaaaaa gcccactgtt ccaataagac t                            41

<210> SEQ ID NO 202
<211> LENGTH: 35
<212> TYPE: DNA
<213> ORGANISM: artificial
<220> FEATURE:
<223> OTHER INFORMATION: cloned psiRNA

<400> SEQUENCE: 202
ggggaattag ggcaaaaaag cccactgttc caata                                   35

<210> SEQ ID NO 203
<211> LENGTH: 45
<212> TYPE: DNA
```

```
<213> ORGANISM: artificial
<220> FEATURE:
<223> OTHER INFORMATION: cloned psiRNA

<400> SEQUENCE: 203
attgaaagtt agcaaattgc cgattattgc acataaaaaa aatag            45

<210> SEQ ID NO 204
<211> LENGTH: 45
<212> TYPE: DNA
<213> ORGANISM: artificial
<220> FEATURE:
<223> OTHER INFORMATION: cloned psiRNA

<400> SEQUENCE: 204
attgaaagtt agcaaattgc cgattattgc acataaaaaa aatag            45

<210> SEQ ID NO 205
<211> LENGTH: 45
<212> TYPE: DNA
<213> ORGANISM: artificial
<220> FEATURE:
<223> OTHER INFORMATION: cloned psiRNA

<400> SEQUENCE: 205
attgaaagac tggattgaga gcaacttgtc gaattatgtc gtcaa            45

<210> SEQ ID NO 206
<211> LENGTH: 43
<212> TYPE: DNA
<213> ORGANISM: artificial
<220> FEATURE:
<223> OTHER INFORMATION: cloned psiRNA

<400> SEQUENCE: 206
aattgaaagt gttcatcagc acttcttctt ctgactctgc tcc              43

<210> SEQ ID NO 207
<211> LENGTH: 42
<212> TYPE: DNA
<213> ORGANISM: artificial
<220> FEATURE:
<223> OTHER INFORMATION: cloned psiRNA

<400> SEQUENCE: 207
aattgaaagt gttcatcgca cttcttcttc tgactctgct cc               42

<210> SEQ ID NO 208
<211> LENGTH: 43
<212> TYPE: DNA
<213> ORGANISM: artificial
<220> FEATURE:
<223> OTHER INFORMATION: cloned psiRNA

<400> SEQUENCE: 208
attgaaagct aatttacgct ttagctcgtg atcaacccta atc              43

<210> SEQ ID NO 209
<211> LENGTH: 38
<212> TYPE: DNA
<213> ORGANISM: artificial
<220> FEATURE:
<223> OTHER INFORMATION: cloned psiRNA

<400> SEQUENCE: 209
attgaaagct aatttacgct ttagctcgtg atcaaccc                    38
```

```
<210> SEQ ID NO 210
<211> LENGTH: 45
<212> TYPE: DNA
<213> ORGANISM: artificial
<220> FEATURE:
<223> OTHER INFORMATION: cloned psiRNA

<400> SEQUENCE: 210
attgaaagtt gagttgaagc gccactcttt gaagcctatc agagt          45

<210> SEQ ID NO 211
<211> LENGTH: 45
<212> TYPE: DNA
<213> ORGANISM: artificial
<220> FEATURE:
<223> OTHER INFORMATION: cloned psiRNA

<400> SEQUENCE: 211
attgaaaggc ttcaggtctt caatattcaa tcccggtccc tttca          45

<210> SEQ ID NO 212
<211> LENGTH: 45
<212> TYPE: DNA
<213> ORGANISM: artificial
<220> FEATURE:
<223> OTHER INFORMATION: cloned psiRNA

<400> SEQUENCE: 212
attgaaaggc ttcaggtctt caatattcaa tcccggtccc tttca          45

<210> SEQ ID NO 213
<211> LENGTH: 42
<212> TYPE: DNA
<213> ORGANISM: artificial
<220> FEATURE:
<223> OTHER INFORMATION: cloned psiRNA

<400> SEQUENCE: 213
gaaagtctct acccttacaa gcttctcgaa tctatcgaat tc             42

<210> SEQ ID NO 214
<211> LENGTH: 41
<212> TYPE: DNA
<213> ORGANISM: artificial
<220> FEATURE:
<223> OTHER INFORMATION: cloned psiRNA

<400> SEQUENCE: 214
gaaaggtcac gtaattcgcc aagttctctt ggataccgtt c              41

<210> SEQ ID NO 215
<211> LENGTH: 39
<212> TYPE: DNA
<213> ORGANISM: artificial
<220> FEATURE:
<223> OTHER INFORMATION: cloned psiRNA

<400> SEQUENCE: 215
attgaaaggt ggataatata atccctgttt ttcccaaga                 39

<210> SEQ ID NO 216
<211> LENGTH: 45
<212> TYPE: DNA
<213> ORGANISM: artificial
<220> FEATURE:
```

<223> OTHER INFORMATION: cloned psiRNA

<400> SEQUENCE: 216
attgaaagtg aactctatc aaggtttgca acaccttgct cccgc   45

<210> SEQ ID NO 217
<211> LENGTH: 38
<212> TYPE: DNA
<213> ORGANISM: artificial
<220> FEATURE:
<223> OTHER INFORMATION: cloned psiRNA

<400> SEQUENCE: 217
gaaaggacaa agaactccct agcgtccctc cccgtgta   38

<210> SEQ ID NO 218
<211> LENGTH: 45
<212> TYPE: DNA
<213> ORGANISM: artificial
<220> FEATURE:
<223> OTHER INFORMATION: cloned psiRNA

<400> SEQUENCE: 218
attgaaagtg gggtctcgtc gcaatcggtg cagtattcct aagcc   45

<210> SEQ ID NO 219
<211> LENGTH: 45
<212> TYPE: DNA
<213> ORGANISM: artificial
<220> FEATURE:
<223> OTHER INFORMATION: cloned psiRNA

<400> SEQUENCE: 219
attgaaagat ctccatcata ccaatgctgt gcaaaatcaa tcttg   45

<210> SEQ ID NO 220
<211> LENGTH: 45
<212> TYPE: DNA
<213> ORGANISM: artificial
<220> FEATURE:
<223> OTHER INFORMATION: cloned psiRNA

<400> SEQUENCE: 220
attgaaagta aacttaagct gggatgggct atatacaaag acaga   45

<210> SEQ ID NO 221
<211> LENGTH: 45
<212> TYPE: DNA
<213> ORGANISM: artificial
<220> FEATURE:
<223> OTHER INFORMATION: cloned psiRNA

<400> SEQUENCE: 221
aattgaaagt caagagttct atcctgcttc acaacaccca tataa   45

<210> SEQ ID NO 222
<211> LENGTH: 43
<212> TYPE: DNA
<213> ORGANISM: artificial
<220> FEATURE:
<223> OTHER INFORMATION: cloned psiRNA

<400> SEQUENCE: 222
attgaaaggc gttaatgaac aataagcctg acacgaacat aaa   43

```
<210> SEQ ID NO 223
<211> LENGTH: 39
<212> TYPE: DNA
<213> ORGANISM: artificial
<220> FEATURE:
<223> OTHER INFORMATION: cloned psiRNA

<400> SEQUENCE: 223
attgaaagcc ggttctgcac ccgaaacttt cataccaaa                    39

<210> SEQ ID NO 224
<211> LENGTH: 39
<212> TYPE: DNA
<213> ORGANISM: artificial
<220> FEATURE:
<223> OTHER INFORMATION: cloned psiRNA

<400> SEQUENCE: 224
aattgaaagc cggttctgca cccgaaactt tcataccaa                    39

<210> SEQ ID NO 225
<211> LENGTH: 39
<212> TYPE: DNA
<213> ORGANISM: artificial
<220> FEATURE:
<223> OTHER INFORMATION: cloned psiRNA

<400> SEQUENCE: 225
attgaaaggt agtgaggcgt tgaacttgac ccaccacca                    39

<210> SEQ ID NO 226
<211> LENGTH: 38
<212> TYPE: DNA
<213> ORGANISM: artificial
<220> FEATURE:
<223> OTHER INFORMATION: cloned psiRNA

<400> SEQUENCE: 226
attgaaagtg agttgtttag tctaactctt acaccatc                     38

<210> SEQ ID NO 227
<211> LENGTH: 39
<212> TYPE: DNA
<213> ORGANISM: artificial
<220> FEATURE:
<223> OTHER INFORMATION: cloned psiRNA

<400> SEQUENCE: 227
attgaaagtg cgctattctc gggtcaagcc tcccagcct                    39

<210> SEQ ID NO 228
<211> LENGTH: 35
<212> TYPE: DNA
<213> ORGANISM: artificial
<220> FEATURE:
<223> OTHER INFORMATION: cloned psiRNA

<400> SEQUENCE: 228
gaaagcacca ccacgatgaa ggtaccgttt tcaac                        35

<210> SEQ ID NO 229
<211> LENGTH: 35
<212> TYPE: DNA
<213> ORGANISM: artificial
<220> FEATURE:
<223> OTHER INFORMATION: cloned psiRNA
```

```
<400> SEQUENCE: 229
gaaagcacca ccacgatgaa ggtaccgttt tcaac                         35

<210> SEQ ID NO 230
<211> LENGTH: 33
<212> TYPE: DNA
<213> ORGANISM: artificial
<220> FEATURE:
<223> OTHER INFORMATION: cloned psiRNA

<400> SEQUENCE: 230
attgaaagtg ttcatcgcac ttcttcttct gac                           33

<210> SEQ ID NO 231
<211> LENGTH: 39
<212> TYPE: DNA
<213> ORGANISM: artificial
<220> FEATURE:
<223> OTHER INFORMATION: cloned psiRNA

<400> SEQUENCE: 231
attgaaagct tcttcgaagt cgtagtttag tgtgtcaag                     39

<210> SEQ ID NO 232
<211> LENGTH: 39
<212> TYPE: DNA
<213> ORGANISM: artificial
<220> FEATURE:
<223> OTHER INFORMATION: cloned psiRNA

<400> SEQUENCE: 232
attgaaagtt ctagaagttc tcttgcgaga gccaggagc                     39

<210> SEQ ID NO 233
<211> LENGTH: 37
<212> TYPE: DNA
<213> ORGANISM: artificial
<220> FEATURE:
<223> OTHER INFORMATION: cloned psiRNA

<400> SEQUENCE: 233
gaaagctaat ttatgcttta gctcgtgatc aaccta                        37

<210> SEQ ID NO 234
<211> LENGTH: 34
<212> TYPE: DNA
<213> ORGANISM: artificial
<220> FEATURE:
<223> OTHER INFORMATION: cloned psiRNA

<400> SEQUENCE: 234
gaaagctaat ttacgcttta gctcgtgatc aacc                          34

<210> SEQ ID NO 235
<211> LENGTH: 33
<212> TYPE: DNA
<213> ORGANISM: artificial
<220> FEATURE:
<223> OTHER INFORMATION: cloned psiRNA

<400> SEQUENCE: 235
aggaatgttg ctcaatgcaa agggctcacc gct                           33

<210> SEQ ID NO 236
<211> LENGTH: 34
```

```
<212> TYPE: DNA
<213> ORGANISM: artificial
<220> FEATURE:
<223> OTHER INFORMATION: cloned psiRNA

<400> SEQUENCE: 236
aaagtctcaa ttggggagtg ctttaatggc tttt                          34

<210> SEQ ID NO 237
<211> LENGTH: 36
<212> TYPE: DNA
<213> ORGANISM: artificial
<220> FEATURE:
<223> OTHER INFORMATION: cloned psiRNA

<400> SEQUENCE: 237
attgaaaggg aactcctcga ttttagtacc tgtgtc                        36

<210> SEQ ID NO 238
<211> LENGTH: 37
<212> TYPE: DNA
<213> ORGANISM: artificial
<220> FEATURE:
<223> OTHER INFORMATION: cloned psiRNA

<400> SEQUENCE: 238
attgaaagcc acataagaca ttgtcataca aagtagg                       37

<210> SEQ ID NO 239
<211> LENGTH: 38
<212> TYPE: DNA
<213> ORGANISM: artificial
<220> FEATURE:
<223> OTHER INFORMATION: cloned psiRNA

<400> SEQUENCE: 239
attgaaaggt cacgtaattc gccaagtcct cttggaga                      38

<210> SEQ ID NO 240
<211> LENGTH: 39
<212> TYPE: DNA
<213> ORGANISM: artificial
<220> FEATURE:
<223> OTHER INFORMATION: cloned psiRNA

<400> SEQUENCE: 240
attgaaaggt ggataatata atccctgttt ttcccaaga                     39

<210> SEQ ID NO 241
<211> LENGTH: 39
<212> TYPE: DNA
<213> ORGANISM: artificial
<220> FEATURE:
<223> OTHER INFORMATION: cloned psiRNA

<400> SEQUENCE: 241
attgaaaggt ggataatata atccctgttt ttcccaaga                     39

<210> SEQ ID NO 242
<211> LENGTH: 39
<212> TYPE: DNA
<213> ORGANISM: artificial
<220> FEATURE:
<223> OTHER INFORMATION: cloned psiRNA

<400> SEQUENCE: 242
```
attgaaaggt ggataatata atccctgttt ttcccaaga                                39

<210> SEQ ID NO 243
<211> LENGTH: 39
<212> TYPE: DNA
<213> ORGANISM: artificial
<220> FEATURE:
<223> OTHER INFORMATION: cloned psiRNA

<400> SEQUENCE: 243
attgaaaggt ggataatata atccctgttt ttcccaaga                                39

<210> SEQ ID NO 244
<211> LENGTH: 39
<212> TYPE: DNA
<213> ORGANISM: artificial
<220> FEATURE:
<223> OTHER INFORMATION: cloned psiRNA

<400> SEQUENCE: 244
attgaaagca gttctacttt gataagactg tggtggtta                                39

<210> SEQ ID NO 245
<211> LENGTH: 39
<212> TYPE: DNA
<213> ORGANISM: artificial
<220> FEATURE:
<223> OTHER INFORMATION: cloned psiRNA

<400> SEQUENCE: 245
attgaaagga caaagaactc cctagcgtcc ctccccgtg                                39

<210> SEQ ID NO 246
<211> LENGTH: 39
<212> TYPE: DNA
<213> ORGANISM: artificial
<220> FEATURE:
<223> OTHER INFORMATION: cloned psiRNA

<400> SEQUENCE: 246
aattgaaagt tctgccgtcc ctttctcgac gaacctcat                                39

<210> SEQ ID NO 247
<211> LENGTH: 39
<212> TYPE: DNA
<213> ORGANISM: artificial
<220> FEATURE:
<223> OTHER INFORMATION: cloned psiRNA

<400> SEQUENCE: 247
attgaaaggc accttcttca ccatcgccgt ctggattgc                                39

<210> SEQ ID NO 248
<211> LENGTH: 36
<212> TYPE: DNA
<213> ORGANISM: artificial
<220> FEATURE:
<223> OTHER INFORMATION: cloned psiRNA

<400> SEQUENCE: 248
agttgtaggc tcgtggactt ggcttccaca caacta                                   36

<210> SEQ ID NO 249
<211> LENGTH: 37
<212> TYPE: DNA
<213> ORGANISM: artificial

<220> FEATURE:
<223> OTHER INFORMATION: cloned psiRNA

<400> SEQUENCE: 249
attgaaagta tctattgtac aggtacttgt tacacgt                37

<210> SEQ ID NO 250
<211> LENGTH: 35
<212> TYPE: DNA
<213> ORGANISM: artificial
<220> FEATURE:
<223> OTHER INFORMATION: cloned psiRNA

<400> SEQUENCE: 250
attgaagctt gcccaacctc tctagaaacg cccac                  35

<210> SEQ ID NO 251
<211> LENGTH: 38
<212> TYPE: DNA
<213> ORGANISM: artificial
<220> FEATURE:
<223> OTHER INFORMATION: cloned psiRNA

<400> SEQUENCE: 251
attgaaaggc gttaatgaac aataagcctg acacgaac               38

<210> SEQ ID NO 252
<211> LENGTH: 39
<212> TYPE: DNA
<213> ORGANISM: artificial
<220> FEATURE:
<223> OTHER INFORMATION: cloned psiRNA

<400> SEQUENCE: 252
attgaaagta atctcaataa ctttggcttc ttttctgtg              39

<210> SEQ ID NO 253
<211> LENGTH: 39
<212> TYPE: DNA
<213> ORGANISM: artificial
<220> FEATURE:
<223> OTHER INFORMATION: cloned psiRNA

<400> SEQUENCE: 253
attgaaagta atctcaataa ctttggcttc ttttctgtg              39

<210> SEQ ID NO 254
<211> LENGTH: 39
<212> TYPE: DNA
<213> ORGANISM: artificial
<220> FEATURE:
<223> OTHER INFORMATION: cloned psiRNA

<400> SEQUENCE: 254
attgaaagac acgaatcccc aacattcttc accaccct              39

<210> SEQ ID NO 255
<211> LENGTH: 36
<212> TYPE: DNA
<213> ORGANISM: artificial
<220> FEATURE:
<223> OTHER INFORMATION: cloned psiRNA

<400> SEQUENCE: 255
attgaaagtg actgcctccc tcagaacctt aatgat                 36

<210> SEQ ID NO 256
<211> LENGTH: 37
<212> TYPE: DNA/RNA
<213> ORGANISM: artificial
<220> FEATURE:
<223> OTHER INFORMATION: target

<400> SEQUENCE: 256
ctguugtgct ctcugccgcu ugguccgcut uctucuu                                37

<210> SEQ ID NO 257
<211> LENGTH: 45
<212> TYPE: RNA
<213> ORGANISM: artificial
<220> FEATURE:
<223> OTHER INFORMATION: wt psiRNA

<400> SEQUENCE: 257
auugaaaguu guaguaugcg guccuugcgg cugagagcac uucag                       45

<210> SEQ ID NO 258
<211> LENGTH: 37
<212> TYPE: RNA
<213> ORGANISM: artificial
<220> FEATURE:
<223> OTHER INFORMATION: tag psiRNA

<400> SEQUENCE: 258
uuguaguaug cgguccuugc ggcugagagc acuucag                                37

<210> SEQ ID NO 259
<211> LENGTH: 45
<212> TYPE: RNA
<213> ORGANISM: artificial
<220> FEATURE:
<223> OTHER INFORMATION: complementary tag psiRNA

<400> SEQUENCE: 259
uaacuuucuu guaguaugcg guccuugcgg cugagagcac uucag                       45

<210> SEQ ID NO 260
<211> LENGTH: 50
<212> TYPE: RNA
<213> ORGANISM: artificial
<220> FEATURE:
<223> OTHER INFORMATION: complementary target RNA

<400> SEQUENCE: 260
aaaaaaacug aagugcucuc agccgcaagg accgcauacu acaaaaaaaa                  50

<210> SEQ ID NO 261
<211> LENGTH: 50
<212> TYPE: RNA
<213> ORGANISM: artificial
<220> FEATURE:
<223> OTHER INFORMATION: complementary target RNA

<400> SEQUENCE: 261
aaaaaaaaac aucauacgcc aggaacgccg acucucguga agucaaaaaa                  50

<210> SEQ ID NO 262
<211> LENGTH: 50
<212> TYPE: DNA/RNA
<213> ORGANISM: artificial
<220> FEATURE:
<223> OTHER INFORMATION: complementary target RNA

```
<400> SEQUENCE: 262
aaaaaaactg aagugcucuc agccgcaagg accgcauacu acaaaaaaaa         50

<210> SEQ ID NO 263
<211> LENGTH: 37
<212> TYPE: RNA
<213> ORGANISM: artificial
<220> FEATURE:
<223> OTHER INFORMATION: complementary target RNA

<400> SEQUENCE: 263
uuguaguaug cgguccuugc ggcugagagc acuucag                       37

<210> SEQ ID NO 264
<211> LENGTH: 50
<212> TYPE: RNA
<213> ORGANISM: artificial
<220> FEATURE:
<223> OTHER INFORMATION: complementary target RNA

<400> SEQUENCE: 264
aaaaaaacug aagugcucuc agccgcaagg accgcauacu acaaaaaaaa         50

<210> SEQ ID NO 265
<211> LENGTH: 37
<212> TYPE: RNA
<213> ORGANISM: artificial
<220> FEATURE:
<223> OTHER INFORMATION: complementary target RNA

<400> SEQUENCE: 265
cugaagugcu cucagccgca aggaccgcau acuacaa                       37

<210> SEQ ID NO 266
<211> LENGTH: 37
<212> TYPE: RNA
<213> ORGANISM: artificial
<220> FEATURE:
<223> OTHER INFORMATION: complementary target RNA

<400> SEQUENCE: 266
uuguaguaug cgguccuugc ggcugagagc acuucag                       37

<210> SEQ ID NO 267
<211> LENGTH: 50
<212> TYPE: RNA
<213> ORGANISM: artificial
<220> FEATURE:
<223> OTHER INFORMATION: complementary target RNA

<400> SEQUENCE: 267
aaaaaaaguu ccacuaagga cauuuguacg ucaaauucuu cacuaaaaaa         50

<210> SEQ ID NO 268
<211> LENGTH: 57
<212> TYPE: DNA
<213> ORGANISM: artificial
<220> FEATURE:
<223> OTHER INFORMATION: complementary target RNA

<400> SEQUENCE: 268
ggggatgatg agttttccc tcactctgat tagtgatgag gagccgatgc actgacc  57

<210> SEQ ID NO 269
```

<211> LENGTH: 287
<212> TYPE: PRT
<213> ORGANISM: artificial
<220> FEATURE:
<223> OTHER INFORMATION: polymerase/nuclease domain

<400> SEQUENCE: 269

```
Leu Lys Leu Lys Thr Leu Thr Pro Leu His Ile Gly Ser Gly Lys Glu
1               5                   10                  15

Glu Gly Glu Ile Gly Gly Ile Val Lys Lys Leu Ile Asp Asn Pro Ile
            20                  25                  30

Val Arg Asp Pro His Leu Phe Lys Asp Glu Ile Ala Lys Lys Lys Thr
        35                  40                  45

Gly Leu Pro Ile Tyr Ile Pro Gly Ser Ser Ile Lys Gly Ala Leu Arg
    50                  55                  60

Trp Trp Phe Arg Ala Leu Tyr Gly Ser Leu Leu Glu Arg Lys Leu Gly
65                  70                  75                  80

Lys Glu Leu Lys Glu Glu Glu Ser Lys Glu Glu Lys Glu Lys Ile Phe
                85                  90                  95

Gly Ser Thr Glu Glu Glu Ser Asp Phe Ala Gly Arg Val Ile Phe Ser
            100                 105                 110

Asp Ala Pro Thr Asp Ala Leu Leu Leu Phe Pro Val Arg Ser Ile Gly
        115                 120                 125

Val Phe Ala Tyr Val Thr Ser Pro Leu Val Leu Arg Phe Leu Glu Val
    130                 135                 140

Leu Val Gly Glu Leu Leu Glu Val Lys Lys Gln Leu Glu Ala Lys Leu
145                 150                 155                 160

Glu Asp Leu Lys Lys Lys Leu Ile Lys Arg Leu Ala Ile Leu Ser Asp
                165                 170                 175

Asp Leu Phe Ser Asp Leu Val Lys Tyr Leu Glu Glu Lys Thr Glu Val
            180                 185                 190

Ala Ile Asn Arg Lys Thr Gly Thr Ala Glu Glu Gly Ile Ala Leu Arg
        195                 200                 205

Tyr Glu Glu Tyr Val Tyr Glu Leu Pro Ala Gly Thr Lys Phe Phe Phe
    210                 215                 220

Phe Glu Leu Ile Leu Lys Ser Glu Asp Glu Leu Tyr Phe Glu Glu Ile
225                 230                 235                 240

Lys Glu Lys Glu Ser Gly Asn Leu Phe Leu Asn Phe Phe Leu Asp Glu
                245                 250                 255

Glu Glu Glu Asp Leu Lys Lys Leu Lys Glu Leu Leu Lys Leu Leu Asp
            260                 265                 270

Leu Gly Leu Gly Gly Lys Thr Ser Arg Gly Tyr Gly Leu Val Lys
        275                 280                 285
```

<210> SEQ ID NO 270
<211> LENGTH: 223
<212> TYPE: PRT
<213> ORGANISM: artificial
<220> FEATURE:
<223> OTHER INFORMATION: polymerase/nuclease domain

<400> SEQUENCE: 270

```
Leu Glu Ala Ile Thr Pro Ile Phe Met Gly Gly Ala Arg Lys Pro Val
1               5                   10                  15

Ser Arg Lys Tyr Arg Gly Tyr Tyr Glu Glu Val Arg Ser Thr Ser
            20                  25                  30

Ile Lys Gly Leu Leu Arg Trp Trp Phe Arg Ala Leu Ala Arg Gly Ile
```

```
                 35                  40                  45
Gly Ser Tyr Phe Gly Asn Asn Leu Glu Lys Leu Lys Glu Ala Glu Lys
 50                  55                  60

Glu Lys Glu Lys Lys Glu Asp Arg Lys Gly Leu Lys Cys Leu Ala Glu
 65                  70                  75                  80

Glu Ile Phe Gly Ser Thr Asn Arg Lys Ser Arg Val Arg Leu Glu Val
                 85                  90                  95

Glu Asp Glu Gly Asn Phe Ile Thr Ile Ser Lys Ala Ile Trp Asp Phe
                100                 105                 110

Ile Ile Arg Ile Val Ser Lys Asn Leu Asn Ile Ala Glu Thr Lys Asn
                115                 120                 125

Ile Lys Leu Gly Asn Val Lys Leu Ser Lys Asn Glu Val Arg Lys Lys
130                 135                 140

Gly Glu Glu Gln Glu Lys Val Lys Lys Arg Glu Leu Arg Asp Pro
145                 150                 155                 160

Asn Asn Thr Leu Arg Ile Leu Leu Glu Gly Asp Asp Lys Lys Ile Ile
                165                 170                 175

Ala Leu Ile Asn Asn Ser Leu Ile Ser Lys Lys Leu Arg Asp Glu Leu
                180                 185                 190

Lys Asn Lys Leu Leu Ile Leu Ser Ser Phe Gly Ile Gly Arg Lys
195                 200                 205

Leu Ala Arg Thr Arg Arg Gly Phe Gly Ser Ile Glu Ile Lys Ser
210                 215                 220
```

<210> SEQ ID NO 271
<211> LENGTH: 665
<212> TYPE: PRT
<213> ORGANISM: artificial
<220> FEATURE:
<223> OTHER INFORMATION: polymerase/nuclease domain

<400> SEQUENCE: 271

```
Val Leu Val Val Ile Thr Ile Gly Pro Val Gln Glu Phe Ile Ala Lys
 1               5                  10                  15

Ala Arg Lys Leu Arg Asp Leu Trp Ala Gly Ser Tyr Leu Leu Ser Tyr
                 20                  25                  30

Leu Ile Trp Lys Ala Ile Glu Phe Leu Val Glu Lys Tyr Gly Pro Asp
                 35                  40                  45

His Val Ile Phe Pro Ala Leu Arg Gly Asn Pro Phe Phe Asp Ala Leu
 50                  55                  60

Leu Ala Asn Lys Val Val Lys Glu Phe Glu Val Asp Val Gly Pro Lys
 65                  70                  75                  80

Glu Val Val Glu Val Lys Glu Thr Ile Leu Ile Lys Leu Lys Glu
                 85                  90                  95

Glu Val Ala Glu Leu Pro Asn Leu Phe Leu Ala Ile Leu Pro Ala Lys
                100                 105                 110

Asp Glu Lys Ile Leu Glu Lys Leu Glu Glu Thr Ile Arg Leu Lys Ile
                115                 120                 125

Lys Ser Glu Leu Ala Glu Leu Leu Lys Lys Ala Val Gly Lys Glu Leu
130                 135                 140

Ile Glu Gly Glu Ala Val Ile Val Asp Leu Glu Gly Leu Lys Gln
145                 150                 155                 160

Leu Glu Glu Ala Leu Lys Lys Leu Leu Glu Lys Arg Ala Asp Leu Arg
                165                 170                 175

Leu Phe Ala Pro Ser Lys Leu Val Val Asp Ile Glu Gly Glu Lys Glu
```

```
                180             185             190
Glu Val Tyr Lys Ser Val Lys Asn Gly Val Glu Ala Gly Leu Asn
            195             200             205

Lys Lys Ile Val Ser Lys Tyr Leu Ser Phe Glu Glu Ile Val Leu Lys
210             215                 220

Leu Ser Glu Lys Glu Lys Arg Lys Glu Leu Ile Arg Ile Tyr Leu Lys
225             230             235             240

Leu Arg Glu Ser Arg Ser Phe Tyr Lys Leu Asp Ala Ile Gly Leu Thr
            245             250             255

Lys Arg Lys Ser Glu Arg Leu Glu Lys Gln Leu Glu Leu Pro Gly Ile
            260             265             270

Lys Cys Leu Leu Cys Gly Glu Asp Leu Ala Ile Ala Gly Val Lys Glu
            275             280             285

Lys Leu Leu Glu Lys Val Tyr Asp Asp Glu Leu Lys Asp Leu Lys Ala
290             295             300

Leu Leu Gln Glu Glu Arg Leu Cys Pro Leu Cys Leu Ile Lys Arg
305             310             315             320

Gln Leu Pro Lys Leu Ile Glu Asp Leu Arg Val Leu Glu Val Glu
            325             330             335

Lys Lys Val Pro Ile Glu Ser Val Lys Asp Val Ala Glu Lys Arg Arg
            340             345             350

Glu Ala Glu Gly Lys Glu Trp Lys Glu Phe Asp Glu Leu Leu Gly
            355             360             365

Arg Leu Phe Pro Lys Lys Glu Leu Leu Pro Ser Ile Lys Glu Val
370             375             380

Ala Glu Ser Glu Lys Glu Gln Lys Leu Leu Val Asp Gly Glu Leu Lys
385             390             395             400

Val Asp Lys Glu Tyr Leu Glu Glu Leu Lys Lys Gly Leu Glu Glu Ser
            405             410             415

Lys Glu Asn Glu Val Glu Lys Leu Lys Val Asp Glu Lys Lys Pro Cys
            420             425             430

Ile Gln Lys Val Lys Glu Val Ser Asp Arg Leu Asn Ala Leu Glu Lys
            435             440             445

Val Arg Lys Asn Pro Arg Pro Tyr Tyr Ala Ile Leu Lys Ala Asp Gly
            450             455             460

Asp Arg Met Gly Lys Leu Leu Arg Gly Glu Ile Arg Pro Glu Lys
465             470             475             480

Glu Arg Ile His Pro Lys Val Ile Glu Val Lys Glu Glu Lys
            485             490             495

Val Lys Lys Asn Ala Ile Lys Arg Ala Leu Lys Phe Leu Ile Lys Thr
            500             505             510

Leu Ser Asn Lys Asp Ser Leu Ala Lys Val Val Leu Lys Lys Lys
            515             520             525

Leu Thr Thr Pro Ala Ala His Arg Ala Ile Ser Arg Ala Leu Ala Glu
            530             535             540

Phe Ser Leu Lys Glu Val Lys Ile Val Val Glu His Arg Asp Asp
545             550             555             560

Trp Ile Tyr Glu Gly Val Leu Val Tyr Ala Gly Gly Asp Asp Val Leu
            565             570             575

Ala Leu Leu Pro Val Asp Thr Asn Ala Leu Asp Val Ala Lys Glu Leu
            580             585             590

Arg Lys Glu Phe Ser Glu Ser Leu Glu Lys Glu Leu Gly Lys Glu Arg
            595             600             605
```

```
Ile Lys Pro Tyr Glu Ser Glu Lys Val Val Arg Tyr Gln Gly Glu Lys
        610                 615                 620

Pro Ser Glu Tyr Thr Ser Leu Glu Glu Pro Thr Leu Ser Ala Gly Leu
625                 630                 635                 640

Val Ile Val His His Lys Glu Pro Leu Tyr Asp Ala Leu Glu Leu Ala
                    645                 650                 655

Arg Glu Leu Leu Lys Arg Ala Lys Glu
            660                 665

<210> SEQ ID NO 272
<211> LENGTH: 456
<212> TYPE: PRT
<213> ORGANISM: artificial
<220> FEATURE:
<223> OTHER INFORMATION: polymerase/nuclease domain

<400> SEQUENCE: 272

Ile Leu Ile Lys Pro Leu Asp Val Leu Phe Arg Glu Ser Arg Pro
1               5                   10                  15

Phe Asp Ala Gly Asn Glu Gly Ser Ala Ala Ser Val Val Ser Ser Ile
                20                  25                  30

Phe Pro Ser Pro Thr Thr Ile Ala Gly Ala Val Arg Thr Ala Leu Leu
            35                  40                  45

Glu Lys Ala Ala Lys Asp Leu Ser Arg Leu Leu Asp Tyr Val Arg Lys
50                  55                  60

Ile Glu Arg Glu Ala Lys Pro Gly Leu Ile Glu Phe Ser Ile Tyr
65                  70                  75                  80

Gly Pro Phe Val Val Glu Lys Gly Pro Glu Ala Ile Ile Arg Glu Leu
                85                  90                  95

Lys Pro Phe Phe Pro Leu Pro Ser Asp Ile Ala Phe Tyr Glu Asp Glu
            100                 105                 110

Asp Gly Ala Leu Ala Val Asp Leu Leu Arg Val Glu Glu Leu Leu Lys
        115                 120                 125

Glu Lys Tyr Phe Lys Val Val Asp Lys Ala Leu Ile Glu Glu Leu Gly
130                 135                 140

Lys Leu Pro Leu Pro Pro Gly Lys Gly Glu Lys Lys Glu Ile Ile Pro
145                 150                 155                 160

Gly Phe Leu Asn Lys Ser Glu Ser Lys Leu Ser Lys Tyr Leu Lys Gly
                165                 170                 175

Glu Ile Ser Glu Leu Lys Lys Tyr Asp Leu Leu Lys Asn Val Ala Gly
            180                 185                 190

Glu Glu Glu Ile Phe Lys Lys Glu Arg Ile Asp Thr Asp Lys Asp
        195                 200                 205

Val His Phe Leu Pro Gly Ile Lys Leu Asp Lys Glu Lys Lys Val Val
210                 215                 220

Arg Glu Ile Gly Ser Arg Lys Glu Lys Glu Gly Ala Leu Tyr Ser Gln
225                 230                 235                 240

Glu Phe Leu Arg Phe Lys Arg Phe Lys Glu Val Asp Gly Val Gly Leu
                245                 250                 255

Ile Val Trp Val Glu Asp Pro Glu Ala Glu Asp Glu Lys Ile Lys
            260                 265                 270

Glu Leu Leu Glu Ser Leu Lys Asp Ile Lys Phe Glu Glu Leu Asn Lys
        275                 280                 285

Lys Ile Val Thr Leu Gly Gly Glu Arg Arg Leu Ala Lys Leu Glu Val
290                 295                 300
```

```
Asp Glu Glu Asn Glu Asp Thr Phe Asn Gly Glu Lys Trp Glu Leu Lys
305                 310                 315                 320

Ser Ser Leu Lys Glu Gly Lys Lys Val Lys Phe Tyr Leu Leu Thr Pro
                325                 330                 335

Ala Ile Phe Leu Glu Gly Gly Tyr Phe Val Val Leu Ser Asp Leu
                340                 345                 350

Lys Asp Leu Leu Leu Glu Asp Glu Ile Phe Ala Lys Leu Leu Glu Arg
                355                 360                 365

Lys Gly Asp Lys Val Leu Val Val Thr Leu Gly Val Arg Lys Gln Glu
    370                 375                 380

Val Ser Gly Trp Asp Tyr Val Glu Lys Lys Gly Asn Glu Pro Lys Pro
385                 390                 395                 400

Thr Leu Glu Ala Val Pro Pro Gly Ser Val Leu Phe Leu Lys Ala Lys
                405                 410                 415

Glu Glu Val Glu Leu Glu Leu Leu Asn Phe Pro Val Ser Glu Asp Glu
                420                 425                 430

Asp Asp Ala Leu Leu Ile Lys Leu Gly Lys Phe Glu Lys Ile Gly Tyr
                435                 440                 445

Gly Leu Ala Leu Ile Gly Glu Trp
    450                 455

<210> SEQ ID NO 273
<211> LENGTH: 326
<212> TYPE: PRT
<213> ORGANISM: artificial
<220> FEATURE:
<223> OTHER INFORMATION: polymerase/nuclease domain

<400> SEQUENCE: 273

Tyr Leu Val Leu Leu Tyr Ala Leu Thr Pro Val His Val Gly Ala Gly
1               5                   10                  15

Gln Ser Ser Ile Gly Val Val Asp Leu Pro Ile Gln Arg Glu Arg His
                20                  25                  30

Thr Gly Tyr Pro Ile Ile Tyr Gly Lys Ser Ser Leu Lys Gly Ala Leu
            35                  40                  45

Arg Ser Tyr Leu Ala Lys Gln Ala Ser Lys Asp Leu Asp Tyr Val Asp
50                  55                  60

Ala Lys Glu Glu Lys Val Glu Ala Val Phe Gly Ser Glu Pro Lys
65                  70                  75                  80

Glu Glu Ala Glu Glu Ser Ala Gly Lys Val Ser Val Ser Asp Ala Arg
                85                  90                  95

Leu Leu Leu Tyr Pro Val Arg Ile Ile Pro Ile Ser Lys Ser Leu Asp
            100                 105                 110

Gly Val Phe Ala Tyr Val Thr Ser Pro Tyr Leu Leu Glu Arg Phe Lys
        115                 120                 125

Arg Asp Leu Glu Ala Ala Gly Val Leu Asn Gly Ser Lys Glu Leu Glu
    130                 135                 140

Glu Asn Glu Gly Leu Glu Lys Lys Leu Ser Leu Asp Glu Asp Ala
145                 150                 155                 160

Leu Leu Ala Ser Gly Glu Glu Val Leu Ala Ile Lys Glu Gly Lys Val
                165                 170                 175

Leu Leu Glu Glu Ile Lys Leu Glu Ala Ile Leu Asn Glu Ala Val Gly
            180                 185                 190

Glu Leu Glu Asp Val Leu Ala Ile Lys Thr Phe Lys Ser Pro Asp Glu
        195                 200                 205
```

```
Leu Val Glu Leu Leu Glu Ser Arg Leu Val Val Ser Asp Asp Leu
            210                 215                 220

Phe Arg Asp Leu Val Asn Ser Ser Leu Glu Val Val Thr Arg Ile Arg
225                 230                 235                 240

Leu Asn Gln Glu Thr Lys Thr Val Glu Glu Gly Gly Leu Trp Tyr Glu
                245                 250                 255

Glu Tyr Ile Pro Ala Glu Thr Ile Phe Tyr Ser Leu Ile Leu Val Asp
                260                 265                 270

Glu Val Ser Asn Asp Tyr Cys Glu Glu Leu Asn Lys Lys Glu Ser Asn
            275                 280                 285

Lys Glu Glu Ile Phe Lys Glu Phe Ser Lys Lys Ile Asn Asn Lys Gly
290                 295                 300

Ile Ser Val Leu Asp Lys Val Leu Gln Ile Gly Gly Lys Glu Thr Val
305                 310                 315                 320

Gly Lys Gly Leu Val Arg
                325

<210> SEQ ID NO 274
<211> LENGTH: 169
<212> TYPE: PRT
<213> ORGANISM: artificial
<220> FEATURE:
<223> OTHER INFORMATION: polymerase/nuclease domain

<400> SEQUENCE: 274

Met Lys Thr Leu Glu Gln Glu Arg Ala Lys Leu Ala Leu Lys Val Val
1               5                   10                  15

Glu Glu Val Glu Lys Lys Lys Asp Lys Lys Leu Arg Glu Lys Tyr
            20                  25                  30

Ala Ser Arg Val Arg Lys Leu Pro Ser Met Ile Leu Ser Asn Gly Leu
            35                  40                  45

Leu Pro Thr Leu Ala Phe Tyr Leu Ser Lys Ala Glu Leu Glu Ala Glu
            50                  55                  60

Asn Lys Ile Leu Ser Ala Leu Asn Asn Tyr Lys Ser Ser Lys Lys Glu
65                  70                  75                  80

Lys Leu Gly Asn Ser Glu Glu Ala Ser Tyr Leu Lys Val Tyr Ala His
                85                  90                  95

Ile Leu Tyr Trp Leu Lys Glu Arg Glu Leu Lys Glu Lys Lys Glu Ile
                100                 105                 110

Leu Leu Asp Glu Leu Lys Pro Lys Asn Asn Val Thr Gln Ser Ala Asp
            115                 120                 125

Ala Leu Lys Glu Leu Leu Glu Lys Asp Tyr Ser Asp Val Arg Thr Tyr
            130                 135                 140

Leu Ile Ala Thr Glu Glu Ala Leu Arg Leu Leu Asn Trp Leu Lys Arg
145                 150                 155                 160

Leu Ala Glu Ala Leu Leu Lys Glu Glu
                165

<210> SEQ ID NO 275
<211> LENGTH: 280
<212> TYPE: PRT
<213> ORGANISM: artificial
<220> FEATURE:
<223> OTHER INFORMATION: polymerase/nuclease domain

<400> SEQUENCE: 275

Phe Lys Leu Lys Thr Cys Ser Ser Arg Leu Leu Val Gly Leu Gly Thr
```

```
1               5                   10                  15
Glu His Glu Ile Asn Lys Pro Ala Asp Glu Lys Gly Lys Lys Val Glu
                20                  25                  30

Gly Asp Lys Glu Asp Asp Ala Pro Glu Val Tyr Glu Thr Gly Leu Thr
                35              40                  45

Leu Asp Pro Ile Tyr Gly Val Pro Tyr Ile Pro Gly Ser Ala Ile Lys
                50              55                  60

Gly Val Leu Arg Ser Ala Thr Phe Glu Val Leu Ala Glu Glu Glu
65                      70                  75                  80

Lys Gly Glu Glu Ile Leu Lys Ile Ala Lys Ser Val Lys Asp Asp Leu
                    85                  90                  95

Lys Lys Arg Ile Ile Lys Glu Asp Glu Leu Lys Asn Gly Val Lys Arg
                    100                 105                 110

Glu Asp Glu Lys Leu Ala Lys Lys Arg Phe Arg Glu Asp Phe Gly Lys
                    115                 120                 125

Lys Lys Arg Pro Glu Leu Pro Glu Glu Leu Ala Asp Lys Leu Phe Gly
                    130                 135                 140

Thr Gln Glu Lys Ser Ile Glu Gly Glu Val Ile Phe Leu Asp Ala Tyr
145                     150                 155                 160

Pro Ile Pro Asp Glu Asn Lys Asp Lys Pro Ser Ile Leu Glu Leu Asp
                    165                 170                 175

Ile Ile Asn Pro His Tyr Gln Pro Tyr Tyr Gln Gly Glu Glu Lys Asn
                    180                 185                 190

Lys Pro Pro Gly Asp Trp Val Asn Pro Ile Pro Ile Lys Phe Leu Thr
                    195                 200                 205

Val Lys Lys Gly Val Thr Phe Gln Phe Val Val Leu Phe Asp Asp Leu
                    210                 215                 220

Arg Ala Glu Glu Leu Lys Lys Glu Lys Ile Phe Glu Glu Val Lys Asn
225                     230                 235                 240

Glu Leu Leu Asp Glu Leu Leu Leu Asp Val Leu Glu Lys Leu Leu Lys
                    245                 250                 255

Glu Leu Leu Lys Glu Ala Leu Thr Glu Phe Gly Ile Gly Ala Lys Thr
                    260                 265                 270

Ser Leu Gly Tyr Gly Arg Phe Glu
                    275                 280

<210> SEQ ID NO 276
<211> LENGTH: 30
<212> TYPE: DNA
<213> ORGANISM: artificial
<220> FEATURE:
<223> OTHER INFORMATION: repeat present in Pyrococcus furiosus

<400> SEQUENCE: 276
gttccaataa gactaaaata gaattgaaag                                  30
```